(12) United States Patent
Mihara et al.

(10) Patent No.: US 8,822,691 B2
(45) Date of Patent: Sep. 2, 2014

(54) PESTICIDAL CARBOXAMIDES

(75) Inventors: Jun Mihara, Osaka (JP); Koichi Araki, Ushiku (JP); Takuma Mori, Tokyo (JP); Tetsuya Murata, Osaka (JP); Yasushi Yoneta, Saitama (JP); Eiichi Shimojo, Osaka (JP); Teruyuki Ichihara, Tochigi (JP); Masashi Ataka, Saitama (JP); Katsuhiko Shibuya, Tochigi (JP); Ulrich Görgens, Ratingen (DE)

(73) Assignee: Bayer CropScience AG, Monheim (DE)

( * ) Notice: Subject to any disclaimer, the term of this patent is extended or adjusted under 35 U.S.C. 154(b) by 0 days.

(21) Appl. No.: 13/386,598

(22) PCT Filed: Jul. 10, 2010

(86) PCT No.: PCT/EP2010/004217
§ 371 (c)(1),
(2), (4) Date: May 3, 2012

(87) PCT Pub. No.: WO2011/009540
PCT Pub. Date: Jan. 27, 2011

(65) Prior Publication Data
US 2012/0277185 A1    Nov. 1, 2012

(30) Foreign Application Priority Data

Jul. 24, 2009  (JP) ................. 2009-172800
Mar. 10, 2010  (JP) ................. 2010-053081

(51) Int. Cl.
*A01N 37/34*    (2006.01)
*A01N 43/42*    (2006.01)
*C07D 215/48*    (2006.01)
*C07D 215/60*    (2006.01)
*C07D 277/68*    (2006.01)

(52) U.S. Cl.
CPC .............. *C07D 215/48* (2013.01); *A01N 37/34* (2013.01); *A01N 43/42* (2013.01); *C07D 215/60* (2013.01); *C07D 277/68* (2013.01)
USPC ............. 546/169; 546/14; 546/162; 546/153; 514/63; 514/510; 514/311; 514/367; 514/617; 514/312; 514/314

(58) Field of Classification Search
CPC .. C07D 215/48; C07D 215/60; C07D 277/68; A01N 37/34; A01N 43/42
See application file for complete search history.

(56) References Cited

U.S. PATENT DOCUMENTS

| | | | |
|---|---|---|---|
| 6,284,796 B1 * | 9/2001 | Geyer et al. ............ | 514/620 |
| 6,603,044 B1 | 8/2003 | Tohnishi et al. | |
| 2002/0198399 A1 | 12/2002 | Onishi et al. | |
| 2003/0181759 A1 | 9/2003 | Kodama et al. | |
| 2004/0009982 A1 | 1/2004 | Tohnishi et al. | |
| 2004/0152898 A1 | 8/2004 | Marhold et al. | |
| 2007/0027154 A1 | 2/2007 | Yoshida et al. | |
| 2007/0275980 A1 | 11/2007 | Yoshida et al. | |
| 2008/0051457 A1 | 2/2008 | Nakao et al. | |
| 2008/0234381 A1 | 9/2008 | Olesen et al. | |
| 2009/0076282 A1 | 3/2009 | Toriyabe et al. | |
| 2009/0099204 A1 | 4/2009 | Yoshida et al. | |
| 2009/0192175 A1 | 7/2009 | Jung et al. | |
| 2009/0233962 A1 | 9/2009 | Kai et al. | |
| 2009/0247551 A1 | 10/2009 | Jeschke et al. | |
| 2009/0253749 A1 | 10/2009 | Jeschke et al. | |
| 2010/0240705 A1 | 9/2010 | Jeschke et al. | |
| 2011/0190493 A1 | 8/2011 | Bretschneider et al. | |
| 2011/0306499 A1 | 12/2011 | Bretschneider et al. | |
| 2012/0149910 A1 | 6/2012 | Mihara et al. | |

FOREIGN PATENT DOCUMENTS

| | | |
|---|---|---|
| EP | 0 539 588 A1 | 5/1993 |
| EP | 1 006 102 A2 | 6/2000 |
| EP | 1 418 171 A1 | 5/2004 |
| JP | 9-50140 A | 2/1997 |
| JP | 2003-335735 A | 11/2003 |
| JP | 2005-145840 A | 6/2005 |
| JP | 2007-099761 A | 4/2007 |
| JP | 2008-302617 A | 12/2008 |
| WO | WO 0121160 A2 * | 3/2001 |
| WO | WO 02/058690 A2 | 8/2002 |
| WO | WO 2006/024412 A2 | 3/2006 |
| WO | WO 2006/068592 A1 | 6/2006 |

(Continued)

OTHER PUBLICATIONS

Carmellino, M.L., et al., "Insecticidal activity of 6-substituted 8-quinolinecarboxylic acids, 8-quinolinecarboxylic acid esters and amides, and 8-quinolinecarboxaldehyde derivatives," *Boll. Chim. Farm.* 129(5):190-194, Societa Editoriale Farmaceutica, Italy (1990).

Caron, S., et al., "A practical, efficient and rapid method for the oxidation of electron deficient pyridines using trifluoroacetic anhydride and hydrogen peroxide-urea complex," *Tetrahedron Letters* 41:2299-2302, Elsevier Science Ltd., England (2000).

Dardonville, C., et al., "Synthesis and pharmacological studies of new hybrid derivatives of fentanyl active at the µ-opioid receptor and I₂-imidazoline binding sites," *Bioorganic & Medicinal Chemistry* 14:6570-6580, Elsevier Ltd., England (2006).

Fife, W.K., "Regioselective Cyanation of Pyridine 1-Oxides Trimethylsilanecarbonitrile: A Modified Reissert-Henze Reaction," *J. Org. Chem.* 48:1375-1377, American Chemical Society, United States (1983).

(Continued)

*Primary Examiner* — Yong Chu
(74) *Attorney, Agent, or Firm* — Sterne, Kessler, Goldstein & Fox P.L.L.C.

(57) ABSTRACT

To provide novel carboxamides which exhibit an excellent pesticidal activity as pesticides. Carboxamides represented by the following Formula (I) and use thereof as pesticides and an animal parasite control agent:

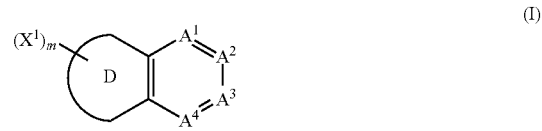

wherein each substituent is as defined in the specification.

7 Claims, No Drawings

(56) References Cited

FOREIGN PATENT DOCUMENTS

| WO | WO 2006/132739 A2 | 12/2006 |
|----|----|----|
| WO | WO 2007/017075 A1 | 2/2007 |
| WO | WO 2007/051560 A1 | 5/2007 |
| WO | WO 2007/133637 A2 | 11/2007 |
| WO | WO 2007/149134 A1 | 12/2007 |
| WO | WO 2008/000438 A1 | 1/2008 |
| WO | WO 2008/074427 A1 | 1/2008 |
| WO | WO 2008/031534 A1 | 3/2008 |
| WO | WO 2008/074427 A1 | 6/2008 |
| WO | WO 2008/107091 A1 | 9/2008 |
| WO | WO 2009/049844 A1 | 4/2009 |
| WO | WO 2009/049845 A2 | 4/2009 |

OTHER PUBLICATIONS

Frère, S., et al., "Novel 6-substituted benzothiazol-2-yl indolo[1,2-c]quinazolines and benzimidazo[1,2-c]quinazolines," *Tetrahedron* 59:773-779, Elsevier Science Ltd., England (2003).

MacDonald, D., et al., "Hunting the Emesis and Efficacy Targets of PDE4 Inhibitors: Identification of the Photoaffinity Probe 8-(3-Azidophenyl)-6-[(4-iodo-1H-1-imidazolyl)methyl]quinoline (APIIMQ)," *J. Med. Chem.* 43:3820-3823, American Chemical Society, United States (2000).

Mazoński, T., et al., "Otrzymywaniu Pochodnych Chinoliny Bezpośrednio Nitrozwiazków. I. 6-Etylochinolina I 8-Chloro-6-Etylochinolina Z p-Nitroetylobenzenu," *Roczniki Chemii* 36:873-877, Państwowe Wydawnictwo Naukowe, Poland (1962).

Miyashita, A., et al., "Preparation by Heteroarenecarbonitriles by Reaction of Heteroarene N-Oxides with Trimethylsilyl Cyanide in the Presence of DBU," *Heterocycles* 33(1):211-218, Elsevier, Netherlands (1992).

Sagi, K., et al., "Optimization of a coagulation factor VIIa inhibitor found in factor Xa inhibitor library," *Bioorganic & Medicinal Chemistry* 13:1487-1496, Elsevier Ltd., England (2005).

English language Abstract of Japanese Patent Publication No. JP 9-50140 A, Japanese Patent Office, Patent & Utility Model Gazette DB, Patent Abstracts of Japan (1997).

English language Abstract of Japanese Patent Publication No. JP 2003-335735 A, European Patent Office, espacenet database—Worldwide (2003).

English language Abstract of Japanese Patent Publication No. JP 2005-145840 A, Japanese Patent Office, Patent & Utility Model Gazette DB, Patent Abstracts of Japan, (2005).

English language Abstract of Japanese Patent Publication No. JP 2007-099761 A, European Patent Office, espacenet database—Worldwide (2007).

English language Abstract of Japanese Patent Publication No. JP 2008-302617 A, Japanese Patent Office, Patent & Utility Model Gazette DB, Patent Abstracts of Japan, (2008).

International Search Report and Written Opinion for International Application No. PCT/EP2010/004217, European Patent Office, The Hague, Netherlands, mailed on Mar. 11, 2011.

Chemical Abstracts Service, Database Registry, Registration No. 847795-79-3, retrieved from STN Entry Apr. 1, 2005.

Chemical Abstracts Service, Database Registry, Registration No. 883102-93-0, retrieved from STN Entry May 5, 2006.

Chemical Abstracts Service, Database Registry, Registration No. 951969-70-3, retrieved from STN Entry Oct. 30, 2007.

\* cited by examiner

PESTICIDAL CARBOXAMIDES

TECHNICAL FIELD

The present invention relates to pesticidal carboxamides and their use as a pesticide.

BACKGROUND ART

In Patent Documents 1 to 17, it is described that pesticidal carboxamide compounds are useful as an agent for controlling harmful organisms.

PRIOR ART LITERATURES

Patent Documents

| | |
|---|---|
| Patent Document 1 | WO 2005/021488 (International Publication Number) |
| Patent Document 2 | WO 2005/073165 (International Publication Number) |
| Patent Document 3 | WO 2006/137376 (International Publication Number) |
| Patent Document 4 | WO 2006/137395 (International Publication Number) |
| Patent Document 5 | WO 2006/306771 (International Publication Number) |
| Patent Document 6 | WO 2007/128410 (International Publication Number) |
| Patent Document 7 | WO 2008/000438 (International Publication Number) |
| Patent Document 8 | WO 2008/012027 (International Publication Number) |
| Patent Document 9 | WO 2008/031534 (International Publication Number) |
| Patent Document 10 | WO 2008/074427 (International Publication Number) |
| Patent Document 11 | WO 2008/107091 (International Publication Number) |
| Patent Document 12 | WO 2009/049844 (International Publication Number) |
| Patent Document 13 | WO 2009/049845 (International Publication Number) |
| Patent Document 14 | WO 2007/017075 (International Publication Number) |
| Patent Document 15 | WO 2007/051560 (International Publication Number) |
| Patent Document 16 | JP-A No. 2007-099761 |
| Patent Document 17 | JP-A No. 2008-302617 |

SUMMARY OF THE INVENTION

Inventors of the present invention extensively studied to develop novel compounds which are highly active as pesticides and have a broad spectrum use. As a result, the inventors found that the novel carboxamides represented by the following Formula (I) have a high activity, a broad spectrum use and safety, and also are effective against harmful pests that are resistant to organic phosphorous agents or carbamate agents.

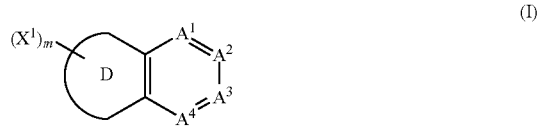

(I)

wherein,

D represents a 6-membered aromatic carbon ring which may be substituted or a 5- to 6-membered aromatic heterocycle which may be substituted;

$A^1$, $A^2$, $A^3$ and $A^4$ each independently represent nitrogen, C—$X^2$ or the following Formula (E):

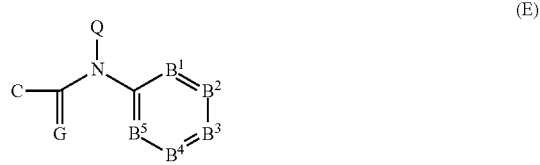

(E)

with the proviso that, at least one of $A^1$, $A^2$, $A^3$ and $A^4$ is the Formula (E);

G represents oxygen or sulfur;

Q represents hydrogen, $C_{1-12}$ alkyl, $C_{1-12}$ haloalkyl, ($C_{1-12}$ alkyl)carbonyl, ($C_{1-12}$ haloalkyl)carbonyl, ($C_{1-12}$ alkoxy)carbonyl or ($C_{1-12}$ haloalkoxy)carbonyl;

$B^1$, $B^2$, $B^3$, $B^4$ and $B^5$ each independently represent nitrogen, C—$X^3$ or C-J, with the proviso that the five groups $B^1$, $B^2$, $B^3$, $B^4$ and $B^5$ are not simultaneously nitrogen and at least one of $B^1$, $B^2$, $B^3$, $B^4$ and $B^5$ is C-J;

$X^1$, $X^2$ and $X^3$ each independently represent hydrogen, cyano, halogen, nitro, oxygen, hydroxy, mercapto, amino, formyl, oxide, $C_{1-12}$ alkyl, $C_{1-12}$ haloalkyl, aryl-($C_{1-12}$)alkyl, heterocyclyl-($C_{1-12}$)alkyl, $C_{1-12}$ alkyl-O—, $C_{1-12}$ alkyl-NH—, $C_{1-12}$ alkyl-S—, $C_{1-12}$ alkyl-S(O)—, $C_{1-12}$ alkyl-S(O)$_2$—, $C_{1-12}$ alkyl-S(O)$_2$O—, $C_{1-12}$ haloalkyl-O—, $C_{1-12}$ haloalkyl-NH—, $C_{1-12}$ haloalkyl-S—, $C_{1-12}$ haloalkyl-S(O)—, $C_{1-12}$ haloalkyl-S(O)$_2$—, $C_{1-12}$ haloalkyl-S(O)$_2$O—, aryl-O—, aryl-NH—, aryl-S—, aryl-S(O)—, aryl-S(O)$_2$—, aryl-S(O)$_2$O—, heterocyclyl-O—, heterocyclyl-NH—, heterocyclyl-S—, heterocyclyl-S(O)—, heterocyclyl-S(O)$_2$—, heterocyclyl-S(O)$_2$O—, $C_{1-12}$ alkyl-O—($C_{1-12}$)alkyl, $C_{1-12}$ alkyl-NH—($C_{1-12}$)alkyl, $C_{1-12}$ alkyl-S—($C_{1-12}$)alkyl, $C_{1-12}$ alkyl-S(O)—($C_{1-12}$)alkyl, $C_{1-12}$ alkyl-S(O)$_2$—($C_{1-12}$)alkyl, $C_{1-12}$ haloalkyl-O—($C_{1-12}$)alkyl, $C_{1-12}$ haloalkyl-NH—($C_{1-12}$)alkyl, $C_{1-12}$ haloalkyl-S—($C_{1-12}$)alkyl, $C_{1-12}$ haloalkyl-S(O)—($C_{1-12}$)alkyl, $C_{1-12}$ haloalkyl-S(O)$_2$—($C_{-12}$)alkyl, aryl-O—($C_{1-12}$)alkyl, aryl-NH—($C_{1-12}$)alkyl, aryl-S(O)—($C_{1-12}$)alkyl, aryl-S(O)$_2$—($C_{1-12}$)alkyl, heterocyclyl-O—($C_{1-12}$)alkyl, heterocyclyl-NH—($C_{1-12}$)alkyl, heterocyclyl-S—($C_{1-12}$)alkyl, heterocyclyl-S(O)—($C_{1-12}$)alkyl, heterocyclyl-S(O)$_2$—($C_{1-12}$)alkyl, $C_{3-8}$ cycloalkyl, $C_{3-8}$ cycloalkyl-($C_{1-12}$)alkyl-, $C_{3-8}$ halocycloalkyl, $C_{3-8}$ halocycloalkyl-($C_{1-12}$)alkyl, $C_{2-12}$ alkenyl, $C_{2-12}$ haloalkenyl, $C_{2-12}$ alkynyl, $C_{2-12}$ haloalkynyl, di($C_{1-12}$ alkylamino, di($C_{1-12}$ haloalkyl)amino, $C_{3-36}$ trialkylsilyl, hydroxyimino($C_{1-12}$) alkyl, $C_{1-12}$ alkyl-O—N=($C_{1-12}$)alkyl, $C_{1-12}$ alkyl-S—N=($C_{1-12}$)alkyl, $C_{1-12}$ alkyl-S(O)—N=($C_{1-12}$)alkyl, $C_{1-12}$ alkyl-S(O)$_2$—N=($C_{1-12}$)alkyl, $C_{1-12}$ alkyl-S(O)$_2$O—N—($C_{1-12}$)alkyl, $C_{1-12}$ haloalkyl-O—N=($C_{1-12}$) alkyl, $C_{1-12}$ haloalkyl-S—N=($C_{1-12}$)alkyl, $C_{1-12}$ haloalkyl-S(O)—N=($C_{1-12}$)alkyl, $C_{1-12}$ haloalkyl-S(O)$_2$—N=($C_{1-12}$)alkyl, $C_{1-12}$ haloalkyl-S(O)$_2$O—N=($C_{1-12}$) alkyl, ($C_{1-12}$ alkoxy)carbonyl, ($C_{1-12}$ haloalkoxy)carbonyl, ($C_{1-12}$ alkyl)carbonyl, ($C_{1-12}$ haloalkyl)carbonyl, $C_{3-8}$ cycloalkyl-($C_{1-12}$)alkyl-carbonyl, $C_{3-8}$ halocycloalkyl-($C_{1-12}$)alkyl-carbonyl, an aryl group, a heterocyclic group, sulf pentafluoride, tri($C_{1-12}$alkyl)silyl-$C_{2-12}$alkynyl, ($C_{3-8}$ cycloalkyl)carbonyl, ($C_{3-8}$ halocycloalkyl)carbonyl, one of the heterocycle or one of the substituents represented by the following Formulae d-1 to d-9:

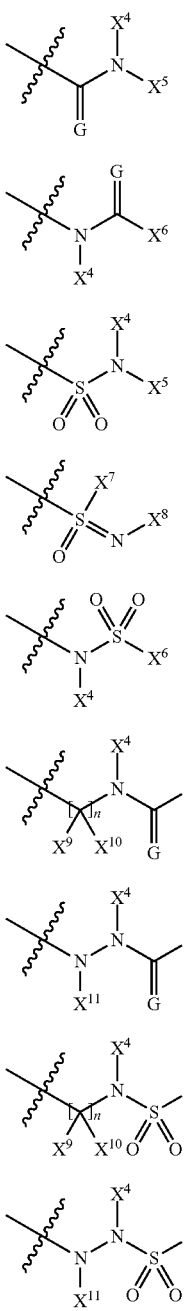

d-1
d-2
d-3
d-4
d-5
d-6
d-7
d-8
d-9 wherein G independently has the same meaning as G described above;

$X^4$, $X^5$, $X^6$, $X^9$, $X^{10}$ and $X^{11}$ each independently represent hydrogen, cyano, halogen, nitro, hydroxy, mercapto, amino, formyl, $C_{1-12}$ alkyl, $C_{1-12}$ haloalkyl, aryl-$(C_{1-12})$alkyl, heterocyclyl-$(C_{1-12})$alkyl, $C_{1-12}$ alkyl-O—, $C_{1-12}$ alkyl-NH—, $C_{1-12}$ alkyl-S—, $C_{1-12}$ alkyl-S(O)—, $C_{1-12}$ alkyl-S(O)$_2$—, $C_{1-12}$ alkyl-S(O)$_2$O—, $C_{1-12}$ haloalkyl-O—, $C_{1-12}$ haloalkyl-NH—, $C_{1-12}$ haloalkyl-S—, $C_{1-12}$ haloalkyl-S(O)—, $C_{1-12}$ haloalkyl-S(O)$_2$—, $C_{1-12}$ haloalkyl-S(O)$_2$O—, aryl-O—, aryl-NH—, aryl-S—, aryl-S(O)—, aryl-S(O)$_2$—, aryl-S(O)$_2$O—, heterocyclyl-O—, heterocyclyl-NH—, heterocyclyl-S—, heterocyclyl-S(O)—, heterocyclyl-S(O)$_2$—, heterocyclyl-S(O)$_2$O—, $C_{1-12}$ alkyl-O—$(C_{1-12})$alkyl, $C_{1-12}$ alkyl-NH—$(C_{1-12})$alkyl, $C_{1-12}$ alkyl-S—$(C_{1-12})$alkyl, $C_{1-12}$ alkyl-S(O)—$(C_{1-12})$alkyl, $C_{1-12}$ alkyl-S(O)$_2$—$(C_{1-12})$alkyl, $C_{1-12}$ haloalkyl-O—$(C_{1-12})$alkyl, $C_{1-12}$ haloalkyl-NH—$(C_{1-12})$alkyl, $C_{1-12}$ haloalkyl-S—$(C_{1-12})$alkyl, $C_{1-12}$ haloalkyl-S(O)$_4C_{1-12}$)alkyl, $C_{1-12}$ haloalkyl-S(O)$_2$—$(C_{1-12})$allyl, aryl-O—$(C_{1-12})$alkyl, aryl-NH—$(C_{1-12})$alkyl, aryl-S—$(C_{1-12})$alkyl, aryl-S(O)—$(C_{1-12})$alkyl, aryl-S(O)$_2$—$(C_{1-12})$alkyl, heterocyclyl-O—$(C_{1-12})$alkyl, heterocyclyl-NH—$(C_{1-12})$alkyl, heterocyclyl-S—$(C_{1-12})$alkyl, heterocyclyl-S(O)—$(C_{1-12})$alkyl, heterocyclyl-S(O)$_2$—$(C_{1-12})$alkyl, $C_{3-8}$ cycloalkyl, $C_{3-8}$ cycloalkyl-$(C_{1-12})$alkyl-, $C_{3-8}$ halocycloalkyl, $C_{3-8}$ halocycloalkyl-$(C_{1-12})$alkyl-, $C_{2-12}$ alkenyl, $C_{2-12}$ haloalkenyl, $C_{2-12}$ alkynyl, $C_{2-12}$ haloalkynyl, di($C_{1-12}$ alkylamino, di($C_{1-12}$ haloalkyl)amino, $C_{3-36}$ trialkylsilyl, hydroxyimino($C_{1-12}$)alkyl, $C_{1-12}$ alkyl-O—N=$(C_{1-12})$alkyl, $C_{1-12}$ alkyl-S—N=$(C_{1-12})$alkyl, $C_{1-12}$ alkyl-S(O)—N=$(C_{1-12})$alkyl, $C_{1-12}$ alkyl-S(O)$_2$—N=$(C_{1-12})$alkyl, $C_{1-12}$ alkyl-S(O)$_2$O—N=$(C_{1-12})$alkyl, $C_{1-12}$ haloalkyl-O—N$(C_{1-12})$alkyl, $C_{1-12}$ haloalkyl-S—N=$(C_{1-12})$alkyl, $C_{1-12}$ haloalkyl-S(O)—N=$(C_{1-12})$alkyl, $C_{1-12}$ haloalkyl-S(O)$C_{1-12}$ haloalkyl-S(O)$_2$O—N=$(C_{1-12})$alkyl, $(C_{1-12}$ alkoxy)carbonyl, $(C_{1-12}$ haloalkoxy)carbonyl, $(C_{1-12}$ alkyl)carbonyl, $(C_{1-12}$ haloalkyl)carbonyl, $C_{3-8}$ cycloalkyl-$(C_{1-12})$alkyl-carbonyl, $C_{3-8}$ halocycloallyl-$(C_{1-12})$alkyl-carbonyl, sulfur pentafluoride, an aryl group, a heterocyclic group, $(C_{3-8}$ cycloalkyl)carbonyl or $(C_{3-8}$ halocycloalkyl)carbonyl;

$X^4$ and $X^5$ may form a heterocycle together with the nitrogen atom, carbon atom, sulfur atom or oxygen atom to which they are bonded;

$X^4$ and $X^6$ may form a heterocycle together with the nitrogen atom, carbon atom, sulfur atom or oxygen atom to which they are bonded;

$X^7$ each independently represents hydrogen, $C_{1-12}$ alkyl, $C_{1-12}$ haloalkyl, $C_{3-8}$ cycloalkyl, $C_{2-12}$ alkenyl, $C_{2-12}$ haloalkenyl, an aryl group, a heterocyclic group, aryl-$(C_{1-12})$alkyl or heterocyclyl-$(C_{1-12})$alkyl;

$X^8$ each independently represents hydrogen, nitro, cyano, formyl, $X^{12}$-carbonyl or $X^{12}$-oxycarbonyl, wherein $X^{12}$ independently has the same meaning as $X^7$ described above;

$X^9$ and $X^{10}$ may form a 3- to 8-membered carbon ring or heterocycle together with the carbon atom to which they are bonded;

J each independently represents $C_{1-12}$ haloalkyl, $C_{1-12}$ haloalkyl-O—, $C_{1-12}$ haloalkyl-S—, $C_{1-12}$ haloalkyl-S(O)—, $C_{1-12}$ haloalkyl-S(O)$_2$—, $C_{3-8}$ halocycloalkyl, —C($J^1$)($J^2$)($J^3$) or —C($J^1$)($J^2$)(O$J^4$), $J^1$ and $J^2$ each independently represent $C_{1-12}$ haloalkyl;

$J^3$ represents a heterocyclic group;

$J^4$ represents hydrogen, $C_{1-12}$ alkyl, $C_{1-12}$ haloalkyl, $C_{1-12}$ alkylsulfonyl, $C_{1-12}$ haloalkylsulfonyl, arylsulfonyl, an aryl group or a heterocyclic group;

m and n each independently represent an integer from 1 to 4; and

Each group defined above may be further substituted with any substituent.

The compounds of the Formula (I) of the present invention can be obtained according to the following preparation methods (a) to (f), for example.

Preparation Method (a)

A method in which compounds represented by the Formula (II):

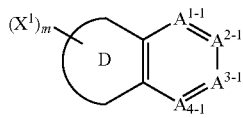

(II)

wherein, $X^1$, m and D are as defined above, $A^{1-1}$, $A^{2-1}$ $A^{3-1}$ and $A^{4-1}$ represent nitrogen, C—$X^2$ or C—C(=O)-$L^1$, at least one of $A^{1-1}$, $A^{2-1}$, $A^{3-1}$ and $A^{4-1}$ represents C—C(=O)-$L^1$, $X^2$ is as defined above, and $L^1$ represents hydroxy or an appropriate leaving group, for example, chlorine, bromine, a $C_{1-4}$ alkyl-carbonyloxy group, a $C_{1-4}$ alkoxy-carbonyloxy group, an azolyl group, a $C_{1-4}$ alkylsulfonyloxy group, a $C_{1-4}$ haloalkylsulfonyloxy group, or an arylsulfonyloxy group are reacted with compounds represented by the Formula (III):

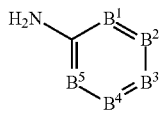

(III)

wherein, $B^1$ to $B^5$ are as defined above in the presence of a condensing agent, a base, or an appropriate diluent, if necessary.

Preparation Method (b)

A method in which compounds represented by the Formula (I-a):

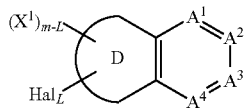

(I-a)

wherein, $A^1$ to $A^4$, $X^1$, m, and D are as defined above, L represents 1, 2, 3 or 4, Hal represents halogen, for example, iodine, chlorine, bromine.

are reacted with a cyanation reagent in the presence of an appropriate catalyst to obtain the compounds represented by the following Formula (I-b):

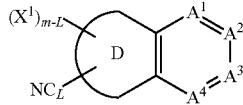

(I-b)

wherein, $A^1$ to $A^4$, $X^1$, m, L and D are as defined above and NC represents a cyano group.

Preparation Method (c-1)

A method in which compounds represented by the Formula (I-c-1):

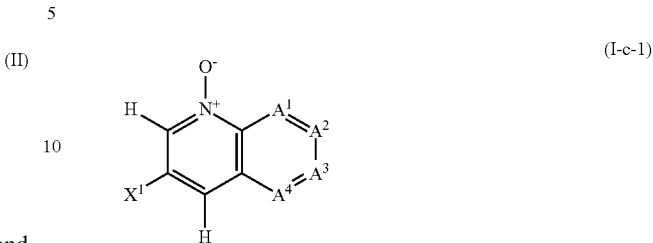

(I-c-1)

wherein, $A^1$ to $A^4$ and $X^1$ are as defiled above.

are reacted with a halogenation reagent to obtain the compounds represented by the following Formula (I-d-1) and/or Formula (I-d-2):

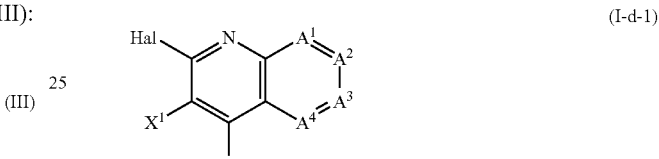

(I-d-1)

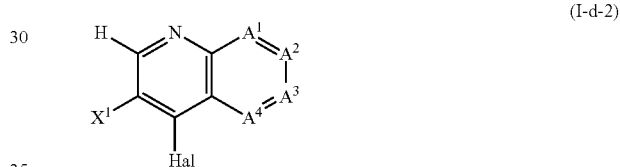

(I-d-2)

wherein, $A^1$ to $A^4$ and $X^1$ are as defined above and Hal represents halogen.

Preparation Method (c-2)

A method in which compounds represented by the Formula (I-c-2):

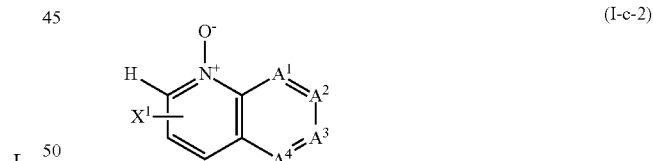

(I-c-2)

wherein, $A^1$ to $A^4$ and $X^1$ are as defined above, with the proviso that $X^1$ is not hydrogen.

are reacted with a halogenation reagent to obtain the compounds represented by the following Formula (I-d-3):

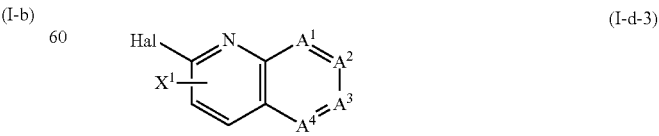

(I-d-3)

wherein, $A^1$ to $A^4$ and $X^1$ are as defined above and Hal represents halogen, with the proviso that $X^1$ is not hydrogen.

Preparation Method (c-3)

A method in which compounds represented by the Formula (I-c-3):

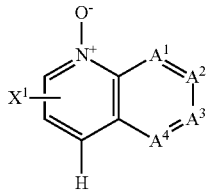
(I-c-3)

wherein, $A^1$ to $A^4$ and $X^1$ are as defined above, with the proviso that $X^1$ is not a hydrogen atom.

are reacted with a halogenation reagent to obtain the compounds represented by the following Formula (I-d-4):

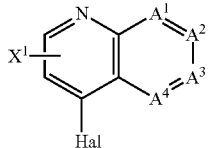
(I-d-4)

wherein, $A^1$ to $A^4$ and $X^1$ are as defined above and Hal represents halogen, with the proviso that $X^1$ is not a hydrogen atom.

Preparation Method (c-4)

A method in which compounds represented by the Formula (I-c-4):

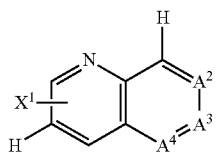
(I-c-4)

wherein, $A^2$ to $A^4$ and $X^1$ are as defined above.

are reacted with a halogenation reagent to obtain the compounds represented by the following Formula (I-d-5):

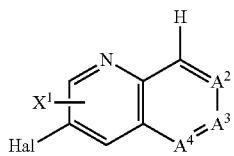
(I-d-5)

wherein, $A^2$ to $A^4$ and $X^1$ are as defined above and Hal represents halogen.

and/or

Formula (I d-6):

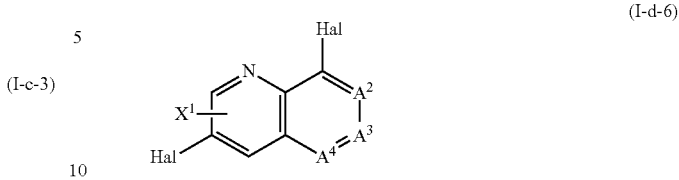
(I-d-6)

wherein, $A^2$ to $A^4$ and $X^1$ are as defined above and Hal represents halogen.

Preparation Method (d)

A method in which compounds represented by the Formula (I-c-2):

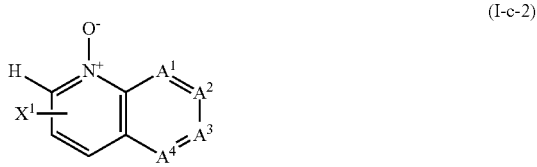
(I-c-2)

wherein, $A^1$ to $A^4$ and $X^1$ are as defined above.

are reacted with a cyanation reagent in the presence of an appropriate diluent to obtain the compounds represented by the following Formula (I-e):

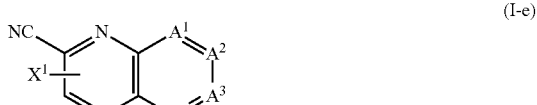
(I-e)

wherein, $A^1$ to $A^4$ and $X^1$ are as defined above and NC represents a cyano group.

Preparation Method (e)

A method in which compounds represented by the Formula (I-f):

(I-f)

wherein, $X^1$, m and D are as defined above, $A^{1-2}$, $A^{2-2}$, $A^{3-2}$ and $A^{4-2}$ represent nitrogen, C—$X^2$ or the following Formula (E1):

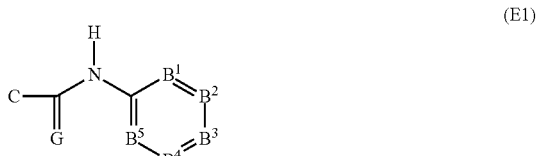
(E1)

at least one of $A^{1-2}$, $A^{2-2}$, $A^{3-2}$ and $A^{4-2}$ represents the Formula (E1), and $X^2$, G and $B^1$ to $B^5$ are as defined above
are reacted with compounds represented by the following Formula (FV):

wherein, Q is as defined above, and $L^2$ represents fluorine, chlorine, bromine, a $C_{1-4}$ alkyl-carbonyloxy group, a $C_{1-4}$ alkoxy-carbonyloxy group, an azolyl group, a $C_{1-4}$ alkylsulfonyloxy group, a $C_{1-4}$ haloalkylsulfonyloxy group, or an arylsulfonyloxy group
in the presence of a base and an appropriate diluent, if necessary.

Preparation Method (f)

A method in which compounds represented by the Formula (I-g):

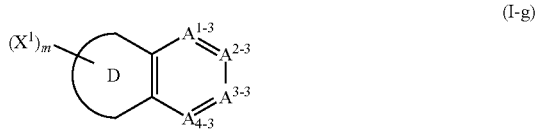

wherein, $X^1$, m and D are as defined above and $A^{1-2}$, $A^{2-2}$, $A^{3-2}$ and $A^{4-2}$ represent nitrogen, C—$X^2$ or the following Formula (E2):

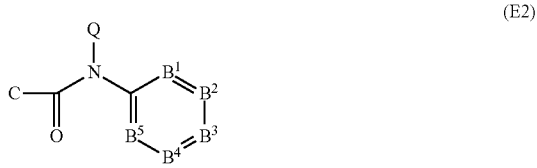

at least one of $A^{1-2}$, $A^{2-2}$, $A^{3-2}$ and $A^{4-2}$ represents the Formula (E2) and $X^2$, Q and $B^1$ to $B^5$ are as defined above are reacted with an appropriate sulfurization reagent in the presence of an appropriate diluent.

Preparation Method (g)

A method in which compounds represented by the Formula (V):

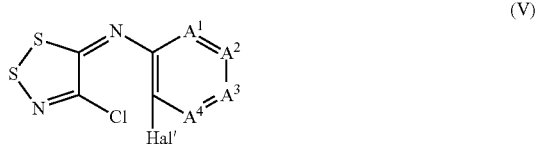

wherein, $A^1$ to $A^4$ are as defined above and Hal' stands for bromo or Iodo,
is reacted with CuI to obtain the compounds represented by the following Formula (I-g-1):

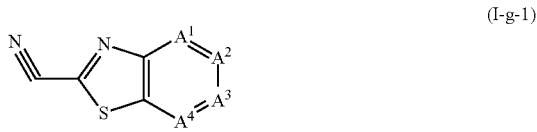

wherein, $A^1$ to $A^4$ are as defined above.

Compounds of the Formula (I-a), (I-b), (I-c-1), (I-c-2), (I-c-3), (I-c-4), (I-d-1), (I-d-2), (I-d-3), (I-d-4), (I-d-5), (I-d-6), (I-e), (I-f) and (I-g) are encompassed by the compounds of the Formula (I) of the present invention.

According to the present invention, carboxamides of the Formula (I) of the present invention have a potent pesticidal activity.

In the present specification, "alkyl" represents linear or branched $C_{1-12}$ alkyl such as methyl, ethyl, n- or iso-propyl, n-, iso-, sec- or tert-butyl, n-pentyl, n-hexyl, n-heptyl, n-octyl, n-nonyl, n-decyl, n-undecyl, and n-dodecyl. Preferably, it represents $C_{1-6}$ alkyl, and more preferably $C_{1-4}$ alkyl. Further, for each alkyl moiety included in a group which includes the alkyl as a part of its constitution, those that are the same as "alkyl" described above can be exemplified.

"Haloalkyl" represents carbon chains in which at least one hydrogen of linear or branched $C_{1-12}$ alkyl, preferably $C_{1-6}$ alkyl, more preferably $C_{1-4}$ alkyl is substituted with halogen, for example, $CH_2F$, $CHF_2$, $CF_3$, $CF_2Cl$, $CFCl_2$, $CF_2Br$, $CF_2CF_3$, $CFHCF_3$, $CH_2CF_3$, $CFClCF_3$, $CCl_2CF_3$, $CF_2CH_3$, $CF_2CH_2F$, $CF_2CHF_2$, $CF_2CF_2Cl$, $CF_2CF_2Br$, $CFHCH_3$, $CFHCHF_2$, $CFHCHF_2$, $CHFCF_3$, $CHFCF_2Cl$, $CHFCF_2Br$, $CFClCF_3$, $CCl_2CF_3$, $CF_2CF_2CF_3$, $CH_2CF_2CF_3$, $CF_2CH_2CF_3$, $CF_2CF_2CH_3$, $CHFCF_2CF_3$, $CF_2CHFCF_3$, $CF_2CF_2CHF_2$, $CF_2CF_2CH_2F$, $CF_2CF_2CF_2Cl$, $CF_2CF_2CF_2Br$, $CH(CF_3)CF_3$, $CF(CF_3)CF_3$, $CF(CF_3)CF_2Br$, $CF_2CF_2CF_2CF_3$, $CH(CF_3)CF_2CF_3$ or $CF(CF_3)CF_2CF_3$. It also includes perfluoroalkyl in which every substitutable hydrogen on alkyl is substituted with fluorine. Furthermore, monobromoperfluoroalkyl is also included in haloalkyl, and it represents an alkyl in which one of the substitutable hydrogens is substituted by bromo while all the remaining substitutable hydrogens are substituted by fluoro. The haloalkyl may be also substituted with any substituent.

"Alkoxy" represents alkoxy of linear or branched $C_{1-12}$, preferably $C_{1-6}$, more preferably $C_{1-4}$, for example, methoxy, ethoxy, n-propoxy, i-propoxy, n-, iso-, sec- or tert-butoxy, pentyloxy or hexyloxy. The alkoxy may be also substituted with any substituent.

Each "halogen" and a halogen moiety included in a group substituted with halogen represent fluorine, chlorine, bromine or iodine, preferably fluorine, chlorine or bromine.

"Cycloalkyl" represents $C_{3-8}$ cycloalkyl including cyclopropyl, cyclobutyl, cyclopentyl, cyclohexyl, cycloheptyl, cyclooctyl, preferably $C_{3-7}$ cycloalkyl, and more preferably $C_{3-6}$ cycloalkyl. Further, for each cycloalkyl moiety included in a group which has cycloalkyl as a part of constitution, those that are the same as "cycloalkyl" described above can be exemplified.

Examples of "halocycloalkyl" include fluorocyclopropyl, chlorocyclopropyl, difluorocyclopropyl, dichlorocyclopropyl and undecafluorocyclohexyl.

"Alkenyl" represents $C_{2-12}$ alkenyl, preferably $C_{2-5}$ alkenyl including vinyl, allyl, 1-propenyl, 1-(or 2-, or 3-)butenyl, 1-pentenyl and the like, and more preferably $C_{2-4}$ alkenyl.

"Alkynyl" represents $C_{2-12}$ alkynyl, preferably $C_{2-5}$ alkynyl including ethynyl, propargyl, 1-propynyl, butan-3-ynyl, pentan-4-ynyl and the like, and more preferably $C_{2-4}$ alkynyl.

"Aryl" represents a $C_{6-12}$ aromatic hydrocarbon group, and examples thereof include phenyl, naphthyl, biphenyl, preferably a $C_{6-10}$ aromatic hydrocarbon group, and more preferably a $C_6$ aromatic hydrocarbon group, i.e., phenyl.

"Heterocycle" represents a 3-, 4-, 5- or 6-membered heterocyclic group which includes at least one of heteroatoms N, O and S, or the cycle represents a fused heterocyclic group which may be benzo-fused. The carbon atom included in the cycle may be substituted with oxo or thioxo.

Specific examples of the heterocycle include pyrrolidinyl, piperidinyl, morpholinyl, thiomorpholinyl, aziridinyl, oxiranyl, thiiranyl, azetidinyl, oxetanyl, thietanyl, pyrrolidinyl, tetrahydrofuranyl, tetrahydrothiophenyl, tetrahydropyranyl, tetrahydrothiopyranyl(i.e., saturated heterocycle), dihydropyrrolyl, dihydroisoxazolyl, dihydropyrazolyl, dihydrooxazolyl, dihydrothiazolyl (i.e., partially saturated heterocycle) furyl, thienyl, pyrrolyl, isoxazolyl, pyrazolyl, oxazolyl, isothiazolyl, thiazolyl, imidazolyl, triazolyl, oxadiazolyl, thiadiazolyl, tetrazolyl, pyridyl, pyrimidinyl, pyridazinyl, pyrazinyl, triazinyl, indolyl, benzoxazolyl, benzothiazolyl, quinolyl and the like. Furthermore, the heterocycle may be substituted with any substituent.

Examples of the substituent described in the expression "may be substituted with any substituent" include amino, hydroxy, oxo, thioxo, halogen, nitro, cyano, isocyano, mercapto, isothiocyanate, carboxy, carboamide, SF$_5$, aminosulfonyl, alkyl, cycloalkyl, alkenyl, cycloalkenyl, alkynyl, monoalkylamino, dialkylamino, N-alkylcarbonyl-amino, alkoxy, alkenyloxy, alkynyloxy, cycloalkyloxy, cycloalkenyloxy, alkoxycarbonyl, alkenyloxycarbonyl, alkynyloxycarbonyl, aryloxycarbonyl, alkylcarbonyl, alkenylcarbonyl, alkynylcarbonyl, arylcarbonyl, alkylthio, cycloalkylthio, alkenylthio, cycloalkenylthio, alkynylthio, alkylsulfenyl, alkylsulfinyl, alkylsulfinyl including isomers, alkylsulfonyl, monoalkylaminosulfonyl, dialkylaminosulfonyl, alkylphosphinyl, alkylphosphonyl, alkylphosphinyl including isomers, alkylphosphonyl including isomers, N-alkyl-aminocarbonyl, N,N-dialkyl-aminocarbonyl, N-alkylcarbonyl-aminocarbonyl, N-alkylcarbonyl-N-alkylaminocarbonyl, aryl, aryloxy, benzyl, benzyloxy, benzylthio, arylthio, acylamino, benzylamino, heterocycle, trialkylsilyl, alkoxyalkyl, alkylthioalkyl, alkylthioalkoxy, alkoxyalkoxy, phenethyl, benzyloxy, haloalkyl, haloalkoxy, haloalkylthio, haloalkylcarbonyl, haloalkoxycarbonyl, haloalkoxyalkoxy, haloalkoxyalkylthio, haloalkoxyalkylcarbonyl and haloalkoxyalkyl, and preferably chloro, fluoro, bromo, iodo, amino, nitro, cyano, hydroxy, thio and carboxy.

Among the compounds of the Formula (I) of the present invention, the compounds which satisfy the followings can be mentioned as preferred examples.

D represents any one of the following Formulae D-1 to D-16, preferably stands for D-9, D-10 or D-16:

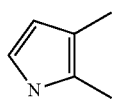
D-1

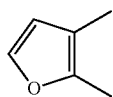
D-2

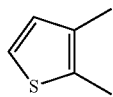
D-3

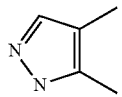
D-4

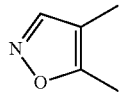
D-5

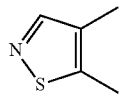
D-6

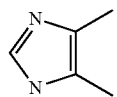
D-7

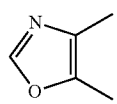
D-8

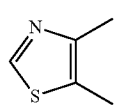
D-9

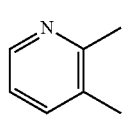
D-10

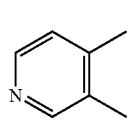
D-11

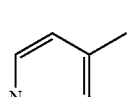
D-12

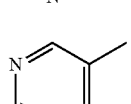
D-13

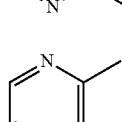
D-14

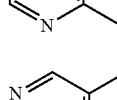
D-15

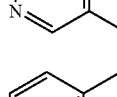
D-16 which may be substituted by $(X^1)_m$, $A^1$, $A^2$, $A^3$ and $A^4$ each independently represent nitrogen, C—$X^2$ or the following Formula (E), preferably $A^1$, $A^2$ and $A^4$ each independently represent nitrogen or C—$X^2$ and $A^3$ stands for the following Formula (E):

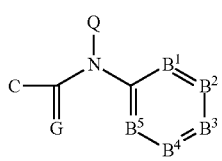
(E)

with the proviso that, at least one of $A^1$, $A^2$, $A^3$ and $A^4$ is the Formula (E);

G represents oxygen or sulfur, preferably stands for oxygen;

Q represents hydrogen, $C_{1-6}$ alkyl, $C_{1-6}$ haloalkyl, ($C_{1-6}$ alkyl)carbonyl, ($C_{1-6}$ haloalkyl)carbonyl, ($C_{1-6}$ alkoxy)carbonyl or ($C_{1-6}$ haloalkoxy)carbonyl, preferably stands for hydrogen or $C_{1-6}$ alkyl;

$B^1$, $B^2$, $B^3$, $B^4$ and $B^5$ each independently represent nitrogen, C—$X^3$ or C-J, with the proviso that the five groups $B^1$, $B^2$, $B^3$, $B^4$ and $B^5$ are not simultaneously nitrogen and at least one of $B^1$, $B^2$, $B^3$, $B^4$ and $B^5$ is C-J, preferably $B^1$, $B^2$, $B^4$ and $B^5$ each independently stand for nitrogen or C—$X^3$ and $B^3$ stands for C-J;

$X^1$, $X^2$ and $X^3$ each independently represent hydrogen, cyano, halogen, nitro, oxygen, hydroxy, mercapto, amino, formyl, $C_{1-6}$ alkyl, $C_{1-6}$ haloalkyl, aryl-($C_{1-6}$)alkyl, heterocyclyl-($C_{1-6}$)alkyl, $C_{1-6}$ alkyl-O—, $C_{1-6}$ alkyl-NH—, $C_{1-6}$ alkyl-S—, $C_{1-6}$ alkyl-S(O)—, $C_{1-6}$ alkyl-S(O)$_2$—, $C_{1-6}$ alkyl-S(O)$_2$O—, $C_{1-6}$ haloalkyl-O—, $C_{1-6}$ haloalkyl-NH—, $C_{1-6}$ haloalkyl-S—, $C_{1-6}$ haloalkyl-S(O)—, $C_{1-6}$ haloalkyl-S(O)$_2$—, $C_{1-6}$ haloalkyl-S(O)$_2$O—, aryl-O—, aryl-NH—, aryl-S—, aryl-S(O)—, aryl-S(O)$_2$—, aryl-S(O)$_2$O—, heterocyclyl-O—, heterocyclyl-NH—, heterocyclyl-S—, heterocyclyl-S(O)—, heterocyclyl-S(O)$_2$—, heterocyclyl-S(O)$_2$O—, $C_{1-6}$ alkyl-O—($C_{1-6}$)alkyl, $C_{1-6}$ alkyl-NH—($C_{1-6}$)alkyl, $C_{1-6}$ alkyl-S—($C_{1-6}$)alkyl, $C_{1-6}$ alkyl-S(O)—($C_{1-6}$)alkyl, $C_{1-6}$ alkyl-S(O)$_2$—($C_{1-6}$)alkyl, $C_{1-6}$ haloalkyl-O—($C_{1-6}$)alkyl, $C_{1-6}$ haloalkyl-NH—($C_{1-6}$)alkyl, $C_{1-6}$ haloalkyl-S—($C_{1-6}$)alkyl, $C_{1-6}$ haloalkyl-S(O)—($C_{1-6}$)alkyl, $C_{1-6}$ haloalkyl-S(O)$_2$—($C_{1-6}$)alkyl, aryl-O—($C_{1-6}$)allyl, aryl-NH—($C_{1-6}$)alkyl, aryl-S—($C_{1-6}$)alkyl, aryl-S(O)—($C_{1-6}$)alkyl, aryl-S(O)$_2$—($C_{1-6}$)alkyl, heterocyclyl-O—($C_{1-6}$)alkyl, heterocyclyl-NH—($C_{1-6}$)alkyl, heterocyclyl-S—($C_{1-6}$)alkyl, heterocyclyl-S(O)—($C_{1-6}$)alkyl, heterocyclyl-S(O)$_2$—($C_{1-6}$)alkyl, $C_{3-7}$ cycloakyl, $C_{3-7}$ cycloalkyl-($C_{1-6}$)alkyl-, $C_{3-7}$ halocycloalkyl, $C_{3-7}$ halocycloalkyl-($C_{1-6}$)alkyl-, $C_{2-5}$ alkenyl, $C_{2-5}$ haloalkenyl, $C_{2-5}$ alkynyl, $C_{2-5}$ haloalkynyl, di($C_{1-6}$ alkyl)amino, di($C_{1-6}$ haloalkyl)amino, $C_{3-18}$ trialkylsilyl, hydroxyimino ($C_{1-6}$)alkyl, $C_{1-6}$ alkyl-O—N—($C_{1-6}$)alkyl, $C_{1-6}$ alkyl-S—N—($C_{1-6}$)alkyl, $C_{1-6}$ alkyl-S(O)—N=($C_{1-6}$)alkyl, $C_{1-6}$ alkyl-S(O)$_2$—N=($C_{1-6}$)alkyl, $C_{1-6}$ alkyl-S(O)$_2$O—N=($C_{1-6}$)alkyl, $C_{1-6}$ haloalkyl-O—N($C_{1-6}$)alkyl, $C_{1-6}$ haloalkyl-S—N—($C_{1-6}$)alkyl, $C_{1-6}$ haloalkyl-S(O)—N=($C_{1-6}$)alkyl, $C_{1-6}$ haloalkyl-S(O)$_2$—N=($C_{1-6}$)allyl, $C_{1-6}$ haloalkyl-S(O)$_2$O—N=($C_{1-6}$)alkyl, ($C_{1-6}$ alkoxy)carbonyl, ($C_{1-6}$ haloalkoxy)carbonyl, ($C_{1-6}$ alkyl)carbonyl, ($C_{1-6}$ haloalkyl)carbonyl, $C_{3-7}$ cycloalkyl-($C_{1-6}$)alkyl-carbonyl, $C_{3-7}$ halocycloalkyl-($C_{1-6}$)alkyl-carbonyl, an aryl group, a heterocyclic group, sulfur pentafluoride, tri($C_{1-6}$alkyl)silyl-$C_{2-6}$alkynyl, ($C_{3-7}$ cycloalkyl)carbonyl, ($C_{3-7}$ halocycloalkyl)carbonyl, one of the heterocycle or one of the substituents represented by the following Formulae d-1 to d-9, preferably stands for hydrogen, cyano, halogen, $C_{1-6}$ alkyl, $C_{1-6}$ haloalkyl, $C_{1-6}$ alkyl-O—, $C_{1-6}$ alkyl-S—, $C_{1-6}$ haloalkyl-O—, $C_{1-6}$ haloalkyl-S—, $C_{1-6}$ haloalkyl-S(O)—, $C_{1-6}$ haloalkyl-S(O)$_2$—, $C_{1-6}$ haloalkyl-S(O)$_2$O—, tri($C_{1-6}$alkyl)silyl-$C_{2-6}$alkynyl, triazoyl or d-6:

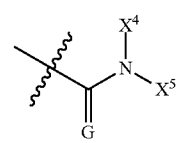
d-1

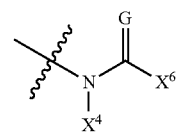
d-2

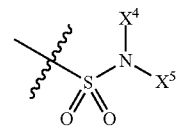
d-3

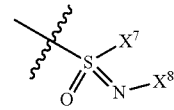
d-4

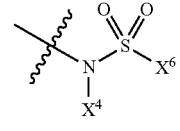
d-5

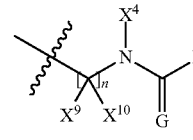
d-6

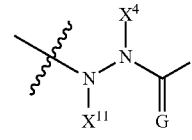
d-7

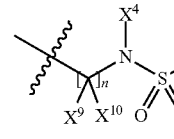
d-8

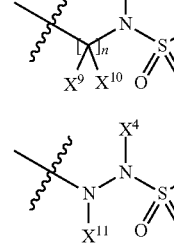
d-9 wherein G independently has the same meaning as G described above, $X^4$, $X^5$, $X^6$, $X^9$, $X^{10}$ and $X^{11}$ each independently represent hydrogen, cyano, halogen, nitro, hydroxy, mercapto, amino, formyl, $C_{1-6}$ alkyl, $C_{1-6}$ haloalkyl, aryl-($C_{1-6}$)alkyl, heterocyclyl-($C_{1-6}$)alkyl, $C_{1-6}$ alkyl-O—, $C_{1-6}$ alkyl-NH—, $C_{1-6}$ alkyl-S—, $C_{1-6}$ alkyl-S(O)—, $C_{1-6}$ alkyl-S(O)$_2$—, $C_{1-6}$ alkyl-S(O)$_2$O—, $C_{1-6}$ haloalkyl-O—, $C_{1-6}$ haloalkyl-NH—, $C_{1-6}$ haloalkyl-S—, $C_{1-6}$ haloalkyl-S(O)—, $C_{1-6}$ haloalkyl-S(O)$_2$—, $C_{1-6}$ haloalkyl-S(O)$_2$O—, aryl-O—, aryl-NH—, aryl-S—, aryl-S(O)—, aryl-S(O)$_2$—, aryl-S(O)$_2$O—, heterocyclyl-O—, heterocyclyl-NH—, heterocyclyl-S—, heterocyclyl-S(O)—, heterocyclyl-S(O)$_2$—, heterocyclyl-S(O)$_2$O—, $C_{1-6}$ alkyl-O—

($C_{1-6}$)alkyl, $C_{1-6}$ alkyl-NH—($C_{1-6}$)alkyl, $C_{1-6}$ alkyl-S—($C_{1-6}$)alkyl, $C_1$ alkyl-S(O)—($C_{1-6}$)alkyl, $C_{1-6}$ alkyl-S(O)$_2$—($C_{1-6}$)alkyl, $C_{1-6}$ haloalkyl-O—($C_{1-6}$)alkyl, $C_{1-6}$ haloalkyl-NH—($C_{1-6}$)alkyl, $C_{1-6}$ haloalkyl-S—($C_{1-6}$)alkyl, $C_{1-6}$ haloalkyl-S(O)—($C_{1-6}$)alkyl, $C_{1-6}$ haloalkyl-S(O)$_2$—($C_{1-6}$)alkyl, aryl-NH—($C_{1-6}$)alkyl, aryl-S—($C_{1-6}$)alkyl, aryl-S(O)—($C_{1-6}$)alkyl, aryl-S(O)$_2$—($C_{1-6}$)alkyl, heterocyclyl-O—($C_{1-6}$)alkyl, heterocyclyl-NH—($C_{1-6}$)alkyl, heterocyclyl-S—($C_{1-6}$)alkyl, heterocyclyl-S(O)—($C_{1-6}$)alkyl, heterocyclyl-S(O)$_2$—($C_{1-6}$)alkyl, $C_{3-7}$ cycloalkyl, $C_{3-7}$ cycloalkyl-($C_{1-6}$)alkyl-, $C_{3-7}$ halocycloalkyl, $C_{3-7}$ halocycloalkyl-($C_{1-6}$)alkyl-, $C_{2-5}$ alkenyl, $C_{2-5}$ haloalkenyl, $C_{2-5}$ alkynyl, $C_{2-5}$ haloalkynyl, alkyl)amino, di($C_{1-6}$ haloalkyl)amino, $C_{3-18}$ trialkylsilyl, hydroxyimino($C_{1-6}$)alkyl, $C_{1-6}$ alkyl-O—N=($C_{1-6}$)alkyl, $C_{1-6}$ alkyl-S—N=($C_{1-6}$)alkyl, $C_{1-6}$ alkyl-S(O)—N=($C_{1-6}$)alkyl, $C_{1-6}$ alkyl-S(O)$_2$—N=($C_{1-6}$)alkyl, $C_{1-6}$ alkyl-S(O)$_2$O—N=($C_{1-6}$)alkyl, $C_{1-6}$ haloalkyl-O—N—($C_{1-6}$)alkyl, $C_{1-6}$ haloalkyl-S—N=($C_{1-6}$)alkyl, $C_{1-6}$ haloalkyl-S(O)—N=($C_{1-6}$)alkyl, $C_{1-6}$ haloalkyl-S(O)$_2$—N—($C_{1-6}$)allyl, $C_{1-6}$ haloalkyl-S(O)$_2$O—N=($C_{1-6}$)alkyl, ($C_{1-6}$ alkoxy)carbonyl, ($C_{1-6}$ haloalkoxy)carbonyl, ($C_{1-6}$ alkyl)carbonyl, ($C_{1-6}$ haloalkyl)carbonyl, $C_{3-7}$ cycloalkyl-($C_{1-6}$)alkyl-carbonyl, $C_{3-7}$ halocycloalkyl-($C_{1-6}$)alkyl-carbonyl, sulfur pentafluoride, an aryl group, a heterocyclic group, ($C_{3-7}$ cycloalkyl)carbonyl or ($C_{3-7}$ cycloalkyl)carbonyl, preferably stands for hydrogen or $C_{1-6}$ alkyl;

$X^4$ and $X^5$ may form a heterocycle together with the nitrogen atom, carbon atom, sulfur atom or oxygen atom to which they are bonded;

$X^4$ and $X^6$ may form a heterocycle together with the nitrogen atom, carbon atom, sulfur atom or oxygen atom to which they are bonded;

$X^7$ each independently represents hydrogen, $C_{1-6}$ alkyl, $C_{1-6}$ haloalkyl, $C_{3-7}$ cycloalkyl, $C_{2-5}$ alkenyl, $C_{2-5}$ haloalkenyl, an aryl group, a heterocyclic group, aryl-($C_{1-6}$)alkyl or heterocyclyl-($C_{1-6}$)allyl;

$X^8$ each independently represents hydrogen, nitro, cyano, formyl, $X^{12}$-carbonyl or $X^{12}$-oxycarbonyl, wherein $X^{12}$ independently has the same meaning as $X^7$ described above;

$X^9$ and $X^{10}$ may form a 3- to 7-membered carbon ring or heterocycle together with the carbon atom to which they are bonded;

J each independently represents $C_{1-6}$ haloalkyl, $C_{1-6}$ haloalkyl-O—, $C_{1-6}$ haloalkyl-S—, $C_{1-6}$ haloalkyl-S(O)—, $C_{1-6}$ haloalkyl-S(O)$_2$—, $C_{3-7}$ halocycloalkyl, —C($J^1$)($J^2$)($J^3$) or —C($J^1$)($J^2$)($OJ^4$), preferably stands for $C_{1-6}$ perfluorohaloalkyl, $C_{1-6}$ monobromoperfluorohaloalkyl or $C_{1-6}$ monochloroperfluorohaloalkyl;

$J^1$ and $J^2$ each independently represent $C_{1-6}$ haloalkyl, preferably stands for $C_{1-6}$ perfluoroalkyl, $J^3$ represents any one of the following G-1 to G-9, preferably stands for G-2:

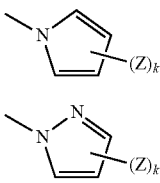
G-1

G-2

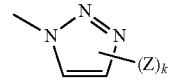
G-3

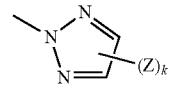
G-4

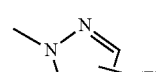
G-5

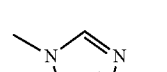
G-6

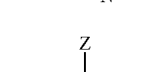
G-7

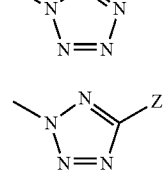
G-8

G-9

Z each independently represents hydrogen, halogen, nitro, cyano, hydroxy, thio, $C_{1-6}$ haloalkyl, $C_{1-6}$ haloalkoxy, $C_{1-6}$ alkylthio, $C_{1-6}$ alkylsulfinyl, $C_{1-6}$ alkylsulfonyl, $C_{1-6}$ haloalkylthio, $C_{1-6}$ haloalkylsulfinyl, or $C_{1-6}$ haloalkylsulfonyl, preferably stands for halogen, k is an integer from 1 to 4, $J^4$ represents hydrogen, $C_{1-6}$ alkyl, $C_{1-6}$ haloalkyl, $C_{1-6}$ alkylsulfonyl, $C_{1-6}$ haloalkylsulfonyl, arylsulfonyl, an aryl group or a heterocyclic group, preferably stands for $C_{1-6}$ alkyl or phenyl, More preferably J stands for one of groups:

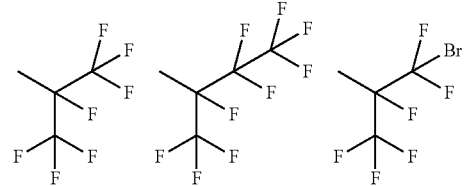

m and n each independently represent an integer from 1 to 4; and

Each group defined above may be further substituted with any substituent.

Among these compounds represented by the Formula (I), the compounds which satisfy the followings can be mentioned as more preferred examples:

D represents any one of the following Formulae D-1 to D-16, preferably stands for D-9, D-10 or D-16:

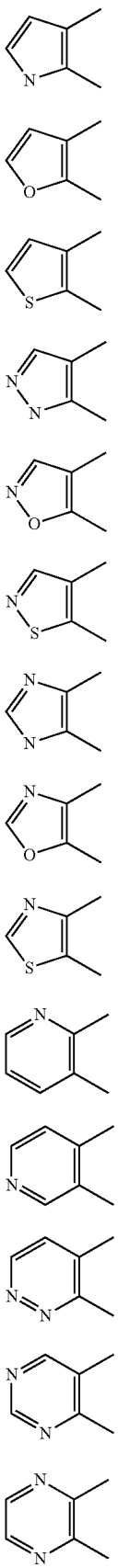

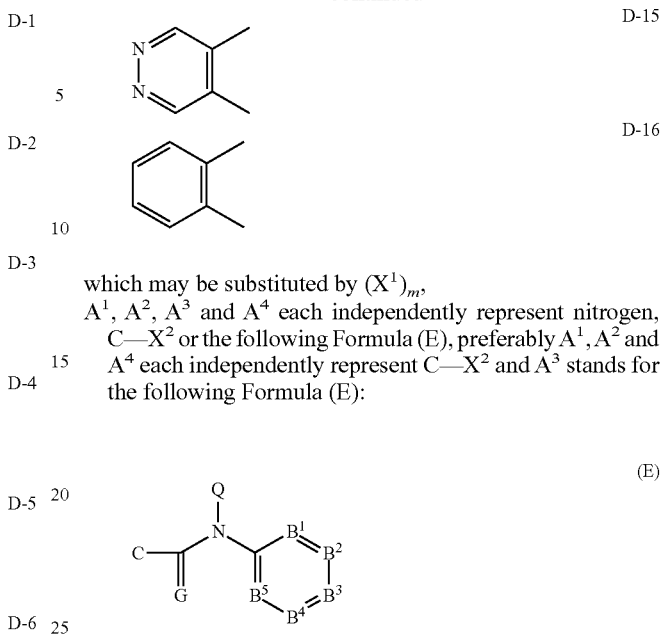

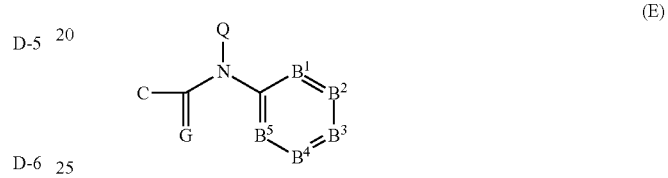

which may be substituted by $(X^1)_m$, $A^1$, $A^2$, $A^3$ and $A^4$ each independently represent nitrogen, C—$X^2$ or the following Formula (E), preferably $A^1$, $A^2$ and $A^4$ each independently represent C—$X^2$ and $A^3$ stands for the following Formula (E):

$$\text{(E)}$$

with the proviso that, at least one of $A^1$, $A^2$, $A^3$ and $A^4$ is the Formula (E);

G represents oxygen or sulfur, preferably stands for oxygen;

Q represents hydrogen, $C_{1-4}$ alkyl, $C_{1-4}$ haloalkyl, ($C_{1-4}$ alkyl) carbonyl, ($C_{1-4}$ haloalkyl)carbonyl, ($C_{1-4}$ alkoxy)carbonyl or ($C_{1-4}$ haloalkoxy)carbonyl, preferably stands for hydrogen or $C_{1-4}$ alkyl;

$B^1$, $B^2$, $B^3$, $B^4$ and $B^5$ each independently represent nitrogen, C—$X^3$ or C-J, with the proviso that the five groups $B^1$, $B^2$, $B^3$, $B^4$ and $B^5$ are not simultaneously nitrogen and at least one of $B^1$, $B^2$, $B^3$, $B^4$ and $B^5$ is C-J, preferably $B^1$, $B^2$, $B^4$ and $B^5$ each independently stand for C—$X^3$ and $B^3$ stands for C-J;

$X^1$, $X^2$ and $X^3$ each independently represent hydrogen, cyano, halogen, nitro, oxygen, hydroxy, mercapto, amino, formyl, $C_{1-4}$ alkyl, $C_{1-4}$ haloalkyl, aryl-($C_{1-4}$)alkyl, heterocyclyl-($C_{1-4}$)alkyl, $C_{1-4}$ alkyl-O—, $C_{1-4}$ alkyl-NH—, $C_{1-4}$ alkyl-S—, $C_{1-4}$ alkyl-S(O)—, $C_{1-4}$ alkyl-S(O)$_2$—, $C_{1-4}$ alkyl-S(O)$_2$O—, $C_{1-4}$ haloalkyl-O—, $C_{1-4}$ haloalkyl-NH—, $C_{1-4}$ haloalkyl-S—, $C_{1-4}$ haloalkyl-S(O)—, $C_{1-4}$ haloalkyl-S(O)$_2$—, $C_{1-4}$ haloalkyl-S(O)$_2$O—, aryl-O—, aryl-NH—, aryl-S—, aryl-S(O)—, aryl-S(O)$_2$—, aryl-S(O)$_2$O—, heterocyclyl-O—, heterocyclyl-NH—, heterocyclyl-S—, heterocyclyl-S(O)—, heterocyclyl-S(O)$_2$—, heterocyclyl-S(O)$_2$O—, $C_{1-4}$ alkyl-O—($C_{1-4}$)alkyl, $C_{1-4}$ alkyl-NH—($C_{1-4}$)alkyl, $C_{1-4}$ alkyl-S—($C_{1-4}$)alkyl, $C_{1-4}$ alkyl-S(O)—($C_{1-4}$)alkyl, $C_{1-4}$ alkyl-S(O)$_2$—($C_{1-4}$)allyl, $C_{1-4}$ haloalkyl-O—($C_{1-4}$)alkyl, $C_{1-4}$ haloalkyl-NH—($C_{1-4}$)alkyl, $C_{1-4}$ haloalkyl-S—($C_{1-4}$)alkyl, $C_{1-4}$ haloalkyl-S(O)—($C_{1-4}$) alkyl, $C_{1-4}$ haloalkyl-S(O)$_2$—($C_{1-4}$)alkyl, aryl-O—($C_{1-4}$) alkyl, aryl-NH—($C_{1-4}$)alkyl, aryl-S—($C_{1-4}$)alkyl, aryl-S (O)—($C_{1-4}$)alkyl, aryl-S(O)$_2$—($C_{1-4}$)alkyl, heterocyclyl-O—($C_{1-4}$)alkyl, heterocyclyl-NH—($C_{1-4}$)alkyl, heterocyclyl-S—($C_{1-4}$)alkyl, heterocyclyl-S(O)—($C_{1-4}$) alkyl, heterocyclyl-S(O)$_2$—($C_{1-4}$)alkyl, $C_{3-6}$ cycloalkyl, $C_{3-6}$ cycloalkyl-($C_{1-4}$)alkyl-, $C_{3-6}$ halocycloalkyl, $C_{3-6}$ halocycloalkyl-($C_{1-4}$)alkyl-, $C_{2-4}$ alkenyl, $C_{2-4}$ haloalkenyl, $C_{2-4}$ alkynyl, $C_{2-4}$ haloalkynyl, di($C_{1-4}$ alkyl)amino, di($C_{1-4}$ haloalkyl)amino, $C_{3-12}$ trialkylsilyl, hydroxyimino ($C_{1-4}$)alkyl, $C_{1-4}$ alkyl-O—N═($C_{1-4}$)alkyl, $C_{1-4}$ alkyl-S—N═($C_{1-4}$)alkyl, $C_{1-4}$ alkyl-S(O)—N═($C_{1-4}$)alkyl, $C_{1-4}$ alkyl-S(O)$_2$—N=(C$_{1-4}$)alkyl, C$_{1-4}$ alkyl-S(O)$_2$O—N=(C$_{1-4}$)alkyl, C$_{1-4}$ haloalkyl-O—N=(C$_{1-4}$)alkyl, C$_{1-4}$ haloalkyl-S—N=(C$_{1-4}$)alkyl, C$_{1-4}$ haloalkyl-S(O)—N=(C$_{1-4}$)alkyl, C$_{1-4}$ haloalkyl-S(O)$_2$—N=(C$_{1-4}$)alkyl, C$_{1-4}$ haloalkyl-S(O)$_2$O—N=(C$_{1-4}$)alkyl, (C$_{1-4}$ alkoxy)carbonyl, (C$_{1-4}$ haloalkoxy)carbonyl, (C$_{1-4}$ alkyl)carbonyl, (C$_{1-4}$ haloalkyl)carbonyl, C$_{3-6}$ cycloalkyl-(C$_{1-4}$)alkyl-carbonyl, C$_{3-6}$ halocycloalkyl-(C$_{1-4}$)alkyl-carbonyl, an aryl group, a heterocyclic group, sulfur pentafluoride, tri(C$_{1-4}$)alkyl)silyl-C$_{2-4}$alkynyl, (C$_{3-6}$ cycloalkyl)carbonyl, (C$_{3-6}$ halocycloalkyl)carbonyl, one of the heterocycle or one of the substituents represented by the following Formulae d-1 to d-9, preferably stands for hydrogen, cyano, halogen, C$_{1-4}$ alkyl, C$_{1-4}$ haloalkyl, C$_{1-4}$ alkyl-O—, C$_{1-4}$ alkyl-S—, C$_{1-4}$ haloalkyl-O—, C$_{1-4}$ haloalkyl-S—, C$_{1-4}$ haloalkyl-S(O)—, C$_{1-4}$ haloalkyl-S(O)$_2$—, C$_{1-4}$ haloalkyl-S(O)$_2$O—, tri(C$_{1-4}$alkyl)silyl-C$_{2-4}$alkynyl, triazoyl or d-6:

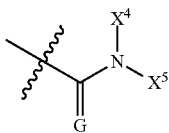

d-1

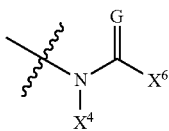

d-2

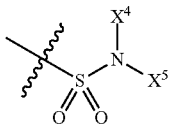

d-3

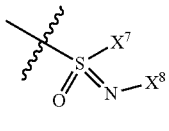

d-4

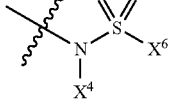

d-5

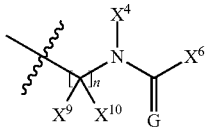

d-6

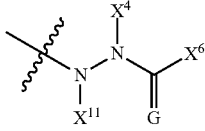

d-7

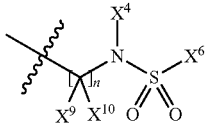

d-8

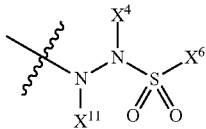

d-9 wherein G independently has the same meaning as G described above,

X$^4$, X$^5$, X$^6$, X$^9$, X$^{10}$ and X$^{11}$ each independently represent hydrogen, cyano, halogen, nitro, hydroxy, mercapto, amino, formyl, C$_{1-4}$ alkyl, C$_{1-4}$ haloalkyl, aryl-(C$_{1-4}$)alkyl, heterocyclyl-(C$_{1-4}$)alkyl, C$_{1-4}$ alkyl-O—, C$_{1-4}$ alkyl-NH—, C$_{1-4}$ alkyl-S—, C$_{1-4}$ alkyl-S(O)—, C$_{1-4}$ alkyl-S(O)$_2$—, C$_{1-4}$ alkyl-S(O)$_2$O—, C$_{1-4}$ haloalkyl-O—, C$_{1-4}$ haloalkyl-NH—, C$_{1-4}$ haloalkyl-S—, C$_{1-4}$ haloalkyl-S(O)—, C$_{1-4}$ haloalkyl-S(O)$_2$—, C$_{1-4}$ haloalkyl-S(O)$_2$O—, aryl-O—, aryl-NH—, aryl-S—, aryl-S(O)—, aryl-S(O)$_2$—, aryl-S(O)$_2$O—, heterocyclyl-O—, heterocyclyl-NH—, heterocyclyl-S—, heterocyclyl-S(O)—, heterocyclyl-S(O)$_2$—, heterocyclyl-S(O)$_2$O—, C$_{1-4}$ alkyl-O—(C$_{1-4}$)alkyl, C$_{1-4}$ alkyl-NH—(C$_{1-4}$)alkyl, C$_{1-4}$ alkyl-S—(C$_{1-4}$)alkyl, C$_{1-4}$ alkyl-S(O)—(C$_{1-4}$)alkyl, C$_{1-4}$ alkyl-S(O)$_2$—(C$_{1-4}$)alkyl, C$_{1-4}$ haloalkyl-O—(C$_{1-4}$)alkyl, C$_{1-4}$ haloalkyl-NH—(C$_{1-4}$)alkyl, C$_{1-4}$ haloalkyl-S—(C$_{1-4}$)alkyl, C$_{1-4}$ haloalkyl-S(O)—(C$_{1-4}$)alkyl, C$_{1-4}$ haloalkyl-S(O)$_2$—(C$_{1-4}$)alkyl, aryl-O—(C$_{1-4}$)alkyl, aryl-NH—(C$_{1-4}$)alkyl, aryl-S—(C$_{1-4}$)alkyl, aryl-S(O)—(C$_{1-4}$)alkyl, aryl-S(O)$_2$—(C$_{1-4}$)alkyl, heterocyclyl-O—(C$_{1-4}$)alkyl, heterocyclyl-NH—(C$_{1-4}$)alkyl, heterocyclyl-S—(C$_{1-4}$)alkyl, heterocyclyl-S(O)—(C$_{1-4}$)alkyl, heterocyclyl-S(O)$_2$—(C$_{1-4}$)alkyl, C$_{3-6}$ cycloalkyl, C$_{3-6}$ cycloalkyl-(C$_{1-4}$)alkyl-, C$_{3-6}$ halocycloalkyl, C$_{3-6}$ halocycloalkyl-(C$_{1-4}$)alkyl-, C$_{2-4}$ alkenyl, C$_{2-4}$ haloalkenyl, C$_{2-4}$ alkynyl, C$_{2-4}$ haloalkynyl, di(C$_{1-4}$ alkyl)amino, di(C$_{1-4}$ haloalkyl)amino, C$_{3-12}$ trialkylsilyl, hydroxyimino(C$_{1-4}$)alkyl, C$_{1-4}$ alkyl-O—N=(C$_{1-4}$)alkyl, C$_{1-4}$ alkyl-S—N=(C$_{1-4}$)alkyl, C$_{1-4}$ alkyl-S(O)—N=(C$_{1-4}$)alkyl, C$_{1-4}$ alkyl-S(O)$_2$—N=(C$_{1-4}$)alkyl, C$_{1-4}$ alkyl-S(O)$_2$O—N=(C$_{1-4}$)alkyl, C$_{1-4}$ haloalkyl-O—N=(C$_{1-4}$)alkyl, C$_{1-4}$ haloalkyl-S—N=(C$_{1-4}$)alkyl, C$_{1-4}$ haloalkyl-S(O)—N=(C$_{1-4}$)alkyl, C$_{1-4}$ haloalkyl-S(O)$_2$—N=(C$_{1-4}$)alkyl, C$_{1-4}$ haloalkyl-S(O)$_2$O—N=(C$_{1-4}$)alkyl, (C$_{1-4}$ alkoxy)carbonyl, (C$_{1-4}$ haloalkoxy)carbonyl, (C$_{1-4}$ alkyl)carbonyl, (C$_{1-4}$ haloalkyl)carbonyl, C$_{3-6}$ cycloalkyl-(C$_{1-4}$)alkyl-carbonyl, C$_{3-6}$ halocycloalkyl-(C$_{1-4}$)alkyl-carbonyl, sulfur pentafluoride, an aryl group, a heterocyclic group, (C$_{3-6}$ cycloalkyl)carbonyl or (C$_{3-6}$ halocycloalkyl)carbonyl, preferably stands for hydrogen or C$_{1-4}$ alkyl;

X$^4$ and X$^5$ may form a heterocycle together with the nitrogen atom, carbon atom, sulfur atom, oxygen atom to which they are bonded;

X$^4$ and X$^6$ may form a heterocycle together with the nitrogen atom, carbon atom, sulfur atom, oxygen atom to which they are bonded;

X$^7$ each independently represents hydrogen, C$_{1-4}$ alkyl, C$_{1-4}$ haloalkyl, C$_{3-6}$ cycloalkyl, C$_{2-4}$ alkenyl, C$_{2-4}$ haloalkenyl, an aryl group, a heterocyclic group, aryl-(C$_{1-4}$)alkyl or heterocyclyl-(C$_{1-4}$)alkyl;

X$^8$ each independently represents hydrogen, nitro, cyano, formyl, X$^{12}$-carbonyl or X$^{12}$-oxycarbonyl, wherein X$^{12}$ independently has the same meaning as X$^7$ described above;

$X^9$ and $X^{10}$ may form a 3- to 7-membered carbon ring or heterocycle together with the carbon atom to which they are bonded;

J each independently represents $C_{1-4}$ haloalkyl, $C_{1-4}$ haloalkyl-O—, $C_{1-4}$ haloalkyl-S—, C haloalkyl-S(O)—, $C_{1-4}$ haloalkyl-S(O)$_2$—, $C_{3-4}$ halocycloalkyl, —C($J^1$)($J^2$)($J^3$) or —C($J^1$)($J^2$)(O$J^4$), preferably stands for $C_{1-4}$ perfluorohaloalkyl, $C_{1-4}$ monobromoperfluorohaloalkyl or $C_{1-4}$ monochloroperfluorohaloalkyl, $J^1$ and $J^2$ each independently represent $C_{1-4}$ haloalkyl, preferably stands for $C_{1-4}$ perfluoroalkyl, $J^3$ represents any one of the following G-1 to G-9, preferably stands for G-2:

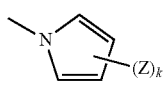
G-1

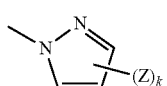
G-2

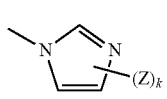
G-3

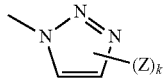
G-4

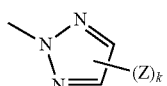
G-5

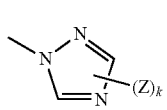
G-6

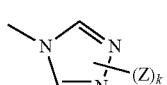
G-7

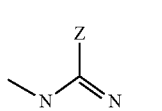
G-8

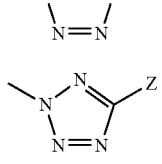
G-9

Z each independently represents hydrogen, halogen, nitro, cyano, hydroxy, thio, $C_{1-4}$ haloalkyl, $C_{1-4}$ haloalkoxy, $C_{1-4}$ alkylthio, $C_{1-4}$ alkylsulfinyl, $C_{1-4}$ alkylsulfonyl, $C_{1-4}$ haloalkylthio, $C_{1-4}$ haloalkylsulfinyl, or $C_{1-4}$ haloalkylsulfonyl, preferably stands for halogen, k is an integer from 1 to 4, $J^4$ represents hydrogen, $C_{1-4}$ alkyl, $C_{1-4}$ haloalkyl, $C_{1-4}$ allylsulfonyl, $C_{1-4}$ haloalkylsulfonyl, arylsulfonyl, an aryl group or a heterocyclic group, preferably stands for $C_{1-4}$ alkyl or phenyl, More preferably J stands for one of groups:

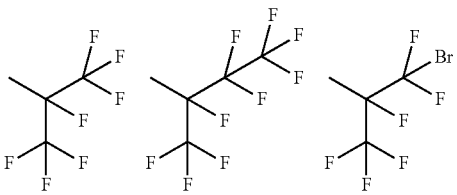

m and n each independently represent an integer from 1 to 4; and

Each group defined above may be further substituted with any substituent.

Among the compounds of the Formula (I) of the present invention, the compounds which satisfy the followings can be mentioned as another preferred aspect of the invention.

D stands for D-9, D-10 or D-16:

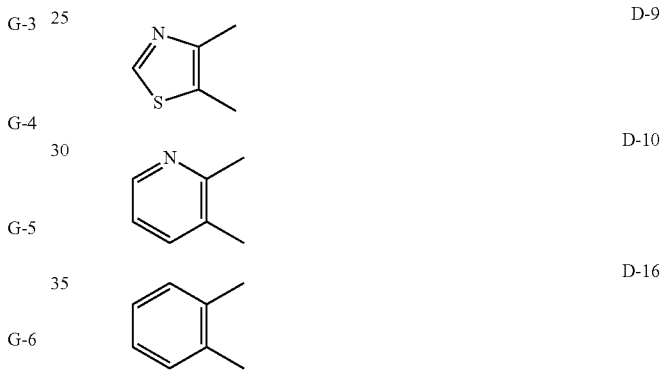

which may be substituted by $(X^1)_m$, $A^1$, $A^2$ and $A^4$ each independently represent C—$X^2$ and $A^3$ stands for the following Formula (E):

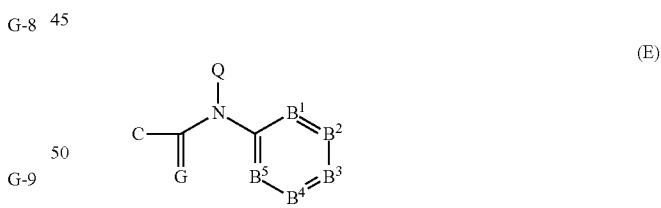

(E)

G stands for oxygen;

Q stands for hydrogen;

$B^1$, $B^2$, $B^4$ and $B^5$ each independently stand for C—$X^3$ and $B^3$ stands for C-J;

$X^1$, $X^2$ and $X^3$ each independently represent hydrogen, cyano, halogen, oxygen, $C_{1-4}$ alkyl, $C_{1-4}$ haloalkyl, $C_{1-4}$ haloalkyl-O—, or haloalkyl-S(O)$_2$—, J each independently represents $C_{1-4}$ perfluoroalkyl, $C_{1-4}$ perfluoroalkyl-O—, $C_{1-4}$ monobromoperfluoroalkyl, $C_{1-4}$ perfluoroalkyl-S(O)$_2$—, $C_{3-6}$ perfluorocycloalkyl, —C($J^1$)($J^2$)($J^3$) or —C($J^1$)($J^2$)(O$J^4$), $J^1$ and $J^2$ each independently represent $C_{1-4}$ perfluoroalkyl,
$J^3$ represents G-2:

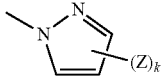

Z each independently represents halogen,
k is an integer from 1 to 4,
$J^4$ represents $C_{1-4}$ alkyl, or phenyl,
m and n each independently represent an integer from 1 to 4; and
each group defined above may be further substituted with any substituent.

Following groups of the novel carboxamides are also preferred, and in any case they are understood as subgroups of the compounds of the Formula (I) described above.

Group 1: Carboxamides Represented by the Formula (I-I):

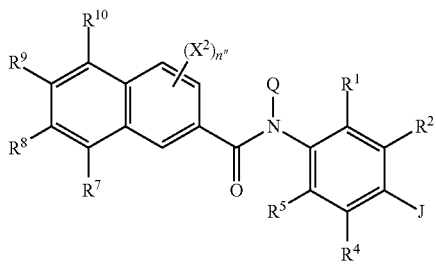

wherein, $X^2$, Q and J are as defined above, $R^1$, $R^2$, $R^4$ and $R^5$ each independently have the same meaning as $X^3$ described above, $R^7$, $R^8$, $R^9$ and $R^{10}$ each independently have the same meaning as $X^1$ described above and n" stands for 1, 2 or 3.

Group 2: Carboxamides Represented by the Formula (I-II):

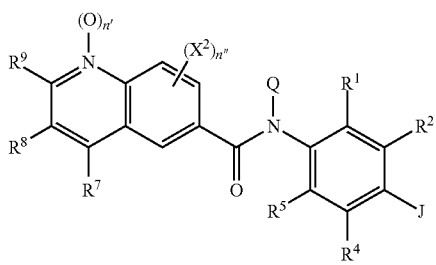

wherein, $X^2$, Q, J and n" are as defined above, $R^1$, $R^2$, $R^4$ and $R^5$ each independently have the same meaning as $X^3$ described above, $R^7$, $R^8$ and $R^9$ each independently have the same meaning as $X^1$ described above and n' is 0 or 1.

Furthermore, each J independently represents $C_{1-4}$ perfluoroalkyl-O—, $C_{1-4}$ monobromoperfluoroalkyl-O—, $C_{1-4}$ perfluoroalkyl-S—, $C_{1-4}$ monobromoperfluoroalkyl-S—, $C_{1-4}$ perfluoroalkyl-S(O)—, $C_{1-4}$ monobromoperfluoroalkyl-S(O)—, $C_{1-4}$ perfluoroalkyl-S(O)$_2$—, $C_{1-4}$ monobromoperfluoroalkyl-S(O)$_2$—, $C_{1-4}$ perfluoroalkyl, $C_{1-4}$ monobromoperfluoroalkyl, $C_{3-6}$ perfluorocycloalkyl, $C_{3-6}$ monobromoperfluorocycloalkyl, —C($J^1$)($J^2$)($J^3$) or —C($J^1$)($J^2$)($OJ^4$),
$J^1$ and $J^2$ each independently represent $C_{1-4}$ perfluoroalkyl,
$J^3$ represents any one of the following G-1 to G-9:

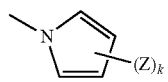
G-1

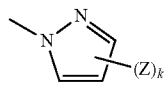
G-2

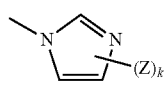
G-3

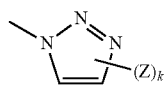
G-4

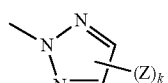
G-5

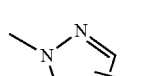
G-6

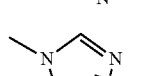
G-7

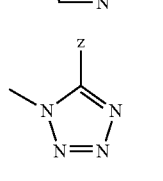
G-8

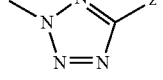
G-9

Z each independently represents hydrogen, halogen, nitro, cyano, hydroxy, thio, $C_{1-4}$ haloalkyl, $C_{1-4}$ haloalkoxy, $C_{1-4}$ alkylthio, $C_{1-4}$ alkylsulfinyl, $C_{1-4}$ alkylsulfonyl, $C_{1-4}$ haloalkylthio, $C_{1-4}$ haloalkylsulfinyl, or $C_{1-4}$ haloalkylsulfonyl,
k represents 1, 2, 3 or 4,
$J^4$ represents hydrogen, $C_{1-4}$ alkyl, $C_{1-4}$ haloalkyl, $C_{1-4}$ alkylsulfonyl, $C_{1-4}$ haloalkylsulfonyl or a phenyl group,
and each group defined above may be substituted with any substituent,
are preferred.

Group 3: Carboxamides Represented by the Formula (I-III):

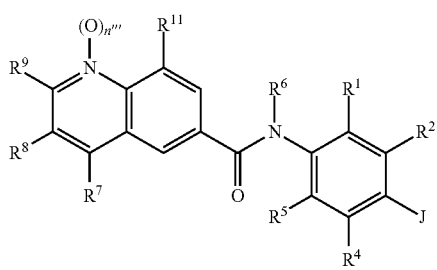

wherein, $R^1$ and $R^5$ each independently represent $C_{1-4}$ alkyl, $C_{1-4}$ haloalkyl, $C_{1-4}$ haloalkoxy, $C_{1-4}$ haloalkylthio, $C_{1-4}$ haloalkylsulfinyl, $C_{1-4}$ haloalkylsulfonyl or halogen, $R^2$ and $R^4$ each independently represent hydrogen, each J independently represents $C_{1-4}$ perfluoroalkyl-O—, $C_{1-4}$ monobromoperfluoroalkyl-O—, $C_{1-4}$ perfluoroalkyl-S—, $C_{1-4}$ monobromoperfluoroalkyl-S—, $C_{1-4}$ perfluoroalkyl-S(O)—, $C_{1-4}$ monobromoperfluoroalkyl-S(O)—, $C_{1-4}$ perfluoroalkyl-S(O)$_2$—, $C_{1-4}$ monobromoperfluoroalkyl-S(O)$_2$—, $C_{1-4}$ perfluoroalkyl, $C_{1-4}$ monobromoperfluoroalkyl, $C_{3-6}$ perfluorocycloalkyl, $C_{3-6}$ monobromoperfluorocycloalkyl, —C(J$^1$)(J$^2$)(J$^3$) or —C(J$^1$)(J$^2$)(OJ$^4$), $J^1$ and $J^2$ each independently represent $C_{1-4}$ perfluoroalkyl, $J^3$ represents any one of the following G-1 to G-9:

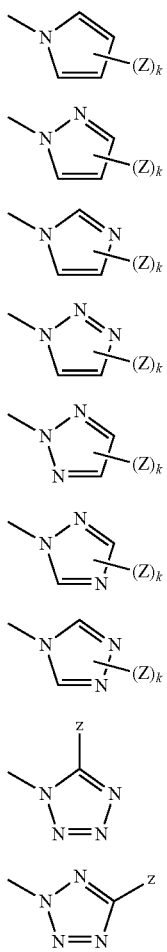

Z each independently represents hydrogen, halogen, nitro, cyano, hydroxy, thio, $C_{1-4}$ haloalkyl, $C_{1-4}$ haloalkoxy, $C_{1-4}$ alkylthio, $C_{1-4}$ alkylsulfinyl, $C_{1-4}$ alkylsulfonyl, $C_{1-4}$ haloalkylthio, $C_{1-4}$ haloalkylsulfinyl, or $C_{1-4}$ haloalkylsulfonyl, k represents 1, 2, 3 or 4, $J^4$ represents hydrogen, $C_{1-4}$ alkyl, $C_{1-4}$ haloalkyl, $C_{1-4}$ alkylsulfonyl, $C_{1-4}$ haloalkylsulfonyl or a phenyl group, $R^4$ represents hydrogen, $R^5$ represents $C_{1-4}$ alkyl, $C_{1-4}$ haloalkyl, $C_{1-4}$ alkoxy, $C_{1-4}$ haloalkoxy, $C_{1-4}$ alkyl-S—, $C_{1-4}$ haloalkyl-S—, $C_{1-4}$ alkyl-S(O)—, $C_{1-4}$ haloalkyl-S(O)—, $C_{1-4}$ alkyl-S(O)$_2$—, $C_{1-4}$ haloalkyl-S(O)$_2$—, or halogen, $R^6$ represents $C_{1-4}$ alkyl or hydrogen, $R^7$ represents halogen or hydrogen, $R^8$ represents halogen or hydrogen, $R^9$ represents hydrogen, cyano, $C_{1-4}$ alkyl, $C_{1-4}$ haloalkyl, $C_{1-4}$ alkoxy, $C_{1-4}$ haloalkoxy, $C_{1-4}$ alkyl-S—, $C_{1-4}$ haloalkyl-S—, $C_{1-4}$ alkyl-S(O)—, $C_{1-4}$ haloalkyl-S(O)—, $C_{1-4}$ alkyl-S(O)$_2$—, $C_{1-4}$ haloalkyl-S(O)$_2$—, halogen, $C_{1-4}$ alkylcarbonylamino, phenylcarbonylamino, $C_{1-4}$ alkylcarbonylamino-$C_{1-4}$ alkyl, 1H-1,2,4-triazol-1-yl or tri($C_{1-4}$ alkyl)silyl $C_{2-4}$ alkynyl, $R^{11}$ represents hydrogen, halogen or cyano, n''' represents 0 or 1, and each group defined above may be further substituted with any substituent, are particularly preferred.

The compounds of the Formula (I) of the present invention may have an asymmetric carbon, and therefore optical isomers are included in such compounds.

Group 4: Carboxamides Represented by the Formula (I-IV):

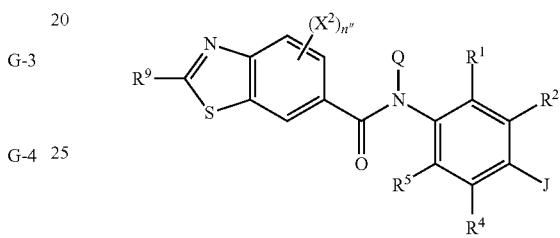

wherein, $X^2$, Q and J are as defined above, $R_1$, $R^2$, $R^4$ and $R^5$ each independently have the same meaning as $X^3$ described above, $R^9$ each independently have the same meaning as $X^1$ described above and n'' stands for 1, 2 or 3.

Furthermore, each J independently represents $C_{1-4}$ perfluoroalkyl-O—, $C_{1-4}$ monobromoperfluoroalkyl-O—, $C_{1-4}$ perfluoroalkyl-S—, $C_{1-4}$ monobromoperfluoroalkyl-S—, $C_{1-4}$ perfluoroalkyl-S(O)—, $C_{1-4}$ monobromoperfluoroalkyl-S(O)—, $C_{1-4}$ perfluoroalkyl-S(O)$_2$—, $C_{1-4}$ monobromoperfluoroalkyl-S(O)$_2$—, $C_{1-4}$ perfluoroalkyl, $C_{1-4}$ monobromoperfluoroalkyl, $C_{3-6}$ perfluorocycloalkyl, $C_{3-6}$ monobromoperfluorocycloalkyl, —C(J$^1$)(J$^2$)(J$^3$) or —C(J$^1$)(J$^2$)(OJ$^4$), $J^1$ and $J^2$ each independently represent $C_{1-4}$ perfluoroalkyl, $J^3$ represents any one of the following G-1 to G-9:

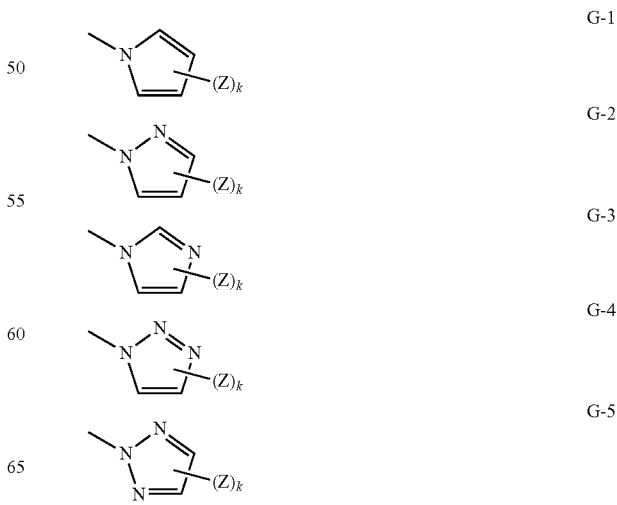

-continued

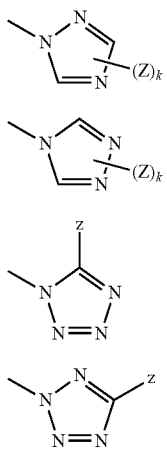

G-6

G-7

G-8

G-9

Z each independently represents hydrogen, halogen, nitro, cyano, hydroxy, thio, $C_{1-4}$ haloalkyl, $C_{1-4}$ haloalkoxy, $C_{1-4}$ alkylthio, $C_{1-4}$ alkylsulfinyl, $C_{1-4}$ alkylsulfonyl, $C_{1-4}$ haloalkylthio, $C_{1-4}$ haloalkylsulfinyl, or $C_{1-4}$ haloalkylsulfonyl, k represents 1, 2, 3 or 4, $J^4$ represents hydrogen, $C_{1-4}$ alkyl, $C_{1-4}$ haloalkyl, $C_{1-4}$ alkylsulfonyl, $C_{1-4}$ haloalkylsulfonyl or a phenyl group, and each group defined above may be substituted with any substituent, are preferred.

Preparation method (a) can be depicted as the following reaction formula when 6-bromo-2-naphthoyl chloride and 2-ethyl-4-(1,1,1,2,3,3,3-heptafluoropropan-2-yl)-6-methylaniline are used as reacting materials.

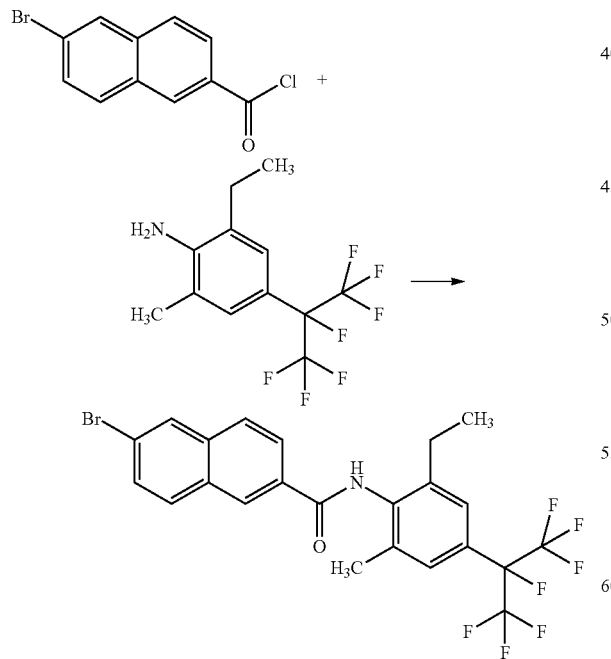

Preparation method (b) can be depicted as the following reaction formula when 6-bromo-N-[2-ethyl-4-(1,1,1,2,3,3,3-heptafluoropropan-2-yl)-6-methylphenyl]-2-naphthamide, zinc cyanide and tetrakis(triphenylphosphine)palladium (0) are used as reacting materials.

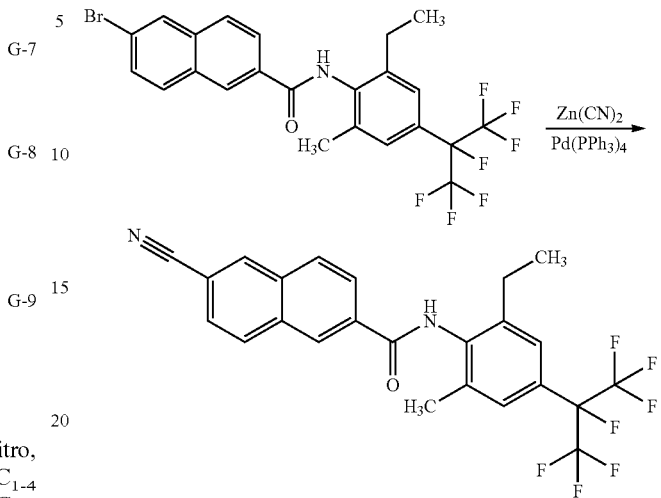

Preparation method (c-1) can be depicted as the following reaction formula when N-[4-(1,1,1,2,3,3,3-heptafluoropropan-2-yl)-2,6-dimethyl-phenyl]quinoline-6-carboxamide-1-oxide and phosphorus oxychloride are used as reacting materials.

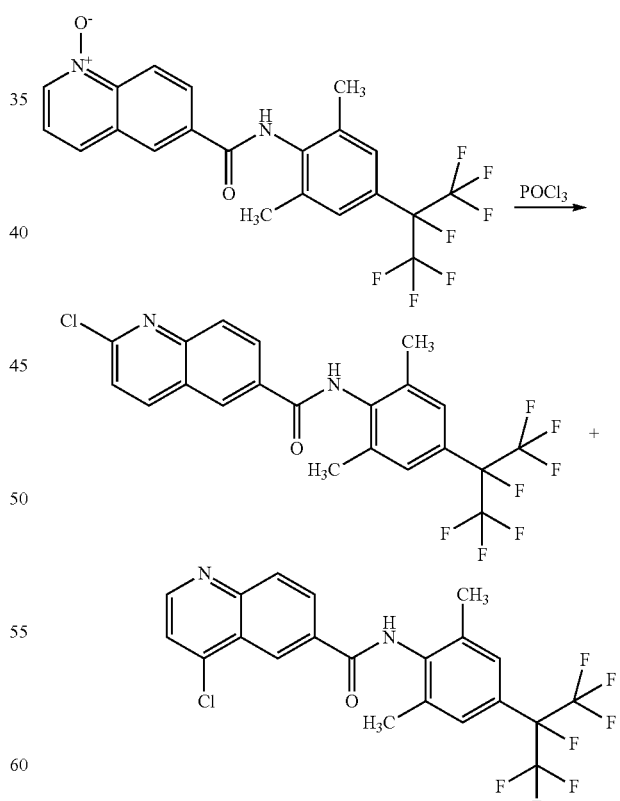

Preparation method (d) can be depicted as the following reaction formula when N-[4-(1,1,1,2,2,3,3-heptafluoropropan-2-yl)-2,6-dimethyl-phenyl]quinoline-6-carboxamide-1-oxide and trimethylsilylnitrile are used as reacting materials.

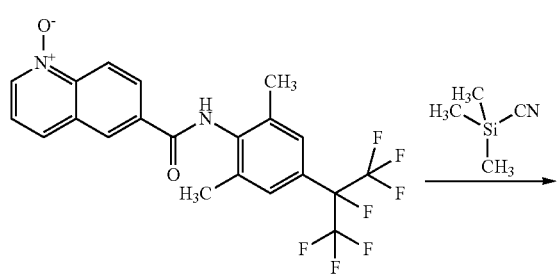

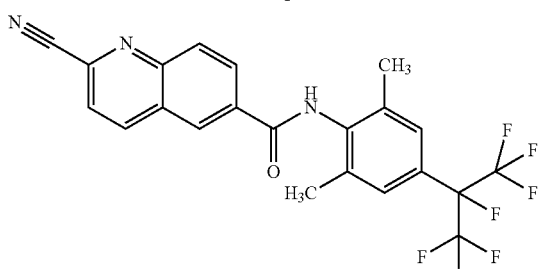

Preparation method (e) can be depicted as the following reaction formula when 6-bromo-N-[2-ethyl-4-(1,1,1,2,3,3,3-heptafluoropropan-2-yl-2-yl)-6-methylphenyl]-2-naphthamide and methyl iodide are used as reacting materials.

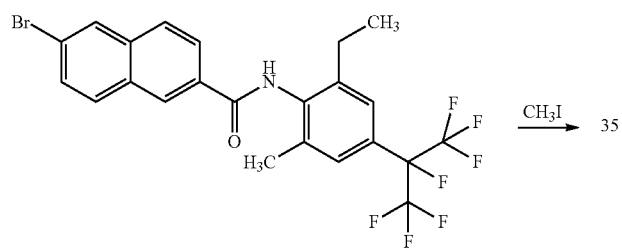

Preparation method (f) can be depicted as the following reaction formula when 6-bromo-N-[2-ethyl-4-(1,1,1,2,3,3,3-heptafluoropropan-2-yl)-6-methylphenyl]-2-naphthamide and a Lawesson reagent are used as reacting materials.

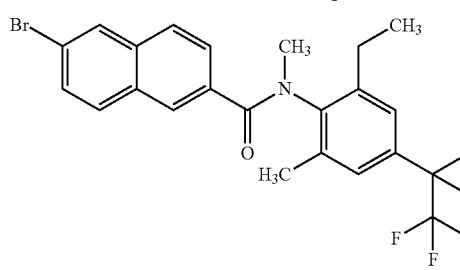

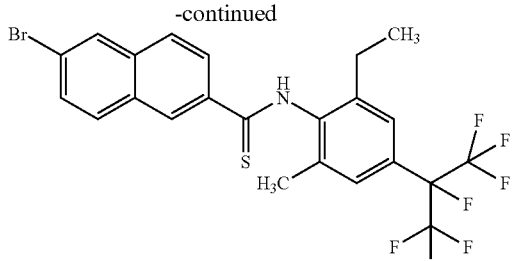

Preparation method (g) can be depicted as the following reaction formula when 3-bromo-4-[(4-chloro-5H-1,2,3-dithiazol-5-yl)amino]-N-[2-ethyl-6-methyl-4-(1,1,1,2,3,3,4,4,4-nonafluorobutan-2-yl)phenyl]cyclohexa-1,5-diene-1-carboxamide and CuI are used as reacting materials.

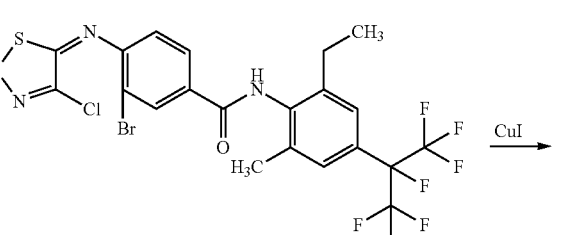

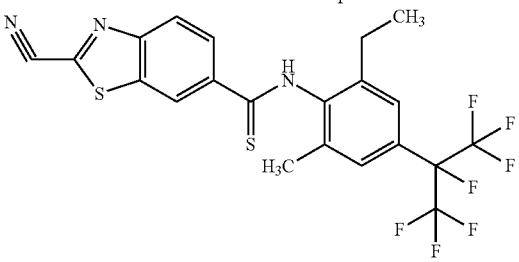

Descriptions about Each Preparation Method and Intermediates

The compounds of the Formula (II) as reacting materials for the Preparation method (a) are known and their representative examples are as follows:

2-naphthalene carboxylic acid,
2-naphthalene carboxylic acid chloride,
6-bromo-2-naphthalene carboxylic acid,
6-bromo-2-naphthalene carboxylic acid chloride,
quinoline-6-carboxylic acid,
quinoline-6-carboxylic acid chloride,
2-(trifluoromethyl)quinoline-6-carboxylic acid,
2-(trifluoromethyl)quinoline-6-carboxylic acid chloride,
2-methylquinoline-6-carboxylic acid,
2-methylquinoline-6-carboxylic acid chloride,
2-chloroquinoline-6-carboxylic acid,
2-chloroquinoline-6-carboxylic acid chloride,
2-cyanoquinoline-6-carboxylic acid,
2-cyanoquinoline-6-carboxylic acid chloride, etc.
8-chloroquinoline-7-carboxylic acid (reference literature: WO2006-132739A2, Roczniki Chemii 1962, 36, 873).
8-chloroquinoline-7-carboxylic acid chloride,
8-bromoquinoline-7-carboxylic acid (reference literature: Journal of Medicinal Chemistry 2000, 43, 3820)
8-bromoquinoline-7-carboxylic acid chloride,
1,3-benzothiazole-6-carbonyl chloride.

When L¹ represents hydroxy in the starting materials of the Formula (II) for the Preparation method (a), they can be reacted with the compounds of the Formula (III) in the presence of a condensing agent.

As a condensing agent, 1,3-dicyclohexylcarbodiimide (DCC), 1-ethyl-3-(3'-dimethylaminopropyl)-carbodiimide hydrochloride salt (WSCI), carbonyldiimidazole (CDI), diethyl phosphocyanate (DEPC), 2-chloro-1-methylpytidinium iodide (Mukaiyama reagent), etc. can be used for the reaction.

When L¹ represents hydroxy in the starting materials of the Formula (II) for the Preparation method (a), L¹ can be easily converted to an appropriate substituent by several methods including, pre-reacting with a chlorination agent such as thionyl chloride, oxalyl chloride or phosphorous pentachloride, reacting with an organic acid halide such as pyvaloyl chloride, or reacting with carbonyldiimidazole or sulfonylimidazole and the like.

As a reacting material for the Preparation method (a), some of the compounds having the Formula (III) are known and they can be synthesized according to the methods that are described in US2002/0198399A1, EP1006102A, JP2003-335735A, WO2005/021488A1, WO2005/073165A1, WO2006/137395A, JP2004-161767A or WO2006/024412A2. As a representative example of the known compounds, the followings can be mentioned.

4-(1,1,1,2,3,3,3-heptafluoropropan-2-yl)-2,6-dimethylaniline,
2-ethyl-4-(1,1,1,2,3,3,3-heptafluoropropan-2-yl)-6-methylaniline,
2,6-diethyl-4-(1,1,1,2,3,3,3-heptafluoropropan-2-yl)aniline,
2-bromo-4-(1,1,1,2,3,3,3-heptafluoropropan-2-yl)-6-methylaniline,
2-bromo-4-(1,1,1,2,3,3,3-heptafluoropropan-2-yl)-6-ethylaniline,
2,6-dichloro-4-(1,1,1,2,3,3,3-heptafluoroptopan-2-yl)aniline,
2,6-dibromo-4-(1,1,1,2,3,3,3-heptafluoropropan-2-yl)aniline,
4-(1,1,1,2,3,3,3-heptafluoropropan-2-yl)-2,6-diiodoaniline,
4-(1,1,1,2,3,3,3-heptafluoropropan-2-yl)-2-(trifluoromethyl)aniline,
2-chloro-4-(1,1,1,2,3,3,3-heptafluoropropan-2-yl)-6-(trifluoromethyl)aniline,
2-bromo-4-(1,1,1,2,3,3,3-heptafluoropropan-2-yl)-6-(trifluoromethyl)aniline,
4-(1,1,1,2,3,3,3-heptafluoropropan-2-yl)-2-iodo-6-(trifluoromethyl)aniline,
4-(1,1,1,2,3,3,3-heptafluoropropan-2-yl)-2-(trifluoromethyl)aniline,
2-chloro-4-(1,1,1,2,3,3,3-heptafluoropropan-2-yl)-6-(trifluoromethoxy)aniline,
2-bromo-4-(1,1,1,2,3,3,3-heptafluoropropan-2-yl)-6-(trifluoromethoxy)aniline,
4-(1,1,1,2,3,3,3-heptafluoropropan-2-yl)-2-iodo-6-(trifluoromethoxy)aniline,
4-(1,1,1,2,3,3,3-heptafluoropropan-2-yl)-2-[(trifluoromethyl)sulfanyl]aniline,
4-(1,1,1,2,3,3,3-heptafluoropropan-2-yl)-2-[(trifluoromethyl)sulfinyl]aniline,
4-(1,1,1,2,3,3,3-heptafluoropropan-2-yl)-2-yl)-6-[(trifluoromethyl)sulfonyl]aniline,
2-chloro-4-(1,1,1,2,3,3,3-heptafluoropropan-2-yl)-6-[(trifluoromethyl)sulfanyl]aniline,
2-chloro-4-(1,1,1,2,3,3,3-heptafluoropropan-2-yl)-6-[(trifluoromethyl)sulfinyl]aniline,
2-chloro-4-(1,1,1,2,3,3,3-heptafluoropropan-2-yl)-6-[(trifluoromethyl)sulfonyl]aniline.
2-bromo-4-(1,1,1,2,3,3,3-heptafluoropropan-2-yl)-6-[(trifluoromethyl)sulfanyl]aniline,
2-bromo-4-(1,1,1,2,3,3,3-heptafluoropropan-2-yl)-6-[(trifluoromethyl)sulfinyl]aniline,
2-bromo-4-(1,1,1,2,3,3,3-heptafluoropropan-2-yl)-6-[trifluoromethyl)sulfonyl]aniline,
4-(1,1,1,2,3,3,3-heptafluoroproan-2-yl)-2-iodo-6-[(trifluoromethyl)sulfanyl]aniline,
4-(1,1,1,2,3,3,3-heptafluoroproan-2-yl)-2-iodo-6-[(trifluoromethyl)sulfinyl]aniline,
4-(1,1,1,2,3,3,3-heptafluoroproan-2-yl)-6-iodo-4-[(trifluoromethyl)sulfonyl]aniline,
2-ethyl-4-(2-ethoxy-1,1,1,3,3,3-hexafluoropropan-2-yl)-6-methylaniline
4-[2-(4-chlorophenoxy)-1,1,1,3,3,3-hexafluoropropan-2-yl]-2-ethyl-6-methylaniline,
4-[2-(4-chloro-1H-pyrazole-1-yl)-1,1,1,3,3,3-hexafluoropropan-2-yl]-2-ethyl-6-methylaniline,
4-(1,1,1,2,3,3,4,4,4-nonafluorobutan-2-yl)-2,6-dimethylaniline,
2-ethyl-4-(1,1,1,2,3,3,4,4,4-nonafluorobutan-2-yl)-6-methylaniline,
2,6-dichloro-4-(1,1,1,2,3,3,4,4,4-nonafluorobutan-2-yl)aniline,
2,6-dibromo-4-(1,1,1,2,3,3,4,4,4-nonafluorobutan-2-yl)aniline,
4-(1,1,1,2,3,3,4,4,4-nonafluorobutan-2-yl)-2,6-diiodoaniline
4-(1,1,1,2,3,3,4,4,4-nonafluorobutan-2-yl)-2-(trifluoromethyl)aniline,
2-chloro-4-(1,1,1,2,3,3,4,4,4-nonafluorobutan-2-yl)-6-(trifluoromethyl)aniline,
2-bromo-4-(1,1,1,2,3,3,4,4,4-nonafluorobutan-2-yl)-6-(trifluoromethyl)aniline,
4-(1,1,1,2,3,3,4,4,4-nonafluorobutan-2-yl)-2-iodo-6-(trifluoromethyl)aniline,
4-(1,1,1,2,3,3,4,4,4-nonafluorobutan-2-yl)-2-(trifluoromethoxy)aniline,
2-chloro-4-(1,1,1,2,3,3,4,4,4-nonafluorobutan-2-yl)-6-(trifluoromethoxy)aniline,
2-bromo-4-(1,1,1,2,3,3,4,4,4-nonafluorobutan-2-yl)-6-(trifluoromethoxy)aniline,
4-(1,1,1,2,3,3,3-heptafluoropropan-2-yl)-2-iodo-6-(trifluoromethoxy)aniline,
4-(1,1,1,2,3,3,4,4,4-nonafluorobutan-2-yl)-2-[(trifluoromethyl)sulfanyl]aniline,
4-(1,1,1,2,3,3,4,4,4-nonafluorobutan-2-yl)-2-[(trifluoromethyl)sulfinyl]aniline,
4-(1,1,1,2,3,3,4,4,4-nonafluorobutan-2-yl)-2-[(trifluoromethyl)sulfonyl]aniline,
2-chloro-4-(1,1,1,2,3,3,4,4,4-nonafluorobutan-2-yl)-6-[(trifluoromethyl)sulfanyl]aniline,
2-chloro-4-(1,1,1,2,3,3,4,4,4-nonafluorobutan-2-yl)-6-[(trifluoromethyl)sulfinyl]aniline,
2-chloro-4-(1,1,1,2,3,3,4,4,4-nonafluorobutan-2-yl)-6-[(trifluoromethyl)sulfonyl]aniline,
2-bromo-4-(1,1,1,2,3,3,4,4,4-nonafluorobutan-2-yl)-6-[(trifluoromethyl)sulfanyl]aniline,
2-bromo-4-(1,1,1,2,3,3,4,4,4-nonafluorobutan-2-yl)-6-[(trifluoromethyl)sulfinyl]aniline,
2-bromo-4-(1,1,1,2,3,3,4,4,4-nonafluorobutan-2-yl)-6-[(trifluoromethyl)sulfonyl]aniline,
4-(1,1,1,2,3,3,4,4,4-nonafluorobutan-2-yl)-2-iodo-6-[(trifluoromethyl)sulfanyl]aniline,
4-(1,1,1,2,3,3,4,4,4-nonafluorobutan-2-yl)-2-iodo-6-[(trifluoromethyl)sulfinyl]aniline, 4-(1,1,1,2,3,3,4,4,4-nonafluorobutan-2-yl)-2-iodo-6-[(trifluoromethyl)sulfonyl]aniline,
2-ethyl-4-[2-ethoxy-1,1,1,3,3,4,4,4-octafluorobutan-2-yl]-6-methylaniline,
4-[2-(4-chlorophenoxy)-1,1,1,3,3,4,4,4-octafluorobutan-2-yl]-2-ethyl-6-methylaniline,
4-[2-(4-chloro-1H-pyrazol-1-yl)-1,1,1,3,3,4,4,4-octafluorobutan-2-yl]-2-ethyl-6-methylaniline,
2,6-dibromo-4-(trifluoromethoxy)aniline,
2,6-dibromo-4-[(trifluoromethyl)sulfanyl]aniline,
2,6-dibromo-4-[(trifluoromethyl)sulfinyl]aniline,
2,6-dibromo-4-[(trifluoromethyl)sulfonyl]aniline,
2,6-dibromo-4-[(pentafluoroethyl)sulfanyl]aniline,
2,6-dibromo-4-[(heptafluoropropyl)sulfanyl]aniline,
2,6-dibromo-4-[(nonafluorobutyl)sulfanyl]aniline,
4-(1-bromo-1,1,2,3,3,3-hexafluoropropan-2-yl)aniline,
4-(1-bromo-1,1,2,3,3,3-hexafluoropropan-2-yl)-2-methylaniline, and the like.

Furthermore, with respect to the compounds having the Formula (III) as a reacting material for the Preparation method (a), those that fall within the concept of the patent literatures, i.e., JP2004-161767A and WO2006/024412A2, but can be mentioned as a novel compound are as follows.

4-(1-bromo-1,1,2,3,3,3-hexafluoropropan-2-yl)-2,6-dimethylaniline
4-(1-bromo-1,1,2,3,3,3-hexafluoropropan-2-yl)-2-ethyl-6-methylaniline
2,6-dichloro-4-(1-bromo-1,1,2,3,3,3-hexafluoropropan-2-yl)aniline
2,6-dichloro-4-(1-bromo-1,1,2,3,3,3-hexafluoropropan-2-yl)aniline
4-(1-bromo-1,1,2,3,3,3-hexafluoropropan-2-yl)-2,6-diiodoaniline,
4-(1-bromo-1,1,2,3,3,3-hexafluoropropan-2-yl)-2-(difluoromethyl)aniline,
2-chloro-4-(1-bromo-1,1,2,3,3,3-hexafluoropropan-2-yl)-6-(difluoromethyl)aniline,
2-bromo-4-(1-bromo-1,1,2,3,3,3-hexafluoropropan-2-yl)-6-(difluoromethyl)aniline,
4-(1-bromo-1,1,2,3,3,3-hexafluoropropan-2-yl)-2-iodo-6-(difluoromethyl)aniline,
4-(1-bromo-1,1,2,3,3,3-hexafluoropropan-2-yl)-2-trifluoromethyl)aniline,
2-chloro-4-(1-bromo-1,1,2,3,3,3-hexafluoropropan-2-yl)-6-(trifluoromethyl)aniline,
2-bromo-4-(1-bromo-1,1,2,3,3,3-hexafluoropropan-2-yl)-6-(rifluoromethyl)aniline,
4-(1-bromo-1,1,2,3,3,3-hexafluoropropan-2-yl)-2-iodo-6-(trifluoromethyl)aniline,
4-(1-bromo-1,1,2,3,3,3-hexafluoropropan-2-yl)-2(difluoromethoxy)aniline,
2-(difluoromethoxy))-4-(1-bromo-1,1,2,3,3,3-hexafloropropan-2-yl)-6-methylaniline,
2-chloro-4-(1-bromo-1,1,2,3,3,3-hexafluoropropan-2-yl)-6-(difluoromethoxy)aniline,
2-bromo-4-(1-bromo-1,1,2,3,3,3-hexafluoropropan-2-yl)-6-(difluoromethoxy)aniline,
4-(1-bromo-1,1,2,3,3,3-hexafluoropropan-2-yl)-2-iodo-6-(difluoromethoxy)aniline,
4-(1-bromo-1,1,2,3,3,3-hexafluoropropan-2-yl)-2-(trifluoromethoxy)aniline,
2-chloro-4-(1-bromo-1,1,2,3,3,3-hexafluoropropan-2-yl)-6-(trifluoromethoxy)aniline,
2-bromo-4-(1-bromo-1,1,2,3,3,3-hexafluoropropan-2-yl)-6-(trifluoromethoxy)aniline,
4-(1-bromo-1,1,2,3,3,3-hexafluoropropan-2-yl)-2-iodo-6-(trifluoromethoxy)aniline,
4-(1-bromo-1,2,3,3,3-hexafluoropropan-2-yl)-2-[(difluoromethyl)sulfanyl]aniline,
4-(1-bromo-1,1,2,3,3,3-hexafluoropropan-2-yl)-2-[(difluoromethyl)sulfinyl]aniline,
4-(1-bromo-1,1,2,3,3,3-hexafluoropropan-2-yl)-2-[(difluoromethyl)sulfonyl]aniline,
2-chloro-4-(1-bromo-1,1,2,3,3,3-hexafluoropropan-2-yl)-6-[(difluoromethyl)sulfanyl]aniline,
2-chloro-4-(1-bromo-1,1,2,3,3,3-hexafluoropropan-2-yl)-6-[(difluoromethyl)sulfinyl]aniline,
2-chloro-4-(1-bromo-1,1,2,3,3,3-hexafluoropropan-2-yl)-6-[(difluoromethyl)sulfonyl]aniline,
2-bromo-4-(1-bromo-1,1,2,3,3,3-hexafluoropropan-2-yl)-6-[(difluoromethyl)sulfanyl]aniline,
2-bromo-4-(1-bromo-1,1,2,3,3,3-hexafluoropropan-2-yl)-6-[(difluoromethyl)sulfinyl]aniline,
2-bromo-4-(1-bromo-1,1,2,3,3,3-hexafluoropropan-2-yl)-6-[(difluoromethyl)sulfonyl]aniline,
4-(1-bromo-1,1,2,3,3,3-hexafluoropropan-2-yl)-2-iodo-6-[(difluoromethyl)sulfanyl]aniline,
4-(1-bromo-1,1,2,3,3,3-hexafluoropropan-2-yl)-2-iodo-6-[(difluoromethyl)sulfinyl]aniline,
4-(1-bromo-1,1,2,3,3,3-hexafluoropropan-2-yl)-2-iodo-6-[(difluoromethyl)sulfonyl]aniline,
4-(1-bromo-1,1,2,3,3,3-hexafluoropropan-2-yl)-2-[(trifluoromethyl)sulfanyl]aniline,
4-(1-bromo-1,1,2,3,3,3-hexafluoropropan-2-yl)-2-[(trifluoromethyl)sulfinyl]aniline,
4-(1-bromo-1,1,2,3,3,3-hexafluoropropan-2-yl)-2-[(trifluoromethyl)sulfonyl]aniline,
2-chloro-4-(1-bromo-1,1,2,3,3,3-hexafluoropropan-2-yl)-6-[(trifluoromethyl)sulfanyl]aniline,
2-chloro-4-(1-bromo-1,1,2,3,3,3-hexafluoropropan-2-yl)-6-[(trifluoromethyl)sulfinyl]aniline,
2-chloro-4-(1-bromo-1,1,2,3,3,3-hexafluoropropan-2-yl)-6-[(trifluoromethyl)sulfonyl]aniline,
2-bromo-4-(1-bromo-1,1,2,3,3,3-hexafluoropropan-2-yl)-6-[(trifluoromethyl)sulfanyl]aniline,
2-bromo-4-(1-bromo-1,1,2,3,3,3-hexafluoropropan-2-yl)-6-[(trifluoromethyl)sulfinyl]aniline,
2-bromo-4 (1-bromo-1,1,2,3,3,3-hexafluoropropan-2-yl)-6-[(trifluoromethyl)sulfonyl]aniline,
4-(1-bromo-1,1,2,3,3,3-hexafluoropropan-2-yl)-2-iodo-6-[(trifluoromethyl)sulfanyl]aniline,
4-(1-bromo-1,1,2,3,3,3-hexafluoropropan-2-yl)-2-iodo-6-[(trifluoromethyl)sulfinyl]aniline,
4-(1-bromo-1,1,2,3,3,3-hexafluoropropan-2-yl)-6-iodo-4-[(trifluoromethyl)sulfonyl]aniline.

It is expressed as follows:

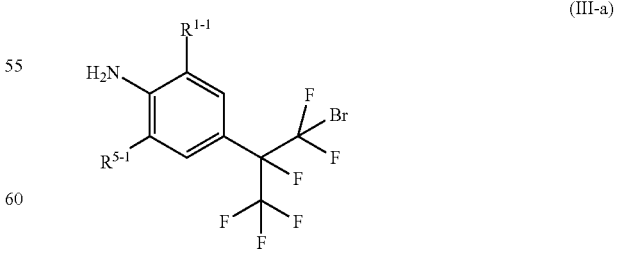

(III-a)

wherein, $R^{1-1}$ and $R^{5-1}$ each independently represent hydrogen, halogen, $C_{1-4}$ alkyl, $C_{1-4}$ haloalkyl, $C_{1-4}$ haloalkoxy, $C_{1-4}$ haloalkylsulfanyl, $C_{1-4}$ haloalkylsulfinyl, $C_{1-4}$ haloalkylsulfonyl, with the proviso that the case is excluded where $R^{1-1}$ is hydrogen and $R^{5-1}$ is hydrogen, $R^{1-1}$ is hydrogen and $R^{5-1}$ is methyl, $R^{1-1}$ is hydrogen and $R^{5-1}$ is fluoro, $R^{1-1}$ is hydrogen and $R^{5-1}$ is chloro, or $R^{1-1}$ is hydrogen and $R^{5-1}$ is bromo. They can be synthesized according to the methods that are described in JP2004-161767A as shown below.

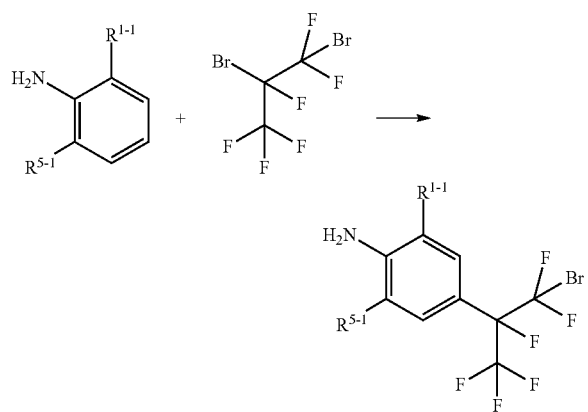

Furthermore, with respect to the compounds having the Formula (III) as a reacting material for the Preparation method (a), those that fall within the concept of the patent literatures, i.e. US2002/0198399A1, EP1006102A and JP2003-335735A, but can be mentioned as a novel compound are as follows.

4-(1,1,1,2,3,3-heptafluoropropan-2-yl)-2-(difluoromethyl)aniline,
2-chloro-(1,1,1,2,3,3,3-heptafluoropropan-2-yl)-6-(difluoromethyl)aniline,
2-bromo-4-(1,1,1,2,3,3,3-heptafluoropropan-2-yl)-6-(difluoromethyl)aniline,
4-(1,1,1,2,3,3,3-heptafluoropropan-2-yl)-2-iodo-6-(difluoromethyl)aniline,
4-(1,1,1,2,3,3,3-heptafluoropropan-2-yl)-2-(difluoromethoxy)aniline,
2-(difluoromethoxy)-4-(1,1,1,2,3,3,3-heptafluoropropan-2-yl)-6-methylaniline,
2-chloro-4-(1,1,2,3,3,3-heptafluoropropan-2-yl)-6-(difluoromethoxy)aniline,
2-bromo-4-(1,1,1,2,3,3,3-heptafluoropropan-2-yl)-6-(difluoromethoxy)aniline,
4-(1,1,1,2,3,3,3-heptafluoropropan-2-yl)-2-iodo-6-(difluoromethoxy)aniline,
4-(1,1,1,2,3,3,3-heptafluoropropan-2-yl)-2-[(difluoromethyl)sulfanyl]aniline,
4-(1,1,1,2,3,3,3-heptafluoropropan-2-yl)-2-[(difluoromethyl)sulfinyl]aniline,
4-(1,1,1,2,3,3,3-heptafluoropropan-2-yl)-2-[(difluoromethyl)sulfonyl]aniline
2-chloro-4-(1,1,1,1,2,3,3,3-heptafluoropropan-2-yl)-6-[(difluoromethyl)sulfanyl]aniline,
2-chloro-4-(1,1,1,2,3,3,3-heptafluoropropan-2-yl)-6-[(difluoromethyl)sulfinyl]aniline,
2-chloro 4-(1,1,1,2,3,3,3-heptafluoropropan-2-yl)-6-[(difluoromethyl)sulfonyl]aniline,
2-bromo-4-(1,1,1,2,3,3,3-heptafluoropropan-2-yl)-6-[(difluoromethyl)sulfanyl]aniline,
2-bromo-4-(1,1,1,2,3,3,3-heptafluoropropan-2-yl)-6-[(difluoromethyl)sulfinyl]aniline,
2-bromo-4-(1,1,1,2,3,3,3-heptafluoropropan-2-yl)-6-[(difluoromethyl)sulfonyl]aniline,
4-(1,1,1,2,3,3,3-heptafluoropropan-2-yl)-2-iodo-6-[(difluoromethyl)sulfanyl]aniline,
4-(1,1,1,2,3,3,3-heptafluoropropan-2-yl)-2-iodo-6-[(difluoromethyl)sulfinyl]aniline,
4-(1,1,1,2,3,3,3-heptafluoropropan-2-yl)-2-iodo-6-[(difluoromethyl)sulfonyl]aniline,
4-(1,1,1,2,3,3,4,4,4-nonafluorobutan-2-yl)-2-(difluoromethyl)aniline,
2-chloro-4-(1,1,1,2,3,3,4,4,4-nonafluorobutan-2-yl)-6-(difluoromethyl)aniline,
2-bromo-4-(1,1,1,2,3,3,4,4,4-nonafluorobutan-2-yl)-6-(difluoromethyl)aniline,
4-(1,1,1,2,3,3,4,4,4-nonafluorobutan-2-yl)-2-iodo-6-(difluoromethyl)aniline,
4-(1,1,1,2,3,3,4,4,4-nonafluorobutan-2-yl)-2-(difluoromethoxy)aniline,
2-(difluoromethoxy)-4-(1,1,1,2,3,3,4,4,4-nonafluorobutan-2-yl)-6-methylaniline,
2-chloro-4-(1,1,1,2,3,3,4,4,4-nonafluorobutan-2-yl)-6-(difluoromethoxy)aniline,
2-bromo-4-(1,1,1,2,3,3,4,4,4-nonafluorobutan-2-yl)-6-(difluoromethoxy)aniline,
4-(1,1,1,2,3,3,4,4,4-nonafluorobutan-2-yl)-2-iodo-6-(difluoromethoxy)aniline,
4-(1,1,1,2,3,3,4,4,4-nonafluorobutan-2-yl)-2-[(difluoromethyl)sulfanyl]aniline,
4-(1,1,1,2,3,3,4,4,4-nonafluorobutan-2-yl)-2-[(difluoromethyl)sulfinyl]aniline,
4-(1,1,1,2,3,3,4,4,4-nonafluorobutan-2-yl)-2-[(difluoromethyl)sulfonyl]aniline,
2-chloro-4-(1,1,1,2,3,3,4,4,4-nonafluorobutan-2-yl)-6-[(difluoromethyl)sulfanyl]aniline,
2-chloro-4-(1,1,1,2,3,3,4,4,4-nonafluorobutan-2-yl)-6-[(difluoromethyl)sulfinyl]aniline,
2-chloro-4-(1,1,1,2,3,3,4,4,4-nonafluorobutan-2-yl)-6-[(difluoromethyl)sulfonyl]aniline,
2-bromo-4-(1,1,1,2,3,3,4,4,4-nonafluorobutan-2-yl)-6-[(difluoromethyl)sulfanyl]aniline,
2-bromo-4-(1,1,1,2,3,3,4,4,4-nonafluorobutan-2-yl)-6-[(difluoromethyl)sulfinyl]aniline,
2-bromo-4-(1,1,1,2,3,3,4,4,4-nonafluorobutan-2-yl)-6-[(difluoromethyl)sulfonyl]aniline,
4-(1,1,1,2,3,3,4,4,4-nonafluorobutan-2-yl)-2-iodo-6-[(difluoromethyl)sulfanyl]aniline,
4-(1,1,1,2,3,3,4,4,4-nonafluorobutan-2-yl)-2-iodo-6-[(difluoromethyl)sulfinyl]aniline,
4-(1,1,1,2,3,3,4,4,4-nonafluorobutan-2-yl)-2-iodo-6-[(difluoromethyl)sulfonyl]aniline
It is expressed as follows:

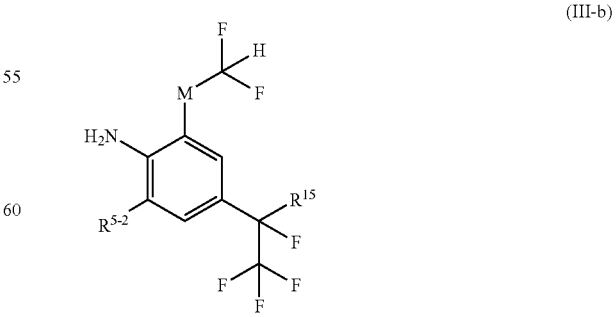

(III-b)

wherein, M represents, single bond, oxygen, sulfur, —S(O)— or —S(O)$_2$—, $R^{15}$ represents fluoro, trifluoromethyl or pentafluoroethyl, $R^{5-2}$ represents hydrogen, halogen, $C_{1-4}$ alkyl, $C_{1-4}$ haloalkyl, $C_{1-4}$ haloalkoxy, $C_{1-4}$ haloalkylsulfanyl, $C_{1-4}$ haloalkylsulfinyl, or $C_{1-4}$ haloalkylsulfanyl. They can be synthesized according to the methods that are described in US2002/0198399A1, EP1006102A, JP2003-335735A, WO2005/021488A1, WO2005/073165A1, WO2006/137395A or JP2004-161767A as shown below.

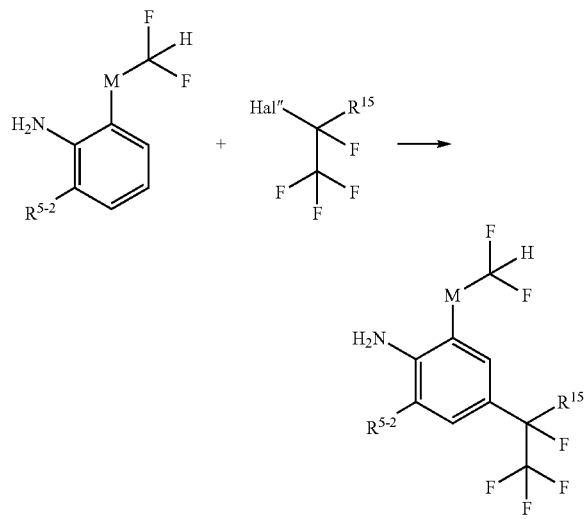

wherein, Hal" represents bromo or ido;
Furthermore, as novel compounds of the Formula (III), the followings can be mentioned,
2,6-dimethyl-4-(undecafluorocyclohexyl)aniline
2-ethyl-6-methyl-4-(undecafluorocyclohexyl)aniline
2,6-dichloro-4-(undecafluorocyclohexyl)aniline
2,6-dibromo-4-(undecafluorocyclohexyl)aniline
2,6-diiodo-4-(undecafluorocyclohexyl)aniline, etc.,
and they are represented by the following formula:

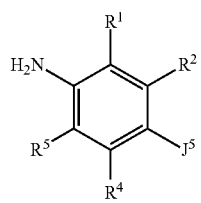

(III-c)

wherein, $R^1$, $R^2$, $R^4$ and $R^5$ each independently have the same meaning as $X^3$ described in claim 1, and $J^5$ represents $C_{3-6}$ perfluorocycloalkyl.

The reaction of the Preparation method (a) can be carried out in the presence of an appropriate diluent, and examples of the diluent which can be used include aliphatic hydrocarbons (hexane, cyclohexane, heptane, etc.), halogenated aliphatic hydrocarbons (dichloromethane, chloroform, carbon tetrachloride, dichloroethane, etc.), aromatic hydrocarbons (benzene, toluene, xylene, chlorobenzene, etc.), ethers (diethyl ether, dibutyl ether; dimethoxyethane (DME), tetrahydrofuran, dioxane, etc.), esters (ethyl acetate, ethyl propionate, etc.), acid amides (dimethylformamide (DMF), dimethyl acetamide (DMA), N-methylpyrrolidone, etc.), nitriles (acetonitrile, propionitrile, etc.), dimethyl sulfoxide (DMSO), water, a mixed solvent including them, etc. Reaction of the Preparation method (a) can be carried out in the presence of an appropriate base and examples of the base which can be used include alkali metal bases (sodium hydroxide, potassium hydroxide, sodium carbonate, potassium carbonate, cesium carbonate, tripotassium phosphate, sodium acetate, potassium acetate, etc.), and organic bases (triethylamine, diisopropylethylamine, tributylamine, N-methylmorpholine, N,N-dimethylaniline, N,N-diethylaniline, 4-tert-butyl-N,N-dimethylaniline, pyridine, picoline, lutidine, diazabicycloundecene (1,8-dizabicyclo[5.4.0]undec-7-ene), diazabicyclooctane, imidazole etc.) and the like.

The Preparation method (a) can be carried out within substantially wide temperature range. It may be generally carried out at the temperature between about –78° C. and about 200° C., preferably between –10° C. and about 150° C. Said reaction is preferably carried out at normal pressure although it may be carried out under elevated or reduced pressure. The reaction time is 0.1 to 72 hours, preferably 0.1 to 24 hours. For carrying out the Preparation method (a), for example, when $L^1$ represents hydroxy, 1 mol of the compound of the Formula (II) can be reacted with 1 to 3 mol of the compound of the Formula (III) using 1 to 3 mol of a condensing agent in a diluent, e.g., DMF to obtain the compounds of the Formula (I).

For carrying out the Preparation method (a), for example, when $L^1$ represents an appropriate leaving group, 1 mol of the compound of the Formula (II) can be reacted with 1 to 3 mol of the compound of the Formula (III) it the presence of an appropriate base, e.g., pyridine, to obtain the compounds of the Formula (I).

The compounds of the Formula (I-a) as reacting materials for the Preparation method (b) are encompassed by the compounds of the Formula (I) of the present invention and their representative examples are as follows:
6-bromo-N-[2-ethyl-4-(1,1,1,2,3,3,3-heptafluoropropan-2-yl)-6-methylphenyl]-2-naphthamide,
2-chloro-N-[4-(1,1,1,2,3,3,3-heptafluoropropan-2-yl)-2,6-dimethylphenyl]quilioline-6-carboxamide,
2-chloro-N-[2-ethyl-4-(1,1,1,2,3,3,3-heptafluoropropan-2-yl)-6-methylphenyl]quinoline-6-carboxamide,
4-bromo-N-[4-(1,1,1,2,3,3,3-heptafluoropropan-2-yl)-2,6-dimethylphenyl]quinoline-6-carboxamide, etc.

The reaction of the Preparation method (b) can be carried out in the presence of an appropriate diluent, and examples of the diluent which can be used are the same as the diluents exemplified for the Preparation method (a). Preferably, dimethylformamide (DMF) can be mentioned.

The reaction of the Preparation method (b) can be carried out in the presence of an appropriate catalyst, and examples of the catalyst which can be used include a transition metal, etc. such as $Pd(PPh_3)_4$, $Pd_2(dba)_3$, $Pd_2(dba)_3CHCl_3$, (dba=dibenzylideneacetone), $Pd(PPh_3)_2Cl_2$, $Pd(OAc)_2$, CuI, CuCN, etc. Further if necessary, the reaction can be carried out by using a phosphine type ligand such as triphenylphosphine, 1,2-bis(diphenylphosphino)ethane, 1,3-bis(diphenylphosphino)propane, 1,4-bis(diphenylphosphino)butane, 1,1'-bis(diphenylphosphino)ferrocene, 2,2'-bis(diphenylphosphino)-1,1'-binaphthalen (BINAP), 4,5-bis(diphenylphosphino)-9,9-dimethylxanthene (Xantphos), tributylphosphine, etc.

Among cyanation reagents which can be used for the reaction of the Preparation method (b), representative examples include zinc cyanide, sodium cyanide, potassium cyanide, silver (I) cyanide, copper (I) cyanide, trimethylsilyl cyanide, potassium hexacyanoiron (II) acid trihydrate, The Preparation method (b) can be carried out within substantially wide temperature range. It may be generally carried out at the temperature between about 0° C. and about 200° C., preferably between 30° C. and about 180° C. Said reaction is preferably carried out at normal pressure although it may be carried out under elevated or reduced pressure. The reaction time is 0.1 to 72 hours, preferably 0.1 to 24 hours.

For carrying out the Preparation method (b), for example, 1 mol of the compound of the Formula (I-a) can be reacted With 0.5 to 3 mol of a cyanation reagent, e.g., zinc cyanide, in the presence of catalytic amount of Pd(PPh$_3$)$_4$ in a diluent such as DMF to obtain the compounds of the Formula (I-h) that are encompassed by the compounds of the Formula (I) of the present invention.

Preparation methods (c-1), (c-2) and (c-3) can be carried out according to the methods described in the literatures (Bioorganic & Medicinal Chemistry 2005, 13, 1487-1496 or WO 2007/133637 A2).

The compounds of the Formula (I-c-1) as reacting materials for the Preparation method (c-1) can be obtained by oxidizing the compounds represented by the following Formula (I-c-5):

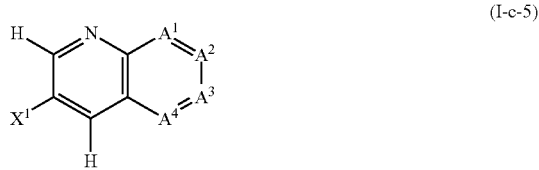

(I-c-5)

with an appropriate oxidizing agent, for example, 3-chloroperbenzoic acid, a combination of trifluoroacetic anhydride and urea-hydrogen peroxide adduct (literature; Tetrahedron Letters, 2000, 41, 2299-2302) and the like.

The compounds of the Formula (I-c-5) are encompassed by the compounds of the Formula (I) of the present invention and they can be synthesized according to the Preparation method (a). Representative examples of the compounds of the Formula (I-c-5) are as ibilows:

N-[4-(1,1,1,2,3,3,3-heptafluoropropan-2-yl)-2,6-dimethylphenyl]quinoline-6-carboxamide,
N-[2-ethyl-4-(1,1,1,2,3,3,3-heptafluoropropan-2-yl)-6-methylphenyl]quinoline-6-carboxamide,
N-[2,6-dibromo-4-(1,1,1,2,3,3,3-heptafluoropropan-2-yl)phenyl]quinoline-6-carboxamide,
N-[4-(1,1,1,2,3,3,3-heptafluoropropan-2-yl)-2,6-diiodophenyl]quinoline-6-carboxamide, etc.

The compounds of the Formula (I-c-1) are encompassed by the compounds of the Formula (I) of the present invention and representative examples of the compounds of the Formula (I-c-1) are as follows:

N-[4-(1,1,1,2,3,3,3-heptafluoropropan-2-yl)-2,6-dimethylphenyl]quinoline-6-carboxamide-1-oxide.
N-[2-ethyl-4-(1,1,1,2,3,3,3-heptafluoropropan-2-yl)-6-methylphenyl]quinoline-6-carboxamide-1-oxide,
N-[2,6-dibromo-4-(1,1,1,2,3,3,3-heptafluoropropan-2-yl)phenyl]quinoline-6-carboxamide-1-oxide,
N-[4-(1,1,1,2,3,3,3-heptafluoropropan-2-yl)-2,6-diiodophenyl]quinoline-6-carboxamide-1-oxide, etc.
N-[2-chloro-4-(1,1,1,2,3,3,3-heptafluoropropan-2-yl)-6-(trifluoromethyl)phenyl]quinoline-7-carboxamide-1-oxide,
N-[2-bromo-4-(1,1,1,2,3,3,3-heptafluoropropan-2-yl)-6-(trifluoromethyl)phenyl]quinoline-7-carboxamide-1-oxide,
N-[4-(1,1,1,2,3,3,3-heptafluoropropan-2-yl)-2-iodo-6-(trifluoromethyl)phenyl]quinoline-7-carboxamide 1-oxide,
N-[2-chloro-6-(difluoromethoxy)-4-(1,1,1,2,3,3,3-heptafluoropropan-2-yl)phentyl]-quinoline-7-carboxamide 1-oxide
N-[2-bromo-6-(difluoromethoxy)-4-(1,1,1,2,3,3,3-heptafluoropropan-2-yl)phenyl]-quinoline-7-carboxamide 1-oxide,
N-[4-(1,1,1,2,3,3,3-heptafluoropropan-2-yl)-2-iodo-6-(difluoromethoxy)phenyl]-quinoline-7-carboxamide 1-oxide,
N-[2-chloro-6-(trifluoromethoxy)-4-(1,1,1,2,3,3,3-heptafluoropropan-2-yl)phenyl]-quinoline-7-carboxamide 1-oxide
N-[2-bromo-6-(trifluoromethoxy)-4-(1,1,1,2,3,3,3-heptafluoropropan-2-yl)phenyl]-quinoline-7-carboxamide 1-oxide,
N-[4-(1,1,1,2,3,3,3-heptafluoropropan-2-yl)-2-iodo-6-(trifluoromethoxy)phenyl]-quinoline-7-carboxamide 1-oxide,
N-{2-chloro-6-[(difluoromethyl)sulfanyl]-4-(1,1,1,2,3,3,3-heptafluoropropan-2-yl)phenyl}-quinoline-7-carboxamide 1-oxide,
N-{2-chloro-6-[(difluoromethyl)sulfinyl]-4-(1,1,1,2,3,3,3-heptafluoropropan-2-yl)phenyl}-quinoline-7-carboxamide 1-oxide,
N-{2-chloro-6-[(difluoromethyl)sulfonyl]-4-(1,1,1,2,3,3,3-heptafluoropropan-2-yl)phenyl}-quinoline-7-carboxamide 1-oxide,
N-{2-bromo-6-[(difluoromethyl)sulfanyl]-4-(1,1,1,2,3,3,3-heptafluoropropan-2-yl)phenyl}quinoline-7-carboxamide 1-oxide,
N-{2-bromo-6-[(difluoromethyl)sulfinyl]-4-(1,1,1,2,3,3,3-heptafluoropropan-2-yl)phenyl}-quinoline-7-carboxamide 1-oxide,
N-{2-bromo-6-[(difluoromethyl)sulfonyl]-4-(1,1,1,2,3,3,3-heptafluoropropan-2-yl)-phenyl}quinoline-7-carboxamide 1-oxide,
N-{6-[(difluoromethyl)sulfanyl]-2-iodo-4-(1,1,1,2,3,3,3-heptafluoropropan-2-yl)phenyl}-quinoline-7-carboxamide 1-oxide,
N-{6-[(difluoromethyl)sulfinyl]-2-iodo-4-(1,1,1,2,3,3,3-heptafluoropropan-2-yl)phenyl}-quinoline-7-carboxamide 1-oxide,
N-{6-[(difluoromethyl)sulfonyl]-2-iodo-4-(1,1,1,2,3,3,3-heptafluoropropan-2-yl)phenyl}-quinoline-7-carboxamide 1-oxide,
N-{2-chloro-6-[(trifluoromethyl)sulfanyl]-4-(1,1,1,2,3,3,3-heptafluoropropan-2-yl)-phenyl}-quinoline-7-carboxamide 1-oxide,
N-{2-chloro-6-[(trifluoromethyl)sulfinyl]-4-(1,1,1,2,3,3,3-heptafluoropropan-2-yl)phenyl}-quinoline-7-carboxamide 1-oxide,
N-{2-chloro-6-[(trifluoromethyl)sulfonyl]-4-(1,1,1,2,3,3,3-heptafluoropropan-2-yl)-phenyl}quinoline-7-carboxamide 1-oxide,
N-{2-bromo-6-[(trifluoromethyl)sulfanyl]-4-(1,1,1,2,3,3,3-heptafluoropropan-2-yl)-phenyl}-quinoline-7-carboxamide 1-oxide,
N-{2-bromo-6-[(trifluoromethyl)sulfinyl]-4-(1,1,1,2,3,3,3-heptafluoropropan-2-yl)-phenyl}-quinoline-7-carboxamide 1-oxide,
N-{2-bromo-6-[(trifluoromethyl)sulfonyl]-4-(1,1,1,2,3,3, 33-heptafluoropropan-2-yl)-phenyl}quinoline-7-carboxamide 1-oxide,
N-{6-[(trifluoromethyl)sulfanyl]-2-iodo-4-(1,1,1,2,3,3,3-heptafluoropropan-2-yl)phenyl}-quinoline-7-carboxamide 1-oxide,
N-{6-[(trifluoromethyl)sulfinyl]-2-iodo-4-(1,1,1,2,3,3,3-heptafluoropropan-2-yl)phenyl}-quinoline-7-carboxamide 1-oxide, N-{6-[(trifluoromethyl)sulfonyl]-2-iodo-4-(1,1,1,2,3,3,3-heptafluoropropan-2-yl)phenyl}-quinoline-7-carboxamide 1-oxide,
N-[4-(1,1,1,2,3,3,3,4,4,4-nonafluorobutan-2-yl)-2,6-dimethylphenyl]quinoline-6-carboxamide-1-oxide,
N-[2-ethyl-4-(1,1,1,2,3,3,3,4,4,4-nonafluorobutan-2-yl)-6-methylphenyl]quinoline-6-carboxamide-1-oxide,
N-[2,6-dichloro-4-(1,1,1,2,3,3,3,4,4,4-nonafluorobutan-2-yl)phenyl]quinoline-6-carboxamide-1-oxide,
N-[2,6-dibromo-4-(1,1,1,2,3,3,3,4,4,4-nonafluorobutan-2-yl)phenyl]quinoline-6-carboxamide-1-oxide,
N-[4-(1,1,1,2,3,3,3,4,4,4-nonafluorobutan-2-yl)-2,6-diiodophenyl]quinoline-6-carboxamide-oxide,
N-[2-chloro-4-(1,1,1,2,3,3,3,4,4,4-nonafluorobutan-2-yl)-6-(trifluoromethyl)phenyl]-quinoline-7-carboxamide 1-oxide
N-[2-bromo-4-(1,1,1,2,3,3,4,4,4-nonafluorobutan-2-yl)-6-(trifluoromethyl)phenyl]-quinoline-7-carboxamide 1-oxide
N-[4-(1,1,1,2,3,3,4,4,4-nonafluorobutan-2-yl)-2-iodo-6-(trifluoromethyl)phenyl]-quinoline-7-carboxamide 1-oxide,
N-[2-chloro-6-(difluoromethoxy)-4-(1,1,1,2,3,3,4,4,4-nonafluorobutan-2-yl)phenyl]-quinoline-7-carboxamide 1-oxide
N-[2-brom-6-(difluoromethoxy)-4-(1,1,1,2,3,3,4,4,4-nonafluorobutan-2-yl)phenyl]-quinoline-7-carboxamide 1-oxide,
N-[4-(1,1,1,2,3,3,4,4,4-nonafluorobutan-2-yl)-2-iodo-6-(difluoroethoxy)phenyl]-quinoline-7-carboxamide 1-oxide,
N-[2-chloro-6-(trifluoromethoxy)-4-(1,1,1,2,3,3,4,4,4-nonafluorobutan-2-yl)phenyl]-quinoline-7-carboxamide 1-oxide
N-[2-bromo-6-(trifluoromethoxy)-4-(1,1,1,2,3,3,4,4,4-nonafluorobutan-2-yl)phenyl]-quinoline-7-carboxamide 1-oxide,
N-[4-(1,1,1,2,3,3,4,4,4-nonafluorobutan-2-yl)-2-iodo-6-(trifluoromethoxy)phenyl]-quinoline-7-carboxamide 1-oxide,
N-{2-chloro-6-[(difluoromethyl)sulfanyl]-4-(1,1,1,2,3,3,4,4,4-nonafluorobutan-2-yl)-phenyl}quinoline-7-carboxamide 1-oxide,
N-{2-chloro-6-[(difluoromethyl)sulfinyl]-4-(1,1,1,2,3,3,4,4,4-nonafluorobutan-2-yl)-phenyl}quinoline-7-carboxamide 1-oxide,
N-{2-chloro-6-[(difluoromethyl)sulfonyl]-4-(1,1,1,2,3,3,4,4,4-nonafluorobutan-2-yl)-phenyl}quinoline-7-carboxamide 1-oxide,
N-{2-bromo-6-[(difluoromethyl)sulfanyl]-4-(1,1,1,2,3,3,4,4,4-nonafluorobutan-2-yl)-phenyl}quinoline-7-carboxamide 1-oxide,
N-{2-bromo-6-[(difluoromethyl)sulfinyl]-4-(1,1,1,2,3,3,4,4,4-nonafluorobutan-2-yl)-phenyl}quinoline-7-carboxamide 1-oxide,
N-{2-bromo-6-[(difluoromethyl)sulfonyl]-4-(1,1,1,2,3,3,4,4,4-nonafluorobutan-2-yl)-phenyl}quinoline-7-carboxamide 1-oxide,
N-{6-[(difluoromethyl)sulfanyl]-2-iodo-4-(1,1,1,2,3,3,4,4,4-nonafluorobutan-2-yl)-phenyl}quinoline-7-carboxamide 1-oxide,
N-{6-[(difluoromethyl)sulfinyl]-2-iodo-4-(1,1,1,2,3,3,4,4,4-nonafluorobutan-2-yl)phenyl}-quinoline-7-carboxamide 1-oxide,
N-{6-[(difluoromethyl)sulfonyl]-2-iodo-4-(1,1,1,2,3,3,4,4,4-nonafluorobutan-2-yl)-phenyl}quinoline-7-carboxamide 1"-oxide,
N-{2-chloro-6-[(trifluoromethyl)sulfanyl]-4-(1,1,1,2,3,3,3,4,4,4-nonafluorobutan-2-yl)-phenyl}quinoline-7-carboxamide 1-oxide,
N-{2-chloro-6-[(trifluoromethyl)sulfinyl]-4-(1,1,1,2,3,3,4,4,4-nonafluorobutan-2-yl)-phenyl}quinoline-7-carboxamide 1-oxide,
N-{2-chloro-6-[(trifluoromethyl)sulfonyl]-4-(1,1,1,2,3,3,4,4,4-nonafluorobutan-2-yl)-phenyl}quinoline-7-carboxamide 1-oxide,
N-{2-bromo-6-[(trifluoromethyl)sulfanyl]-4-(1,1,1,2,3,3,4,4,4-nonafluorobutan-2-yl)-phenyl}quinoline-7-carboxamide 1-oxide,
N-{2-bromo-6-[(trifluoromethyl)sulfinyl]-4-(1,1,1,2,3,3,4,4,4-nonafluorobutan-2-yl)-phenyl}quinoline-7-carboxamide 1-oxide,
N-{2-bromo-6-[(trifluoromethyl)sulfonyl]-4-(1,1,1,2,3,3,4,4,4-nonafluorobutan-2-yl)-phenyl}quinoline-7-carboxamide 1-oxide,
N-{6-[(trifluoromethyl)sulfanyl]-2-iodo-4-(1,1,1,2,3,3,4,4,4-nonafluorobutan-2-yl)-phenyl}quinoline-7-carboxamide 1-oxide,
N-{6-[(trifluoromethyl)sulfinyl]-2-iodo-4-(1,1,1,2,3,3,4,4,4-nonafluorobutan-2-yl)phenyl}-quinoline-7-carboxamide 1-oxide,
N-{6-[(trifluoromethyl)sulfonyl]-2-iodo-4-(1,1,1,2,3,3,4,4,4-nonafluorobutan-2-yl)-phenyl}quinoline-7-carboxamide 1-oxide,
N-[4-(1-bromo-1,1,2,3,3,3-hexafluoropropan-2-yl-2,6-dimethylphenyl]quinoline-6-carboxamide-1-oxide,
N-[2-ethyl-4-(1-bromo-1,1,2,3,3,3-hexafluoropropan-2-yl-6-methylphenyl)quinoline-6-carboxamide-1-oxide,
N-[2,6-dibromo-4-(1-bromo-1,1,2,3,3,3-hexafluoropropan-2-yl)phenyl]quinoline-6-carboxamide-1-oxide,
N-[4-(1-bromo-1,1,2,3,3,3-hexafluoropropan-2-yl)-2,6-diiodophenyl]quinoline-6-carboxamide-1-oxide,
N-[2-chloro-4-(1-bromo-1,1,2,3,3,3-hexafluoropropan-2-yl)-6-(trifluoromethyl)phenyl]-quinoline-7-carboxamide 1-oxide
N-[2-bromo-4-(1-bromo-1,1,2,3,3,3-hexafluoropropan-2-yl)-6-(trifluormethyl)phenyl]-quinoline-7-carboxamide 1-oxide
N-[4-(1-bromo-1,1,2,3,3,3-hexafluoropropan-2-yl)-2-iodo-6-(trifluoromethyl)phenyl]-quinoline-7-carboxamide 1-oxide,
N-[2-chloro-6-(difluoromethoxy)-4-(1-bromo-1,1,2,3,3,3-hexafluoropropan-2-yl)phenyl]-quinoline-7-carboxamide 1-oxide
N-[2-bromo-6-(difluoromethoxy)-4-(1-bromo-1,1,2,3,3,3-hexafluoropropan-2-yl)phenyl]-quinoline-7-carboxamide 1-oxide,
N-[4-(1-bromo-1,1,2,3,3,3-hexafluoropropan-2-yl)-2-iodo-6-(difluoromethoxy)phenyl]-quinoline-7-carboxamide 1-oxide,
N-[2-chloro-6-(trifluoromethoxy)-4-(1-bromo-1,1,2,3,3,3-hexafluoropropan-2-yl)phenyl]-quinoline-7-carboxamide 1-oxide
N-[2-bromo-6-(trifluoromethoxy)-4-(1-bromo-1,1,2,3,3,3-hexafluoropropan-2-yl)phenyl]-quinoline-7-carboxamide 1-oxide,
N-[4-(1-bromo-1,1,2,3,3,3-hexafluoropropan-2-yl)-2-iodo-6-(trifluoromethoxy)phenyl]-quinoline-7-carboxamide 1-oxide,
N-{2-chloro-6-[(difluoromethyl)sulfanyl]-4-(1-bromo-1,1,2,3,3,3-hexafluoropropan-2-yl)-phenyl}quinoline-7-carboxamide 1-oxide, N-{2-chloro-6-[(difluoromethyl)sulfinyl]-4-(1-bromo-1,1,2,3,3,3-hexafluoropropan-2-yl)-phenyl}quinoline-7-carboxamide 1-oxide, N-{2-chloro-6-[(difluoromethyl)sulfonyl]-4-(1-bromo-1,1,2,3,3,3-hexafluoropropan-2-yl)-phenyl}quinoline-7-carboxamide 1-oxide, N-{2-bromo-6-[(difluoromethyl)sulfanyl]-4-(1-bromo-1,1,2,3,3,3-hexafluoropropan-2-yl)phenyl}quinoline-7-carboxamide 1-oxide, N-{2-bromo-6-[(difluoromethyl)sulfinyl]-4-(1-bromo-1,1,2,3,3,3-hexafluoropropan-2-yl)-phenyl}quinoline-7-carboxamide 1-oxide, N-{2-bromo-6-[(difluoromethyl)sulfonyl]-4-(1-bromo-1,1,2,3,3,3-hexafluoropropan-2-yl)-phenyl}quinoline-7-carboxamide 1-oxide, N-{6-[(difluoromethyl)sulfanyl]-2-iodo-4-(1-bromo-1,1,2,3,3,3-hexafluoropropan-2-yl)-phenyl}quinoline-7-carboxamide 1-oxide, N-{6-[(difluoromethyl)sulfinyl]-2-iodo-4-(1-bromo-1,1,2,3,3,3-hexafluoropropan-2-yl)-phenyl}quinoline-7-carboxamide 1-oxide, N-{6-[(difluoromethyl)sulfonyl]-2-iodo-4-(1-bromo-1,1,2,3,3,3-hexafluoropropan-2-yl)-phenyl}quinoline-7-carboxamide 1-oxide, N-{2-chloro-6-[(trifluoromethyl)sulfanyl]-4-(1-bromo-1,1,2,3,3,3-hexafluoropropan-2-yl)-phenyl}quinoline-7-carboxamide 1-oxide, N-{2-chloro-6-[(trifluoromethyl)sulfinyl]-4-(1-bromo-1,1,2,3,3,3-hexafluoropropan-2-yl)-phenyl}quinoline-7-carboxamide 1-oxide, N-{2-chloro-6-[(trifluoromethyl)sulfonyl]-4-(1-bromo-1,1,2,3,3,3-hexafluoropropan-2-yl)-phenyl}quinoline-7-carboxamide 1-oxide, N-{2-bromo-6-[(trifluoromethyl)sulfanyl]-4-(1-bromo-1,1,2,3,3,3-hexafluoropropan-2-yl)-phenyl}quinoline-7-carboxamide 1-oxide, N-{2-bromo-6-[(trifluoromethyl)sulfinyl]-4-(1-bromo-1,1,2,3,3,3-hexafluoropropan-2-yl)-phenyl}quinoline-7-carboxamide 1-oxide, N-{2-bromo-6-[(trifluoromethyl)sulfonyl]-4-(1-bromo-1,1,2,3,3,3-hexafluoropropan-2-yl)-phenyl}quinoline-7-carboxamide 1-oxide, N-{6-[(trifluoromethyl)sulfanyl]-2-iodo-4-(1-bromo-1,1,2,3,3,3-hexafluoropropan-2-yl)-phenyl}quinoline-7-carboxamide 1-oxide, N-{6-[(trifluoromethyl)sulfinyl]-2-iodo-4-(1-bromo-1,1,2,3,3,3-hexafluoropropan-2-yl)-phenyl}quinoline-7-carboxamide 1-oxide, N-{6-[(trifluoromethyl)sulfonyl]-2-iodo-4-(1-bromo-1,1,2,3,3,3-hexafluoropropan-2-yl)-phenyl}quinoline-7-carboxamide 1-oxide.

Among halogenation reagents which can be used for the reaction of the Preparation method (c-1), representative examples include phosphorus oxychloride, phosphorus pentachloride, and phosphorus oxybromide.

Temperature range, pressure and time for the reaction of the Preparation method (c-1) are the same as the Preparation method (b).

For carrying out the Preparation method (c-1), for example, 1 mol of the compounds of the Formula (I-c-1) can be reacted with 1 to 10 mol of a halogenation reagent, e.g., phosphorus oxychloride, to obtain the compounds of the Formula (I-d-1) and/or the compounds of the Formula (I-d-2) that are encompassed by the compounds of the Formula (I) of the present invention.

The compounds of the Formula (I-d-1) and the Formula (I-d-2) can be easily isolated according to a general isolation method used in organic chemistry, for example, column chromatography.

The Preparation methods (c-2), (c-3) and (c-4) can be carried out in accordance with the Preparation method (c-1).

The Preparation method (d) can be carried out according to the method described in the following literatures:

The Journal of Organic Chemistry 1983, 48, 1375-1377,
HETEROCYCLES, 1992, 33, 211-218,
Bioorganic & Medicinal Chemistry 2006, 14, 6570-6580,
WO 2007/133637A2.

Among cyanation reagents of the Preparation method (d), representative examples include trimethylsilyl cyanide, sodium cyanide, potassium cyanide, and diethyl cyanophosphate.

The reaction of the Preparation method (d) can be carried out in the presence of an appropriate diluent, and examples of the diluent which can be used are the same as the diluents exemplified for the Preparation method (a). Preferably; tetrahydrofuran can be mentioned.

Reaction of the Preparation method (d) can be carried out in the presence of an appropriate base and/or acyl chloride, and examples of the base which can be used are the same as the bases exemplified for the Preparation method (a). Preferred examples include organic bases such as trimethylamine, triethylamine, diisopropylethylamine, tributylamine, N-methylmorpholine, diazabicycloundecene (1,8-diazabicyclo[5.4.0]undec-7-ene), and diazabicyclooctane. Particularly preferred examples include 1,8-diazabicyclo[5.4.0]undec-7-ene Further, examples of an appropriate acyl chloride include benzoyl chloride, dimethyl carbamoyl chloride, chloroethyl carbonate and the like.

Temperature range, pressure and time for the reaction of the Preparation method (d) are the same as the Preparation method (b).

For carrying out the Preparation method (d), for example, 1 mol of the compound of the Formula (I-c-2) can be reacted with 1 to 5 mol of a cyanation reagent, e.g., trimethylsilyl cyanide, in the presence of 1 to 5 mol of a base, e.g., 1,8-diazabicyclo[5.4.0]undec-7-ene, to obtain the compounds of the Formula (I-e) that are encompassed by the compounds of the Formula (I) of the present invention.

The compounds of the Formula (I-f) as reacting materials for the Preparation method (e) are encompassed by the compounds of the Formula (I) of the present invention and their representative examples are as follows:

6-cyano-N-[2-ethyl-4-(1,1,1,2,3,3,3-heptafluoropropan-2-yl)-6-methylphenyl]-2-naphthamide, 2-cyano-N-[4-(1,1,1,2,3,3,3-heptafluoropropan-2-yl)-2,6-dimethylphenyl]quinoline-6-carboxamide, 2-cyano-N-[2-ethyl-4-(1,1,1,2,3,3,3-heptafluoropropan-2-yl)-6-methylphenyl]quinoline-6-carboxamide, etc.

The compounds of the Formula (IV) as reacting materials for the Preparation method (e) are known compounds, and representative examples include methyl iodide, ethyl iodide, benzyl bromide, dimethyl sulfate, diethyl sulfate, etc.

The reaction of the Preparation method (e) can be carried out in the presence of an appropriate diluent, and examples of the diluent which can be used are the same as the diluents exemplified for the Preparation method (a). Preferably, DMF can be mentioned.

The reaction of the Preparation method (e) can be carried out in the presence of an appropriate base, and examples of the base which can be used are the same as the base exemplified for the Preparation method (a). Preferably, sodium hydride can be mentioned.

Temperature range, pressure and time for the react on of the Preparation method (e) are the same as the Preparation method (b).

For carrying out the Preparation method (e), for example, 1 mol of the compound of the Formula (I-f) can be reacted with 1 to 3 mol of the compound of the Formula (IV), e.g., methyl iodide, in the presence of an appropriate base, e.g., sodium hydride, in an appropriate diluent, e.g., DMF, to obtain the compounds of the Formula (I) of the present invention.

The compounds of the Formula (I-g) as reacting materials for the Preparation method (f) are encompassed by the compounds of the Formula (I) of the present invention and their representative examples are as follows:
6-bromo-N-[2-ethyl-4-(1,1,1,2,3,3,3-heptafluoropropan-2-yl)-6-methylphenyl]-2-naphthamide,
N-[4-(1,1,1,2,3,3,3-heptafluoropropan-2-yl)-2,6-dimethylphenyl]quinoline-6-carboxamide,
N-[2-ethyl-4-(1,1,1,2,3,3,3-heptafluoropropan-2-yl)-6-methylphenyl]quinoline-6-carboxamide, etc.

Among sulfurizing agents which can be used for the Preparation method (f), representative examples include phosphorus pentasulfide, Lawesson reagent, etc.

The reaction of the Preparation method (f) can be carried out in the presence of an appropriate diluent, and examples of the diluent which can be used are the same as the diluents exemplified for the Preparation method (a). Preferably, toluene can be mentioned.

Temperature range, pressure and time for the reaction of the Preparation method (f) are the same as the Preparation method (b).

For carrying out the Preparation method (f), for example, 1 mol of the compound of the Formula (I-g) can be reacted with 0.5 to 3 mol of a Lawesson reagent in an appropriate diluent, e.g., toluene, to obtain the compounds of the Formula (I).

The reaction of the Preparation method (g) and the preparation of the compounds of formula (VI) can be carried out by following procedure desclived in the literature: Tetrahedron, 2003, 59, 773-779.

The starting material (V) of the reaction method (g) is prepared by reaction of the compounds Formula (Vi):

wherein, $A^1$ to $A^4$ are as defined above,
with a reagent represented by the following formula:

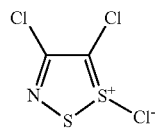

The compounds of formula (VI) can be prepared by the method desclived in the Japanese patent application: Japanese patent application number 2010-055470.

The active compounds according to the invention may be used in combination with suitable synergists or other active compounds, such as for example insecticides, acaricides, nematicides, fungicides, biological control agents, and bacterizides. Such combinations can also result in a synergistic effect, i.e. the biological activity of such a combination is synergistically increased. Examples of such combination partners are the following insecticides, acaricides, nematicides:

The active ingredients specified herein by their "common name" are known and described, for example, in the Pesticide Manual ("TI e Pesticide Manual", 14th Ed., British Crop Protection Council 2006) or can be searched in the internet (e.g. http://www.alanwood.net/pesticides).

(1) Acetylcholinesterase (AChE) inhibitors, for example carbamates, e.g. alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC, and xylylcarb; or
organophosphates, e.g. acephate, azamethiphos, azinphos (-methyl, -ethyl), cadusafos, chlorethoxyfos, chlorfenvinphos, chlorfenvinphos, chlormephos, chlorpyrifos (-methyl), coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, isofenphos, isopropyl O-(methoxyaminothio-phosphoryl) salicylate, isoxathion, malathion, mecarbam, methamidophos, methidathion, mevinphos, monocrotophos, naled, omethoate, oxydemeton-methyl, parathion (-methyl), phenthoate, phorate, phosalone, phosmet, phosphamidon, phoxim, pirimiphos (-methyl), profenofos, propetamphos, prothiofos, pyraclofos, pyridaphenthion, quinalphos, sulfotep, tebupirimfos, temephos, terbufos, tetrachlorvinphos, thiometon, triazophos, triclorfon, and vamidothion.

(2) GABA-gated chloride channel antagonists, for example organochlorines, e.g. chlordane, endosulfan (alpha-); or fiproles (phenylpyrazoles), e.g. ethiprole, fipronil, pyrafluprole, and pyriprole.

(3) Sodium channel modulators/voltage-dependent sodium channel blockers, for example pyrethroids, e.g. acrinathrin, allethrin (d-cis-trans, d-trans), bifenthrin, bioallethrin, bioallethrin S-cyclopentenyl, bioresmethrin, cycloprothrin, cyfluthrin (beta-), cyhalothrin (gamma-, lambda-), cypermethrin (alpha-, beta-, theta-, zeta-), cyphenothrin [(1R)-trans-isomers], deltamethrin, dimefluthrin, empenthrin [(EZ)-(1R)-isomers), esfenvalerate, etofenprox, fenpropathrin, fenvalerate, flucythrinate, flumethrin, fluvalinate (tau-), halfenprox, imiprothrin, metofluthrin, permethrin, phenothrin [(1R)-trans-isomer), prallethrin, profluthrin, pyrethrin (pyrethrum), resmethrin, RU 15525, silafluofen, tefluthrin, tetramethrin [(1R)-isomers)], tralomethrin, transfluthrin and ZXI 8901; or DDT; or methoxychlor.

(4) Nicotinergic acetylcholine receptor agonists, for example chloronicotinyls, e.g. acetamiprid, clothianidin, dinotefaran, imidacloprid, nitenpyram, thiacloprid, thiamethoxam; or nicotine.

(5) Allosteric acetylcholine receptor modulators (agonists), for example spinosyns, e.g. spinetoram and spinosad.

(6) Chloride channel activators, for example avermectins/milbemycins, e.g. abamectin, emamectin benzoate, lepimectin, and milbemectin.

(7) Juvenile hormone mimics, e.g. hydroprene, kinoprene, methoprene; or fenoxycarb; pyriproxyfen.

(8) Miscellaneous non-specific (multi-site) inhibitors, for example gassing agents, e.g. methyl bromide and other alkyl halides; or chloropicrin; sulfuryl fluoride; borax; tartar emetic.
(9) Selective homopteran feeding blockers, e.g. pymetrozine or flonicamid.
(10) Mite growth inhibitors, e.g. clofentezine, diflovidazin, hexythiazox, etoxazole.
(11) Microbial disruptors of insect midgut membranes, e.g. *Bacillus thuringiensis* subspecies *israelensis, Bacillus sphaericus, Bacillus thuringiensis* subspecies *aizawai, Bacillus thuringiensis* subspecies *kurstaki, Bacillus thuringiensis* subspecies *tenebrionis*, and BT crop proteins: Cry1Ab, Cry1Ac, Cry1Fa, Cry2Ab, mCry3A, Cry3Ab, Cry3Bb, Cry34/35Ab1.
(12) Inhibitors of mitochondrial ATP synthase, for example diafenthiuron; or organotin miticides, e.g. azocyclotin, cyhexatin, and fenbutatin oxide; or propargite; tetradifon.
(13) Uncouplers of oxidative phoshorylation via disruption of the proton gradient, for example chlorfenapyr, and DNOC.
(14) Nicotinic acetylcholine receptor channel blockers, for example bensultap, cartap hydrochloride, thiocyclam, and thiosultap-sodium.
(15) Inhibitors of chitin biosynthesis, type 0, for example benzoylureas, e.g. bistrifluoron, chlorfluazuron, diflubenzuron, flucycloxuron, flufenoxuron, hexaflumuron, lufenuron, novaluron, noviflumuron, penfluoron, tefluben-zuron, and triflumuron.
(16) Inhibitors of chitin biosynthesis, type 1, for example buprofezin.
(17) Moulting disruptors, for example cyromazine.
(18) Ecdysone receptor agonists/disruptors, for example diacylhydrazines, e.g. chromafenozide, halofenozide, methoxyfenozide, and tebufenozide.
(19) Octopamine receptor agonists, for example amitraz.
(20) Mitochondrial complex III electron transport inhibitors, for example hydramethylnon; acequinocyl or fluacrypyrim.
(21) Mitochondrial complex I electron transport inhibitors, for example METI acaricides, e.g. fehazaquin, fenpyroximate, pyrimidifen, pyridaben, tebufenpyrad, tolfenpyrad or rotenone. (Derris).
(22) Voltage-dependent sodium channel blockers, e.g. indoxacarb; metaflumizone.
(23) Inhibitors of acetyl CoA carboxylase, for example tetronic acid derivatives, e.g. spirodiclofen and spiromesifen; or tramic acid derivatives, e.g. spirotetramat.
(24) Mitochondrial complex IV electron inhibitors, for example phosphines, e.g. aluminium phosphide, calcium phosphide, phosphine, and zinc phosphide or cyanide.
(25) Mitochondrial complex II electron transport inhibitors, for example cyenopyrafen.
(28) Ryanodine receptor modulators, for example diamides, e.g. chlorantraniliprole (Rynaxypyr), Cyantraniliprole (Cyazypyr), and flubendiamide.

Further active ingredients with unknown or uncertain mode of action, for example azadirachtin, amidoflumet, benzoximate, bifenazate, chinomethionat, cryolite, cyflumetofen, dicofol, fluensulfone (5-chloro-2-[(3,4,4-trifluorobut-3-en-1-yl)sulfonyl]-1,3-thiazole), flufenerim, pyridalyl, and pyrifluquinazon; furthermore products based on *Bacillus firmus* (I-1582, BioNeem, Votivo) or one of the following known active compounds:
4-{[(6-brompyrid-3-yl)methyl](2-fluorethyl)amino}furan-2 (5H)-on (known from WO 2007/115644),
4-{[(6-fluorpyrid-3-yl)methyl](2,2-difluorethyl) amino}furan-2(5H)-on (known from WO 2007/115644),
4-{[(2-chlor-1,3-thiazol-5-yl)methyl](2-fluorethyl) amino}furan-2(5H)-on (known from WO 2007/115644),
4-{[(6-chlorpyrid-3-yl)methyl](2-fluorethyl)amino}furan-2 (5H)-on (known from WO 2007/115644),
4-{[(6-chlorpyrid-3-yl)methyl](2,2-difluorethyl) amino}furan-2(5H)-on known from WO 2007/115644),
4-{[(6-chlor-5-fluorpyrid-3-yl)methyl](methyl) amino}furan-2(5H)-on (known from WO 2007/115643),
4-{[(5,6-dichlorpyrid-3-yl)methyl](2-fluorethyl) amino}furan-2(5H)-on (known from WO 2007/115646),
4-{[(6-chlor-5-fluorpyrid-3-yl)methyl](cyclopropyl) amino}furan-2(5H)-on (known from WO 2007/115643),
4-{[(6-chlorpyrid-3-yl)methyl](cyclopropyl)amino}furan-2 (5H)-on (known from EP-A-0 539 588),
4-{[(6-chlorpyrid-3-yl)methyl](methyl)amino}furan-2(5H)-on (known from EP-A-0 539 588),
[(6-chlorpyridin-3-yl)methyl](methyl)oxido-λ4-sulfanylidencyanamnid (known from WO 2007/149134),
[1-(6-chlorpyridin-3-yl)ethyl](methyl)oxido-λ4-sulfanylidencyanamid (known from WO 2007/149134) and its diastereomeres (A) and (B)

(A)

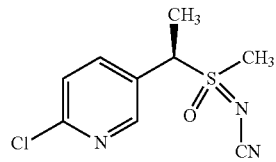

(B)

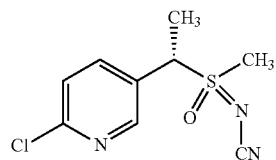

(also known from WO 2007/149134), [(6-trifluoromethylpyridin-3-yl)methyl](methyl)oxido-λ4-sulfanylidencyanamid (known from WO 2007/095229), or sulfoxaflor (also known from WO 2007/149134), 11-(4-chloro-2,6-dimethylphenyl)-12-hydroxy-1,4-dioxa-9-azadispiro[4.2.4.2]tetradec-11-en-10-one (known from WO 2006/089633), 3-(4'-fluoro-2,4-dimethylbiphenyl-3-yl)-4-hydroxy-8-oxa-1-azaspiro[4.5] dec-3-en-2-one (known from WO 2008/067911), and 1-[2-fluoro-4-methyl-5-[2,2,2-trifluoroethyl)sulfinyl]phenyl]-3-(trifluoromethyl)-1H-1,2,4-Triazol-5-amine (known from WO 2006/043635).

Examples of further combination partners are the following fungicides:
(1) Inhibitors of the ergosterol biosynthesis, for example aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, ferbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifine, nuarimol, oxpoconazole, paclobutrazol, pefurazoate, penconazole, piperalin, prochloraz, propiconazole, prothioconazole, pyributicarb, pyrifenox, quinconazole, simeconazole, spuoxamine, tebuconazole, terbinafine, tetraconazole, triadimefon, triadimenol, tridemorph, triflumizole, triforine, triticonazole, uniconazole, uniconazole-p, viniconazole, voriconazole, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N'-{5-(difluoromethyl)-2-methyl-4-[3-(trimethylsilyl)propoxy]phenyl}-N-ethyl-N-methylimidoformamide, N-ethyl-N-methyl-N'-{2-methyl-5-(trifluoromethyl)-4-[3-(trimethylsilyl)propoxy]phenyl}imidoformamide and O-[1-(4-methoxyphenoxy)-3,3-dimethylbutan-2-yl]1H-imidazole 1-carbothioate.

(2) inhibitors of the respiratory chain at complex I or II, for example bixafen, boscalid, carboxin, diflumetorim, fenfuram, fluopyram, flutolanil, fluxapyroxad, furametpyr, fumecyclox, isopyrazam (mixture of syn-epimeric racemate 1RS,4SR,9RS and anti-epimeric racemate 1RS,4SR,9SR), isopyrazam (anti-epimeric racemate 1 RS,4SR,9SR), isopyrazam (anti-epimeric enantiomer 1R,4S,9S), isopyrazam (anti-epimeric enantiomer 1S,4R,9R), isopyrazam (syn epimeric racemate 1 RS,4SR,9RS), isopyrazam (syn-epimeric enantiomer 1R,4S,9R), isopyrazam (syn-epimeric enantiomer 1S,4R,9S), mepronil, oxycarboxin, penflufen, penthiopyrad, sedaxane, thifluzamide, 1-methyl-N-[2-(1,2,2-tetrafluoroethoxy)phenyl]-3-(trifluoromethyl)-1H-pyrazole-4-carboxamide, 3-(difluoromethyl)-1-methyl-N-[2-(1,1,2,2-tetrafluoroethoxy)phenyl]-1H-pyrazole-4-carboxamide, 3-(difluoromethyl)-N-[4-fluoro-2-(1,1,2,3,3,3-hexafluoropropoxy)phenyl]-1-methyl-1H-pyrazole-4-carboxamide, N-[1-(2,4-dichlorophenyl)-1-methoxypropan-2-yl]-3-(difluoromethyl)-1-methyl-1H-pyrazole-4-carboxamide and salts thereof (3) inhibitors of the respiratory chain at complex III, for example ametoctradin, amisuibrom, azoxystrobin, cyazofamid, dimoxystrobin, enestroburin, anoxadone, fenamidone, fluoxastrobin, kresoxim-methyl, metominostrobin, orysastrobin, picoxystrobin, pyraclostrobin, pyrametostrobin, pyraoxystrobin, pyribencarb, trifloxystrobin, (2E)-2-(2-{[6-(3-chloro-2-methylphenoxy)-5-fluoropyrimidin-4-yl]oxy}phenyl)-2-(methoxyimino)-N-methylethanamide, (2E)-2-(methoxyimino)-N-methyl-2-(2-{[({(1E)-1-[3-(trifluoromethyl)phenyl]ethylidene}amino)oxy]methyl}phenyl)ethanamide, (2E)-2-(methoxyimino)-N-methyl-2-{2-[(E)-({-[3-(trifluoroethyl)phenyl]ethoxy}-imino)methyl]phenyl}ethanamide, (2E)-2-{2-[({[(1E)-1-(3-{[(E)-1-fluoro-2-phenylethenyl]oxy}-phenyl)ethylidene]amino}oxy)methyl]phenyl}-2-(methoxyimino)-N-methylethanamide, (2E)-2-{2-[({[(2E,3E)-4-(2,6-dichlorophenyl)but-3-en-2-ylidene]amino}oxy)-methyl]phenyl}-2-(methoxyimino)-N-methylethanamide, 2-chloro-N-(1,1,3-trimethyl-2,3-dihydro-1H-inden-4-yl)pyridine-3-carboxamide, 5-methoxy-2-methyl-4-(2-{[({(1E)-1-[3-(trifluoro-methyl)phenyl]ethylidene}amino)oxy]methyl}phenyl)-2,4-dihydro-3H-1,2,4-triazol-3-one, methyl (2E)$_2$-{2-[({cyclopropyl[(4-methoxyphenyl)imino]methyl}sulfanyl)methyl]phenyl}-3-methoxy-prop-2-enoate, N-(3-ethyl-3,5,5-trimethylcyclohexyl)-3-(formylamino)-2-hydroxybenzamide, 2-{2-[(2,5-dimethylphenoxy)methyl]phenyl}-2-methoxy-N-methylacetamide, (2R)-2-{2-[(2,5-dimethylphenoxy)methyl]phenyl}-2-methoxy-N-methylacetamide and salts thereof (4) Inhibitors of the mitosis and cell division, for example benomyl, carbendazim, chlorfenazol, diethofencarb, ethaboxam, fluopicolide, fuberidazole, pencycuron, thiabendazole, thiophanate-methyl, thiophanate, zoxamide, 5-chloro-7-(4-methylpiperidin-1-yl)-6-(2,4,6-trifluorophenyl)[1,2,4]triazolo[1,5-a]pyrimidine, 3-chloro-5-(6-chloropyridin-3-yl)-6-methyl-4-(2,4,6-trifluorophenyl) pyridazine and salts thereof.

(5) Compounds capable to have a multisite action, like for example bordeaux mixture, captafol, captan, chlorothalonil, copper hydroxide, copper naphthenate, copper oxide, copper oxychloride, copper(2+) sulfate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propamidine, propineb, sulphur and sulphur preparations including calcium polysulphide, thiram, tolylfluanid, zineb, ziram and salts thereof.

(6) Compounds capable to induce a host defense, like for example acibenzolar-S-methyl, isotianil, probenazole, tiadinil and salts thereof.

(7) Inhibitors of the amino acid and/or protein biosynthesis, for example andoprim, blasticidin-S, cyprodinil, kasugamycin, kasugamycin hydrochloride hydrate, mepanipyrim, pyrimethanil and salts thereof.

(8) Inhibitors of the ATP production, for example fentin acetate, fentin chloride, fentin hydroxide and silthiofam.

(9) Inhibitors of the cell wall synthesis, for example benthiavalicarb, dimethomorph, flumorph, iprovalicarb, mandipropamid, polyoxins, polyoxorim, validamycin A and valifenalate.

(10) Inhibitors of the lipid and membrane synthesis, for example biphenyl, chloroneb, dicloran, edifenphos, etridiazole, iodocarb, iprobenfos, isoprothiolane, propamocarb, propamocarb hydrochloride, prothiocarb, pyrazophos, quintozene, tecnazene and tolclofos-methyl.

(11) Inhibitors of the melanine biosynthesis, for example carpropainid, diclocymet, fenoxanil, phthalide, pyroquilon and tricyclazole.

(12) Inhibitors of the nucleic acid synthesis, for example benalaxyl, benalaxyl-M (kiralaxyl), bupirimate, clozylacon, dimethirimol, ethirimol, furalaxyl, hymexazol, metalaxyl, metalaxyl-M (mefenoxam), ofurace, oxadixyl and oxolinic acid.

(13) Inhibitors of the signal transduction, for example chlozolinate, fenpiclonil, fludioxonil, iprodione, procymidone, quinoxyfen and vinclozolin.

(14) Compounds capable to act as an uncoupler, like for example binapacryl, dinocap, ferimzone, fluazinam and meptyldinocap.

(15) Further compounds, like for example benthiazole, bethoxazin, capsimycin, carvone, chinomethionat, chlazafenone, cufraneb, cyflufenamid, cymoxanil, cyprosulfamide, dazomet, debacarb, dichlorophen, diclomezine, difenzoquat, difenzoquat methylsulphate, diphenylamine, ecomate, fenpyrazamine, flumetover, fluoroimide, flusulfamide, flutianil, fosetyl-aluminium, fosetyl-calcium, fosetyl-sodium, hexachlorobenzene, irumamycin, methasulfocarb, methyl isothiocyarate, metrafenone, mildiomycin, natamycin, nickel dimethyldithiocarbamate, nitrothal-isopropyl, octhilinone, oxanocarb, oxyfenthiin, pentachlorophenol and salts, phenothrin, phosphorous acid and its salts, propamocarb-fosetylate, propanosine-sodium, proquinazid, pyrrolnitrine, tebufloquin, tecloftalam, tolnifanide, triazoxide, trichlamide, zarilamid, 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[5-

(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-methoxyphenoxy)-3,3-dimethylbutan-2-yl 1H-imidazole-1-carboxylate, 2,3,5,6-tetrachloro-4-(methylsulfonyl) pyridine, 2,3-dibutyl-6-chlorothieno[2,3-d]pyrimidin-4(3H)-one, 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, 2-butoxy-6-iodo-3-propyl-4H-chromen-4-one, 2-chloro-5-[2-chloro-1-(2,6-difluoro-4-methoxyphenyl)-4-methyl-1H-imidazol-5-yl]pyridine, 2-phenylphenol and salts, 3,4,5-trichloropyridine-2,6-dicarbonitrile, 3-[5-(4-chlorophenyl)-2,3-dimethyl-1,2-oxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 5-amino-1,3,4-thiadiazole-2-thiol, 5-chloro-N'-phenyl-N'-(prop-2-yn-1-yl)thiophene-2-sulfonohydrazide, 5-methyl-6-octyl[1,2,4]triazolo[1,5-a]pyrimidin-7-amine, ethyl (2Z)-3-amino-2-cyano-3-phenylprop-2-enoate, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloropyridine-3-carboxamide, N-[1-(5-bromo-3-chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-{(E)-[(cyclopropylmethoxy)imino][6-(difluoromethoxy)-2,3-difluorophenyl]methyl}-2-phenylacetamide, N-{(Z)-[(cyclopropylmethoxy)imino][6-(difluoromethoxy)-2,3-difluorophenyl]methyl}-2-phenylacetamide, N-methyl-2-(1-{[5-methyl-3-(trifluoromethyl)-1H-pyrazol-1-yl]acetyl}piperidin-4-yl)-N-(1,2,3,4-tetrahydro naphthalen-1-yl)-1,3-thiazole-4-carboxamide, N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, pentyl {6-[({[(1-methyl-1H-tetrazol-5-yl)(phenyl)methylidene]amino}oxy)methyl]pyridin-2-yl}carbamate, phenazine-1-carboxylic acid, quinolin-8-ol and quinolin-8-ol sulfate (2:1).

(16) Further compounds like for example 1-methyl-3-(trifluoromethyl)-N-[2-(trifluoromethyl)biphenyl-2-yl]-1H-pyrazole-4-carboxamide, N-(4'-chlorobiphenyl-2-yl)-3-(difluormethyl)-1-methyl-1H-pyrazole-4-carboxamide N-(2',4'-dichlorobiphenyl-2-yl)-3-(difluoromethyl)-1-methyl-1H-pyrazole-4-carboxamide, 3-(difluoromethyl)-1-methyl-N-[4'-(trifluoromethyl)biphenyl-2-yl]-1H-pyrazole-4-carboxamide, N-(2',5'-difluorobiphenyl-2-yl)-1-methyl-3-(trifluoromethyl)-1H-pyrazole-4-carboxamide, 3-(difluoromethyl)-1-methyl-N-[4'-(prop-1-yn-1-yl)biphenyl-2-yl]-1H-pyrazole-4-carboxamide, 5-fluoro-1,3-dimethyl-N-[4'(prop-1-yn-1-yl)biphenyl-2-yl]-1H-pyrazole-4-carboxamide, 2-chloro-N-[4'-(prop-1-yn-1-yl)biphenyl-2-yl]pyridine-3-carboxamide, 3-(difluoromethyl)-N-[4'-(3,3-diethylbut-1-yn-1-yl)biphenyl-2-yl]-1-methyl-1H-pyrazole-4-carboxamide, N-[4'-(3,3-diimethylbut-1-yn-1-yl)biphenyl-2-yl]-5-fluoro-1,3-dimethyl-1H-pyrazole-4-carboxamide, 3-(difluoromethyl)-N-(4'-ethynylbiphenyl-2-yl)-1-methyl-1H-pyrazole-4-carboxamide, N-(4'-ethynylbiphenyl-2-yl)-5-fluoro-1,3-dimethyl-1H-pyrazole-4-carboxamide, 2-chloro-N-(4'-ethynylbiphenyl-2-yl)pyridine-3-carboxamide, 2-chloro-N-[4'-(3,3-dimethylbut-1-yn-1-yl)biphenyl-2-yl]pyridine-3-carboxamide, 4-(difluoromethyl)-2-methyl-N-[4'-(trifluoromethyl)biphenyl-2-yl]-1,3-thiazole-5-carboxamide, 5-fluoro-N-[4'-(3-hydroxy-3-methylbut-1-yn-1-yl)biphenyl-2-yl]-1,3-dimethyl-1H-pyrazole-4-carboxamide, 2-chloro-N-[4'-(3-hydroxy-3-methylbut-1-yn-1-yl)biphenyl-2-yl]pyridine-3-carboxamide, 3-(difluoromethyl)-N-[4'-(3-methoxy-3-methylbut-1-yn-1-yl)biphenyl-2-yl]-1-methyl-1H-pyrazole-4-carboxamide, 5-fluoro-N-[4'-(3-methoxy-3-methylbut-1-yn-1-yl)biphenyl-2-yl]-1,3-dimethyl-1H-pyrazole-4-carboxamide 2-chloro-N-[4'-(3-methoxy-3-methylbut-1-yn-1-yl)biphenyl-2-yl]pyridine-3-carboxamide, (5-bromo-2-methoxy-4-methylpyridin-3-yl)(2,3,4-trimethoxy-6-methylphenyl)methanone and N-[2-(4-{[3-(4-chlorophenyl)prop-2-yn-1-yl]oxy}-3-methoxyphenyl)ethyl]-N2-(methylsulfonyl)valinamide.

The compounds according to the present invention show a potent insecticidal action and can, therefore, be used as an insecticide. Furthermore, the compounds according to the present invention exhibit a strong control effect against harmful animal pests, in particular arthropods and/or insects, particularly to agricultural pests, without imposing any harmful side effects of drug to the animal or the cultivated plants. The compounds of the present invention can thus be used for the control of a wide range of pest species, for example, harmful sucking insects, chewing insects, as well as other plant parasitic pests, storage insects, hygiene pests and the like, and can be applied for the purpose of disinfestations and extermination thereof. The active compounds and active compound combinations according to the invention, in combination with good plant tolerance and favourable toxicity to warm-blooded animals and being tolerated well by the environment, are suitable for protecting plants and plant organs, for increasing harvest yields, for improving the quality of the harvested material and for controlling animal pests, in particular insects, arachnids, helminths, nematodes and molluscs, which are encountered in agriculture, in horticulture, in animal husbandry in forests, in gardens and leisure facilities, in the protection of stored products and of materials, and in the hygiene sector. They can be preferably employed as plant protection agents. They are active against normally sensitive and resistant species and against all or some stages of development. The abovementioned pests include:

Order: Arthropoda:

From the class of the Arachnida, for example *Acarus* spp., *Aceria sheldoni, Aculops* spp., *Aculus* spp., *Amblyomma* spp., *Amphitetranychus viennensis, Argas* spp., *Boophilus* spp., *Brevipalpus* spp., *Bryobia praetiosa, Centruroides* spp., *Chorioptes* spp., *Dermanyssus gallinae, Dermatophagoides pteronyssius, Dermatophagoides farinae, Dermacentor* spp., *Fotetranychus* spp., *Epitrimerus pyri, Eutetranychus* spp., *Eriophyes* spp., *Halotydeus destructor, Hemitarsonemus* spp., *Hyalomma* spp., *Nodes* spp., *Latrodectus* spp., *Loxosceles* spp., *Metatetranychus* spp., *Nuphersa* spp., *Oligonychus* spp., *Ornithodorus* spp., *Ornithonyssus* spp., *Panonvehus* spp., *Phyllocoptruta oleivora, Polyphagotarsonemus latus, Psoroptes* spp., *Rhipicephalus* spp., *Rhizoglyphus* spp., *Sar-*

*coptes* spp., *Scorpio maurus*, *Stenotarsonemus* spp., *Tarsonemus* spp., *Tetranychus* spp., *Vaejovis* spp., *Vasates lycopersici*.

From the order of the Anoplura (Phthiraptera), for example, *Damalinia* spp., *Haematopinus* spp., *Linognathus* spp., *Pediculus* spp., *Ptirus pubis*, *Trichodectes* spp.

From the order of the Chilopoda, for example, *Geophilus* spp., *Scutigera* spp.

From the order of the Coleoptera, for example, *Acalymma vittatum*, *Acanthoscelides obtectus*, *Adoretus* spp., *Agelastica alni*, *Agriotes* spp., *Alphitobius diaperinus*, *Amphimallon solstitialis*, *Anobium punctatum*, *Anoplophora* spp., *Anthonomus* spp., *Anthrenus* spp., *Apion* spp., *Apogonia* spp., *Atomaria* spp., *Attagenus* spp., *Bruchidius obtectus*, *Bruchus* spp., *Cassida* spp., *Cerotoma trifurcata*, *Ceutorrhynchus* spp., *Chaetocnema* spp., *Cleonus mendicus*, *Conoderus* spp., *Cosmopolites* spp., *Costelytra zealandica*, *Ctenicera* spp., *Curculio* spp., *Cryptorhynchus lapathi*, *Cylindrocopturus* spp., *Dennestes* spp., *Diabrotica* spp., *Dichocrocis* spp., *Diloboderus* spp., *Epilachna* spp., *Epitrix* spp., *Faustinus* spp., *Gibbium psylloides*, *Hellula undalis*, *Heteronychus arator*, *Heteronyx* spp., *Hylamorpha elegans*, *Hylotrupes bajulus*, *Hypera postica*, *Hypothlenemus* spp., *Lachnostema consanguinea*, *Lema* spp., *Leptinotarsa decemlineata*, *Leucoptera* spp., *Lissorhoptrus oryzophilus*, *Lixus* spp., *Luperodes* spp., *Lyctus* spp., *Megascelis* spp., *Melanotus* spp., *Meligethes aeneus*, *Melolontha* spp., *Migdolus* spp., *Monochamus* spp., *Naupactus xanthographus*, *Niptus hololeucus*, *Oryctes rhinoceros*, *Oryzaephilus surinamensis*, *Oryzaphagus oryzae*, *Otiorrhynchus* spp., *Oxycetonia jucunda*, *Phaedon cochleariae*, *Phyllophaga* spp., *Phyllotreta* spp., *Popillia japonica*, *Premnotrypes* spp., *Prostephanus truncatus*, *Psylliodes* spp., *Ptinus* spp., *Rhizobius ventralis*, *Rhizopertha dominica*, *Sitophilus* spp., *Sphenophorus* spp., *Stegobium paniceum*, *Stemechus* spp., *Symphyletes* spp., *Tanymecus* spp., *Tenebrio molitor*, *Tribolium* spp., *Trogoderma* spp., *Tychius* spp., *Xylotrechus* spp., *Zabrus* spp.

From the order of the Collembola, for example, *Onychiurus armatus*.

From the order of the Diplopoda, for example, *Blaniulus guttulatus*.

From the order of the Diptera, for example, *Aedes* spp., *Agromyza* spp., *Anastrepha* spp., *Anopheles* spp., *Asphondylia* spp., *Bactrocera* spp., *Bibio hortulanus*, *Calliphora erythrocephala*, *Ceratitis capitata*, *Chironomus* spp., *Chrysomyia* spp., *Chrysops* spp., *Cochliomyia* spp., *Contarinia* spp., *Cordylobia anthropophaga*, *Culex* spp., *Culicoides* spp., *Culiseta* spp., *Cuterebra* spp., *Dacus oleae*, *Dasyneura* spp., *Delia* spp., *Dermatobia hominis*, *Drosophila* spp., *Echinocnemus* spp., *Fannia* spp., *Gasterophilus* spp., *Glossina* spp., *Haematopota* spp., *Hydrellia* spp., *Hylemyia* spp., *Hyppobosca* spp., *Hypodenna* spp., *Liriomyza* spp. *Lucilia* spp., *Lutzomia* spp., *Mansonia* spp., *Musca* spp., *Nezara* spp., *Oestrus* spp., *Oscinella frit*, *Pegomyia* spp., *Phlebotomus* spp., *Phorbia* spp., *Phormia* spp., *Prodiplosis* spp., *Psila rosae*, *Rhagoletis* spp., *Sarcophaga* spp., *Simulium spp*, *Stomoxys* spp., *Tabanus* spp., *Tannia* spp., *Tetanops* spp., *Tipula* spp.

From the order of the Heteroptera, for example, *Anasa tristis*, *Antestiopsis* spp., *Boisea* spp., *Blissus* spp., *Calocoris* spp., *Campylomma livida*, *Cavelerius* spp., *Cimex* spp., *Cimex lectularius*, *Cimex hemipterus*, *Collaria* spp., *Creontiades dilutus*, *Dasynus piperis*, *Dichelops farcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, *Miridae*, *Monalonion atratum*, *Nezara* spp., *Oebalus* spp., *Pentomidae*, *Piesma quadrata*, *Piezodorus* spp., *Psallus* spp., *Pseudacysta persea*, *Rhodnius* spp., *Sahlbergella singularis*, *Scaptocoris castanea*, *Scotinophora* spp., *Stephanitis nashi*, *Tibraca* spp., *Triatoma* spp.

From the order of the Homoptera, for example, *Acyrthosipon* spp., *Acrogonia* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aonidiella* spp., *Aphanostigma piri*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona marginata*, *Cameocephala fulgda*, *Ceratovacuna lanigera*, *Cercopidae*, *Ceroplastes* spp., *Chaetosiphon fiagaefolii*, *Chionaspis tegalensis*, *Chlorita onukii*, *Chromaphis juglandicola*, *Chrysomphalus ficus*, *Cicadulina mbila*, *Coccomytilus halli*, *Coccus* spp., *Cryptomyzus ribis*, *Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erytlroneura* spp., *Euscelis bilobatus*, *Ferrisia* spp., *Geococcus coffeae*, *Hieroglyphus* spp., *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Mahanarva* spp., *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nilaparvata lugens*, *Oncometopia* spp., *Orthezia praelonga*, *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoides titanus*, *Schizaphis graminum*, *Selenaspidus articulatus*, *Sogata* spp., *Sogatella furcifera*, *Sogatodes* spp., *Stictocephala festina*, *Tenalaphara malayensis*, *Tinocallis caryaefoliae*, *Tomaspis* spp., *Toxoptera* spp., *Trialeurodes* spp., *Trioza* spp., *Typhlocyba* spp., *Unaspis* spp., *Viteus vitifolii*, *Zygina* spp.

From the order of the Hymenoptera, for example, *Acrornyrmex* spp., *Athalia* spp., *Atta* spp., *Diprion* spp., *Hoplocampa* spp., *Lasius* spp., *Monomorium pharaonis*, *Solenopsis invicta*, *Tahpinoma* spp., *Vespa* spp.

From the order of the Isopoda, for example, *Armadillidium vulgare*, *Oniscus asellus*, *Porcellio scaber*.

From the order of the Isoptera, for example, *Coptotermes* spp., *Cornitermes cumulans*, *Cryptotermes* spp., *Incisitermes* spp., *Microtennes obesi*, *Odontotermes* spp., *Reticulitermes* spp., From the order of the Lepidoptera, for example, *Acronicta major*, *Adoxophyes* spp., *Aedia leucomelas*, *Agrotis* spp., *Alabama* spp., *Amyelois transitella*, *Anarsia* spp., *Anticarsia* spp., *Argyroploce* spp., *Barathra brassicae*, *Borbo cinnara*, *Bucculatrix thurberiella*, *Bupalus piniarius*, *Busseola* spp., *Cacoecia* spp., *Caloptilia theivora*, *Capua reticulana*, *Carpocapsa pornonella*, *Carposina niponensis*, *Cheimatobia brumata*, *Chilo* spp., *Choristoneura* spp., *Clysia ambiguella*, *Cnaphalocerus* spp., *Cnephasia* spp., *Conopomorpha* spp., *Conotrachelus* spp., *Copitarsia* spp., *Cydia* spp., *Dalaca noctuides*, *Diaphania* spp., *Diatraea saccharalis*, *Earias* spp., *Ecdytolopha aurantium*, *Elasmopalpus lignosellus*, *Eldana saccharina*, *Ephestia* spp., *Epinotia* spp., *Epiphyas postvittana*, *Etiella* spp., *Eulia* spp., *Eupoecilia ambiguella*, *Euproctis* spp., *Euxoa* spp., *Feltia* spp., *Galleria mellonella*, *Gracillaria* spp., *Grapholitha* spp., *Hedylepta* spp., *Helicoverpa* spp., *Heliothis* spp., *Hofmamnnophila pseudospretella, Homoeosoma* spp., *Homona* spp., *Hyponomeuta padella, Kakivoria flavofasciata, Laphygmaa* spp., *Laspeyresia molesta, Leucinodes orbonalis, Leucoptera* spp., *Lithocolletis* spp., *Lithophane antennata, Lobesia* spp., *Loxagrotis albicosta, Lymantria* spp., *Lyonetia* spp., *Malacosoma neustria, Maruca testulalis, Mamestra brassicae, Mocis* spp., *Mythimna separata, Nymphula* spp., *Oiketicus* spp., *Oria* spp, *Orthaga* spp., *Ostrinia* spp., *Oulema oryzae, Panolis flammea, Parnara* spp., *Pectinophora* spp., *Perileucoptera* spp., *Phthorimaea* spp., *Phyllocnistis citrella, Phyllonorycter* spp., *Pieris* spp., *Platynota stultana, Plodia interpunctella, Plusia* spp., *Plutella xylostella, Prays* spp., *Prodenia* spp., *Protoparce* spp., *Pseudaletia* spp., *Pseudoplusia includens, Pyrausta nubilalis, Rachiplusia nu, Schoenobius* spp., *Scirpophaga* spp., *Scotia segetum, Sesamia* spp., *Sparganothis* spp., *Spodoptera* spp., *Stathmopoda* spp., *Stomopteryx subsecivella, Synanthedon* spp., *Tecia solanivora, Thermesia gemmatalis, Tinea pellionella, Tineola bisselliela, Tortrix* spp., *Trichophaga tapetzella, Trichoplusia* spp., *Tuta absoluta, Virachola* spp.

From the order of the Orthoptera, for example, *Acheta domesticus, Blatta orientalis, Blattella germanica, Dichroplus* spp., *Gryllotalpa* spp., *Leucophaea maderae, Locusta* spp., *Melanoplus* spp., *Periplaneta* spp., *Pulex irritans, Schistocerca gregaria, Supella longipalpa*.

From the order of the Siphonaptera, for example, *Ceratophyllus* spp., *Ctenocephalides* spp., *Tunga penetrans, Xenopsylla cheopis*.

From the order of the Symphyla, for example, *Scutigerella* spp.

From the order of the Thysanoptera, for example, *Anaphothrips obscurus, Baliofthrips biformis, Drepanothris reuteri, Enneothrips flavens, Frankliniella* spp., *Heliothrips* spp., *Hercinothrips femoralis, Rhipiphorothrips cruentatus, Scirtothrips* spp., *Taeniothrips cardamoni, Thrips* spp.

From the order of the Zygentoma (=Thysanura), for example, *Lepisma saccharina, Thermobia domestica*.

Order: Mollusca:

From the class of the Bivalvia, for example, *Dreissena* spp,

From the class of the Gastropoda, for example, *Arion* spp., *Biomphalaria* spp., *Bulinus* spp., *Deroceras* spp., *Galba* spp., *Lymnaea* spp., *Oncomelania* spp., *Pomacea* spp., *Succinea* spp.

Order: Plathelminthes, Nematodes (Animal Parasites)

From the class of the Helminths, for example, *Ancylostoma duodenale, Ancylostoma ceylanicum, Acylostoma braziliensis, Ancylostoma* spp., *Ascaris* spp., *Brugia malayi, Brugia timori, Bunostomum* spp., *Chabertia* spp., *Clonorchis* spp., *Cooperia* spp., *Dicrococlium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp, *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinelia pseudopsiralis, Trichostrongulus* spp., *Trichuris trichuria, Wuchereria bancrofti,*

Order: Nematodes (Plant Parasites, Phytoparasites)

From the group of the phytoparasitic nematodes, for example, *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus similis, Trichodorus* spp., *Tylenchulus semipenetrans, Xiphinema* spp.

Subphylum: Protozoa:

It is furthermore possible to control protozoa, such as Eimeria.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds is carried out directly or by allowing the compounds to act on their surroundings, habitat or storage space by the customary treatment methods, for example by immersion, spraying, evaporation, fogging, scattering, painting on, injecting and, in the case of propagation material, in particular in the case of seed, also by applying one or more coats.

The compounds according to the present invention show a systemic action which means that the compounds can permeate plants body and translocate from the underground part of plants to the aerial part of plants.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof, are treated. The terms "parts", "parts of plants" and "plant parts" have been explained above.

Particularly preferably, plants of the plant cultivars which are in each case commercially available or in use are treated according to the invention. Plant cultivars are understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive "synergistic" effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The preferred transgenic plants or plant cultivars (obtained by genetic engineering) which are to be treated according to the invention include all plants which, by virtue of the genetic modification, received genetic material which imparts particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized in particular are the increased defence of the plants against insects, arachnids, nematodes and slugs and snails by virtue of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (referred to hereinbelow as "Bt plants"). Traits that are also particularly emphasized are the increased defence of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya beans), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The plants listed can be treated according to the invention in a particularly advantageous manner with the compounds according to the invention at a suitable concentration.

In veterinary medicine field, i.e., veterinary science, the active compounds of the present invention can be effectively used against various harmful animal parasites, particularly, endoparasites and ectoparasites. The term "endoparasites" include in particular worms (tapeworm, eelworm, trematode and the like) and *plasmodium* (coccidium and the like). The term "ectoparasites" include in general and preferably an arthropod, in particular insects (fly (a fly which can sting and suck), larva of parasitic fly, sucking lice, crab lice, bird lice, flea and the like) or acaroid mites (ticks and the like, for example, hard tick and soft tick) or mites (itch mite, chigger mite, bird mite and the like).

These parasites are as follows:

from Anoplurida, for example, *Haematopinus* spp., *Linognathus* spp., *Pediculus* spp., *Phtirus* spp., *Solenopotes* spp.; particularly, for representative examples, *Linognathus setosus*, *Linognathus vituli*, *Linognathus ovillus*, *Linognathus oviformis*, *Linognathus pedalis*, *Linognathus stenopsis*, *Haematopinus asini macrocephalus*, *Haematopinus eurysternus*, *Haematopinus suis*, *Pediculus humanus capitis*, *Pediculus humanus corporis*, *Phylloera vastatrix*, *Phthirus pubis*, *Solenopotes capillatus*;

from Mallophagida, Amblycerina, and Ischnocerina, for example, *Trimenopon* spp., *Menopon* spp., *Trinoton* spp., *Bovicola* spp., *Wemeckiella* spp., *Lepikentron* spp., *Damalina* spp., *Trichodectes* spp., *Felicola* spp.; particularly, for representative examples, *Bovicola bovis*, *Bovicola ovis*, *Bovicola limbata*, *Damalina bovis*, *Trichodectes canis*, *Felicola subrostratus*, *Bovicola caprae*, *Lepikentron ovis*, *Werneckiella equi*;

from Diptera, Nematocerina, and Brachycerina, for example, *Aedes* spp., *Anopheles* ssp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; particularly, for representative examples, *Aedes aegypti*, *Aedes albopictus*, *Aedes taeniorhynchus*, *Anopheles gambiae*, *Anopheles maculipennis*, *Calliphora erythrocephala*, *Chrysozona pluvialis*, *Culex quinquefasciatus*, *Culex pipiens*, *Culex tarsalis*, *Farnia canicularis*, *Sarcophaga carnaria*, *Stomoxys calcitrans*, *Tipula paludosa*, *Lucilia cuprina*, *Lucilia sericata*, *Simulium reptans*, *Phlebotomus papatasi*, *Phlebotomus longipalpis*, *Odagmia omata*, *Wilhelmia equina*, *Boophthora erythrocephala*, *Tabanus bromius*, *Tabanus spodopterus*, *Tabanus atratus*, *Tabanus sudeticus*, *Hybomitra ciurea*, *Chrysops caecutiens*, *Chrysops relictus*, *Haematopota pluvialis*, *Haematopota italica*, *Musca autumnalis*, *Musca domestica*, *Haematobia irritans irritans*, *Haematobia irritans exigua*, *Haematobia stimulans*, *Hydrotaea irritans*, *Hydrotaea albipuncta*, *Chrysomya chloropyga*, *Chrysomya bezziana*, *Oestrus ovis*, *Hypoderma bovis*, *Hypoderma lineatum*, *Przhevalskiana silenus*, *Dermatobia hominis*, *Melophagus ovinus*, *Lipoptena capreoli*, *Lipoptena cervi*, *Hippobosca variegata*, *Hippobosca equina*, *Gasterophilus intestinalis*, *Gasterophilus haemorroidalis*, *Gasterophilus intermis*, *Gasterophilus nasalis*, *Gasterophilus nigricomis*, *Gasterophilus pecorum*, *Braula coeca*;

from Siphonapterida, for example, *Pulex* spp., *Ctenocephalides* spp., *Tunga* spp., *Xenopsylla* spp., *Ceratophyllus* spp.; particularly, for representative examples, *Ctenocephalides canis, Ctenocephalides felis, Pulex irritans, Tunga penetrans, Xenopsylla* cheopis;

from Heteropterida, for example, *Cimex* spp., *Triatoma* spp., *Rhodnius* spp., *Panstrongylus* spp.;

from Blattarida, for example, *Blatta orientalis, Periplaneta americana, Blattela germanica, Supella* spp. (for example, *Suppella longipalpa*);

from Acari (Acarina), Metastigmata, and Mesostigmata, for example, *Argas* spp., *Ornithodorus* spp., *Otobius* spp., *Ixodes* spp., *Amblyomma* spp., *Rhipicephalus (Boophilus)* spp., *Dermacentor* spp., *Haemophysalis* spp., *Hyalomma* spp., *Dermanyssus* spp., *Rhipicephalus* spp. (original genus of heteroxenous mites), *Ornithonyssus* spp., *Pneumonyssus* spp., *Raillietia* spp., *Pneumonyssus* spp., *Sternostoma* spp., *Varroa* spp., *Acarapis* spp.); particularly, for representative examples, *Argas persicus, Argas reflexus, Ornithodorus moubata, Otobius megnini, Rhipicephalus (Boophilus) microplus, Rhipicephalus (Boophilus) decoloratus, Rhipicephalus (Boophilus) annulatus, Rhipicephalus (Boophilus) calceratus, Hyalomma anatolicum, Hyalomma aegypticum, Hyalomma marginatum, Hyalomma transiens, Rhipicephalus evertsi, Ixodes ricinus, Ixodes hexagonus, Ixodes canisuga, Ixodes pilosus, Ixodes rubicundus, Ixodes scapularis, Ixodes holocyclus, Haemaphysalis concinna, Haemaphysalis punctata, Haemaphysalis cinnabarina, Haemaphysalis otophila, Haemaphysalis leachi, Haemaphysalis longicorni, Dermacentor marginatus, Dermacentor reticulatus, Dermacentor pictus, Dermacentor albipictus, Dermacentor andersoni, Dermacentor variabilis, Hyalomma mauritanicum, Rhipicephalus sanguineus, Rhipicephalus bursa, Rhipicephalus appendiculatus, Rhipicephalus capensis, Rhipicephalus turanicus, Rhipicephalus zambeziensis, Amblyomma americanum, Amblyomma variegatum, Amblyomma maculatum, Amblyomma hebraeumn, Amblyomma cajennense, Dermanyssus gallinae, Ornithonyssus bursa, Ornithonyssus sylviarum, Varroa jacobsconi*;

from Actinedida (Prostigmata), and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.; particularly, *Cheyletiella yasguri, Cheyletiella blakei, Demodex canis, Demodex bovis, Demodex ovis, Demodex caprae, Demodex equi, Demodex caballi, Demodex suis, Neotrombicula autumnalis, Neotrombicula desaleli, Neoschonegastia xerothermobia, Trombicula akamnushi, Otodectes cynotis, Notoedres cati, Sarcoptis canis, Sarcoptes bovis, Sarcoptes ovis, Sarcoptes rupicaprae (=S. caprae), Sarcoptes equi, Sarcoptes suis, Psoroptes ovis, Psoroptes cuniculi, Psoroptes equi, Chorioptes bovis, Psoergates ovis, Pneumonyssoidic mange, Pneumonyssoides caninum, Acarapis woodi*.

The active compounds of the present invention are also useful for controlling an arthropod, a worm and a *plasmodium* which attacks an animal. Examples of the animal include an agricultural animals such as a cow, a sheep, a goat, a horse, a pig, a donkey, a camel, a buffalo, a rabbit, a chicken, a turkey, a duck, a goose, a nursery fish, a honey bee, etc. In addition, a pet which is also called as a companion animal, for example, a dog, a cat, a caged bird, an aquarium fish, and an animal for experimental testing (e.g., a hamster, a guinea pig, a rat, a mouse and the like) is also included.

With control of the arthropod, worm and/or *plasmodium* by using the active compounds of the present invention, death ratio of a host animal can be reduced and productivity (for meat, milk, wool, leather, egg, and honey) and health of the animal can be improved. As a result, it is intended to achieve economically more favorable and simple animal breeding.

For example, it is preferable that introduction of blood from a parasite to a host is either prevented or inhibited (if possible). Parasite control can be useful for preventing infection which is caused by inflammatory pathogens.

The term "control" that is used in the present specification regarding a veterinary medicine field means that the active compounds are effective for reducing the occurrence ratio of each parasite in the animal infected with it to an innoxious level. More specifically, the term "to control" means that the active compounds of the present invention are effective for destroying parasites, inhibiting growth or propagation thereof.

In the present invention, substances having pesticidal effects against harmful pests encompassing all of such pests are referred to as pesticides.

When used as a pesticide, the active compounds of the present invention can be prepared in a form of a common preparation. Such preparation form may include, for example, liquids, emulsions, wettable powders, granulated wettable powders, suspensions, powders, foams, pastes, tablets, granules, aerosols, natural or synthetic agents impregnated with the active compounds, microcapsules, coating agents for seeds, formulations equipped with a combustion device (the combustion device can be a smoke or fog cartridge, a can or a coil, etc.) and ULV (cold mist, warm mist), and the like.

These formulations can be produced by known methods per se. For example, they can be prepared by mixing the active compounds with extenders, namely, liquid diluents or carriers; liquefied gas diluents or carriers; solid diluents or carriers and, optionally, with surfactants, namely, emulsifiers and/or dispersants and/or foam formers and the like.

In case of using water as an extender, for example, organic solvents can be used as auxiliary solvents.

Liquid diluents or carriers may include, for example, aromatic hydrocarbons (e.g. xylene, toluene, alkylnaphthalene etc.), chlorinated aromatic or chlorinated aliphatic hydrocarbons (e.g. chlorobenzenes, ethylene chlorides, methylene chlorides etc.), aliphatic hydrocarbons (e.g. cyclohexanes or paraffins (e.g. mineral oil fractions)), alcohols (e.g. butanol, glycol and ethers or esters thereof, etc.), ketones (e.g. acetone, methylethylketone, methylisobutylketone, cyclohexanone etc.), strong polar solvents (e.g. dimethylformamide, dimethylsulfoxide etc.), water and the like.

Liquefied gas diluent or carrier may include those present as gas at atmospheric pressure and temperature, for example, bulan, propane, nitrogen gas, carbon dioxide, and aerosol propellant such as halogenated hydrocarbons.

Examples of the solid diluents may include ground natural minerals (for example, kaolins, clay, talc, chalk, quartz, attapulgite, montmorillonite or diatomaceous earth, etc.) and ground synthetic minerals (for example, highly dispersed silicic acid, alumina and silicate, etc.) and the like.

Examples of the solid carriers for granules may include crushed and fractionated rocks (for example, calcite, marble, pumice, sepiolite and dolomite, etc.), synthetic granules of inorganic or organic powders, and fine granules of organic materials (for example, sawdust, coconut shells, maize cobs and tobacco stalks, etc.) and the like.

Examples of the emulsifiers and/or foam formers may include nonionic and anionic emulsifiers [for example, polyoxyethylene fatty acid esters, polyoxyethylene fatty acid alcohol ethers (for example, alkylaryl polyglycol ether), alkyl sulfonates, alkyl sulfates and aryl sulfonates] and albumin hydrolysates and the like. The dispersants include lignin sulfite waste liquor and methylcellulose.

Binders may also be used in the formulations (powders, granules and emulsion). Examples of the binders may include carboxymethyl cellulose, natural or synthetic polymers (for example, gum arabic, polyvinyl alcohol and polyvinyl acetate, etc).

Colorants may also be used. Examples of the colorants may include inorganic pigments (for example, iron oxide, titanium oxide and Prussian blue, etc.), organic dyes such as Alizarin dyes, azo dyes or metal phthalocyanine dyes, and further, trace elements such as salts of iron, manganese, boron, copper, cobalt, molybdenum or zinc.

The formulation may include the above active components in an amount of 0.1 to 95 wt %, preferably 0.5 to 90 wt %.

The active compounds of the Formula (I) of the present invention can be provided as mixtures with other active compounds such as pesticides, poison baits, sterilizing agents, acaricidal agents, nematocides, fungicides, growth regulating agents, herbicides, and the like in a form of commercially useful formulation or an application form prepared from formulation thereof. The amount of the active compounds of the Formula (I) of the present invention in a commercially useful form may vary over a broad range. The concentration of the active compounds of the Formula (I) of the present invention for actual use can be, for example, between 0.0000001 and 100% by weight, preferably between 0.00001 and 1% by weight.

The compounds of the Formula (I) of the present invention can be used according to any common methods that are appropriate for an application form.

The active compounds of the present invention have stability that is effective for alkaline substances present in lime materials when the compounds are used against hygienic pests and storage pests. In addition, they exhibit excellent residual effectiveness in woods and soils.

Generally, when the active compounds of the present invention are used for the treatment of animals, they can be directly applied to the animal. Preferably, the compounds are applied in a form of pharmaceutical composition which may include a vehicle, an auxiliary agent, or both, that are known in the field and pharmaceutically acceptable.

For a veterinary medicine field and animal breeding, the active compounds can be applied (administered) according to various known ways, for example; intraintestinal administration with a tablet, a capsule, a drink, a drinkable medicine, granules, paste, and bolus administration, feed-through method, suppository; non-intraintestinal administration based on skin application such as injection (intramuscular, subcutaneous, intravenous, intraperitoneal, etc.), embedding, intranasal application, bathing or immersion, spray, pouring, dropping, washing and scattering, and by using a molding article containing the active compounds such as a necklace, an earnmark, a tag a leg brace, a net, a marking device and the like. The active compounds of the present invention can be formulated into an appropriate formulation form that can be applied with a shampoo, aerosol, a non-pressurized spray, for example a pump spray and a vaporizer spray, etc.

When used for livestock, fouls, pets and the like, the active compounds of the present invention can be used as a formulation which includes them in an amount of 1 to 80 wt % (for example, powders, wettable powders (WP), emulsion, emulsifiable concentrate (EC), fluid, homogeneous solution and suspension concentrate (SC)), and the formulation can be applied as it is or after dilution (for example, dilution of 100 to 10,000 times), or as a chemical shower as an alternative method.

When used in a veterinary medicine field, the active compounds of the present invention can be used in combination with other appropriate synergistic agents or other active compounds, for example, acaricides, insecticides, parasticides, anti-*plasmodium* agents, etc.

The active compounds of the present invention have low toxicity and can be safely used for warm-blooded animals.

EXAMPLES

Herein below, the present invention is described in greater detail with reference to the following examples.

However, it is evident that the present invention is not limited thereto only

Synthetic Example 1

Synthesis of 6-cyano-N-[2-ethyl-(1,1,1,2,3,3,3-heptafluoropropan-2-yl)-6-methylphenyl]-2-naphthamide (Compound No. 1-4)

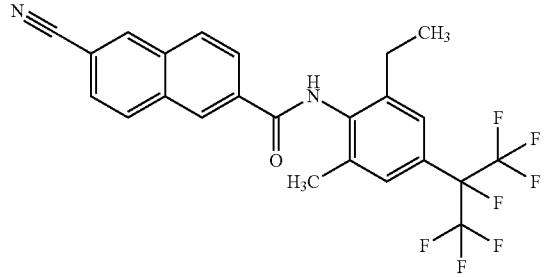 [SMILES: CCc1cc(C(F)(C(F)(F)F)C(F)(F)F)cc(C)c1NC(=O)c1ccc2cc(C#N)ccc2c1]

Step 1-1: Synthesis of 6-bromo-N-[2-ethyl-4-(1,1,1,2,3,3,3-heptafluoropropan-2-yl-2-yl)-6-methylphenyl]-2-naphthamide (Compound No. 1-3)

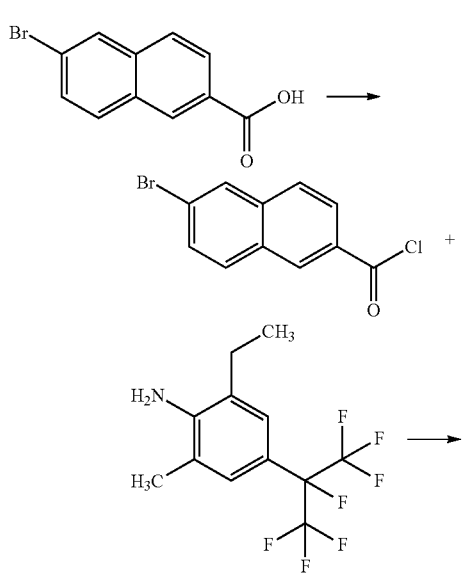

-continued

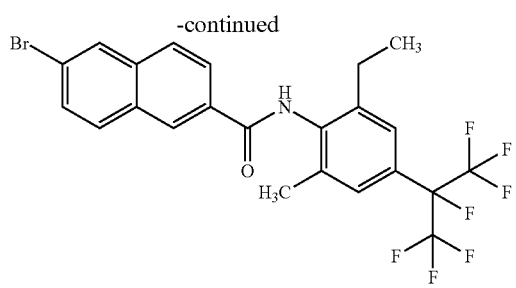

To methylene chloride solution including 6-bromo-2-naphthonic acid (0.42 g) and N,N-dimethylformamide (300 μL), oxalyl dichloride (2.6 ml) was added under stirring at room temperature (18 to 30° C., the same shall apply hereinafter) followed by further stirring for 2 hours. Subsequently, the solvent was distilled off under the reduced pressure (760 to 20 mmHg, the same shall apply hereinafter). Resulting 6-bromo-2-naphthoyl chloride was dissolved in methylene chloride, added with pyridine (2.1 ml) and 2-ethyl-4-(1,1,1,2,3,3,3-heptafluoropropan-2-yl)-6-methylaniline (0.45 g), followed by stirring for 5 hours. After dilution with methylene chloride and water, the organic phase was separated and dried over magnesium sulfate. The drying agent (magnesium sulfate) was removed by filtration and the solvent was distilled off under the reduced pressure. The residue was separated and purified by column chromatography to obtain 6-bromo-N-[2-ethyl-4-(1,1,1,2,3,3,3-heptafluoropropan-2-yl-2-yl)-6-methylphenyl]-2-naphthamide (0.75 g, yield 84%).

$^1$H-NMR (CDCl$_3$) δ: 1.23 (3H, t), 2.35 (3H, s), 2.71 (2H, q), 7.39 (2H, s), 7.63-7.66 (2H, m), 7.80 (1H, d), 7.85 (1H, d), 7.96 (1H, dd), 8.08 (1H, s), 8.40 (1H, s).

Step 1-2: Synthesis of 6-cyano-N-[2-ethyl-4-(1,1,1,2,3,3,3-heptafluoropropan-2-yl)-6-methylphenyl]-2-naphthamide

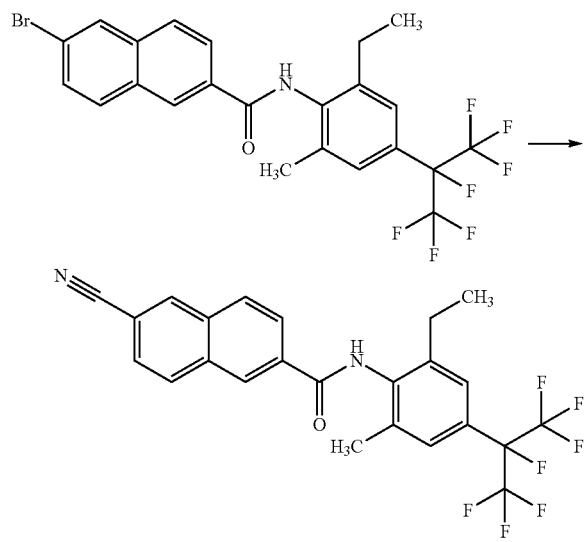

6-Bromo-N-[2-ethyl-4-(1,1,1,2,3,3,3-heptafluoropropan-2-yl)-6-methylphenyl]-2-naphthamide (0.49 g) was dissolved in N,N-dimethylformamide (4 ml), and deaeration was carried out three times under argon atmosphere (i.e., the reaction solution was de-pressurized to 20 mmHg and brought back to atmospheric pressure under argon atmosphere). Zinc cyanide (0.07 g) and tetrakis (triphenylphosphine) palladium(0) (0.11 g) were added thereto and stirred with heating at 80° C. for 7 hours under argon atmosphere. After cooling to room temperature, the reaction solution was diluted with ethyl acetate, and washed with water and saturated brine. The organic phase was dried over anhydrous magnesium sulfate. The drying agent (anhydrous magnesium sulfate) was removed by filtration and the solvent was distilled off under the reduced pressure. The residue was purified by silica gel chromatography to obtain 6-cyano-N-[2-ethyl-4-(1,1,1,2,3,3,3-heptafluoropropan-2-yl)-6-methylphenyl]-2-naphthamide (0.04 g, yield 9%).

$^1$H-NMR (CDCl$_3$) δ: 1.25 (3H, t), 2.39 (3H, s), 2.74 (2H, q), 7.41 (2H, brs), 7.60 (1H, s), 7.73 (1H, d), 8.07-8.09 (4H, m), 8.32 (1H, s), 8.50 (1H, s)<

Synthetic Example 2

Synthesis of 2-chloro-N-[4-(1,1,1,2,3,3,3-heptafluoropropan-2-yl)-2,6-dimethylphenyl]quinoline-6-carboxamide (Compound No. 2-17) and 4-chloro-N-[4-(1,1,1,2,3,3,3-heptafluoropropan-2-yl)-2,6-dimethylphenyl]quioline-6-carboxamide (Compound No. 2-12)

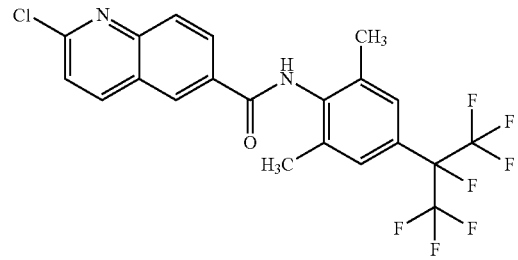

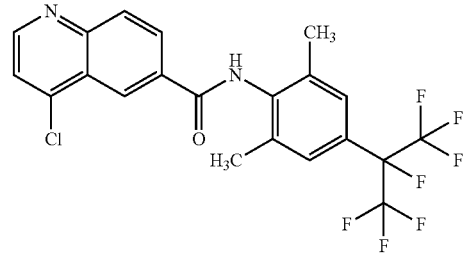

Step 2-1: Synthesis of N-[4-(1,2,3,3,3-heptafluoropropan-2-yl)-2,6-dimethylphenyl]quinoline-6-carboxamide (Compound No. 2-10)

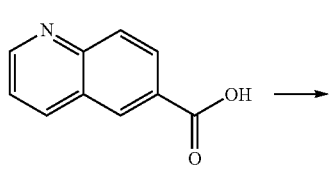

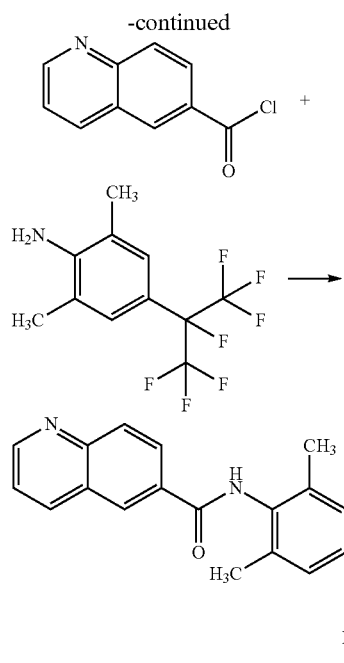

Quinoline-6-carboxylic acid (1.0 g) was dissolved in dichloromethane. N,N-dimethylformamide (300 μL) and oxalyl chloride (1.2 g) were added to this solution at room temperature and stirred for two hours followed by reflux for 20 minutes. The solvent was removed under the reduced pressure, and quinoline-6-carbonyl chloride was obtained as a crude product, which was then dissolved in dichloromethane. To this solution, 4-(1,1,1,2,3,3,3-heptafluoropropan-2-yl)-2,6-dimethylaniline (1.6 g) dissolved in dichloromethane and pyridine (1.2 g) were added and stirred at room temperature for 5 hours. The reaction solution was diluted with water and extracted twice with ethyl acetate. The organic phases were combined and washed with 1N hydrochloric acid and water, and dried over anhydrous magnesium sulfate. The drying agent (anhydrous magnesium sulfate) was removed by filtration and the solvent was distilled off under the reduced pressure. The residue was purified by column chromatography to obtain N-[4-(1,1,1,2,3,3,3-heptafluoropropan-2-yl)-2,6-dimethylphenyl]quinoline-6-carboxamide (2.0 g, yield 78%).

¹H-NMR: see Table 7.

Step 2-2: Synthesis of N-[4-(1,1,1,2,3,3,3-heptafluoropropan-2-yl)-2,6-dimethylphenyl]quinoline-6-carboxamide-1-oxide (Compound No. 2-11)

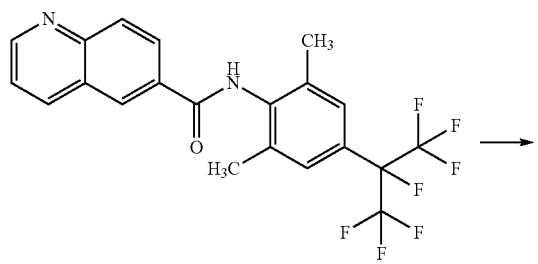

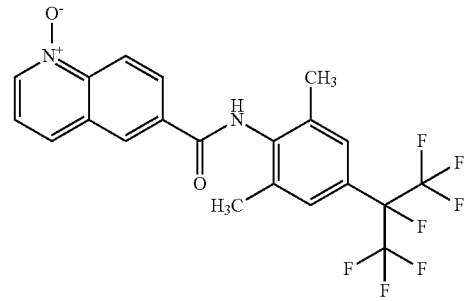

Dichloromethane was added to N-[4-(1,2,3,3,3-heptafluoropropan-2-yl)-2,6-dimethylphenyl]quinoline-6-carboxamide (1.9 g). To the resulting solution, 3-chloroperbenzoic acid (purity 70%) (1.4 g) was added and the mixture was stirred at room temperature for 3 hours. The solvent was distilled off under the reduced pressure and the residue was dissolved in ethyl acetate. Sodium hydrocarbonate solution and potassium carbonate were added thereto. After extracting the mixture twice with ethyl acetate, the organic phases were combined and washed with water, and dried over anhydrous magnesium sulfate. The drying agent (anhydrous magnesium sulfate) was removed by filtration and the solvent was distilled off under the reduced pressure to obtain N-[4-(1,1,1,2,3,3,3-heptafluoropropan-2-yl)-2,6-dimethylphenyl]quinoline-6-carboxyamide-1-oxide as a crude product (2.0 g). Without further purification, the compound was used for the next reaction.

¹H-NMR: see Table 7.

Step 2-3: Synthesis of 2-chloro-N-[4-(1,1,1,2,3,3,3-heptafluoropropan-2-yl)-2,6-dimethylphenyl]quinoline-6-carboxamide (Compound No. 2-17) and 4-chloro-N-[4-(1,1,1,2,3,3,3-heptafluoropropan-2-yl)-2,6-dimethylphenyl]quinoline-6-carboxamide (Compound No. 2-12):

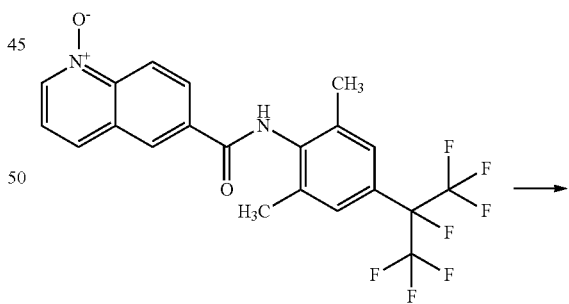

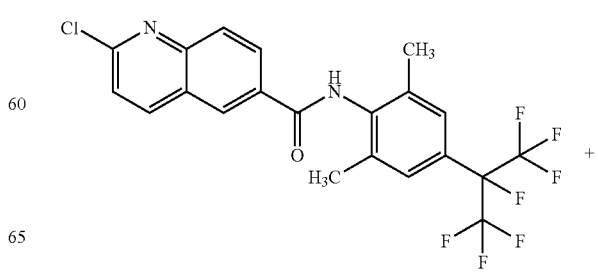

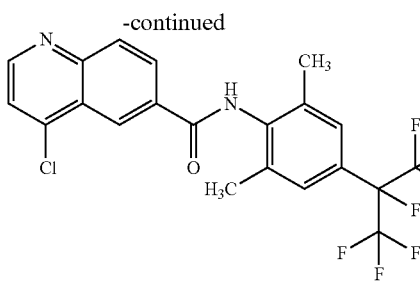

To crude product of N-[4-(1,1,1,2,3,3,3-heptafluoropropan-2-yl)-2,6-dimethylpheyl]quinoline-6-carboxamide-1-oxide (97 mg), phosphorus oxychloride (3.0 g) was added and the mixture was stirred under heating at 100° C. for 1 hour. The reaction solution was poured into ice water, neutralized with potassium carbonate and extracted twice with ethyl acetate. The organic phases were combined and washed with water, and dried over anhydrous magnesium sulfate. The drying agent (anhydrous magnesium sulfate) was removed by filtration and the solvent was distilled off under the reduced pressure. The residue was purified by column chromatography to obtain 2-chloro-N-[4-(,1,1,2,3,3,3-heptafluoropropan-2-yl)-2,6-dimethylphenyl]quinoline-6-carboxamide (35 mg, yield 35%) and 4-chloro-N-[4-(1,1,1,2,3,3,3-heptafluoropropan-2-yl)-2,6-dimethylphenyl]quinoline-6-carboxamide (23 mg, yield 23%).

$^1$H-NMR: see Table 7.

Synthetic Example 3

Synthesis of 2-cyano-N-[4-(1,1,1,2,3,3,3-heptafluoropropan-2-yl)-2,6-dimethylphenyl]quinoline-6-carboxamide (Compound No. 2-20)

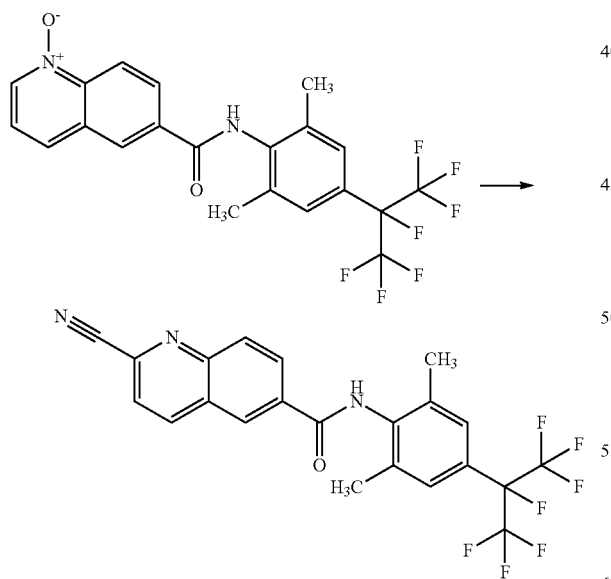

Crude product of N-[4-(1,1,1,2,3,3,3-heptafluoropropan-2-yl)-2,6-dimethylphenyl]quinoline-6-carboxamide-1-oxide (0.18 g) was dissolved in tetrahydrofuran. Trimethylsilylnitrile (0.14 g) and 1,8-diazacyclo[5.4.0]undec-7-ene (0.24 g) were added to this solution and stirred for 5 hours under heating at 70° C. Water was added to the reaction solution and extraction was carried out twice using ethyl acetate. The organic phases were combined and washed with water, and dried over anhydrous magnesium sulfate. The drying agent (anhydrous magnesium sulfate) was removed by filtration and the solvent was distilled off under the reduced pressure. The residue was purified by column chromatography to obtain 2-cyano-N-[4-(1,1,1,2,3,3,3-heptafluoropropan-2-yl)-2,6-dimethylphenyl]quinoline-6-carboxamide (0.13 g, yield 72%).

$^1$H-NMR: see Table 7.

Synthetic Example 4

Synthesis of N-[4-(1,1,1,2,3,3,3-heptafluoropropan-2-2,6-dimethylphenyl]-2-(trifluormethyl)quinoline-6-carboxamide (Compound No. 2-19):

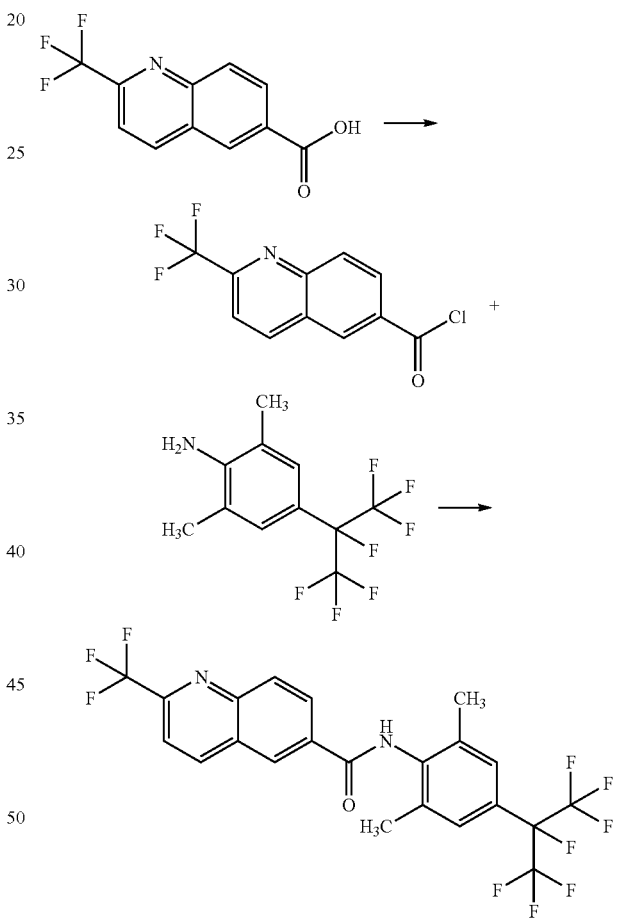

The reaction material of 2-(trifluoromethyl)quioline-6-carboxylic acid can be synthesized according to the method described in the patent document (International Publication No. 08/059370).

2-(Trifluoromethyl)quinoline-6-carboxylic acid (0.20 g) was dissolved in dichloromethane. To this solution, a small amount of N,N-dimethylformamide (300 μL) and oxalyl chloride (0.17 g) were added at room temperature and stirred for two hours. After refluxing for 20 minutes, the solvent was distilled off under the reduced pressure and 2-(trifluoromethyl)quinoline-6-carbonyl chloride was obtained as a crude product. To this crude product, 4-(1,1,1,2,3,3,3-heptafluoropropan-2-yl)-2,6-dimethylaniline (0.49 g) dissolved in pyridine was added and refluxed for 5 hours. The reaction solution was diluted with water and extracted twice with ethyl acetate. The organic phases were combined and washed with 1N hydrochloric acid and water, and dried over anhydrous magnesium sulfate. The drying agent (anhydrous magnesium sulfate) was removed by filtration and the solvent was distilled off under the reduced pressure. The residue was purified by column chromatography to obtain N-[4-(1,1,1,2,3,3,3-heptafluoropropan-2-yl)-2,6-dimethylphenyl]-2-(trifluoromethyl)quinoline-6-carboxamide (0.10 g, yield 24%).
$^1$H-NMR: see Table 7.

Synthetic Example 5

Synthesis of 3-chloro-N-[4-(1,1,1,2,3,3,3-heptafluoropropan-2-yl)-2,6-dimethylphenyl]quinoline-6-carboxamide (Compound No. 2-213) and 3,8-dichloro-N-[4-(1,1,1,2,3,3,3-heptafluoropropan-2-yl)-2,6-dimethylphenyl]quinoline-6-carboxamide (Compound No. 2-2.14)

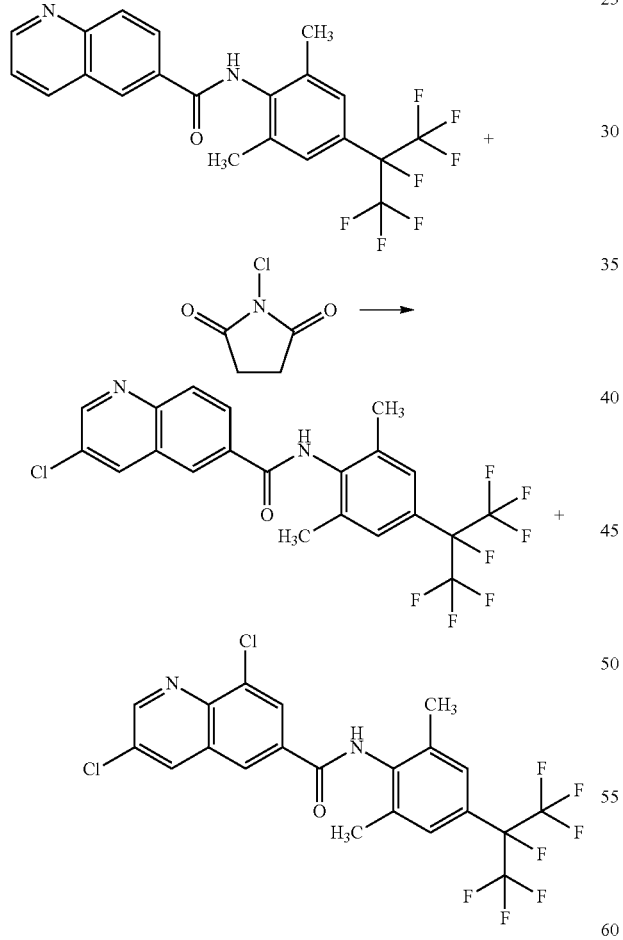

N-[4-(1,1,1,2,3,3,3-Heptafluoropropan-2-yl)-2,6-dimethylphenyl]quinoline-6-carboxamide (250 mg) was dissolved in acetic acid (20 ml), added with N-chlorosuccinimide (160 mg), and stirred at 110° C. for hours. After cooling to room temperature, the reaction solution was added with water and extracted twice with ethyl acetate. The organic layer was combined, neutralized with aqueous solution of sodium hydrogen carbonate, and dried over anhydrous magnesium sulfate. The drying agent was filtered off and the solvent was removed by distillation under the reduced pressure. The resulting residues were purified by column chromatography to obtain 3-chloro-N-[4-(1,1,1,2,3,3,3-heptafluoropropan-2-yl)-2,6-dimethylphenyl]quinoline-6-carboxamide (90 mg, 33%) and 3,8-dichloro-N-[4-(1,1,1,2,3,3,3-heptafluoropropan-2-yl)-2,6-dimethylphenyl]quinoline-6-carboxamide (25 mg, 8%).
$^1$H-NMR: see Table 7.

Synthetic Example 6

Synthesis of N-[2-bromo-4-(1-bromo-1,1,2,3,3,3-hexafluoropropan-2-yl)-6-(difluoromethoxy)phenyl]-2-cyanoquinoline-6-carboxamide (Compound No. 2-203)

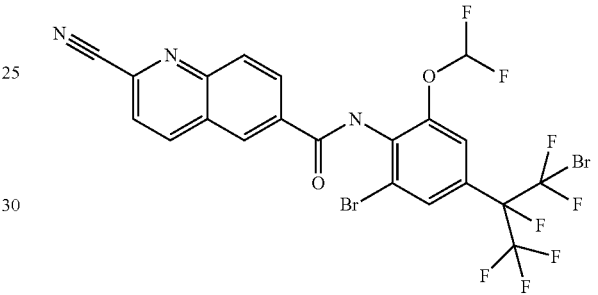

Step 6-1

Synthesis of 4-(1-bromo-1,1,2,3,3,3-hexafluoropropan-2-yl)-6-(difluoromethoxy)aniline (Compound No. b-6)

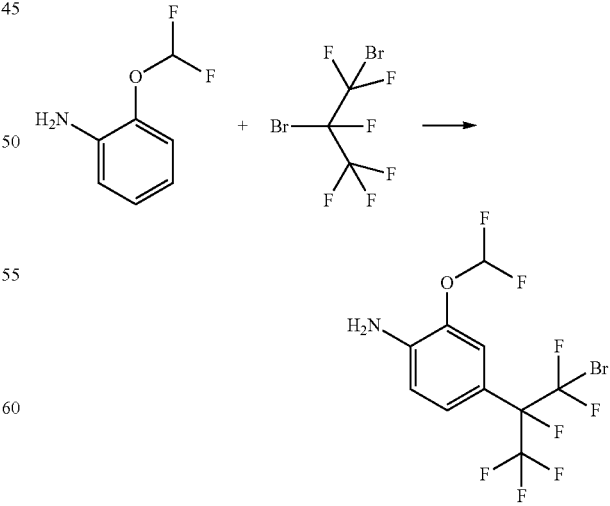

2-(Difluoromethoxy)aniline (1280 mg) and 1,2-dibromo-1,1,2,3,3,3-hexafluoropropane (8610 mg) were dissolved in tert-butylmethyl ether (30 ml) and water (30 ml), and added with tetrabutylammonium hydrogen sulfate salt (270 mg), sodium hydrogen carbonate (2030 mg) and sodium dithionite (4200 mg) in order. The mixture was stirred vigorously at room temperature for 2 days. The reaction solution was extracted twice with ethyl acetate. The organic phases were combined and washed with water, and dried over anhydrous magnesium sulfate. The drying agent was filtered off and the solvent was removed by distillation under the reduced pressure. The resulting residues were purified by column chromatography to obtain 1-(1-bromo-1,1,2,3,3,3-hexafluoropropan-2-yl)-6-(difluoromethoxy)aniline (810 mg, 26%).

$^1$H-NMR: see Table 7.

Step 6-2

Synthesis of 2-bromo-4-(1-bromo-1,1,2,3,3,3-hexafluoropropan-2-yl)-6-(difluoromethoxy)aniline (Compound No. b-8)

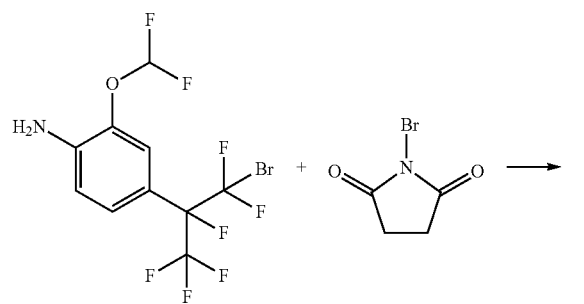

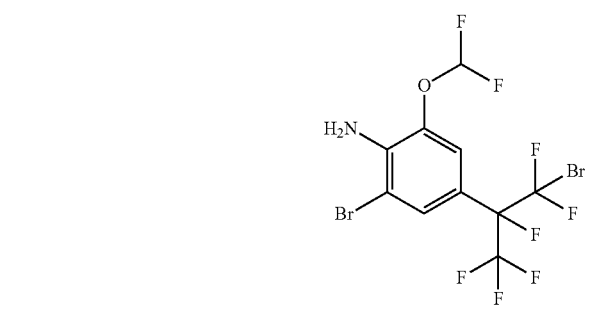

4-(1-Bromo-1,1,2,3,3,3-hexafluoropropan-2-yl)-6-(difluoromethoxy)aniline (810 mg) was dissolved in acetic acid, added with N-bromosuccinimide (390 mg), and stirred at 70° C. for 3 hours. Water was added to the reaction solution and extraction was carried out twice using ethyl acetate. The organic phases were combined and neutralized with sodium hydrogen carbonate solution and dried over anhydrous magnesium sulfate. The drying agent was filtered off and the solvent was removed by distillation under the reduced pressure. The resulting residues were purified by column chromatography to obtain 2-bromo-4-(1-bromo-1,1,2,3,3,3-hexafluoroprop-2-yl)-6-(difluoromethoxy)aniline (730 mg, 75%).

$^1$H-NMR: see Table 7.

Step 6-3

Synthesis of N-[2-bromo-4-(1-bromo-1,1,2,3,3,3-hexafluoropropan-2-yl)-6-(difluoromethoxy)phenyl]quinoline-6-carboxamide (Compound No. 2-201)

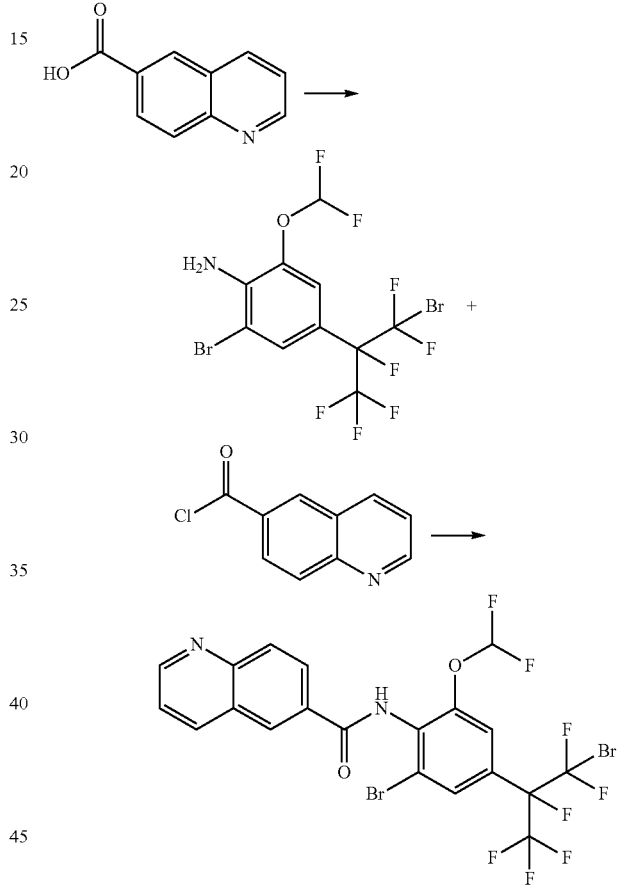

Quinoline-6-carboxylic acid (1.4 g) was dissolved in dichloromethane (50 ml). N,N-dimethylformamide (100 μL) and oxalyl chloride (1.6 g) were added to this solution at room temperature and stirred for two hours followed by reflux for 20 minutes. The solvent was removed by distillation under the reduced pressure to obtain crude quinoline-6-carbonyl chloride. It was dissolved in pyridine and added to 2-bromo-4-(1-bromo-1,1,2,3,3,3-hexafluoropropan-2-yl)-6-(difluoromethoxy)aniline (0.73 g) also dissolved in pyridine, and the resulting mixture was heated under reflux for 5 hours. After cooling to room temperature, the reaction solution was diluted with 1 N hydrochloric acid and extracted twice with ethyl acetate. The solvent was removed by distillation under the reduced pressure. The resulting residues were dissolved in tetrahydrofuran (30 ml), added with 1 M aqueous solution of lithium hydroxide (50 ml), and stirred at room temperature for 2 hours. The reaction solution was extracted twice with ethyl acetate. The organic phases were combined, washed with water, and dried over anhydrous magnesium sulfate. The drying agent (anhydrous magnesium sulfate) was removed by filtration and the solvent was distilled off under the reduced pressure. The resulting residues were purified by column chromatography to obtain N-[2-bromo-4-(1-bromo-1,1,2,3,3,3-hexafluoropropan-2-yl)-6-(difluoromethoxy)phenyl]quinoline-6-carboxamide (0.84 g, 86%).

1H-NMR: see Table 7.

Step 6-4

Synthesis of N-[2-bromo-4-(1-bromo-1,1,2,3,3,3-hexafluoropropan-2-yl)-6-(difluoromethoxy)phenyl]quinoline-6-carboxamide 1-oxide (Compound No. 2-202)

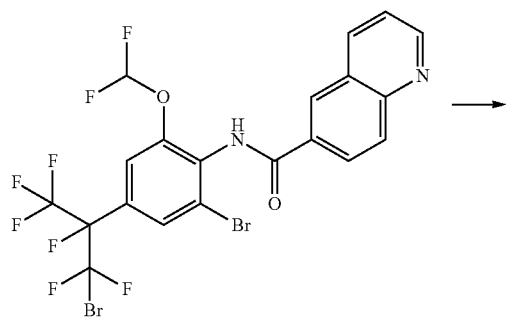

N-[2-Bromo-4-(1-bromo-1,1,2,3,3,3-hexafluoropropan-2-yl)-6-(difluoromethoxy)phenyl]-quinoline-6-carboxamide (0.73 g) was dissolved in dichloromethane (50 ml), added with 3-chloroperbenzoic acid (purity 70%, 0.48 g), and sited at room temperature for S hours. The solvent was distilled off under the reduced pressure and the residue was dissolved in ethyl acetate, Sodium hydrocarbonate solution and potassium carbonate were added thereto. After extracting the mixture twice with ethyl acetate, the organic phases were combined and washed with water, and dried over anhydrous magnesium sulfate. The drying agent (anhydrous magnesium sulfate) was filtered off and the solvent was removed by distillation under the 1.5 reduced pressure to obtain N-[2-bromo-4-(1-bromo-1,1,2,3,3,3-hexafluoropropan-2-yl)-6-(difluoromethoxy)phenyl]quinoline-6-carboxamide-1-oxide (0.81 g, 98%).

1H-NMR: see Table 7.

Step 6-5

Synthesis of N-[2-bromo-4-(1-bromo-1,1,2,3,3,3-hexafluoropropan-2-yl)-6-(difluoromethoxy)phenyl]-2-cyanoquinoline-6-carboxamide (Compound No. 2-203)

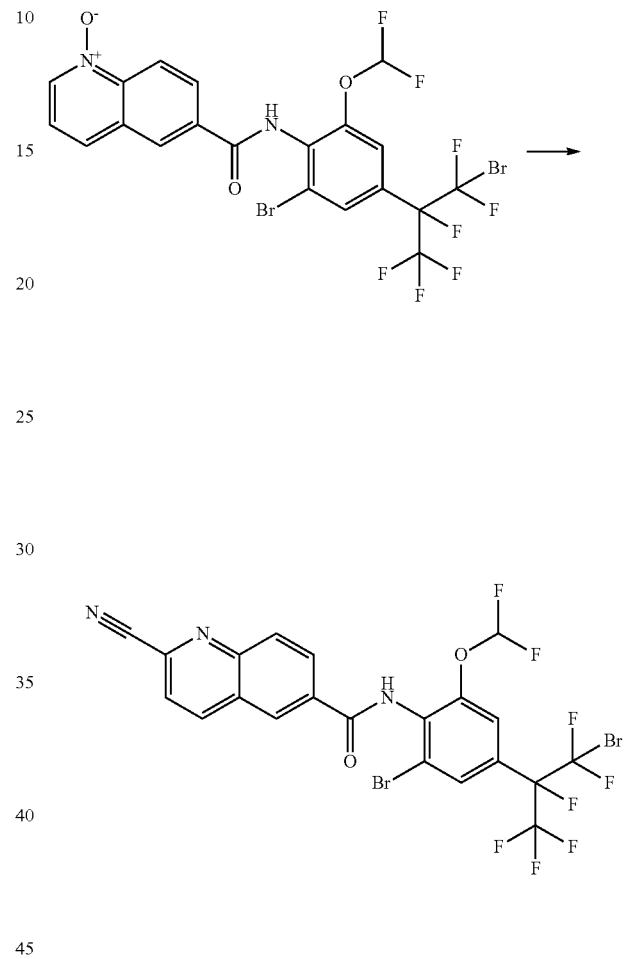

N-[2-Bromo-4-(1-bromo-1,1,2,3,3,3-hexafluoropropan-2-yl)-6-(difluoromethoxy)phenyl]-quinoline-6-carboxamide-1-oxide (0.41 g) was dissolved in tetrahydrofuran (50 ml), added with trimethylsilylnitrile (0.23 g) and 1,8-diazabicyclo[5.4.0]undec-7-ene (0.39 g), and stirred at 60° C. for 5 hours. Water was added to the reaction solution and extraction was carried out twice using ethyl acetate. The organic phases were combined and washed with water, and dried over anhydrous magnesium sulfate. The drying agent (anhydrous magnesium sulfate) was removed by filtration and the solvent was distilled off under the reduced pressure. The resulting residues were purified by column chromatography to obtain N-[2-bromo-4-(1-bromo-1,1,2,3,3,3-hexafluoropropan-2-yl)-6-(difluoromethoxy)phenyl]-2-cyanoquinoline-6-carboxamide (0.15 g, 36%).

1H-NMR: see Table 7.

Synthetic Example 7

Synthesis of N-[2-bromo-6-(difluoromethoxy)-4-(1,1,1,2,3,3,4,4,4-nonafluorobutan-2-yl)phenyl]-2-cyanoquinoline-6-carboxamide (Compound No. 2-173)

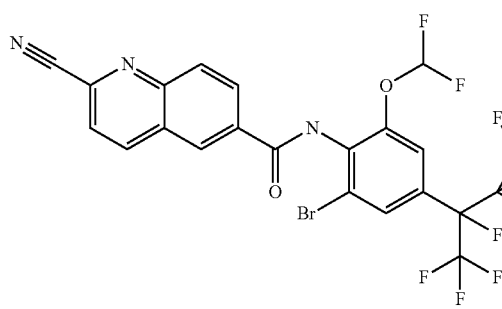

Step 7-1

Synthesis of 4-(1,1,1,2,3,3,4,4,4-Nonafluorobutan-2-yl)-6-(difluoromethoxy)aniline (Compound No. c-5)

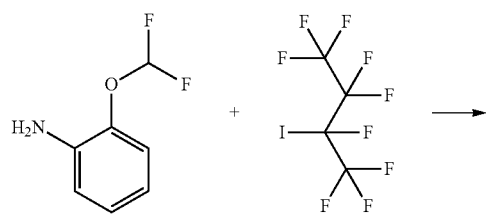

By using 1,1,1,2,2,3,4,4,4-nonafluoro-3-iodobutane instead of 1,2-dibromo-1,1,2,3,3,3-hexafluoropropane, the title compound was obtained according to the method of Step 6-1 of Synthetic example 6.

$^1$H-NMR: see Table 7.

Step 7-2

Synthesis of 2-bromo-4-(1,1,1,2,3,3,4,4,4-nonafluorobutan-2-yl)-6-(difluoromethoxy)aniline (Compound No. c-7)

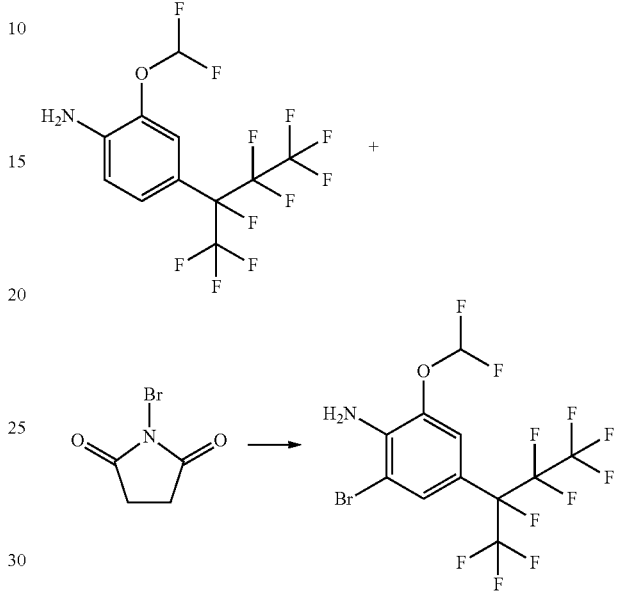

The title compound was obtained from 4-(1,1,1,2,3,3,4,4,4-nonafluorobutan-2-yl)-6-(difluoromethoxy)aniline, which had been obtained in Step 7-1, according to the method of Step 6-2 of Synthetic example 6.

$^1$H-NMR: see Table 7.

Step 7-3

Synthesis of N-[2-bromo-(1,1,1,2,3,3,4,4,4-nonafluorobutan-2-yl)-6-(difluoromethoxy)phenyl]quinoline-6-carboxamide (Compound No. 2-171)

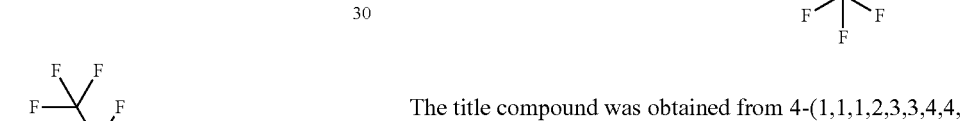

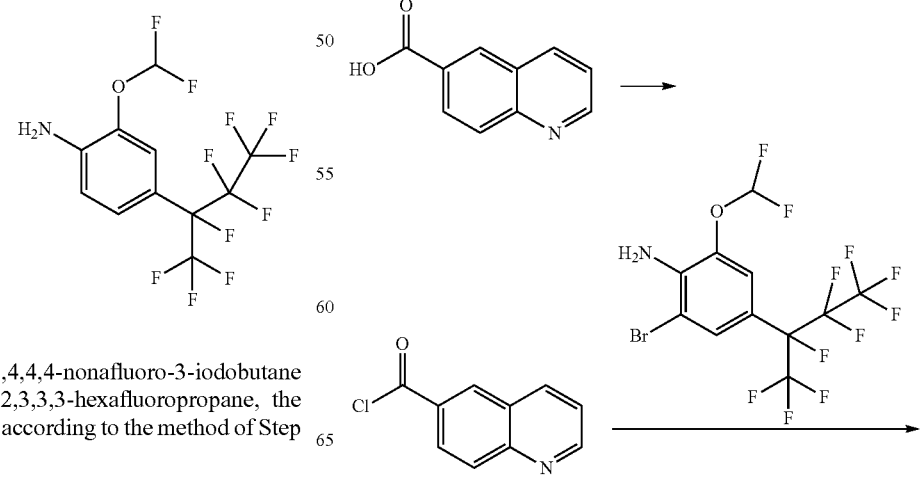

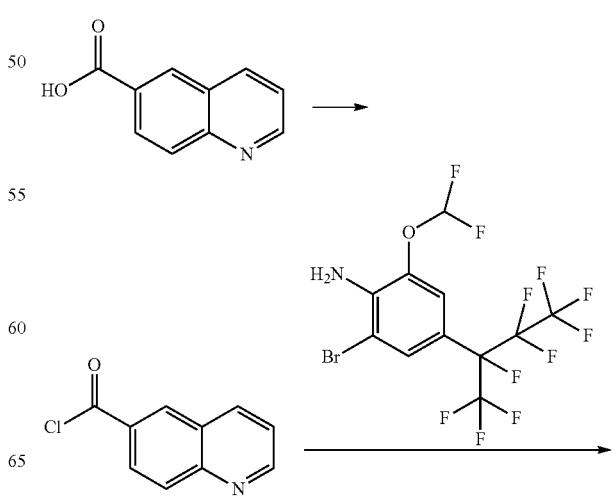

-continued

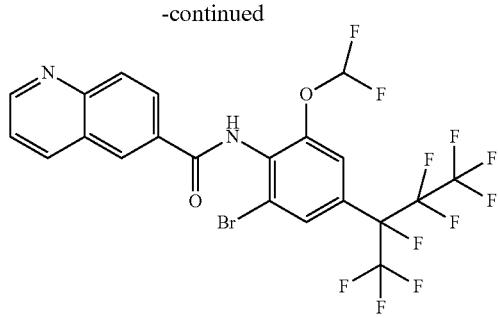

The title compound was obtained from 2-bromo-4-(1,1,1,2,3,4,4,4-nonafluorobutan-2-yl)-6-(difluoromethoxy)aniline, which had been obtained in Step 7-2, according to the method of Step 6-3 of Synthetic example 6.
$^1$H-NMR: see Table 7.

Step 7-4

Synthesis of N-[2-bromo-4-(1,1,1,2,3,3,4,4,4-nonafluorobutan-2-yl)-6-(difluoromethoxy)phenyl]quinoline-6-carboxamide 1-oxide (Compound No. 2-172)

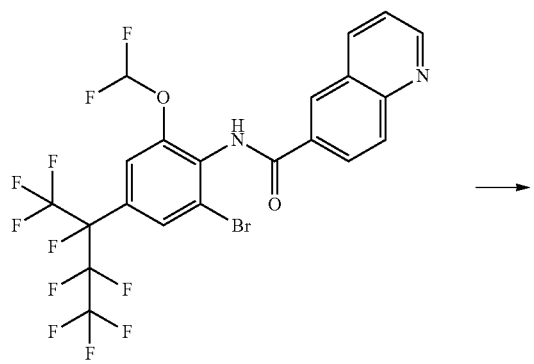

The title compound was obtained from N-[2-bromo-(1,1,1,2,3,3,4,4,4-nonafluorobutan-2-yl)-6-(difluoromethoxy)phenyl]quinoline-6-carboxamide, which had been obtained in Step 7-3, according to the method of Step 6-4 of Synthetic example 6.
$^1$H-NMR: see Table 7.

Step 7-5

Synthesis of N-[2-bromo-4-(1,1,1,2,3,3,4,4,4-nonafluorobutan-2-yl)-6-(difluoromethoxy)phenyl]-2-cyanoquinoline-6-carboxamide (Compound No. 2-173)

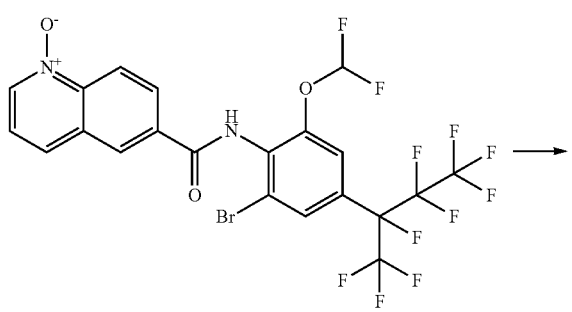

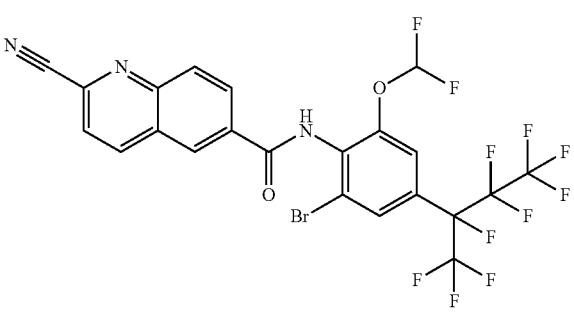

The title compound was obtained from N-[2-bromo-4-(1,1,1,2,3,3,4,4,4-nonafluorobutan-2-yl)-6-(difluoromethoxy)phenyl]quinoline-6-carboxamide 1-oxide, which had been obtained in Step 7-4, according to the method of Step 6-5 of Synthetic example 6.
$^1$H-NMR: see Table 7.

Synthetic Example 8

Synthesis of 2-cyano-N-[2-(difluoromethoxy)-6-iodo-4-(1,1,1,2,3,3,4,4,4-nonafluorobutan-2-yl)phenyl]-quinoline-6-carboxamide (Compound No. 2-176):

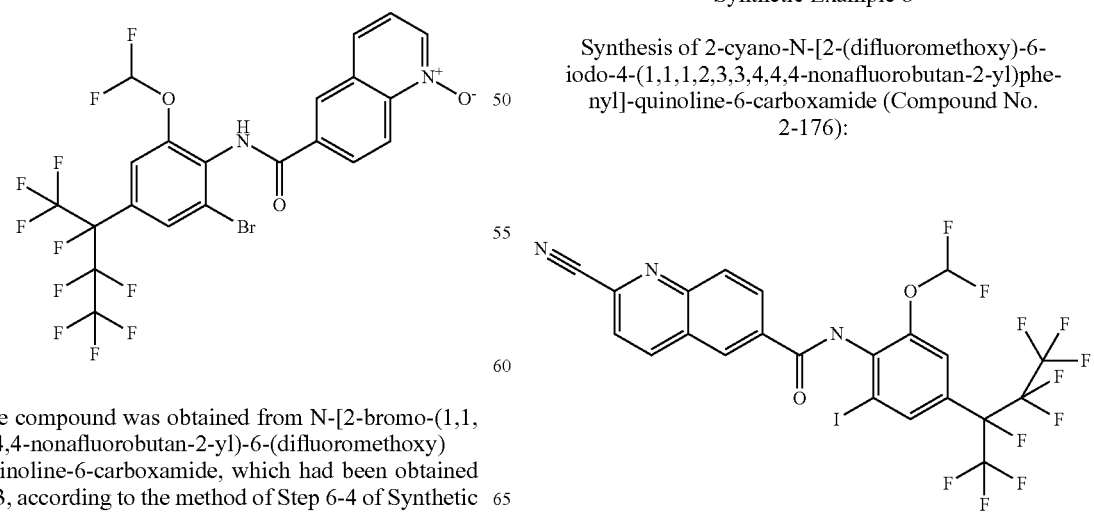

Step 8-1

Synthesis of 2-(difluoromethoxy)-6-iodo-4-(1,1,1,2,3,3,4,4,4-nonafluorobutan-2-yl)aniline (Compound No. c-8)

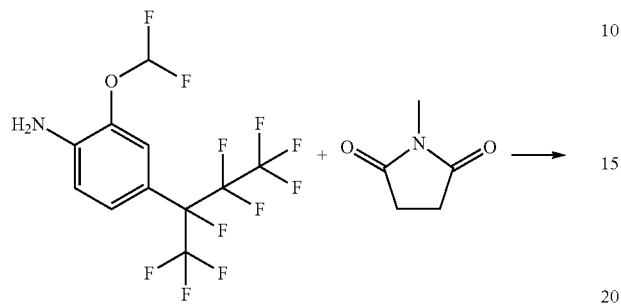

By using N-iodosuccinimide instead of N-bromosuccinimide, the title compound was obtained from 4-(1,1,1,2,3,3,3,4,4,4-nonafluorobutan-2-yl)-6-(difluoromethoxy)aniline, which had been obtained in Step 7-1 of Synthetic example 7, according to the method of Step 6-2 of Synthetic example 6.

$^1$H-NMR: see Table 7.

Step 8-2

Synthesis of N-[2-(difluoromethoxy)-6-iodo-4-(1,1,1,2,3,3,4,4,4-nonafluorobutan-2-yl)phenyl]quinoline-6-carboxamide (Compound No. 2-174)

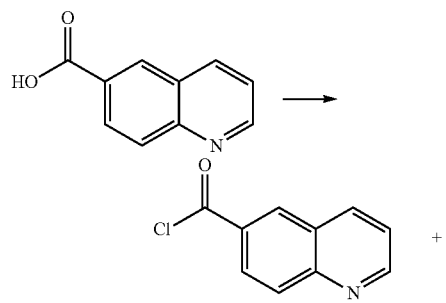

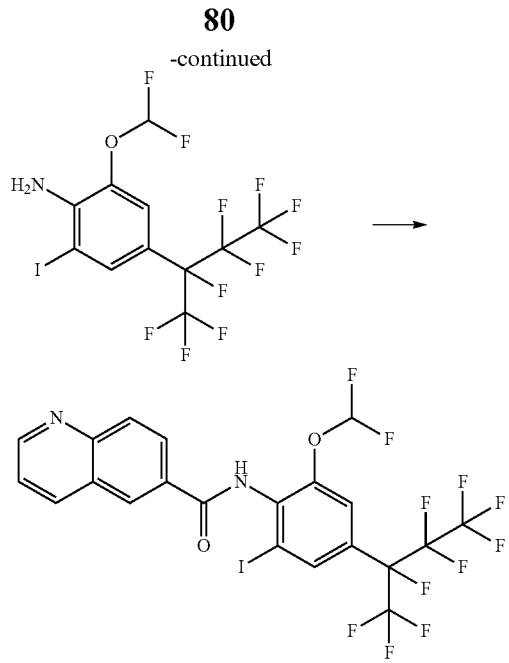

The title compound was obtained from 2-(difluoromethoxy)-6-iodo-4-(1,1,1,2,3,3,4,4,4-nonafluorobutan-2-yl)aniline, which had been obtained in Step 8-1, according to the method of Step 6-3 of Synthetic example 6.

$^1$H-NMR: see Table 7.

Step 8-3

Synthesis of N-[2-(difluoromethoxy)-6-iodo-4-(1,1,1,2,3,3,4,4,4-nonafluorobutan-2-yl)phenyl]quinoline-6-carboxamide N-oxide (Compound No. 2-175)

The title compound was obtained from N-[2-(difluoromethoxy)-6-iodo-4-(1,1,1,2,3,3,4,4,4-nonafluorobutan-2- yl)phenyl]quinoline-6-carboxamide, which had been obtained in Step 8-2, according to the method of Step 6-4 of Synthetic example 6.

¹H-NMR: see Table 7.

Step 8-4

Synthesis of 2-cyano-N-[2-(difluoromethoxy)-6-iodo-4-(1,1,1,2,3,3,4,4,4-nonafluorobutan-2-yl)phenyl]quinoline-6-carboxamide (Compound No. 2-176)

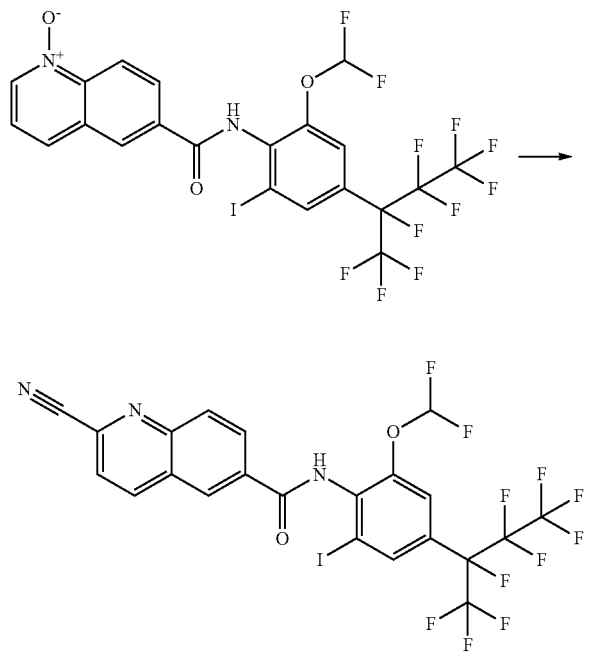 [SMILES: O=C(Nc1c(Br)cc(C(F)(C(F)(F)F)C(F)(F)C(F)(F)F)cc1OC(F)F)c1ccc2c(ccc[n+]2[O-])c1 ; N#Cc1ccc2cc(C(=O)Nc3c(Br)cc(C(F)(C(F)(F)F)C(F)(F)C(F)(F)F)cc3OC(F)F)ccc2n1]

The title compound was obtained from N-[2-(difluoromethoxy)-6-iodo-4-(1,1,1,2,3,3,4,4,4-nonafluorobutan-2-yl)phenyl]-quinoline-6-carboxamide N-oxide, which had been obtained in Step 8-3, according to the method of Step 6-5 of Synthetic example 6.

¹H-NMR: see Table 7.

Synthetic Example 9

Synthesis of N-[2-bromo-6-(difluoromethoxy)-4-(1,1,1,2,3,3,3-heptafluoropropan-2-yl)phenyl]-2-cyano-quinoline-6-carboxamide (Compound No. 2-154)

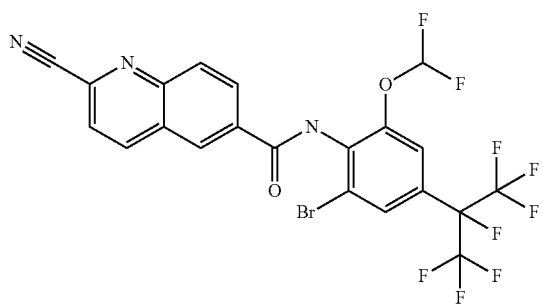 [SMILES: N#Cc1ccc2cc(C(=O)Nc3c(Br)cc(C(F)(C(F)(F)F)C(F)(F)F)cc3OC(F)F)ccc2n1]

Step 9-1

Synthesis of 4-(1,1,1,2,3,3,3-heptafluoropropan-2-yl)-6-(difluoromethoxy)aniline (Compound No. c-1)

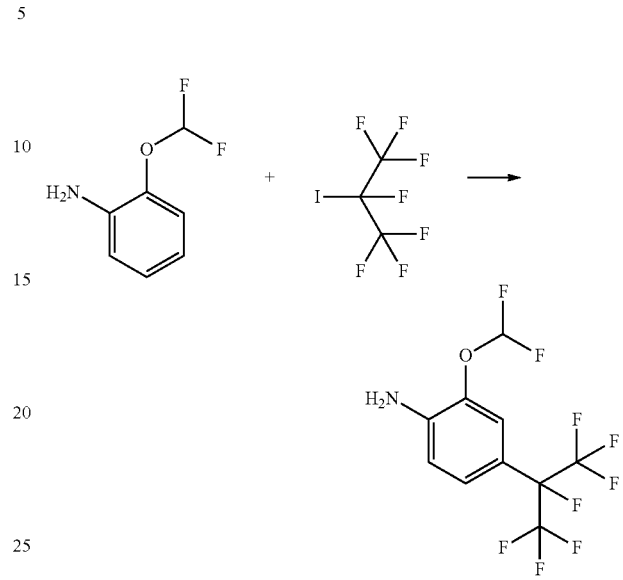

By using 1,1,1,2,3,3,3-heptafluoro-2-iodopropane instead of 1,2-dibromo-1,1,2,3,3,3-hexafluoropropane, the title compound was obtained according to the method of Step 6-1 of Synthetic example 6.

¹H-NMR: see Table 7.

Step 9-2

Synthesis of 2-bromo-4-(1,1,1,2,3,3,3-heptafluoropropan-2-yl)-6-(difluoromethoxy)aniline (Compound No. c-3):

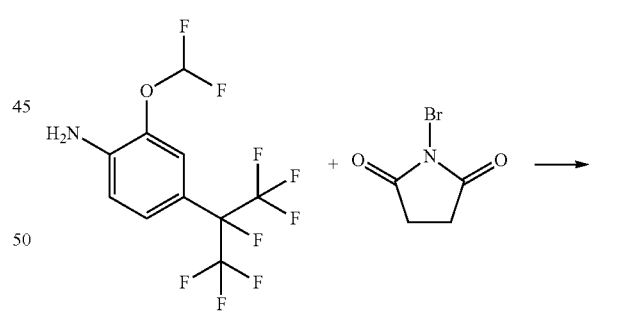

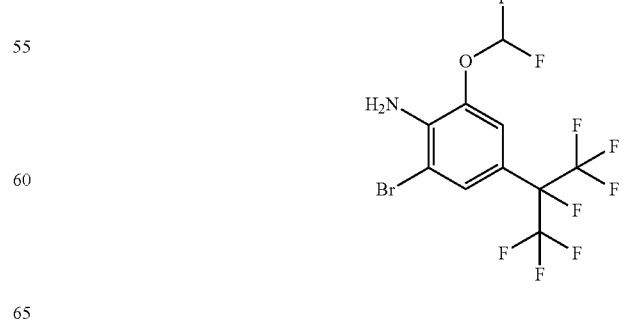

The title compound was obtained from 4-(1,1,1,2,3,3,3-heptafluoropropan-2-yl)-6-(difluoromethoxy)aniline, which had been obtained in Step 9-1, according to the method of Step 6-2 of Synthetic example 6.

¹H-NMR: see Table 7.

Step 9-3

Synthesis of N-[2-bromo-(1,1,1,2,3,3,3-heptafluoro-propan-2-yl)-6-(difluoromethoxy)phenyl]quinoline-6-carboxamide (Compound No. 2-152):

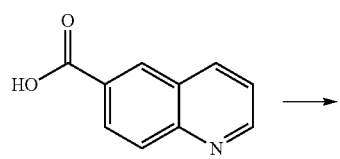

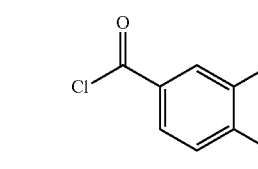

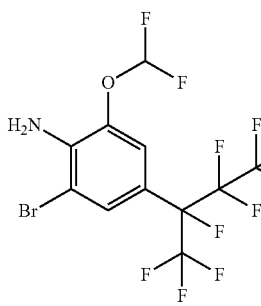

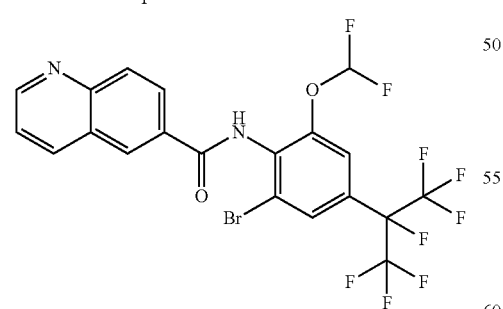

The title compound was obtained from 2-bromo-4-(1,1,1,2,3,3,3-heptafluoropropan-2-yl)-6-(difluoromethoxy) aniline, which had been obtained in Step 9-2, according to the method of Step 6-3 of Synthetic example 6.

¹H-NMR: see Table 7.

Step 9-4

Synthesis of N-[2-bromo-(1,1,1,2,3,3,3-heptafluoro-propan-2-yl)-6-(difluoromethoxy)phenyl]quinoline-6-carboxamide 1-oxide (Compound No. 2-153)

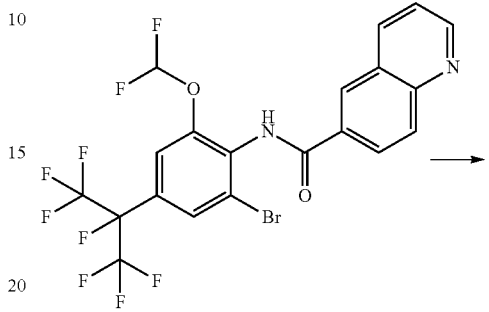

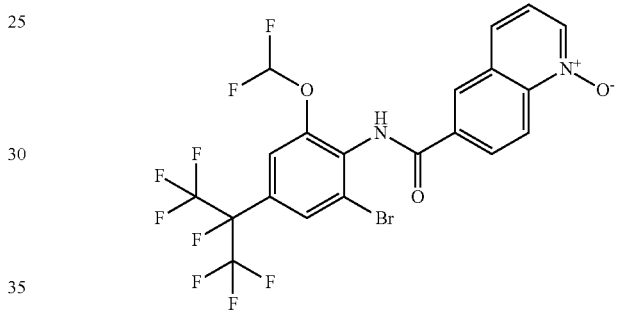

The title compound was obtained from N-[2-bromo-(1,1,1,2,3,3,3-heptafluoropropan-2-yl)-6-(difluoromethoxy)phenyl]quinoline-6-carboxamide, which had been obtained in Step 9-3, according to the method of Step 6-4 of Synthetic example 6.

¹H-NMR: see Table 7.

Step 9-5

Synthesis of N-[2-bromo-4-(1-bromo-1,1,2,3,3,3-hexafluoropropan-2-yl)-6-(difluoromethoxy)phenyl]-2-cyanoquinoline-6-carboxamide (Compound No. 2-154)

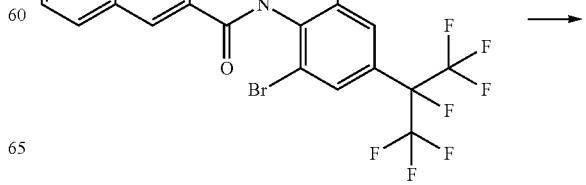

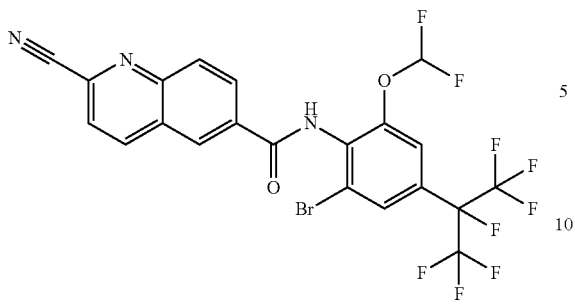

The title compound was obtained from N-[2-bromo-(1,1,1,2,3,3,3-heptafluoropropan-2-yl)-6-(difluoromethoxy)phenyl]quinoline-6-carboxamide 1-oxide, which had been obtained in Step 9-4, according to the method of Step 6-5 of Synthetic example 6.

¹H-NMR: see Table 7.

Synthetic Example 10

Synthesis of N-[2-chloro-6-(difluoromethoxy)-4-(1,1,1,2,3,3,3-heptafluoropropan-2-yl)phenyl]-2-cyano-quinoline-6-carboxamide (Compound No. 2-229)

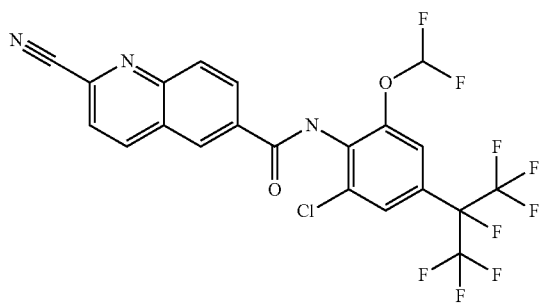 [SMILES: N#Cc1ccc2cc(C(=O)Nc3c(Cl)cc(C(F)(C(F)(F)F)C(F)(F)F)cc3OC(F)F)ccc2n1]

Step 10-1

Synthesis of 2-chloro-4-(1,1,1,2,3,3,3-heptafluoropropan-2-yl)-6-(difluoromethoxy)aniline (Compound No. c-2)

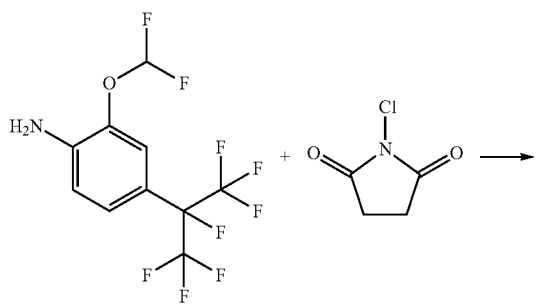

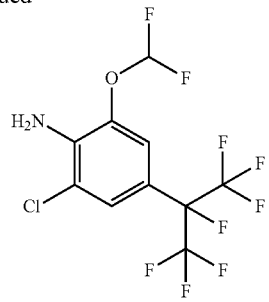

By using chlorosuccinimide instead of bromosuccinimide, the title compound was obtained from 4-(1,1,1,2,3,3,3-heptafluoropropan-2-yl)-6-(difluoromethoxy)aniline, which had been obtained in Step 9-1 of Synthetic example 9, according to the method of Step 6-2 of Synthetic example 6.

¹H-NMR: see Table 7.

Step 10-2

Synthesis of N-[2-chloro-(1,1,1,2,3,3,3-heptafluoropropan-2-yl)-6-(difluoromethoxy)phenyl]quinoline-6-carboxamide (Compound No. 2-229):

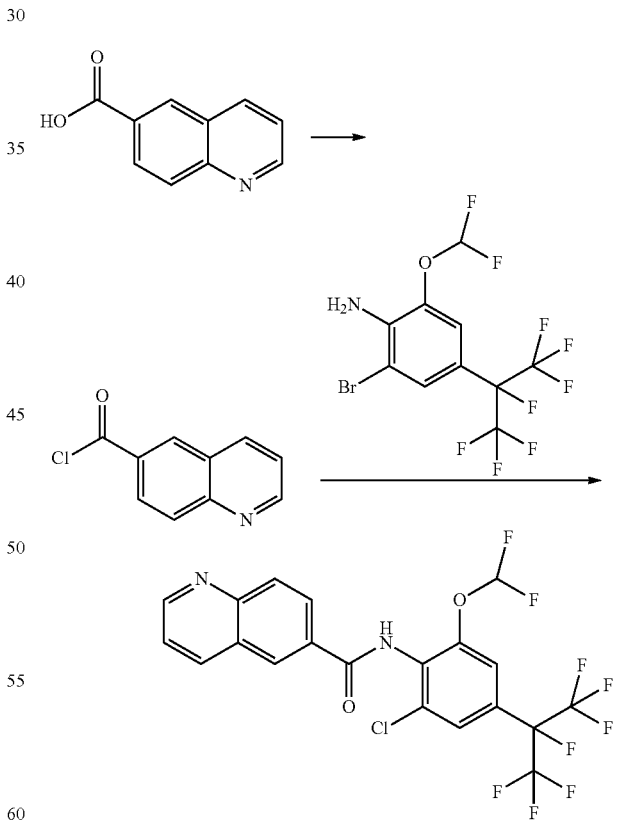

The title compound was obtained irom 2-chloro-4-(1,1,1,2,3,3,3-heptafluoropropan-2-yl)-6-(difluoromethoxy)aniline, which had been obtained in Step 10-1, according to the method of Step 6-3 of Synthetic example 6.

¹H-NMR: see Table 7.

Step 10-3

Synthesis of N-[2-chloro-(1,1,1,2,3,3,3-heptafluoropropan-2-yl)-6-(difluoromethoxy)phenyl]quinoline-6-carboxamide 1-oxide (Compound No. 2-230)

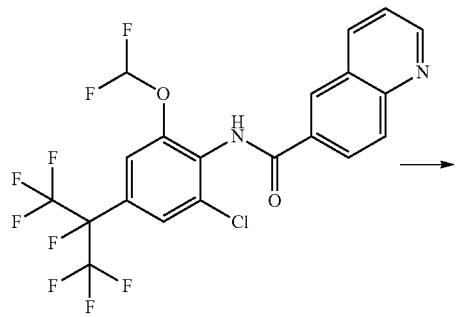

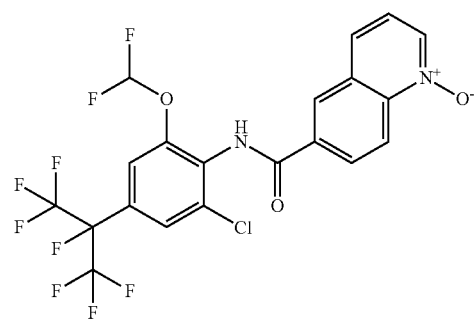

The title compound was obtained from N-[2-chloro-(1,1,1,2,3,3,3-heptafluoropropan-2-yl) 6-(difluoromethoxy)phenyl]quinoline-6-carboxamide, which had been obtained in Step 10-2, according to the method of Step 6-4 of Synthetic example 6.

¹H-NMR: see Table 7.

Step 10-4

Synthesis of N-[2-chloro-4-(1-bromo-1,1,1,2,3,3,3-heptafluoropropan-2-yl)-6-(difluoromethoxy)phenyl]-2-cyanoquinoline-6-carboxamide (Compound No. 2-231)

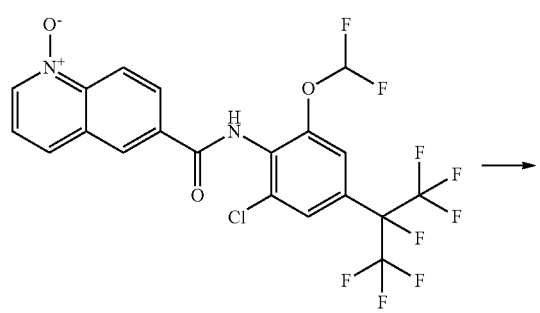

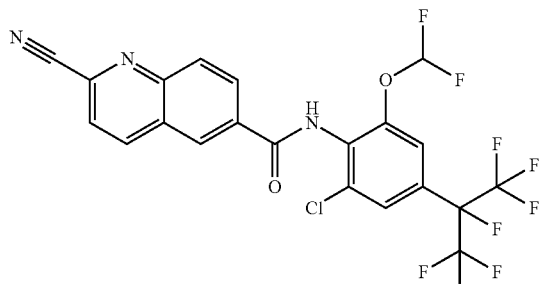

The title compound was obtained from N-[2-chloro-(1,1,1,2,3,3,3-heptafluoropropan-2-yl)-6-(difluoromethoxy)phenyl]quinoline-6-carboxamide 1-oxide, which had been obtained in Step 10-3, according to the method of Step 6-5 of Synthetic example 6.

¹H-NMR: see Table 7.

Synthetic Example 11

Synthesis of 4-bromo-2-cyano-N-[2-ethyl-6-methyl-4-(1,1,1,2,3,3,4,4,4-nonafluorobutan-2-yl)phenyl]quinoline-6-carboxamide (Compound No. 2-269)

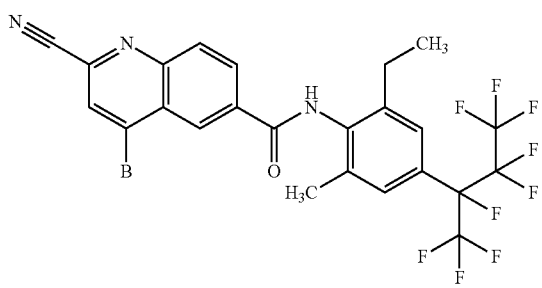

Step 11-1

Synthesis of 2-cyano-N-[2-ethyl-6-methyl-4-(1,1,1,2,3,3,4,4,4-nonafluorobutan-2-yl)phenyl]quinoline-6-carboxamide-1-oxide (Compound No. 2-268)

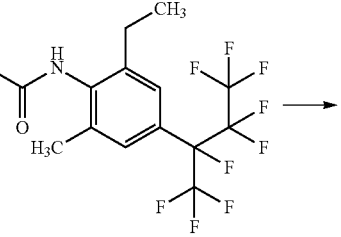

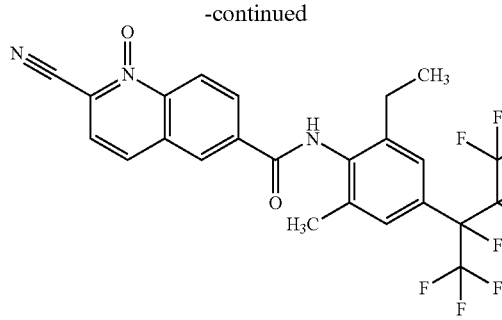

2-Cyano-N-[2-ethyl-6-methyl-4-(1,1,1,2,3,3,4,4,4-nonafluorobutan-2-yl)phenyl]quinoline-6-carboxamide (240 mg) was dissolved in dichloromethane, added with urea-hydrogen peroxide adduct (85 mg) and trifluoroacetic anhydride (190 mg), and stirred at room temperature for 20 hours. The reaction solution was concentrated under the reduced pressure, and the resulting residues were dissolved in ethyl acetate. The solution was washed with water and dried over anhydrous magnesium sulfate. The drying agent was filtered off and the solvent was removed by distillation under the reduced pressure. The resulting residues were purified by column chromatography to obtain 2-cyano-N-[2-ethyl-6-methyl-4-(1,1,1,2,3,3,4,4,4-nonafluorobutan-2-yl)phenyl]quinoline-6-carboxamide-1-oxide (0.20 g, 81%).

$^1$H-NMR: see Table 7.

Step 11-2

Synthesis of 4-bromo-2-cyano-N-[2-ethyl-6-methyl-4-(1,1,1,2,3,3,4,4,4-nonafluorobutan-2-yl)phenyl]quinoline-6-carboxamide (Compound No. 2-269)

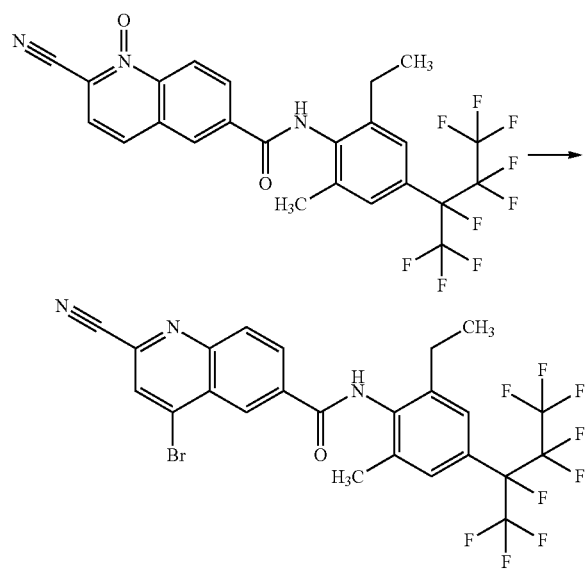

2-Cyano-N-[2-ethyl-6-methyl-4-(1,1,1,2,3,3,4,4,4-nonafluorobutan-2-yl)phenyl]-quinoline-6-carboxamide-1-oxide (96 mg) was dissolved in acetonitrile, added with phosphoryl bromide (250 mg), and stirred at 100° C. for 5 hours. After cooling to room temperature, the reaction solution was poured into ice water and neutralized with sodium hydrogen carbonate. After extracting the mixture twice with ethyl acetate, the organic phases were combined and washed with water, and dried over anhydrous magnesium sulfate. The drying agent was filtered off and the solvent was removed by distillation under the reduced pressure. The resulting residues were purified by column chromatography to obtain 4-bromo-2-cyano-N-[2-ethyl-6-methyl-4-(1,1,1,2,3,3,4,4,4-nonafluorobutan-2-yl)phenyl]quinoline-6-carboxamide (46 mg, 43%).

$^1$H-NMR: see Table 7,

Synthetic Example 12

Synthesis of 2-cyano-N-[2-ethyl-6-methyl-4-(1,1,1,2,3,3,4,4,4-nonafluorobutan-2-yl)phenyl]-1,3-benzothiazole-6-carboxamide (Compound No. 4-34)

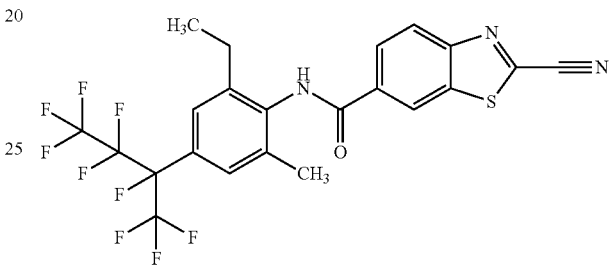

Step 12-1

Synthesis of 3-bromo-4-{[4-chloro-5H-1,2,3-dithiazol-5-ylidene]amino}-N-[2-ethyl-6-methyl-4-(1,1,1,2,3,3,4,4,4-nonafluorobutan-2-yl)phenyl]benzamide

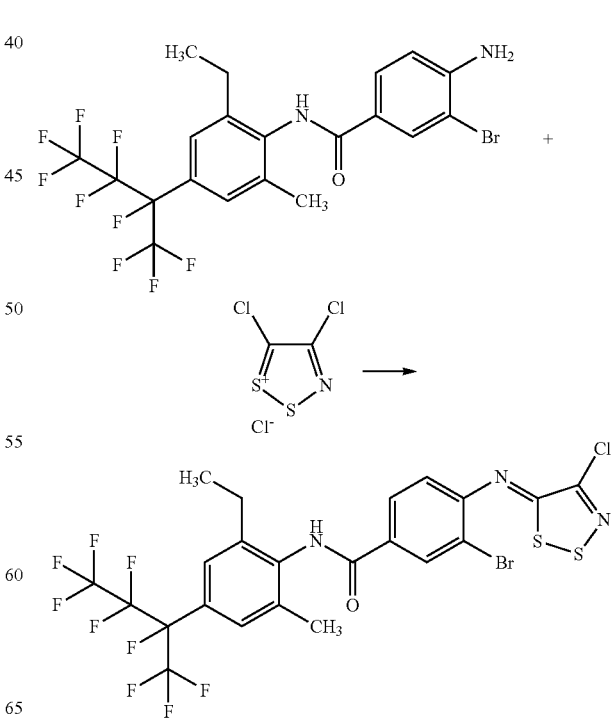

4-amino-3-bromo-N-[2-ethyl-6-methyl-4-(1,1,1,2,3,3,4,4,4-nonafluorobutan-2-yl)phenyl]benzamide (0.254 g) was dissolved in tetrahydrofuran (20 ml). To the mixture was added 4,5-dichloro-1,2,3-dithiazol-1-ium chloride (0.106 g), and stirred at room temperature for 2 hours. To the reaction mixture was added pyridine (0.091 g) in dichloromethane, and stirred at room temperature for 1 hour. The solvent was removed under reduced pressure. To the residue was added water and extracted twice with ethyl acetate. The organic phases were combined and washed with water, and dried over anhydrous magnesium sulfate. The drying agent (anhydrous magnesium sulfate) was removed by filtration and the solvent was distilled off under the reduced pressure. The residue was purified by column chromatography to obtain 3-bromo-4-{[4-chloro-5H-1,2,3-dithiazol-5-ylidene]amino}-N-[2-ethyl-6-methyl-4-(1,1,1,2,3,3,4,4,4-nonafluorobutan-2-yl)phenyl]benzamide (0.270 g, 85%).
(ref Frere, S. et al., Tetrahedron 2003, 59, 773-779.)

Step 12-2

Synthesis of 2-cyano-N-[2-ethyl-6-methyl-4-(1,1,2,3,3,4,4,4-nonafluorobutan-2-yl)phenyl]-1,3-benzothiazole-6-carboxamide

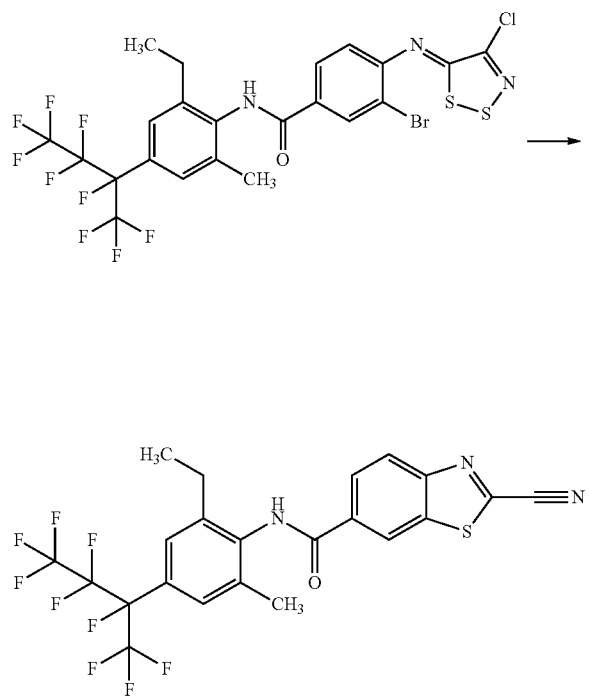

3-bromo-4-{[4-chloro-5H-1,2,3-dithiazol-5-ylidene]amino}-N-[2-ethyl-6-methyl-4-(1,1,1,2,3,3,4,4,4-nonafluorobutan-2-yl)phenyl]benzamide (0.195 g) and copper(I) iodide (0.057 g) were suspended in pyridine (5 ml), and irradiated(150° C., 20 minutes). After cooling, to the reaction mixture was added ethyl acetate. The mixture was washed with 1N hydrochloric acid and water, and dried over anhydrous magnesium sulfate. The drying agent (anhydrous magnesium sulfate) was removed by filtration and the solvent was distilled off under the reduced pressure. The residue was purified by column chromatography to obtain 2-cyano-N-[2-ethyl-6-methyl-4-(1,1,1,2,3,3,4,4,4-nonafluorobutan-2-yl)phenyl]-1,3-benzothiazole-6-carboxamide (0.076 g, 49%).

Synthesis Examples for Novel Intermediates

Synthesis of 4-(undecafluorocyclohexyl)-2,6-bromoaniline (Compound No. a-6)

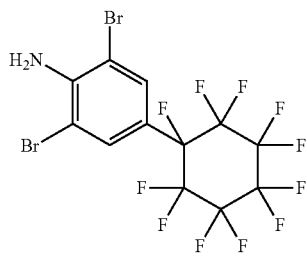 [SMILES: Nc1c(Br)cc(C2(F)C(F)(F)C(F)(F)C(F)(F)C(F)(F)C2(F)F)cc1Br]

Step 1: Synthesis of 4-(undecafluorocyclohexyl)aniline (Compound No. a-1)

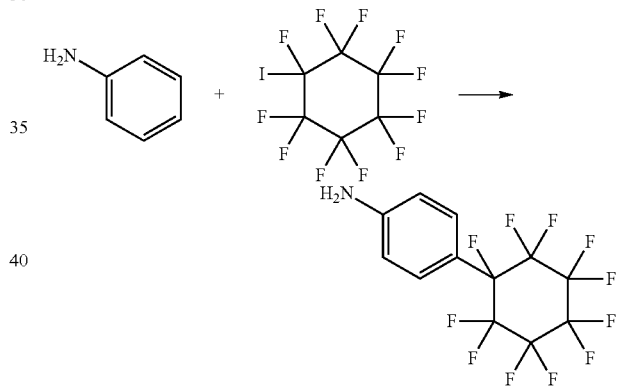

Aniline (1.0 g) was dissolved in tert-butylmethyl ether (15 ml) and water (15 ml), and added with undecafluoroiodocyclohexane (5.5 g), sodium dithionite (2.3 g), sodium hydrogen carbonate (1.1 g) and tetrabutylammonium hydrogen sulfate (0.46 g) in order. The resulting mixture was stirred vigorously at room temperature for 18 hours. After separating the reaction solution, the aqueous phase was extracted twice with ethyl acetate. The organic phases were combined and washed with 2N hydrochloric acid and sodium hydrogen carbonate solution in order, and dried over anhydrous magnesium sulfate, The drying agent (anhydrous magnesium sulfate) was removed by filtration and the solvent was distilled off under the reduced pressure. The residue was purified by column chromatography to obtain 4-(undecafluorocyclohexyl)aniline (2.7 g, yield 68%).

$^1$H-NMR: see Table 7.

Step 2: Synthesis of 4-(undecafluorocyclohexyl)-2,6-dibromoaniline (Compound No. a-6)

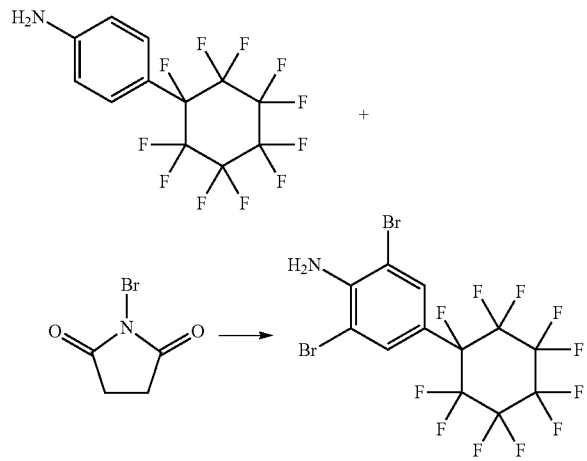

4-(Undecafluorocyclohexyl)aniline (2.7 g) was dissolved in acetic acid (30 ml), and then N-bomosuccinimide (2.4 g) was added thereto, followed by stirring the reaction solution for 2 hours at 60° C. After cooling down to room temperature, the reaction solution was poured into water and extracted twice with ethyl acetate. The organic phases were combined and washed with water and sodium hydrogen carbonate solution, and dried over anhydrous magnesium sulfate. The drying agent (anhydrous magnesium sulfate) was removed by filtration and the solvent was distilled off under the reduced pressure. The residue was purified by column chromatography to obtain 4-(undecafluorocyclohexyl)-2,6-dibromoaniline (3.7 g, yield 96%).

$^1$H-NMR: see Table 7.

The compounds of the Formula (I) and the intermediates of the present invention that are obtained by the same methods as those of the above synthetic examples and according to the methods described above in detail, as well as their physical values are given in Table 1 to 6. Each compound obtained in the above synthetic examples is also shown in a corresponding table.

Abbreviations included in the tables are as follows.

$Ch_3$: methyl, h: hydrogen,

TABLE 1

| Exa | $R^1$ | $R^2$ | J | $R^4$ | $R^5$ | Q | $R^7$ | $R^8$ | $R^9$ | $R^{10}$ |
|---|---|---|---|---|---|---|---|---|---|---|
| 1-1 | $CH_3$ | H | 1,1,1,2,3,3,3-heptafluoropropan-2-yl | H | $CH_3$ | H | H | H | bromo | H |
| 1-2 | $CH_3$ | H | 1,1,1,2,3,3,3-heptafluoropropan-2-yl | H | $CH_3$ | H | H | H | cyano | H |
| 1-3 | $CH_3$ | H | 1,1,1,2,3,3,3-heptafluoropropan-2-yl | H | ethyl | H | H | H | bromo | H |
| 1-4 | $CH_3$ | H | 1,1,1,2,3,3,3-heptafluoropropan-2-yl | H | ethyl | H | H | H | cyano | H |
| 1-5 | $CH_3$ | H | 1,1,1,2,3,3,3-heptafluoropropan-2-yl | H | ethyl | H | H | H | acetamidomethyl | H |
| 1-6 | $CH_3$ | H | 1,1,1,2,3,3,3-heptafluoropropan-2-yl | H | ethyl | H | H | H | acetylamino | H |
| 1-7 | bromo | H | 1,1,1,2,3,3,3-heptafluoropropan-2-yl | H | bromo | H | H | H | cyano | H |
| 1-8 | iodo | H | 1,1,1,2,3,3,3-heptafluoropropan-2-yl | H | iodo | H | H | H | cyano | H |
| 1-9 | $CH_3$ | H | 1,1,1,2,3,3,4,4,4-nonafluorobutan-2-yl | H | $CH_3$ | H | H | H | bromo | H |
| 1-10 | $CH_3$ | H | 1,1,1,2,3,3,4,4,4-nonafluorobutan-2-yl | H | $CH_3$ | H | H | H | cyano | H |
| 1-11 | $CH_3$ | H | 1,1,1,2,3,3,4,4,4-nonafluorobutan-2-yl | H | ethyl | H | H | H | bromo | H |
| 1-12 | $CH_3$ | H | 1,1,1,2,3,3,4,4,4-nonafluorobutan-2-yl | H | ethyl | H | H | H | cyano | H |
| 1-13 | bromo | H | 1,1,1,2,3,3,4,4,4-nonafluorobutan-2-yl | H | bromo | H | H | H | cyano | H |
| 1-14 | iodo | H | 1,1,1,2,3,3,4,4,4-nonafluorobutan-2-yl | H | iodo | H | H | H | cyano | H |
| 1-15 | $CH_3$ | H | undecafluorocyclohexyl | H | $CH_3$ | H | H | H | bromo | H |
| 1-16 | $CH_3$ | H | undecafluorocyclohexyl | H | $CH_3$ | H | H | H | cyano | H |
| 1-17 | $CH_3$ | H | undecafluorocyclohexyl | H | ethyl | H | H | H | bromo | H |
| 1-18 | $CH_3$ | H | undecafluorocyclohexyl | H | ethyl | H | H | H | cyano | H |
| 1-19 | bromo | H | undecafluorocyclohexyl | H | bromo | H | H | H | cyano | H |
| 1-20 | iodo | H | undecafluorocyclohexyl | H | iodo | H | H | H | cyano | H |

TABLE 2

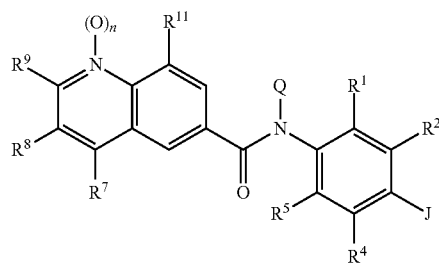

wherein $R^{11}$ are the same as $X^2$.

| Exa | n | $R^1$ | $R^2$ | J | $R^4$ | $R^5$ | Q | $R^7$ | $R^8$ | $R^9$ | $R^{11}$ |
|---|---|---|---|---|---|---|---|---|---|---|---|
| 2-1 | 0 | bromo | H | trifluoromethyl | H | bromo | H | H | H | H | H |
| 2-2 | 1 | bromo | H | trifluoromethyl | H | bromo | H | H | H | H | H |
| 2-3 | 0 | bromo | H | trifluoromethyl | H | bromo | H | H | H | cyano | H |
| 2-4 | 0 | H | H | 1,1,1,2,3,3,3-heptafluoropropan-2-yl | H | H | H | H | H | H | H |
| 2-5 | 1 | H | H | 1,1,1,2,3,3,3-heptafluoropropan-2-yl | H | H | H | H | H | H | H |
| 2-6 | 0 | H | H | 1,1,1,2,3,3,3-heptafluoropropan-2-yl | H | H | H | H | H | cyano | H |
| 2-7 | 0 | H | H | 1,1,1,2,3,3,3-heptafluoropropan-2-yl | H | $CH_3$ | H | H | H | H | H |
| 2-8 | 1 | H | H | 1,1,1,2,3,3,3-heptafluoropropan-2-yl | H | $CH_3$ | H | H | H | H | H |
| 2-9 | 0 | H | H | 1,1,1,2,3,3,3-heptafluoropropan-2-yl | H | $CH_3$ | H | H | H | cyano | H |
| 2-10 | 0 | $CH_3$ | H | 1,1,1,2,3,3,3-heptafluoropropan-2-yl | H | $CH_3$ | H | H | H | H | H |
| 2-11 | 1 | $CH_3$ | H | 1,1,1,2,3,3,3-heptafluoropropan-2-yl | H | $CH_3$ | H | H | H | H | H |
| 2-12 | 0 | $CH_3$ | H | 1,1,1,2,3,3,3-heptafluoropropan-2-yl | H | $CH_3$ | H | chloro | H | H | H |
| 2-13 | 0 | $CH_3$ | H | 1,1,1,2,3,3,3-heptafluoropropan-2-yl | H | $CH_3$ | H | bromo | H | H | H |
| 2-14 | 0 | $CH_3$ | H | 1,1,1,2,3,3,3-heptafluoropropan-2-yl | H | $CH_3$ | H | cyano | H | H | H |
| 2-15 | 0 | $CH_3$ | H | 1,1,1,2,3,3,3-heptafluoropropan-2-yl | H | $CH_3$ | H | H | H | ethynyl | H |
| 2-16 | 0 | $CH_3$ | H | 1,1,1,2,3,3,3-heptafluoropropan-2-yl | H | $CH_3$ | H | H | H | (trimethylsilyl)ethynyl | H |
| 2-17 | 0 | $CH_3$ | H | 1,1,1,2,3,3,3-heptafluoropropan-2-yl | H | $CH_3$ | H | H | H | chloro | H |
| 2-18 | 0 | $CH_3$ | H | 1,1,1,2,3,3,3-heptafluoropropan-2-yl | H | $CH_3$ | H | H | H | bromo | H |
| 2-19 | 0 | $CH_3$ | H | 1,1,1,2,3,3,3-heptafluoropropan-2-yl | H | $CH_3$ | H | H | H | trifluoromethyl | H |
| 2-20 | 0 | $CH_3$ | H | 1,1,1,2,3,3,3-heptafluoropropan-2-yl | H | $CH_3$ | H | H | H | cyano | H |
| 2-21 | 1 | $CH_3$ | H | 1,1,1,2,3,3,3-heptafluoropropan-2-yl | H | $CH_3$ | H | H | H | cyano | H |
| 2-22 | 0 | $CH_3$ | H | 1,1,1,2,3,3,3-heptafluoropropan-2-yl | H | $CH_3$ | $CH_3$ | H | H | cyano | H |
| 2-23 | 0 | $CH_3$ | H | 1,1,1,2,3,3,3-heptafluoropropan-2-yl | H | $CH_3$ | H | H | H | methylsulfanyl | H |
| 2-24 | 0 | $CH_3$ | H | 1,1,1,2,3,3,3-heptafluoropropan-2-yl | H | $CH_3$ | H | H | H | acetylamino | H |
| 2-25 | 0 | $CH_3$ | H | 1,1,1,2,3,3,3-heptafluoropropan-2-yl | H | $CH_3$ | H | H | H | (phenylcarbonyl)amino | H |
| 2-26 | 0 | $CH_3$ | H | 1,1,1,2,3,3,3-heptafluoropropan-2-yl | H | ethyl | H | H | H | H | H |
| 2-27 | 1 | $CH_3$ | H | 1,1,1,2,3,3,3-heptafluoropropan-2-yl | H | ethyl | H | H | H | H | H |
| 2-28 | 0 | $CH_3$ | H | 1,1,1,2,3,3,3-heptafluoropropan-2-yl | H | ethyl | H | H | H | $CH_3$ | H |
| 2-29 | 0 | $CH_3$ | H | 1,1,1,2,3,3,3-heptafluoropropan-2-yl | H | ethyl | H | H | H | chloro | H |
| 2-30 | 0 | $CH_3$ | H | 1,1,1,2,3,3,3-heptafluoropropan-2-yl | H | ethyl | H | H | H | methoxy | H |
| 2-31 | 0 | $CH_3$ | H | 1,1,1,2,3,3,3-heptafluoropropan-2-yl | H | ethyl | H | H | H | cyano | H |
| 2-32 | 0 | $CH_3$ | H | 1,1,1,2,3,3,3-heptafluoropropan-2-yl | H | ethyl | $CH_3$ | H | H | cyano | H |
| 2-33 | 0 | $CH_3$ | H | 1,1,1,2,3,3,3-heptafluoropropan-2-yl | H | ethyl | H | H | H | acetamidomethyl | H |
| 2-34 | 0 | $CH_3$ | H | 1,1,1,2,3,3,3-heptafluoropropan-2-yl | H | ethyl | H | H | H | 1H-1,2,4-triazol-1-yl | H |
| 2-35 | 0 | $CH_3$ | H | 1,1,1,2,3,3,3-heptafluoropropan-2-yl | H | propan-2-yl | H | H | H | H | H |
| 2-36 | 1 | $CH_3$ | H | 1,1,1,2,3,3,3-heptafluoropropan-2-yl | H | propan-2-yl | H | H | H | H | H |
| 2-37 | 0 | $CH_3$ | H | 1,1,1,2,3,3,3-heptafluoropropan-2-yl | H | propan-2-yl | H | H | H | cyano | H |
| 2-38 | 0 | $CH_3$ | H | 1,1,1,2,3,3,3-heptafluoropropan-2-yl | H | bromo | H | H | H | H | H |
| 2-39 | 1 | $CH_3$ | H | 1,1,1,2,3,3,3-heptafluoropropan-2-yl | H | bromo | H | H | H | H | H |
| 2-40 | 0 | $CH_3$ | H | 1,1,1,2,3,3,3-heptafluoropropan-2-yl | H | bromo | H | H | H | cyano | H |
| 2-41 | 0 | $CH_3$ | H | 1,1,1,2,3,3,3-heptafluoropropan-2-yl | H | iodo | H | H | H | H | H |
| 2-42 | 1 | $CH_3$ | H | 1,1,1,2,3,3,3-heptafluoropropan-2-yl | H | iodo | H | H | H | H | H |
| 2-43 | 0 | $CH_3$ | H | 1,1,1,2,3,3,3-heptafluoropropan-2-yl | H | iodo | H | H | H | cyano | H |
| 2-44 | 0 | ethyl | H | 1,1,1,2,3,3,3-heptafluoropropan-2-yl | H | ethyl | H | H | H | H | H |
| 2-45 | 1 | ethyl | H | 1,1,1,2,3,3,3-heptafluoropropan-2-yl | H | ethyl | H | H | H | H | H |
| 2-46 | 0 | ethyl | H | 1,1,1,2,3,3,3-heptafluoropropan-2-yl | H | ethyl | H | H | H | cyano | H |
| 2-47 | 0 | ethyl | H | 1,1,1,2,3,3,3-heptafluoropropan-2-yl | H | bromo | H | H | H | H | H |
| 2-48 | 1 | ethyl | H | 1,1,1,2,3,3,3-heptafluoropropan-2-yl | H | bromo | H | H | H | H | H |
| 2-49 | 0 | ethyl | H | 1,1,1,2,3,3,3-heptafluoropropan-2-yl | H | bromo | H | H | H | cyano | H |
| 2-50 | 0 | ethyl | H | 1,1,1,2,3,3,3-heptafluoropropan-2-yl | H | iodo | H | H | H | H | H |
| 2-51 | 1 | ethyl | H | 1,1,1,2,3,3,3-heptafluoropropan-2-yl | H | iodo | H | H | H | H | H |
| 2-52 | 0 | ethyl | H | 1,1,1,2,3,3,3-heptafluoropropan-2-yl | H | iodo | H | H | H | cyano | H |
| 2-53 | 0 | propyl | H | 1,1,1,2,3,3,3-heptafluoropropan-2-yl | H | iodo | H | H | H | H | H |
| 2-54 | 1 | propyl | H | 1,1,1,2,3,3,3-heptafluoropropan-2-yl | H | iodo | H | H | H | H | H |
| 2-55 | 0 | propyl | H | 1,1,1,2,3,3,3-heptafluoropropan-2-yl | H | iodo | H | H | H | cyano | H |
| 2-56 | 0 | propan-2-yl | H | 1,1,1,2,3,3,3-heptafluoropropan-2-yl | H | propan-2-yl | H | H | H | H | H |
| 2-57 | 1 | propan-2-yl | H | 1,1,1,2,3,3,3-heptafluoropropan-2-yl | H | propan-2-yl | H | H | H | H | H |
| 2-58 | 0 | propan-2-yl | H | 1,1,1,2,3,3,3-heptafluoropropan-2-yl | H | propan-2-yl | H | H | H | cyano | H |

TABLE 2-continued

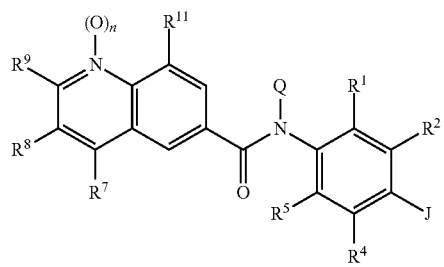

wherein R¹¹ are the same as X².

| Exa | n | R¹ | R² | J | R⁴ | R⁵ | Q | R⁷ | R⁸ | R⁹ | R¹¹ |
|---|---|---|---|---|---|---|---|---|---|---|---|
| 2-59 | 0 | chloro | H | 1,1,1,2,3,3,3-heptafluoropropan-2-yl | H | chloro | H | H | H | H | H |
| 2-60 | 1 | chloro | H | 1,1,1,2,3,3,3-heptafluoropropan-2-yl | H | H | chloro | H | H | H | H |
| 2-61 | 0 | chloro | H | 1,1,1,2,3,3,3-heptafluoropropan-2-yl | H | chloro | H | H | H | cyano | H |
| 2-62 | 0 | bromo | H | 1,1,1,2,3,3,3-heptafluoropropan-2-yl | H | bromo | H | H | H | H | H |
| 2-63 | 1 | bromo | H | 1,1,1,2,3,3,3-heptafluoropropan-2-yl | H | bromo | H | H | H | H | H |
| 2-64 | 0 | bromo | H | 1,1,1,2,3,3,3-heptafluoropropan-2-yl | H | bromo | H | H | H | cyano | H |
| 2-65 | 0 | bromo | H | 1,1,1,2,3,3,3-heptafluoropropan-2-yl | H | (trifluoromethyl)sulfanyl | H | H | H | H | H |
| 2-66 | 0 | bromo | H | 1,1,1,2,3,3,3-heptafluoropropan-2-yl | H | (trifluoromethyl)sulfanyl | H | H | H | cyano | H |
| 2-67 | 0 | iodo | H | 1,1,1,2,3,3,3-heptafluoropropan-2-yl | H | iodo | H | H | H | H | H |
| 2-68 | 1 | iodo | H | 1,1,1,2,3,3,3-heptafluoropropan-2-yl | H | iodo | H | H | H | H | H |
| 2-69 | 0 | iodo | H | 1,1,1,2,3,3,3-heptafluoropropan-2-yl | H | iodo | H | H | H | cyano | H |
| 2-70 | 0 | CH₃ | H | 1,1,1,3,3,3-hexafluoro-2-hydroxypropan-2-yl | H | ethyl | H | H | H | H | H |
| 2-71 | 0 | CH₃ | H | 1,1,1,3,3,3-hexafluoro-2-[(methylsulfonyl)oxy]propan-2-yl | H | ethyl | H | H | H | H | H |
| 2-72 | 0 | CH₃ | H | 2-ethoxy-1,1,1,3,3,3-hexafluoropropan-2-yl | H | ethyl | H | H | H | H | H |
| 2-73 | 1 | CH₃ | H | 2-ethoxy-1,1,1,3,3,3-hexafluoropropan-2-yl | H | ethyl | H | H | H | H | H |
| 2-74 | 0 | CH₃ | H | 2-ethoxy-1,1,1,3,3,3-hexafluoropropan-2-yl | H | ethyl | H | H | H | cyano | H |
| 2-75 | 0 | CH₃ | H | 1,1,1,3,3,3-hexafluoro-2-(2,2,2-trifluoroethoxy)propan-2-yl | H | ethyl | H | H | H | H | H |
| 2-76 | 1 | CH₃ | H | 1,1,1,3,3,3-hexafluoro-2-(2,2,2-trifluoroethoxy)propan-2-yl | H | ethyl | H | H | H | H | H |
| 2-77 | 0 | CH₃ | H | 1,1,1,3,3,3-hexafluoro-2-(2,2,2-trifluoroethoxy)propan-2-yl | H | ethyl | H | H | H | cyano | H |
| 2-78 | 0 | CH₃ | H | 2-(4-chlorophenoxy)-1,1,1,3,3,3-hexafluoropropan-2-yl | H | ethyl | H | H | H | H | H |
| 2-79 | 1 | CH₃ | H | 2-(4-chlorophenoxy)-1,1,1,3,3,3-hexafluoropropan-2-yl | H | ethyl | H | H | H | H | H |
| 2-80 | 0 | CH₃ | H | 2-(4-chlorophenoxy)-1,1,1,3,3,3-hexafluoropropan-2-yl | H | ethyl | H | H | H | cyano | H |
| 2-81 | 0 | CH₃ | H | 2-(4-chloro-1H-pyrazol-1-yl)-1,1,1,3,3,3-hexafluoropropan-2-yl | H | ethyl | H | H | H | H | H |
| 2-82 | 1 | CH₃ | H | 2-(4-chloro-1H-pyrazol-1-yl)-1,1,1,3,3,3-hexafluoropropan-2-yl | H | ethyl | H | H | H | H | H |
| 2-83 | 0 | CH₃ | H | 2-(4-chloro-1H-pyrazol-1-yl)-1,1,1,3,3,3-hexafluoropropan-2-yl | H | ethyl | H | H | H | cyano | H |
| 2-84 | 0 | CH₃ | H | 1,1,1,3,3,3-hexafluoro-2-(1H-1,2,4-triazol-1-yl)propan-2-yl | H | ethyl | H | H | H | 1H-1,2,4-triazol-1-yl | H |
| 2-85 | 0 | CH₃ | H | 1,1,1,2,3,3,4,4,4-nonafluorobutan-2-yl | H | CH₃ | H | H | H | H | H |
| 2-86 | 1 | CH₃ | H | 1,1,1,2,3,3,4,4,4-nonafluorobutan-2-yl | H | CH₃ | H | H | H | H | H |
| 2-87 | 0 | CH₃ | H | 1,1,1,2,3,3,4,4,4-nonafluorobutan-2-yl | H | CH₃ | H | H | H | cyano | H |
| 2-88 | 0 | CH₃ | H | 1,1,1,2,3,3,4,4,4-nonafluorobutan-2-yl | H | ethyl | H | H | H | H | H |
| 2-89 | 1 | CH₃ | H | 1 1 1,2,3,3,4,4,4-nonafluorobutan-2-yl | H | ethyl | H | H | H | H | H |
| 2-90 | 0 | CH₃ | H | 1,1,1,2,3,3,4,4,4-nonafluorobutan-2-yl | H | ethyl | H | H | H | cyano | H |
| 2-91 | 0 | CH₃ | H | 1,1,1,2,3,3,4,4,4-nonafluorobutan-2-yl | H | bromo | H | H | H | H | H |
| 2-92 | 1 | CH₃ | H | 1,1,1,2,3,3,4,4,4-nonafluorobutan-2-yl | H | bromo | H | H | H | H | H |
| 2-93 | 0 | CH₃ | H | 1,1,1,2,3,3,4,4,4-nonafluorobutan-2-yl | H | bromo | H | H | H | cyano | H |
| 2-94 | 0 | CH₃ | H | 1,1,1,2,3,3,4,4,4-nonafluorobutan-2-yl | H | iodo | H | H | H | H | H |
| 2-95 | 1 | CH₃ | H | 1,1,1,2,3,3,4,4,4-nonafluorobutan-2-yl | H | iodo | H | H | H | H | H |
| 2-96 | 0 | ethyl | H | 1,1,1,2,3,3,4,4,4-nonafluorobutan-2-yl | H | bromo | H | H | H | H | H |
| 2-97 | 1 | ethyl | H | 1,1,1,2,3,3,4,4,4-nonafluorobutan-2-yl | H | bromo | H | H | H | H | H |
| 2-98 | 0 | ethyl | H | 1,1,1,2,3,3,4,4,4-nonafluorobutan-2-yl | H | bromo | H | H | H | cyano | H |
| 2-99 | 0 | ethyl | H | 1,1,1,2,3,3,4,4,4-nonafluorobutan-2-yl | H | iodo | H | H | H | H | H |
| 2-100 | 1 | ethyl | H | 1,1,1,2,3,3,4,4,4-nonafluorobutan-2-yl | H | iodo | H | H | H | H | H |
| 2-101 | 0 | ethyl | H | 1,1,1,2,3,3,4,4,4-nonafluorobutan-2-yl | H | iodo | H | H | H | cyano | H |
| 2-102 | 0 | propyl | H | 1,1,1,2,3,3,4,4,4-nonafluorobutan-2-yl | H | iodo | H | H | H | H | H |
| 2-103 | 1 | propyl | H | 1,1,1,2,3,3,4,4,4-nonafluorobutan-2-yl | H | iodo | H | H | H | H | H |
| 2-104 | 0 | propyl | H | 1,1,1,2,3,3,4,4,4-nonafluorobutan-2-yl | H | iodo | H | H | H | cyano | H |
| 2-105 | 0 | chloro | H | 1,1,1,2,3,3,4,4,4-nonafluorobutan-2-yl | H | chloro | H | H | H | H | H |
| 2-106 | 1 | chloro | H | 1,1,1,2,3,3,4,4,4-nonafluorobutan-2-yl | H | chloro | H | H | H | H | H |
| 2-107 | 0 | chloro | H | 1,1,1,2,3,3,4,4,4-nonafluorobutan-2-yl | H | chloro | H | H | H | cyano | H |

TABLE 2-continued

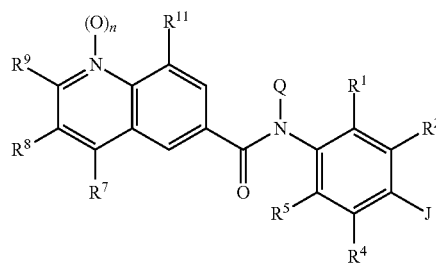

wherein R¹¹ are the same as X².

| Exa | n | R¹ | R² | J | R⁴ | R⁵ | Q | R⁷ | R⁸ | R⁹ | R¹¹ |
|---|---|---|---|---|---|---|---|---|---|---|---|
| 2-108 | 0 | bromo | H | 1,1,1,2,3,3,4,4,4-nonafluorobutan-2-yl | H | bromo | H | H | H | H | H |
| 2-109 | 1 | bromo | H | 1,1,1,2,3,3,4,4,4-nonafluorobutan-2-yl | H | bromo | H | H | H | H | H |
| 2-110 | 0 | bromo | H | 1,1,1,2,3,3,4,4,4-nonafluorobutan-2-yl | H | bromo | H | H | H | cyano | H |
| 2-111 | 0 | iodo | H | 1,1,1,2,3,3,4,4,4-nonafluorobutan-2-yl | H | iodo | H | H | H | H | H |
| 2-112 | 1 | iodo | H | 1,1,1,2,3,3,4,4,4-nonafluorobutan-2-yl | H | iodo | H | H | H | H | H |
| 2-113 | 0 | iodo | H | 1,1,1,2,3,3,4,4,4-nonafluorobutan-2-yl | H | iodo | H | H | H | cyano | H |
| 2-114 | 0 | CH₃ | H | 1,1,1,3,3,4,4,4-octafluoro-2-hydroxybutan-2-yl | H | ethyl | H | H | H | H | H |
| 2-115 | 0 | CH₃ | H | 1,1,1,3,3,4,4,4-octafluoro-2-[(methylsulfonyl)oxy]butan-2-yl | H | ethyl | H | H | H | H | H |
| 2-116 | 0 | CH₃ | H | 2-ethoxy-1,1,1,3,3,4,4,4-octafluorobutan-2-yl | H | ethyl | H | H | H | H | H |
| 2-117 | 1 | CH₃ | H | 2-ethoxy-1,1,1,3,3,4,4,4-octafluorobutan-2-yl | H | ethyl | H | H | H | H | H |
| 2-118 | 0 | CH₃ | H | 2-ethoxy-1,1,1,3,3,4,4,4-octafluorobutan-2-yl | H | ethyl | H | H | H | cyano | H |
| 2-119 | 0 | CH₃ | H | 2-[(4-chlorobenzyl)oxy]-1,1,1,3,3,4,4,4-octafluorobutan-2-yl | H | ethyl | H | H | H | H | H |
| 2-120 | 1 | CH₃ | H | 2-[(4-chlorobenzyl)oxy]-1,1,1,3,3,4,4,4-octafluorobutan-2-yl | H | ethyl | H | H | H | H | H |
| 2-121 | 0 | CH₃ | H | 2-[(4-chlorobenzyl)oxy]-1,1,1,3,3,4,4,4-octafluorobutan-2-yl | H | ethyl | H | H | H | cyano | H |
| 2-122 | 0 | CH₃ | H | 2-(4-chloro-1H-pyrazol-1-yl)-1,1,1,3,3,4,4,4-octafluorobutan-2-yl | H | ethyl | H | H | H | H | H |
| 2-123 | 1 | CH₃ | H | 2-(4-chloro-1H-pyrazol-1-yl)-1,1,1,3,3,4,4,4-octafluorobutan-2-yl | H | ethyl | H | H | H | H | H |
| 2-124 | 0 | CH₃ | H | 2-(4-chloro-1H-pyrazol-1-yl)-1,1,1,3,3,4,4,4-octafluorobutan-2-yl | H | ethyl | H | H | H | cyano | H |
| 2-125 | 0 | CH₃ | H | undecafluorocyclohexyl | H | CH₃ | H | H | H | H | H |
| 2-126 | 1 | CH₃ | H | undecafluorocyclohexyl | H | CH₃ | H | H | H | H | H |
| 2-127 | 0 | CH₃ | H | undecafluorocyclohexyl | H | CH₃ | H | H | H | cyano | H |
| 2-128 | 0 | CH₃ | H | undecafluorocyclohexyl | H | ethyl | H | H | H | H | H |
| 2-129 | 1 | CH₃ | H | undecafluorocyclohexyl | H | ethyl | H | H | H | H | H |
| 2-130 | 0 | CH₃ | H | undecafluorocyclohexyl | H | ethyl | H | H | H | cyano | H |
| 2-131 | 0 | bromo | H | undecafluorocyclohexyl | H | bromo | H | H | H | H | H |
| 2-132 | 1 | bromo | H | undecafluorocyclohexyl | H | bromo | H | H | H | H | H |
| 2-133 | 0 | bromo | H | undecafluorocyclohexyl | H | bromo | H | H | H | cyano | H |
| 2-134 | 0 | iodo | H | undecafluorocyclohexyl | H | iodo | H | H | H | H | H |
| 2-135 | 1 | iodo | H | undecafluorocyclohexyl | H | iodo | H | H | H | H | H |
| 2-136 | 0 | iodo | H | undecafluorocyclohexyl | H | iodo | H | H | H | cyano | H |
| 2-137 | 0 | bromo | H | trifluoromethoxy | H | bromo | H | H | H | H | H |
| 2-138 | 1 | bromo | H | trifluoromethoxy | H | bromo | H | H | H | H | H |
| 2-139 | 0 | bromo | H | trifluoromethoxy | H | bromo | H | H | H | cyano | H |
| 2-140 | 0 | bromo | H | (trifluoromethyl)sulfanyl | H | bromo | H | H | H | cyano | H |
| 2-141 | 0 | bromo | H | (pentafluoroethyl)sulfanyl | H | bromo | H | H | H | cyano | H |
| 2-142 | 0 | bromo | H | (heptafluoropropyl)sulfanyl | H | bromo | H | H | H | cyano | H |
| 2-143 | 0 | bromo | H | (nonafluorobutyl)sulfanyl | H | bromo | H | H | H | cyano | H |
| 2-144 | 0 | bromo | H | (trifluoromethyl)sulfinyl | H | bromo | H | H | H | cyano | H |
| 2-145 | 0 | bromo | H | (trifluoromethyl)sulfonyl | H | bromo | H | H | H | H | H |
| 2-146 | 1 | bromo | H | (trifluoromethyl)sulfonyl | H | bromo | H | H | H | H | H |
| 2-147 | 0 | bromo | H | (trifluoromethyl)sulfonyl | H | bromo | H | H | H | cyano | H |
| 2-148 | 0 | bromo | H | (trifluoromethyl)sulfanyl | H | bromo | H | H | H | H | H |
| 2-149 | 1 | bromo | H | (trifluoromethyl)sulfanyl | H | bromo | H | H | H | H | H |
| 2-150 | 0 | bromo | H | (trifluoromethyl)sulfinyl | H | bromo | H | H | H | H | H |
| 2-151 | 1 | bromo | H | (trifluoromethyl)sulfinyl | H | bromo | H | H | H | H | H |
| 2-152 | 0 | bromo | H | 1,1,1,2,3,3,3-heptafluoropropan-2-yl | H | difluoromethoxy | H | H | H | H | H |
| 2-153 | 1 | bromo | H | 1,1,1,2,3,3,3-heptafluoropropan-2-yl | H | difluoromethoxy | H | H | H | H | H |
| 2-154 | 0 | bromo | H | 1,1,1,2,3,3,3-heptafluoropropan-2-yl | H | difluoromethoxy | H | H | H | cyano | H |
| 2-155 | 0 | iodo | H | 1,1,1,2,3,3,3-heptafluoropropan-2-yl | H | difluoromethoxy | H | H | H | H | H |
| 2-156 | 1 | iodo | H | 1,1,1,2,3,3,3-heptafluoropropan-2-yl | H | difluoromethoxy | H | H | H | H | H |
| 2-157 | 0 | iodo | H | 1,1,1,2,3,3,3-heptafluoropropan-2-yl | H | difluoromethoxy | H | H | H | cyano | H |
| 2-158 | 1 | bromo | H | 1,1,1,2,3,3,3-heptafluoropropan-2-yl | H | (trifluoromethyl)sulfanyl | H | H | H | H | H |
| 2-159 | 0 | iodo | H | 1,1,1,2,3,3,3-heptafluoropropan-2-yl | H | (trifluoromethyl)sulfanyl | H | H | H | H | H |

TABLE 2-continued

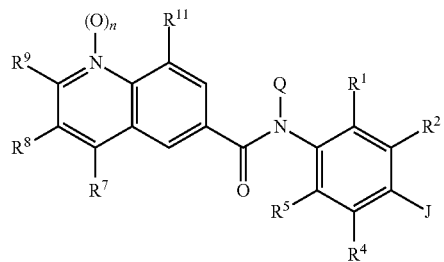

wherein $R^{11}$ are the same as $X^2$.

| Exa | n | $R^1$ | $R^2$ | J | $R^4$ | $R^5$ | Q | $R^7$ | $R^8$ | $R^9$ | $R^{11}$ |
|---|---|---|---|---|---|---|---|---|---|---|---|
| 2-160 | 1 | iodo | H | 1,1,1,2,3,3,3-heptafluoropropan-2-yl | H | (trifluoromethyl)sulfanyl | H | H | H | H | H |
| 2-161 | 0 | iodo | H | 1,1,1,2,3,3,3-heptafluoropropan-2-yl | H | (trifluoromethyl)sulfanyl | H | H | H | cyano | H |
| 2-162 | 0 | propyl | H | 1,1,1,2,3,3,4,4,4-nonafluorobutan-2-yl | H | bromo | H | H | H | H | H |
| 2-163 | 1 | propyl | H | 1,1,1,2,3,3,4,4,4-nonafluorobutan-2-yl | H | bromo | H | H | H | H | H |
| 2-164 | 0 | propyl | H | 1,1,1,2,3,3,4,4,4-nonafluorobutan-2-yl | H | bromo | H | H | H | cyano | H |
| 2-165 | 0 | propan-2-yl | H | 1,1,1,2,3,3,4,4,4-nonafluorobutan-2-yl | H | iodo | H | H | H | H | H |
| 2-166 | 1 | propan-2-yl | H | 1,1,1,2,3,3,4,4,4-nonafluorobutan-2-yl | H | iodo | H | H | H | H | H |
| 2-167 | 0 | propan-2-yl | H | 1,1,1,2,3,3,4,4,4-nonafluorobutan-2-yl | H | iodo | H | H | H | cyano | H |
| 2-168 | 0 | bromo | H | 1,1,1,2,3,3,4,4,4-nonafluorobutan-2-yl | H | hydroxy | H | H | H | H | H |
| 2-169 | 0 | bromo | H | 1,1,1,2,3,3,4,4,4-nonafluorobutan-2-yl | H | [(trifluoromethyl)Sulfonyl]oxy | H | H | H | H | H |
| 2-170 | 0 | bromo | H | 1,1,1,2,3,3,4,4,4-nonafluorobutan-2-yl | H | methoxy | H | H | H | H | H |
| 2-171 | 0 | bromo | H | 1,1,1,2,3,3,4,4,4-nonafluorobutan-2-yl | H | difluoromethoxy | H | H | H | H | H |
| 2-172 | 1 | bromo | H | 1,1,1,2,3,3,4,4,4-nonafluorobutan-2-yl | H | difluoromethoxy | H | H | H | H | H |
| 2-173 | 0 | bromo | H | 1,1,1,2,3,3,4,4,4-nonafluorobutan-2-yl | H | difluoromethoxy | H | H | H | cyano | H |
| 2-174 | 0 | iodo | H | 1,1,1,2,3,3,4,4,4-nonafluorobutan-2-yl | H | difluoromethoxy | H | H | H | H | H |
| 2-175 | 1 | iodo | H | 1,1,1,2,3,3,4,4,4-nonafluorobutan-2-yl | H | difluoromethoxy | H | H | H | H | H |
| 2-176 | 0 | iodo | H | 1,1,1,2,3,3,4,4,4-nonafluorobutan-2-yl | H | difluoromethoxy | H | H | H | cyano | H |
| 2-177 | 0 | bromo | H | 1,1,1,2,3,3,4,4,4-nonafluorobutan-2-yl | H | trifluoromethoxy | H | H | H | H | H |
| 2-178 | 1 | bromo | H | 1,1,1,2,3,3,4,4,4-nonafluorobutan-2-yl | H | trifluoromethoxy | H | H | H | H | H |
| 2-179 | 0 | bromo | H | 1,1,1,2,3,3,4,4,4-nonafluorobutan-2-yl | H | trifluoromethoxy | H | H | H | cyano | H |
| 2-180 | 0 | bromo | H | 1,1,1,2,3,3,4,4,4-nonafluorobutan-2-yl | H | (difluoromethyl)sulfanyl | H | H | H | H | H |
| 2-181 | 1 | bromo | H | 1,1,1,2,3,3,4,4,4-nonafluorobutan-2-yl | H | (difluoromethyl)sulfanyl | H | H | H | H | H |
| 2-182 | 0 | bromo | H | 1,1,1,2,3,3,4,4,4-nonafluorobutan-2-yl | H | (difluoromethyl)sulfanyl | H | H | H | cyano | H |
| 2-183 | 0 | bromo | H | 1,1,1,2,3,3,4,4,4-nonafluorobutan-2-yl | H | (trifluoromethyl)sulfanyl | H | H | H | H | H |
| 2-184 | 1 | bromo | H | 1,1,1,2,3,3,4,4,4-nonafluorobutan-2-yl | H | (trifluoromethyl)sulfanyl | H | H | H | H | H |
| 2-185 | 0 | bromo | H | 1,1,1,2,3,3,4,4,4-nonafluorobutan-2-yl | H | (trifluoromethyl)sulfanyl | H | H | H | cyano | H |
| 2-186 | 0 | iodo | H | 1,1,1,2,3,3,4,4,4-nonafluorobutan-2-yl | H | (trifluoromethyl)sulfanyl | H | H | H | H | H |
| 2-187 | 1 | iodo | H | 1,1,1,2,3,3,4,4,4-nonafluorobutan-2-yl | H | (trifluoromethyl)sulfanyl | H | H | H | H | H |
| 2-188 | 0 | iodo | H | 1,1,1,2,3,3,4,4,4-nonafluorobutan-2-yl | H | (trifluoromethyl)sulfanyl | H | H | H | cyano | H |
| 2-189 | 0 | $CH_3$ | H | 1-bromo-1,1,2,3,3,3-hexafluoropropan-2-yl | H | $CH_3$ | H | H | H | H | H |
| 2-190 | 1 | $CH_3$ | H | 1-bromo-1,1,2,3,3,3-hexafluoropropan-2-yl | H | $CH_3$ | H | H | H | H | H |
| 2-191 | 0 | $CH_3$ | H | 1-bromo-1,1,2,3,3,3-hexafluoropropan-2-yl | H | $CH_3$ | H | H | H | cyano | H |
| 2-192 | 0 | $CH_3$ | H | 1-bromo-1,1,2,3,3,3-hexafluoropropan-2-yl | H | ethyl | H | H | H | H | H |
| 2-193 | 1 | $CH_3$ | H | 1-bromo-1,1,2,3,3,3-hexafluoropropan-2-yl | H | ethyl | H | H | H | H | H |
| 2-194 | 0 | $CH_3$ | H | 1-bromo-1,1,2,3,3,3-hexafluoropropan-2-yl | H | ethyl | H | H | H | cyano | H |
| 2-195 | 0 | bromo | H | 1-bromo-1,1,2,3,3,3-hexafluoropropan-2-yl | H | bromo | H | H | H | H | H |
| 2-196 | 1 | bromo | H | 1-bromo-1,1,2,3,3,3-hexafluoropropan-2-yl | H | bromo | H | H | H | H | H |
| 2-197 | 0 | bromo | H | 1-bromo-1,1,2,3,3,3-hexafluoropropan-2-yl | H | bromo | H | H | H | cyano | H |
| 2-198 | 0 | iodo | H | 1-bromo-1,1,2,3,3,3-hexafluoropropan-2-yl | H | iodo | H | H | H | H | H |
| 2-199 | 1 | iodo | H | 1-bromo-1,1,2,3,3,3-hexafluoropropan-2-yl | H | iodo | H | H | H | H | H |
| 2-200 | 0 | iodo | H | 1-bromo-1,1,2,3,3,3-hexafluoropropan-2-yl | H | iodo | H | H | H | cyano | H |
| 2-201 | 0 | bromo | H | 1-bromo-1,1,2,3,3,3-hexafluoropropan-2-yl | H | difluoromethoxy | H | H | H | H | H |
| 2-202 | 1 | bromo | H | 1-bromo-1,1,2,3,3,3-hexafluoropropan-2-yl | H | difluoromethoxy | H | H | H | H | H |
| 2-203 | 0 | bromo | H | 1-bromo-1,1,2,3,3,3-hexafluoropropan-2-yl | H | difluoromethoxy | H | H | H | cyano | H |
| 2-204 | 0 | iodo | H | 1-bromo-1,1,2,3,3,3-hexafluoropropan-2-yl | H | difluoromethoxy | H | H | H | H | H |
| 2-205 | 1 | iodo | H | 1-bromo-1,1,2,3,3,3-hexafluoropropan-2-yl | H | difluoromethoxy | H | H | H | H | H |
| 2-206 | 0 | iodo | H | 1-bromo-1,1,2,3,3,3-hexafluoropropan-2-yl | H | difluoromethoxy | H | H | H | cyano | H |
| 2-207 | 0 | bromo | H | 1-bromo-1,1,2,3,3,3-hexafluoropropan-2-yl | H | (trifluoromethyl)sulfanyl | H | H | H | H | H |

TABLE 2-continued

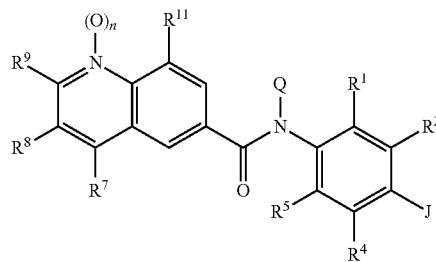

wherein R[11] are the same as X[2].

| Exa | n | R[1] | R[2] | J | R[4] | R[5] | Q | R[7] | R[8] | R[9] | R[11] |
|---|---|---|---|---|---|---|---|---|---|---|---|
| 2-208 | 1 | bromo | H | 1-bromo-1,1,2,3,3,3-hexafluoropropan-2-yl | H | (trifluoromethyl)sulfanyl | H | H | H | H | H |
| 2-209 | 0 | bromo | H | 1-bromo-1,1,2,3,3,3-hexafluoropropan-2-yl | H | (trifluoromethyl)sulfanyl | H | H | H | cyano | H |
| 2-210 | 0 | iodo | H | 1-bromo-1,1,2,3,3,3-hexafluoropropan-2-yl | H | (trifluoromethyl)sulfanyl | H | H | H | H | H |
| 2-211 | 1 | iodo | H | 1-bromo-1,1,2,3,3,3-hexafluoropropan-2-yl | H | (trifluoromethyl)sulfanyl | H | H | H | H | H |
| 2-212 | 0 | iodo | H | 1-bromo-1,1,2,3,3,3-hexafluoropropan-2-yl | H | (trifluoromethyl)sulfanyl | H | H | H | cyano | H |
| 2-213 | 0 | CH₃ | H | 1,1,1,2,3,3,3-heptafluoropropan-2-yl | H | CH₃ | H | H | chloro | H | H |
| 2-214 | 0 | CH₃ | H | 1,1,1,2,3,3,3-heptafluoropropan-2-yl | H | CH₃ | H | H | chloro | H | chloro |
| 2-215 | 0 | CH₃ | H | 1,1,1,2,3,3,3-heptafluoropropan-2-yl | H | CH₃ | H | H | bromo | H | H |
| 2-216 | 0 | CH₃ | H | 1,1,1,2,3,3,3-heptafluoropropan-2-yl | H | CH₃ | H | H | bromo | H | bromo |
| 2-217 | 0 | CH₃ | H | 1,1,1,2,3,3,4,4,4-nonafluorobutan-2-yl | H | ethyl | H | H | H | H | chloro |
| 2-218 | 0 | CH₃ | H | 1,1,1,2,3,3,4,4,4-nonafluorobutan-2-yl | H | ethyl | H | H | H | H | bromo |
| 2-219 | 0 | bromo | H | pentafluoroethyl | H | difluoromethoxy | H | H | H | H | H |
| 2-220 | 1 | bromo | H | pentafluoroethyl | H | difluoromethoxy | H | H | H | H | H |
| 2-221 | 0 | bromo | H | pentafluoroethyl | H | difluoromethoxy | H | H | H | cyano | H |
| 2-222 | 0 | CH₃ | H | 1,1,1,2,3,3,4,4,4-nonafluorobutan-2-yl | H | iodo | H | H | H | cyano | H |
| 2-223 | 0 | bromo | H | 1,1,1,2,3,3,4,4,4-nonafluorobutan-2-yl | H | bromo | CH₃ | H | H | cyano | H |
| 2-224 | 0 | bromo | H | 1,1,1,2,3,3,4,4,4-nonafluorobutan-2-yl | H | difluoromethoxy | CH₃ | H | H | cyano | H |
| 2-225 | 0 | iodo | H | 1,1,1,2,3,3,4,4,4-nonafluorobutan-2-yl | H | iodo | CH₃ | H | H | cyano | H |
| 2-226 | 0 | bromo | H | 1-bromo-1,1,2,3,3,3-hexafluoropropan-2-yl | H | bromo | CH₃ | H | H | cyano | H |
| 2-227 | 0 | bromo | H | 1-bromo-1,1,2,3,3,3-hexafluoropropan-2-yl | H | difluoromethoxy | CH₃ | H | H | cyano | H |
| 2-228 | 0 | iodo | H | 1-bromo-1,1,2,3,3,3-hexafluoropropan-2-yl | H | iodo | CH₃ | H | H | cyano | H |
| 2-229 | 0 | chloro | H | 1,1,1,2,3,3,3-heptafluoropropan-2-yl | H | difluoromethoxy | H | H | H | H | H |
| 2-230 | 1 | chloro | H | 1,1,1,2,3,3,3-heptafluoropropan-2-yl | H | difluoromethoxy | H | H | H | H | H |
| 2-231 | 0 | chloro | H | 1,1,1,2,3,3,3-heptafluoropropan-2-yl | H | difluoromethoxy | H | H | H | cyano | H |
| 2-232 | 0 | iodo | H | 1,1,1,2,3,3,4,4,4-nonafluorobutan-2-yl | H | (difluoromethyl)sulfanyl | H | H | H | H | H |
| 2-233 | 1 | iodo | H | 1,1,1,2,3,3,4,4,4-nonafluorobutan-2-yl | H | (difluoromethyl)sulfanyl | H | H | H | H | H |
| 2-234 | 0 | iodo | H | 1,1,1,2,3,3,4,4,4-nonafluorobutan-2-yl | H | (difluoromethyl)sulfanyl | H | H | H | cyano | H |
| 2-235 | 0 | bromo | H | 1-bromo-1,1,2,3,3,3-hexafluoropropan-2-yl | H | (difluoromethyl)sulfanyl | H | H | H | H | H |
| 2-236 | 1 | bromo | H | 1-bromo-1,1,2,3,3,3-hexafluoropropan-2-yl | H | (difluoromethyl)sulfanyl | H | H | H | H | H |
| 2-237 | 0 | bromo | H | 1-bromo-1,1,2,3,3,3-hexafluoropropan-2-yl | H | (difluoromethyl)sulfanyl | H | H | H | cyano | H |
| 2-238 | 0 | iodo | H | 1-bromo-1,1,2,3,3,3-hexafluoropropan-2-yl | H | (difluoromethyl)sulfanyl | H | H | H | H | H |
| 2-239 | 1 | iodo | H | 1-bromo-1,1,2,3,3,3-hexafluoropropan-2-yl | H | (difluoromethyl)sulfanyl | H | H | H | H | H |
| 2-240 | 0 | iodo | H | 1-bromo-1,1,2,3,3,3-hexafluoropropan-2-yl | H | (difluoromethyl)sulfanyl | H | H | H | cyano | H |
| 2-241 | 0 | bromo | H | 1-bromo-1,1,2,3,3,3-hexafluoropropan-2-yl | H | trifluoromethyl | H | H | H | H | H |
| 2-242 | 1 | bromo | H | 1-bromo-1,1,2,3,3,3-hexafluoropropan-2-yl | H | trifluoromethyl | H | H | H | H | H |
| 2-243 | 0 | bromo | H | 1-bromo-1,1,2,3,3,3-hexafluoropropan-2-yl | H | trifluoromethyl | H | H | H | cyano | H |
| 2-244 | 0 | iodo | H | 1-bromo-1,1,2,3,3,3-hexafluoropropan-2-yl | H | trifluoromethyl | H | H | H | H | H |
| 2-245 | 1 | iodo | H | 1-bromo-1,1,2,3,3,3-hexafluoropropan-2-yl | H | trifluoromethyl | H | H | H | H | H |
| 2-246 | 0 | iodo | H | 1-bromo-1,1,2,3,3,3-hexafluoropropan-2-yl | H | trifluoromethyl | H | H | H | cyano | H |
| 2-247 | 0 | bromo | H | 1,1,1,2,3,3,3-heptafluoropropan-2-yl | H | trifluoromethyl | H | H | H | H | H |
| 2-248 | 1 | bromo | H | 1,1,1,2,3,3,3-heptafluoropropan-2-yl | H | trifluoromethyl | H | H | H | H | H |
| 2-249 | 0 | bromo | H | 1,1,1,2,3,3,3-heptafluoropropan-2-yl | H | trifluoromethyl | H | H | H | cyano | H |
| 2-250 | 0 | iodo | H | 1,1,1,2,3,3,3-heptafluoropropan-2-yl | H | trifluoromethyl | H | H | H | H | H |
| 2-251 | 1 | iodo | H | 1,1,1,2,3,3,3-heptafluoropropan-2-yl | H | trifluoromethyl | H | H | H | H | H |
| 2-252 | 0 | iodo | H | 1,1,1,2,3,3,3-heptafluoropropan-2-yl | H | trifluoromethyl | H | H | H | cyano | H |
| 2-253 | 0 | bromo | H | 1,1,1,2,3,3,4,4,4-nonafluorobutan-2-yl | H | trifluoromethyl | H | H | H | H | H |
| 2-254 | 1 | bromo | H | 1,1,1,2,3,3,4,4,4-nonafluorobutan-2-yl | H | trifluoromethyl | H | H | H | H | H |
| 2-255 | 0 | bromo | H | 1,1,1,2,3,3,4,4,4-nonafluorobutan-2-yl | H | trifluoromethyl | H | H | H | cyano | H |

TABLE 2-continued

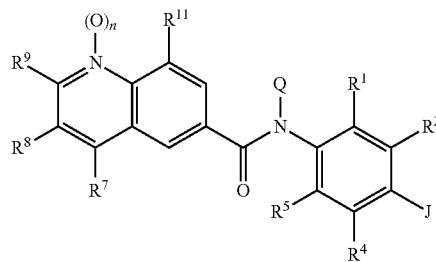

wherein R[11] are the same as X[2].

| Exa | n | R[1] | R[2] | J | R[4] | R[5] | Q | R[7] | R[8] | R[9] | R[11] |
|---|---|---|---|---|---|---|---|---|---|---|---|
| 2-256 | 0 | iodo | H | 1,1,1,2,3,3,4,4,4-nonafluorobutan-2-yl | H | trifluoromethyl | H | H | H | H | H |
| 2-257 | 1 | iodo | H | 1,1,1,2,3,3,4,4,4-nonafluorobutan-2-yl | H | trifluoromethyl | H | H | H | H | H |
| 2-258 | 0 | iodo | H | 1,1,1,2,3,3,4,4,4-nonafluorobutan-2-yl | H | trifluoromethyl | H | H | H | cyano | H |
| 2-259 | 0 | CH$_3$ | H | 1,1,1,2,3,3,3-heptafluoropropan-2-yl | H | difluoromethoxy | H | H | H | H | H |
| 2-260 | 1 | CH$_3$ | H | 1,1,1,2,3,3,3-heptafluoropropan-2-yl | H | difluoromethoxy | H | H | H | H | H |
| 2-261 | 0 | CH$_3$ | H | 1,1,1,2,3,3,3-heptafluoropropan-2-yl | H | difluoromethoxy | H | H | H | cyano | H |
| 2-262 | 0 | CH$_3$ | H | 1,1,1,2,3,3,4,4,4-nonafluorobutan-2-yl | H | difluoromethoxy | H | H | H | H | H |
| 2-263 | 1 | CH$_3$ | H | 1,1,1,2,3,3,4,4,4-nonafluorobutan-2-yl | H | difluoromethoxy | H | H | H | H | H |
| 2-264 | 0 | CH$_3$ | H | 1,1,1,2,3,3,4,4,4-nonafluorobutan-2-yl | H | difluoromethoxy | H | H | H | cyano | H |
| 2-265 | 0 | CH$_3$ | H | 1-bromo-1,1,2,3,3,3-hexafluoropropan-2-yl | H | difluoromethoxy | H | H | H | H | H |
| 2-266 | 1 | CH$_3$ | H | 1-bromo-1,1,2,3,3,3-hexafluoropropan-2-yl | H | difluoromethoxy | H | H | H | H | H |
| 2-267 | 0 | CH$_3$ | H | 1-bromo-1,1,2,3,3,3-hexafluoropropan-2-yl | H | difluoromethoxy | H | H | H | cyano | H |
| 2-268 | 1 | CH$_3$ | H | 1,1,1,2,3,3,4,4,4-nonafluorobutan-2-yl | H | ethyl | H | H | H | cyano | H |
| 2-269 | 0 | CH$_3$ | H | 1,1,1,2,3,3,4,4,4-nonafluorobutan-2-yl | H | ethyl | H | bromo | H | Cyano | H |
| 2-270 | 1 | bromo | H | 1,1,1,2,3,3,4,4,4-nonafluorobutan-2-yl | H | bromo | H | H | H | cyano | H |
| 2-271 | 0 | CH$_3$ | H | 1,1,1,2,3,3,4,4,4-nonafluorobutan-2-yl | H | ethyl | H | H | chloro | H | H |
| 2-272 | 0 | chloro | H | 1,1,1,2,3,3,4,4,4-nonafluorobutan-2-yl | H | difluoromethoxy | H | H | H | H | H |
| 2-273 | 1 | chloro | H | 1,1,1,2,3,3,4,4,4-nonafluorobutan-2-yl | H | difluoromethoxy | H | H | H | H | H |
| 2-274 | 0 | chloro | H | 1,1,1,2,3,3,4,4,4-nonafluorobutan-2-yl | H | difluoromethoxy | H | H | H | cyano | H |
| 2-275 | 0 | chloro | H | 1-bromo-1,1,2,3,3,3-hexafluoropropan-2-yl | H | difluoromethoxy | H | H | H | H | H |
| 2-276 | 1 | chloro | H | 1-bromo-1,1,2,3,3,3-hexafluoropropan-2-yl | H | difluoromethoxy | H | H | H | H | H |
| 2-277 | 0 | chloro | H | 1-bromo-1,1,2,3,3,3-hexafluoropropan-2-yl | H | difluoromethoxy | H | H | H | cyano | H |
| 2-278 | 0 | chloro | H | 1,1,1,2,3,3,3-heptafluoropropan-2-yl | H | trifluoromethyl | H | H | H | H | H |
| 2-279 | 1 | chloro | H | 1,1,1,2,3,3,3-heptafluoropropan-2-yl | H | trifluoromethyl | H | H | H | H | H |
| 2-280 | 0 | chloro | H | 1,1,1,2,3,3,3-heptafluoropropan-2-yl | H | trifluoromethyl | H | H | H | cyano | H |
| 2-281 | 0 | chloro | H | 1,1,1,2,3,3,4,4,4-nonafluorobutan-2-yl | H | trifluoromethyl | H | H | H | H | H |
| 2-282 | 1 | chloro | H | 1,1,1,2,3,3,4,4,4-nonafluorobutan-2-yl | H | trifluoromethyl | H | H | H | H | H |
| 2-283 | 0 | chloro | H | 1,1,1,2,3,3,4,4,4-nonafluorobutan-2-yl | H | trifluoromethyl | H | H | H | cyano | H |
| 2-284 | 0 | chloro | H | 1-bromo-1,1,2,3,3,3-hexafluoropropan-2-yl | H | trifluoromethyl | H | H | H | H | H |
| 2-285 | 1 | chloro | H | 1-bromo-1,1,2,3,3,3-hexafluoropropan-2-yl | H | trifluoromethyl | H | H | H | H | H |
| 2-286 | 0 | chloro | H | 1-bromo-1,1,2,3,3,3-hexafluoropropan-2-yl | H | trifluoromethyl | H | H | H | cyano | H |
| 2-287 | 0 | CH$_3$ | H | 1,1,1,2,3,3,4,4,4-nonafluorobutan-2-yl | H | ethyl | H | H | H | H | cyano |
| 2-288 | 1 | bromo | H | 1,1,1,2,3,3,4,4,4-nonafluorobutan-2-yl | H | [(trifluoromethyl)sulfonyl]oxy | H | H | H | H | H |
| 2-289 | 0 | bromo | H | 1,1,1,2,3,3,4,4,4-nonafluorobutan-2-yl | H | [(trifluoromethyl)sulfonyl]oxy | H | H | H | cyano | H |
| 2-290 | 0 | chloro | H | 1,1,1,2,3,3,3-heptafluoropropan-2-yl | H | (trifluoromethyl)sulfanyl | H | H | H | H | H |
| 2-291 | 1 | chloro | H | 1,1,1,2,3,3,3-heptafluoropropan-2-yl | H | (trifluoromethyl)sulfanyl | H | H | H | H | H |
| 2-292 | 0 | chloro | H | 1,1,1,2,3,3,3-heptafluoropropan-2-yl | H | (trifluoromethyl)sulfanyl | H | H | H | cyano | H |
| 2-293 | 0 | chloro | H | 1,1,1,2,3,3,4,4,4-nonafluorobutan-2-yl | H | (trifluoromethyl)sulfanyl | H | H | H | H | H |
| 2-294 | 1 | chloro | H | 1,1,1,2,3,3,4,4,4-nonafluorobutan-2-yl | H | (trifluoromethyl)sulfanyl | H | H | H | H | H |
| 2-295 | 0 | chloro | H | 1,1,1,2,3,3,4,4,4-nonafluorobutan-2-yl | H | (trifluoromethyl)sulfanyl | H | H | H | cyano | H |
| 2-296 | 0 | chloro | H | 1-bromo-1,1,2,3,3,3-hexafluoropropan-2-yl | H | (trifluoromethyl)sulfanyl | H | H | H | H | H |
| 2-297 | 1 | chloro | H | 1-bromo-1,1,2,3,3,3-hexafluoropropan-2-yl | H | (trifluoromethyl)sulfanyl | H | H | H | H | H |
| 2-298 | 0 | chloro | H | 1-bromo-1,1,2,3,3,3-hexafluoropropan-2-yl | H | (trifluoromethyl)sulfanyl | H | H | H | cyano | H |
| 2-299 | 0 | bromo | H | 1,1,1,2,3,3,3-heptafluoropropan-2-yl | H | (trifluoromethyl)sulfinyl | H | H | H | cyano | H |
| 2-300 | 0 | bromo | H | 1,1,1,2,3,3,3-heptafluoropropan-2-yl | H | (trifluoromethyl)sulfonyl | H | H | H | cyano | H |
| 2-301 | 0 | chloro | H | 1,1,1,2,3,3,4,4,4-nonafluorobutan-2-yl | H | (difluoromethyl)sulfanyl | H | H | H | H | H |
| 2-302 | 1 | chloro | H | 1,1,1,2,3,3,4,4,4-nonafluorobutan-2-yl | H | (difluoromethyl)sulfanyl | H | H | H | H | H |

TABLE 2-continued

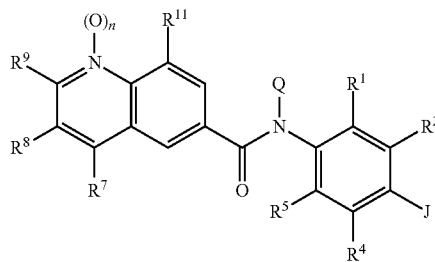

wherein R¹¹ are the same as X².

| Exa | n | R¹ | R² | J | R⁴ | R⁵ | Q | R⁷ | R⁸ | R⁹ | R¹¹ |
|---|---|---|---|---|---|---|---|---|---|---|---|
| 2-303 | 0 | chloro | H | 1,1,1,2,3,3,4,4,4-nonafluorobutan-2-yl | H | (difluoromethyl)sulfanyl | H | H | H | cyano | H |
| 2-304 | 0 | chloro | H | 1-bromo-1,1,2,3,3,3-hexafluoropropan-2-yl | H | (difluoromethyl)sulfanyl | H | H | H | H | H |
| 2-305 | 1 | chloro | H | 1-bromo-1,1,2,3,3,3-hexafluoropropan-2-yl | H | (difluoromethyl)sulfanyl | H | H | H | H | H |
| 2-306 | 0 | chloro | H | 1-bromo-1,1,2,3,3,3-hexafluoropropan-2-yl | H | (difluoromethyl)sulfanyl | H | H | H | cyano | H |
| 2-307 | 0 | chloro | H | 1,1,1,2,3,3-heptafluoropropan-2-yl | H | (difluoromethyl)sulfanyl | H | H | H | H | H |
| 2-308 | 1 | chloro | H | 1,1,1,2,3,3-heptafluoropropan-2-yl | H | (difluoromethyl)sulfanyl | H | H | H | H | H |
| 2-309 | 0 | chloro | H | 1,1,1,2,3,3-heptafluoropropan-2-yl | H | (difluoromethyl)sulfanyl | H | H | H | cyano | H |
| 2-310 | 0 | bromo | H | 1,1,1,2,3,3-heptafluoropropan-2-yl | H | (difluoromethyl)sulfanyl | H | H | H | H | H |
| 2-311 | 1 | bromo | H | 1,1,1,2,3,3-heptafluoropropan-2-yl | H | (difluoromethyl)sulfanyl | H | H | H | H | H |
| 2-312 | 0 | bromo | H | 1,1,1,2,3,3-heptafluoropropan-2-yl | H | (difluoromethyl)sulfanyl | H | H | H | cyano | H |
| 2-313 | 0 | iodo | H | 1,1,1,2,3,3-heptafluoropropan-2-yl | H | (difluoromethyl)sulfanyl | H | H | H | H | H |
| 2-314 | 1 | iodo | H | 1,1,1,2,3,3-heptafluoropropan-2-yl | H | (difluoromethyl)sulfanyl | H | H | H | H | H |
| 2-315 | 0 | iodo | H | 1,1,1,2,3,3-heptafluoropropan-2-yl | H | (difluoromethyl)sulfanyl | H | H | H | cyano | H |
| 2-316 | 0 | bromo | H | 1,1,1,2,3,3-heptafluoropropan-2-yl | H | (difluoromethyl)sulfinyl | H | H | H | cyano | H |
| 2-317 | 0 | bromo | H | 1,1,1,2,3,3-heptafluoropropan-2-yl | H | (difluoromethyl)sulfonyl | H | H | H | cyano | H |
| 2-318 | 0 | chloro | H | 1,1,1,2,3,3-heptafluoropropan-2-yl | H | difluoromethyl | H | H | H | H | H |
| 2-319 | 1 | chloro | H | 1,1,1,2,3,3-heptafluoropropan-2-yl | H | difluoromethyl | H | H | H | H | H |
| 2-320 | 0 | chloro | H | 1,1,1,2,3,3-heptafluoropropan-2-yl | H | difluoromethyl | H | H | H | cyano | H |
| 2-321 | 0 | bromo | H | 1,1,1,2,3,3-heptafluoropropan-2-yl | H | difluoromethyl | H | H | H | H | H |
| 2-322 | 1 | bromo | H | 1,1,1,2,3,3-heptafluoropropan-2-yl | H | difluoromethyl | H | H | H | H | H |
| 2-323 | 0 | bromo | H | 1,1,1,2,3,3-heptafluoropropan-2-yl | H | difluoromethyl | H | H | H | cyano | H |
| 2-324 | 0 | iodo | H | 1,1,1,2,3,3-heptafluoropropan-2-yl | H | difluoromethyl | H | H | H | H | H |
| 2-325 | 1 | iodo | H | 1,1,1,2,3,3-heptafluoropropan-2-yl | H | difluoromethyl | H | H | H | H | H |
| 2-326 | 0 | iodo | H | 1,1,1,2,3,3-heptafluoropropan-2-yl | H | difluoromethyl | H | H | H | cyano | H |
| 2-327 | 0 | chloro | H | 1,1,1,2,3,3,4,4,4-nonafluorobutan-2-yl | H | difluoromethyl | H | H | H | H | H |
| 2-328 | 1 | chloro | H | 1,1,1,2,3,3,4,4,4-nonafluorobutan-2-yl | H | difluoromethyl | H | H | H | H | H |
| 2-329 | 0 | chloro | H | 1,1,1,2,3,3,4,4,4-nonafluorobutan-2-yl | H | difluoromethyl | H | H | H | cyano | H |
| 2-330 | 0 | bromo | H | 1,1,1,2,3,3,4,4,4-nonafluorobutan-2-yl | H | difluoromethyl | H | H | H | H | H |
| 2-331 | 1 | bromo | H | 1,1,1,2,3,3,4,4,4-nonafluorobutan-2-yl | H | difluoromethyl | H | H | H | H | H |
| 2-332 | 0 | bromo | H | 1,1,1,2,3,3,4,4,4-nonafluorobutan-2-yl | H | difluoromethyl | H | H | H | cyano | H |
| 2-333 | 0 | iodo | H | 1,1,1,2,3,3,4,4,4-nonafluorobutan-2-yl | H | difluoromethyl | H | H | H | H | H |
| 2-334 | 1 | iodo | H | 1,1,1,2,3,3,4,4,4-nonafluorobutan-2-yl | H | difluoromethyl | H | H | H | H | H |
| 2-335 | 0 | iodo | H | 1,1,1,2,3,3,4,4,4-nonafluorobutan-2-yl | H | difluoromethyl | H | H | H | cyano | H |
| 2-336 | 0 | chloro | H | 1-bromo-1,1,2,3,3,3-hexafluoropropan-2-yl | H | difluoromethyl | H | H | H | H | H |
| 2-337 | 1 | chloro | H | 1-bromo-1,1,2,3,3,3-hexafluoropropan-2-yl | H | difluoromethyl | H | H | H | H | H |
| 2-338 | 0 | chloro | H | 1-bromo-1,1,2,3,3,3-hexafluoropropan-2-yl | H | difluoromethyl | H | H | H | cyano | H |
| 2-339 | 0 | bromo | H | 1-bromo-1,1,2,3,3,3-hexafluoropropan-2-yl | H | difluoromethyl | H | H | H | H | H |
| 2-340 | 1 | bromo | H | 1-bromo-1,1,2,3,3,3-hexafluoropropan-2-yl | H | difluoromethyl | H | H | H | H | H |
| 2-341 | 0 | bromo | H | 1-bromo-1,1,2,3,3,3-hexafluoropropan-2-yl | H | difluoromethyl | H | H | H | cyano | H |
| 2-342 | 0 | iodo | H | 1-bromo-1,1,2,3,3,3-hexafluoropropan-2-yl | H | difluoromethyl | H | H | H | H | H |
| 2-343 | 1 | iodo | H | 1-bromo-1,1,2,3,3,3-hexafluoropropan-2-yl | H | difluoromethyl | H | H | H | H | H |
| 2-344 | 0 | iodo | H | 1-bromo-1,1,2,3,3,3-hexafluoropropan-2-yl | H | difluoromethyl | H | H | H | cyano | H |
| 2-345 | 0 | CH₃ | H | 1,1,1,2,3,3-heptafluoropropan-2-yl | H | CH₃ | H | H | H | H | cyano |
| 2-346 | 0 | CH₃ | H | 1,1,1,2,3,3-heptafluoropropan-2-yl | H | ethyl | H | H | H | H | cyano |
| 2-347 | 0 | chloro | H | 1,1,1,2,3,3-heptafluoropropan-2-yl | H | chloro | H | H | H | H | cyano |
| 2-348 | 0 | bromo | H | 1,1,1,2,3,3-heptafluoropropan-2-yl | H | bromo | H | H | H | H | cyano |
| 2-349 | 0 | iodo | H | 1,1,1,2,3,3-heptafluoropropan-2-yl | H | iodo | H | H | H | H | cyano |

TABLE 2-continued

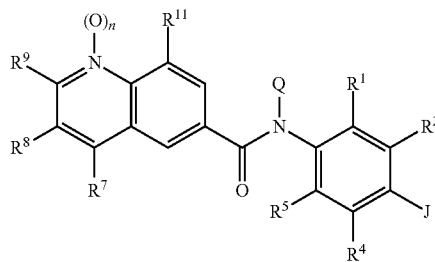

wherein R[11] are the same as X[2].

| Exa | n | R[1] | R[2] | J | R[4] | R[5] | Q | R[7] | R[8] | R[9] | R[11] |
|---|---|---|---|---|---|---|---|---|---|---|---|
| 2-350 | 0 | chloro | H | 1,1,1,2,3,3,3-heptafluoropropan-2-yl | H | difluoromethyl | H | H | H | H | cyano |
| 2-351 | 0 | bromo | H | 1,1,1,2,3,3,3-heptafluoropropan-2-yl | H | difluoromethyl | H | H | H | H | cyano |
| 2-352 | 0 | iodo | H | 1,1,1,2,3,3,3-heptafluoropropan-2-yl | H | difluoromethyl | H | H | H | H | cyano |
| 2-353 | 0 | chloro | H | 1,1,1,2,3,3,3-heptafluoropropan-2-yl | H | trifluoromethyl | H | H | H | H | cyano |
| 2-354 | 0 | bromo | H | 1,1,1,2,3,3,3-heptafluoropropan-2-yl | H | trifluoromethyl | H | H | H | H | cyano |
| 2-355 | 0 | iodo | H | 1,1,1,2,3,3,3-heptafluoropropan-2-yl | H | trifluoromethyl | H | H | H | H | cyano |
| 2-356 | 0 | chloro | H | 1,1,1,2,3,3,3-heptafluoropropan-2-yl | H | difluoromethoxy | H | H | H | H | cyano |
| 2-357 | 0 | bromo | H | 1,1,1,2,3,3,3-heptafluoropropan-2-yl | H | difluoromethoxy | H | H | H | H | cyano |
| 2-358 | 0 | iodo | H | 1,1,1,2,3,3,3-heptafluoropropan-2-yl | H | difluoromethoxy | H | H | H | H | cyano |
| 2-359 | 0 | chloro | H | 1,1,1,2,3,3,3-heptafluoropropan-2-yl | H | trifluoromethoxy | H | H | H | H | cyano |
| 2-360 | 0 | bromo | H | 1,1,1,2,3,3,3-heptafluoropropan-2-yl | H | trifluoromethoxy | H | H | H | H | cyano |
| 2-361 | 0 | iodo | H | 1,1,1,2,3,3,3-heptafluoropropan-2-yl | H | trifluoromethoxy | H | H | H | H | cyano |
| 2-362 | 0 | chloro | H | 1,1,1,2,3,3,3-heptafluoropropan-2-yl | H | difluoromethyl sulfanyl | H | H | H | H | cyano |
| 2-363 | 0 | bromo | H | 1,1,1,2,3,3,3-heptafluoropropan-2-yl | H | difluoromethyl sulfanyl | H | H | H | H | cyano |
| 2-364 | 0 | iodo | H | 1,1,1,2,3,3,3-heptafluoropropan-2-yl | H | difluoromethyl sulfanyl | H | H | H | H | cyano |
| 2-365 | 0 | chloro | H | 1,1,1,2,3,3,3-heptafluoropropan-2-yl | H | trifluoromethyl sulfanyl | H | H | H | H | cyano |
| 2-366 | 0 | bromo | H | 1,1,1,2,3,3,3-heptafluoropropan-2-yl | H | trifluoromethyl sulfanyl | H | H | H | H | cyano |
| 2-367 | 0 | iodo | H | 1,1,1,2,3,3,3-heptafluoropropan-2-yl | H | trifluoromethyl sulfanyl | H | H | H | H | cyano |
| 2-368 | 0 | CH$_3$ | H | 1,1,1,2,3,3,4,4,4-nonafluorobutan-2-yl | H | CH$_3$ | H | H | H | H | cyano |
| 2-369 | 0 | chloro | H | 1,1,1,2,3,3,4,4,4-nonafluorobutan-2-yl | H | chloro | H | H | H | H | cyano |
| 2-370 | 0 | bromo | H | 1,1,1,2,3,3,4,4,4-nonafluorobutan-2-yl | H | bromo | H | H | H | H | cyano |
| 2-371 | 0 | iodo | H | 1,1,1,2,3,3,4,4,4-nonafluorobutan-2-yl | H | iodo | H | H | H | H | cyano |
| 2-372 | 0 | chloro | H | 1,1,1,2,3,3,4,4,4-nonafluorobutan-2-yl | H | difluoromethyl | H | H | H | H | cyano |
| 2-373 | 0 | bromo | H | 1,1,1,2,3,3,4,4,4-nonafluorobutan-2-yl | H | difluoromethyl | H | H | H | H | cyano |
| 2-374 | 0 | iodo | H | 1,1,1,2,3,3,4,4,4-nonafluorobutan-2-yl | H | difluoromethyl | H | H | H | H | cyano |
| 2-375 | 0 | chloro | H | 1,1,1,2,3,3,4,4,4-nonafluorobutan-2-yl | H | trifluoromethyl | H | H | H | H | cyano |
| 2-376 | 0 | bromo | H | 1,1,1,2,3,3,4,4,4-nonafluorobutan-2-yl | H | trifluoromethyl | H | H | H | H | cyano |
| 2-377 | 0 | iodo | H | 1,1,1,2,3,3,4,4,4-nonafluorobutan-2-yl | H | trifluoromethyl | H | H | H | H | cyano |
| 2-378 | 0 | chloro | H | 1,1,1,2,3,3,4,4,4-nonafluorobutan-2-yl | H | difluoromethoxy | H | H | H | H | cyano |
| 2-379 | 0 | bromo | H | 1,1,1,2,3,3,4,4,4-nonafluorobutan-2-yl | H | difluoromethoxy | H | H | H | H | cyano |
| 2-380 | 0 | iodo | H | 1,1,1,2,3,3,4,4,4-nonafluorobutan-2-yl | H | difluoromethoxy | H | H | H | H | cyano |
| 2-381 | 0 | chloro | H | 1,1,1,2,3,3,4,4,4-nonafluorobutan-2-yl | H | trifluoromethoxy | H | H | H | H | cyano |
| 2-382 | 0 | bromo | H | 1,1,1,2,3,3,4,4,4-nonafluorobutan-2-yl | H | trifluoromethoxy | H | H | H | H | cyano |
| 2-383 | 0 | iodo | H | 1,1,1,2,3,3,4,4,4-nonafluorobutan-2-yl | H | trifluoromethoxy | H | H | H | H | cyano |
| 2-384 | 0 | chloro | H | 1,1,1,2,3,3,4,4,4-nonafluorobutan-2-yl | H | difluoromethyl sulfanyl | H | H | H | H | cyano |
| 2-385 | 0 | bromo | H | 1,1,1,2,3,3,4,4,4-nonafluorobutan-2-yl | H | difluoromethyl sulfanyl | H | H | H | H | cyano |
| 2-386 | 0 | iodo | H | 1,1,1,2,3,3,4,4,4-nonafluorobutan-2-yl | H | difluoromethyl sulfanyl | H | H | H | H | cyano |
| 2-387 | 0 | chloro | H | 1,1,1,2,3,3,4,4,4-nonafluorobutan-2-yl | H | trifluoromethyl sulfanyl | H | H | H | H | cyano |
| 2-388 | 0 | bromo | H | 1,1,1,2,3,3,4,4,4-nonafluorobutan-2-yl | H | trifluoromethyl sulfanyl | H | H | H | H | cyano |
| 2-389 | 0 | iodo | H | 1,1,1,2,3,3,4,4,4-nonafluorobutan-2-yl | H | trifluoromethyl sulfanyl | H | H | H | H | cyano |
| 2-390 | 0 | CH$_3$ | H | 1-bromo-1,1,2,3,3,3-hexafluoropropan-2-yl | H | CH$_3$ | H | H | H | H | cyano |
| 2-391 | 0 | CH$_3$ | H | 1-bromo-1,1,2,3,3,3-hexafluoropropan-2-yl | H | ethyl | H | H | H | H | cyano |
| 2-392 | 0 | chloro | H | 1-bromo-1,1,2,3,3,3-hexafluoropropan-2-yl | H | chloro | H | H | H | H | cyano |
| 2-393 | 0 | bromo | H | 1-bromo-1,1,2,3,3,3-hexafluoropropan-2-yl | H | bromo | H | H | H | H | cyano |
| 2-394 | 0 | iodo | H | 1-bromo-1,1,2,3,3,3-hexafluoropropan-2-yl | H | iodo | H | H | H | H | cyano |
| 2-395 | 0 | chloro | H | 1-bromo-1,1,2,3,3,3-hexafluoropropan-2-yl | H | difluoromethyl | H | H | H | H | cyano |
| 2-396 | 0 | bromo | H | 1-bromo-1,1,2,3,3,3-hexafluoropropan-2-yl | H | difluoromethyl | H | H | H | H | cyano |
| 2-397 | 0 | iodo | H | 1-bromo-1,1,2,3,3,3-hexafluoropropan-2-yl | H | difluoromethyl | H | H | H | H | cyano |
| 2-398 | 0 | chloro | H | 1-bromo-1,1,2,3,3,3-hexafluoropropan-2-yl | H | trifluoromethyl | H | H | H | H | cyano |
| 2-399 | 0 | bromo | H | 1-bromo-1,1,2,3,3,3-hexafluoropropan-2-yl | H | trifluoromethyl | H | H | H | H | cyano |

TABLE 2-continued

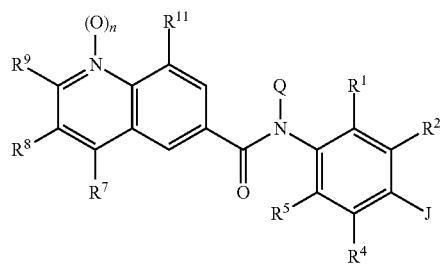

wherein $R^{11}$ are the same as $X^2$.

| Exa | n | $R^1$ | $R^2$ | J | $R^4$ | $R^5$ | Q | $R^7$ | $R^8$ | $R^9$ | $R^{11}$ |
|---|---|---|---|---|---|---|---|---|---|---|---|
| 2-400 | 0 | iodo | H | 1-bromo-1,1,2,3,3,3-hexafluoropropan-2-yl | H | trifluoromethyl | H | H | H | H | cyano |
| 2-401 | 0 | chloro | H | 1-bromo-1,1,2,3,3,3-hexafluoropropan-2-yl | H | difluoromethoxy | H | H | H | H | cyano |
| 2-402 | 0 | bromo | H | 1-bromo-1,1,2,3,3,3-hexafluoropropan-2-yl | H | difluoromethoxy | H | H | H | H | cyano |
| 2-403 | 0 | iodo | H | 1-bromo-1,1,2,3,3,3-hexafluoropropan-2-yl | H | difluoromethoxy | H | H | H | H | cyano |
| 2-404 | 0 | chloro | H | 1-bromo-1,1,2,3,3,3-hexafluoropropan-2-yl | H | difluoromethoxy | H | H | H | H | cyano |
| 2-405 | 0 | bromo | H | 1-bromo-1,1,2,3,3,3-hexafluoropropan-2-yl | H | trifluoromethoxy | H | H | H | H | cyano |
| 2-406 | 0 | iodo | H | 1-bromo-1,1,2,3,3,3-hexafluoropropan-2-yl | H | trifluoromethoxy | H | H | H | H | cyano |
| 2-407 | 0 | chloro | H | 1-bromo-1,1,2,3,3,3-hexafluoropropan-2-yl | H | difluoromethyl sulfanyl | H | H | H | H | cyano |
| 2-408 | 0 | bromo | H | 1-bromo-1,1,2,3,3,3-hexafluoropropan-2-yl | H | difluoromethyl sulfanyl | H | H | H | H | cyano |
| 2-409 | 0 | iodo | H | 1-bromo-1,1,2,3,3,3-hexafluoropropan-2-yl | H | difluoromethyl sulfanyl | H | H | H | H | cyano |
| 2-410 | 0 | chloro | H | 1-bromo-1,1,2,3,3,3-hexafluoropropan-2-yl | H | trifluoromethyl sulfanyl | H | H | H | H | cyano |
| 2-411 | 0 | bromo | H | 1-bromo-1,1,2,3,3,3-hexafluoropropan-2-yl | H | trifluoromethyl sulfanyl | H | H | H | H | cyano |
| 2-412 | 0 | iodo | H | 1-bromo-1,1,2,3,3,3-hexafluoropropan-2-yl | H | trifluoromethyl sulfanyl | H | H | H | H | cyano |

TABLE 3a

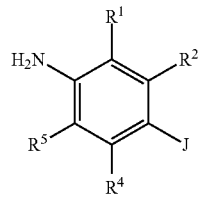

| Exa | $R^1$ | $R^2$ | J | $R^4$ | $R^5$ |
|---|---|---|---|---|---|
| a-1 | H | H | undecafluorocyclohexyl | H | H |
| a-2 | H | H | undecafluorocyclohexyl | H | $CH_3$ |
| a-3 | $CH_3$ | H | undecafluorocyclohexyl | H | $CH_3$ |
| a-4 | $CH_3$ | H | undecafluorocyclohexyl | H | ethyl |
| a-5 | chloro | H | undecafluorocyclohexyl | H | chloro |
| a-6 | bromo | H | undecafluorocyclohexyl | H | bromo |
| a-7 | iodo | H | undecafluorocyclohexyl | H | iodo |

TABLE 3b

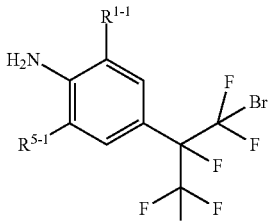

| Exa | $R^{1-1}$ | $R^{5-1}$ |
|---|---|---|
| b-1 | $CH_3$ | $CH_3$ |
| b-2 | $CH_3$ | ethyl |
| b-3 | chloro | chloro |
| b-4 | bromo | bromo |
| b-5 | iodo | iodo |
| b-6 | H | difluoromethoxy |
| b-7 | chloro | difluoromethoxy |
| b-8 | bromo | difluoromethoxy |
| b-9 | iodo | difluoromethoxy |
| b-10 | methyl | difluoromethoxy |

TABLE 3c

| Exa | M | R⁵⁻² | R¹⁵ |
|---|---|---|---|
| c-1 | O | H | trifluoromethyl |
| c-2 | O | chloro | trifluoromethyl |
| c-3 | O | bromo | trifluoromethyl |
| c-4 | O | iodo | trifluoromethyl |
| c-5 | O | H | pentafluoroethyl |
| c-6 | O | chloro | pentafluoroethyl |
| c-7 | O | bromo | pentafluoroethyl |
| c-8 | O | iodo | pentafluoroethyl |
| c-9 | O | methyl | trifluoromethyl |
| c-10 | O | methyl | pentafluoroethyl |

TABLE 4

| Exa | R¹ | R² | J | R⁴ | R⁵ | Q | R⁹ |
|---|---|---|---|---|---|---|---|
| 4-1 | CH₃ | H | 1,1,1,2,3,3,3-heptafluoropropan-2-yl | H | CH₃ | H | H |
| 4-2 | CH₃ | H | 1,1,1,2,3,3,3-heptafluoropropan-2-yl | H | CH₃ | H | cyano |
| 4-3 | CH₃ | H | 1,1,1,2,3,3,3-heptafluoropropan-2-yl | H | ethyl | H | H |
| 4-4 | CH₃ | H | 1,1,1,2,3,3,3-heptafluoropropan-2-yl | H | ethyl | H | cyano |
| 4-5 | chloro | H | 1,1,1,2,3,3,3-heptafluoropropan-2-yl | H | chloro | H | H |
| 4-6 | chloro | H | 1,1,1,2,3,3,3-heptafluoropropan-2-yl | H | chloro | H | cyano |
| 4-7 | bromo | H | 1,1,1,2,3,3,3-heptafluoropropan-2-yl | H | bromo | H | H |
| 4-8 | bromo | H | 1,1,1,2,3,3,3-heptafluoropropan-2-yl | H | bromo | H | cyano |
| 4-9 | iodo | H | 1,1,1,2,3,3,3-heptafluoropropan-2-yl | H | iodo | H | H |
| 4-10 | iodo | H | 1,1,1,2,3,3,3-heptafluoropropan-2-yl | H | iodo | H | cyano |
| 4-11 | CH₃ | H | 1,1,1,2,3,3,3-heptafluoropropan-2-yl | H | difluoromethoxy | H | H |
| 4-12 | CH₃ | H | 1,1,1,2,3,3,3-heptafluoropropan-2-yl | H | difluoromethoxy | H | cyano |
| 4-13 | chloro | H | 1,1,1,2,3,3,3-heptafluoropropan-2-yl | H | difluoromethoxy | H | H |
| 4-14 | chloro | H | 1,1,1,2,3,3,3-heptafluoropropan-2-yl | H | difluoromethoxy | H | cyano |
| 4-15 | bromo | H | 1,1,1,2,3,3,3-heptafluoropropan-2-yl | H | difluoromethoxy | H | H |
| 4-16 | bromo | H | 1,1,1,2,3,3,3-heptafluoropropan-2-yl | H | difluoromethoxy | H | cyano |
| 4-17 | iodo | H | 1,1,1,2,3,3,3-heptafluoropropan-2-yl | H | difluoromethoxy | H | H |
| 4-18 | iodo | H | 1,1,1,2,3,3,3-heptafluoropropan-2-yl | H | difluoromethoxy | H | cyano |
| 4-19 | chloro | H | 1,1,1,2,3,3,3-heptafluoropropan-2-yl | H | trifluoromethyl | H | H |
| 4-20 | chloro | H | 1,1,1,2,3,3,3-heptafluoropropan-2-yl | H | trifluoromethyl | H | cyano |
| 4-21 | bromo | H | 1,1,1,2,3,3,3-heptafluoropropan-2-yl | H | trifluoromethyl | H | H |
| 4-22 | bromo | H | 1,1,1,2,3,3,3-heptafluoropropan-2-yl | H | trifluoromethyl | H | cyano |
| 4-23 | iodo | H | 1,1,1,2,3,3,3-heptafluoropropan-2-yl | H | trifluoromethyl | H | H |
| 4-24 | iodo | H | 1,1,1,2,3,3,3-heptafluoropropan-2-yl | H | trifluoromethyl | H | cyano |
| 4-25 | chloro | H | 1,1,1,2,3,3,3-heptafluoropropan-2-yl | H | (trifluoromethyl)sulfanyl | H | H |
| 4-26 | chloro | H | 1,1,1,2,3,3,3-heptafluoropropan-2-yl | H | (trifluoromethyl)sulfanyl | H | cyano |
| 4-27 | bromo | H | 1,1,1,2,3,3,3-heptafluoropropan-2-yl | H | (trifluoromethyl)sulfanyl | H | H |
| 4-28 | bromo | H | 1,1,1,2,3,3,3-heptafluoropropan-2-yl | H | (trifluoromethyl)sulfanyl | H | cyano |
| 4-29 | iodo | H | 1,1,1,2,3,3,3-heptafluoropropan-2-yl | H | (trifluoromethyl)sulfanyl | H | H |
| 4-30 | iodo | H | 1,1,1,2,3,3,3-heptafluoropropan-2-yl | H | (trifluoromethyl)sulfanyl | H | cyano |
| 4-31 | CH₃ | H | 1,1,1,2,3,3,4,4,4-nonafluorobutan-2-yl | H | CH₃ | H | H |
| 4-32 | CH₃ | H | 1,1,1,2,3,3,4,4,4-nonafluorobutan-2-yl | H | CH₃ | H | cyano |
| 4-33 | CH₃ | H | 1,1,1,2,3,3,4,4,4-nonafluorobutan-2-yl | H | ethyl | H | H |
| 4-34 | CH₃ | H | 1,1,1,2,3,3,4,4,4-nonafluorobutan-2-yl | H | ethyl | H | cyano |
| 4-35 | chloro | H | 1,1,1,2,3,3,4,4,4-nonafluorobutan-2-yl | H | chloro | H | H |
| 4-36 | chloro | H | 1,1,1,2,3,3,4,4,4-nonafluorobutan-2-yl | H | chloro | H | cyano |
| 4-37 | bromo | H | 1,1,1,2,3,3,4,4,4-nonafluorobutan-2-yl | H | bromo | H | H |
| 4-38 | bromo | H | 1,1,1,2,3,3,4,4,4-nonafluorobutan-2-yl | H | bromo | H | cyano |
| 4-39 | iodo | H | 1,1,1,2,3,3,4,4,4-nonafluorobutan-2-yl | H | iodo | H | H |
| 4-40 | iodo | H | 1,1,1,2,3,3,4,4,4-nonafluorobutan-2-yl | H | iodo | H | cyano |

TABLE 4-continued

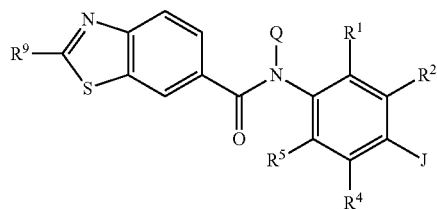

| Exa | R¹ | R² | J | R⁴ | R⁵ | Q | R⁹ |
|---|---|---|---|---|---|---|---|
| 4-41 | CH₃ | H | 1,1,1,2,3,3,4,4,4-nonafluorobutan-2-yl | H | difluoromethoxy | H | H |
| 4-42 | CH₃ | H | 1,1,1,2,3,3,4,4,4-nonafluorobutan-2-yl | H | difluoromethoxy | H | cyano |
| 4-43 | chloro | H | 1,1,1,2,3,3,4,4,4-nonafluorobutan-2-yl | H | difluoromethoxy | H | H |
| 4-44 | chloro | H | 1,1,1,2,3,3,4,4,4-nonafluorobutan-2-yl | H | difluoromethoxy | H | cyano |
| 4-45 | bromo | H | 1,1,1,2,3,3,4,4,4-nonafluorobutan-2-yl | H | difluoromethoxy | H | H |
| 4-46 | bromo | H | 1,1,1,2,3,3,4,4,4-nonafluorobutan-2-yl | H | difluoromethoxy | H | cyano |
| 4-47 | iodo | H | 1,1,1,2,3,3,4,4,4-nonafluorobutan-2-yl | H | difluoromethoxy | H | H |
| 4-48 | iodo | H | 1,1,1,2,3,3,4,4,4-nonafluorobutan-2-yl | H | difluoromethoxy | H | cyano |
| 4-49 | chloro | H | 1,1,1,2,3,3,4,4,4-nonafluorobutan-2-yl | H | trifluoromethyl | H | H |
| 4-50 | chloro | H | 1,1,1,2,3,3,4,4,4-nonafluorobutan-2-yl | H | trifluoromethyl | H | cyano |
| 4-51 | bromo | H | 1,1,1,2,3,3,4,4,4-nonafluorobutan-2-yl | H | trifluoromethyl | H | H |
| 4-52 | bromo | H | 1,1,1,2,3,3,4,4,4-nonafluorobutan-2-yl | H | trifluoromethyl | H | cyano |
| 4-53 | iodo | H | 1,1,1,2,3,3,4,4,4-nonafluorobutan-2-yl | H | trifluoromethyl | H | H |
| 4-54 | iodo | H | 1,1,1,2,3,3,4,4,4-nonafluorobutan-2-yl | H | trifluoromethyl | H | cyano |
| 4-55 | chloro | H | 1,1,1,2,3,3,4,4,4-nonafluorobutan-2-yl | H | (trifluoromethyl)sulfanyl | H | H |
| 4-56 | chloro | H | 1,1,1,2,3,3,4,4,4-nonafluorobutan-2-yl | H | (trifluoromethyl)sulfanyl | H | cyano |
| 4-57 | bromo | H | 1,1,1,2,3,3,4,4,4-nonafluorobutan-2-yl | H | (trifluoromethyl)sulfanyl | H | H |
| 4-58 | bromo | H | 1,1,1,2,3,3,4,4,4-nonafluorobutan-2-yl | H | (trifluoromethyl)sulfanyl | H | cyano |
| 4-59 | iodo | H | 1,1,1,2,3,3,4,4,4-nonafluorobutan-2-yl | H | (trifluoromethyl)sulfanyl | H | H |
| 4-60 | iodo | H | 1,1,1,2,3,3,4,4,4-nonafluorobutan-2-yl | H | (trifluoromethyl)sulfanyl | H | cyano |
| 4-61 | CH3 | H | 1-bromo-1,1,2,3,3,3-hexafluoropropan-2-yl | H | CH3 | H | H |
| 4-62 | CH3 | H | 1-bromo-1,1,2,3,3,3-hexafluoropropan-2-yl | H | CH3 | H | cyano |
| 4-63 | CH3 | H | 1-bromo-1,1,2,3,3,3-hexafluoropropan-2-yl | H | ethyl | H | H |
| 4-64 | CH3 | H | 1-bromo-1,1,2,3,3,3-hexafluoropropan-2-yl | H | ethyl | H | cyano |
| 4-65 | chloro | H | 1-bromo-1,1,2,3,3,3-hexafluoropropan-2-yl | H | chloro | H | H |
| 4-66 | chloro | H | 1-bromo-1,1,2,3,3,3-hexafluoropropan-2-yl | H | chloro | H | cyano |
| 4-67 | bromo | H | 1-bromo-1,1,2,3,3,3-hexafluoropropan-2-yl | H | bromo | H | H |
| 4-68 | bromo | H | 1-bromo-1,1,2,3,3,3-hexafluoropropan-2-yl | H | bromo | H | cyano |
| 4-69 | iodo | H | 1-bromo-1,1,2,3,3,3-hexafluoropropan-2-yl | H | iodo | H | H |
| 4-70 | iodo | H | 1-bromo-1,1,2,3,3,3-hexafluoropropan-2-yl | H | iodo | H | cyano |
| 4-71 | CH3 | H | 1-bromo-1,1,2,3,3,3-hexafluoropropan-2-yl | H | difluoromethoxy | H | H |
| 4-72 | CH3 | H | 1-bromo-1,1,2,3,3,3-hexafluoropropan-2-yl | H | difluoromethoxy | H | cyano |
| 4-73 | chloro | H | 1-bromo-1,1,2,3,3,3-hexafluoropropan-2-yl | H | difluoromethoxy | H | H |
| 4-74 | chloro | H | 1-bromo-1,1,2,3,3,3-hexafluoropropan-2-yl | H | difluoromethoxy | H | cyano |
| 4-75 | bromo | H | 1-bromo-1,1,2,3,3,3-hexafluoropropan-2-yl | H | difluoromethoxy | H | H |
| 4-76 | bromo | H | 1-bromo-1,1,2,3,3,3-hexafluoropropan-2-yl | H | difluoromethoxy | H | cyano |
| 4-77 | iodo | H | 1-bromo-1,1,2,3,3,3-hexafluoropropan-2-yl | H | difluoromethoxy | H | H |
| 4-78 | iodo | H | 1-bromo-1,1,2,3,3,3-hexafluoropropan-2-yl | H | difluoromethoxy | H | cyano |
| 4-79 | chloro | H | 1-bromo-1,1,2,3,3,3-hexafluoropropan-2-yl | H | trifluoromethyl | H | H |
| 4-80 | chloro | H | 1-bromo-1,1,2,3,3,3-hexafluoropropan-2-yl | H | trifluoromethyl | H | cyano |
| 4-81 | bromo | H | 1-bromo-1,1,2,3,3,3-hexafluoropropan-2-yl | H | trifluoromethyl | H | H |
| 4-82 | bromo | H | 1-bromo-1,1,2,3,3,3-hexafluoropropan-2-yl | H | trifluoromethyl | H | cyano |
| 4-83 | iodo | H | 1-bromo-1,1,2,3,3,3-hexafluoropropan-2-yl | H | trifluoromethyl | H | H |
| 4-84 | iodo | H | 1-bromo-1,1,2,3,3,3-hexafluoropropan-2-yl | H | trifluoromethyl | H | cyano |
| 4-85 | chloro | H | 1-bromo-1,1,2,3,3,3-hexafluoropropan-2-yl | H | (trifluoromethyl)sulfanyl | H | H |
| 4-86 | chloro | H | 1-bromo-1,1,2,3,3,3-hexafluoropropan-2-yl | H | (trifluoromethyl)sulfanyl | H | cyano |
| 4-87 | bromo | H | 1-bromo-1,1,2,3,3,3-hexafluoropropan-2-yl | H | (trifluoromethyl)sulfanyl | H | H |
| 4-88 | bromo | H | 1-bromo-1,1,2,3,3,3-hexafluoropropan-2-yl | H | (trifluoromethyl)sulfanyl | H | cyano |
| 4-89 | iodo | H | 1-bromo-1,1,2,3,3,3-hexafluoropropan-2-yl | H | (trifluoromethyl)sulfanyl | H | H |
| 4-90 | iodo | H | 1-bromo-1,1,2,3,3,3-hexafluoropropan-2-yl | H | (trifluoromethyl)sulfanyl | H | cyano |

TABLE 5

| Exa | R¹ | R² | J | R⁴ | R⁵ | Q | R¹¹ |
|---|---|---|---|---|---|---|---|
| 5-1 | $CH_3$ | H | 1,1,1,2,3,3,3-heptafluoropropan-2-yl | H | $CH_3$ | H | bromo |
| 5-2 | $CH_3$ | H | 1,1,1,2,3,3,3-heptafluoropropan-2-yl | H | ethyl | H | bromo |
| 5-3 | $CH_3$ | H | 1,1,1,2,3,3,4,4,4-nonafluorobutan-2-yl | H | $CH_3$ | H | bromo |
| 5-4 | $CH_3$ | H | 1,1,1,2,3,3,4,4,4-nonafluorobutan-2-yl | H | ethyl | H | bromo |

TABLE 6

| Exa | R¹ | R² | J | R⁴ | R⁵ | Q |
|---|---|---|---|---|---|---|
| 6-1 | $CH_3$ | H | 1,1,1,2,3,3,3-heptafluoropropan-2-yl | H | $CH_3$ | H |
| 6-2 | $CH_3$ | H | 1,1,1,2,3,3,3-heptafluoropropan-2-yl | H | ethyl | H |
| 6-3 | $CH_3$ | H | 1,1,1,2,3,3,4,4,4-nonafluorobutan-2-yl | H | $CH_3$ | H |
| 6-4 | $CH_3$ | H | 1,1,1,2,3,3,4,4,4-nonafluorobutan-2-yl | H | ethyl | H |
| 6-5 | $CH_3$ | H | 1-bromo-1,1,2,3,3,3-hexafluoropropan-2-yl | H | $CH_3$ | H |
| 6-6 | $CH_3$ | H | 1-bromo-1,1,2,3,3,3-hexafluoropropan-2-yl | H | ethyl | H |

TABLE 7

| Exa | NMR |
|---|---|
| 1-3 | $^1$H-NMR (CDCl$_3$) δ: 1.23 (3H, t), 2.35 (3H, s), 2.71 (2H, q), 7.39 (2H, s), 7.63-7.66 (2H, m), 7.80 (1H, d), 7.85 (1H, d), 7.96 (1H, dd), 8.08 (1H, s), 8.40 (1H, s). |
| 1-4 | $^1$H-NMR (CDCl$_3$) δ: 1.25 (3H, t), 2.39 (3H, s), 2.74 (2H, q), 7.41 (2H, br s), 7.60 (1H, s), 7.73 (1H, d), 8.07-8.09 (4H, m), 8.32 (1H, s), 8.50 (1H, s). |
| 1-6 | $^1$H-NMR (CDCl$_3$) δ: 0.88 (3H, t), 2.26 (3H, s), 2.39 (3H, s), 2.74 (2H, q), 7.39 (2H, s), 7.53-7.56 (3H, m), 7.90-7.92 (3H, m), 8.34 (1H, s), 8.40 (1H, s). |
| 2-1 | $^1$H-NMR (CDCl$_3$) δ: 7.53 (1H, dd), 7.88 (1H, s), 7.93 (2H, s), 8.21-8.34 (3H, m), 8.53 (1H, s), 9.05 (1H, dd). |
| 2-2 | $^1$H-NMR (DMSO-d6) δ: 7.56 (1H, dd), 8.10 (1H, d), 8.18 (2H, s), 8.34 (1H, d), 8.63-8.68 (2H, m), 8.74 (1H, s). |
| 2-3 | $^1$H-NMR (DMSO-d6) δ: 8.18 (1H, d), 8.26 (2H, s), 8.33 (1H, d), 8.44 (1H, d), 8.83 (1H, s), 8.90 (1H, d), 11.01 (1H, s). |
| 2-4 | $^1$H-NMR (DMSO-d6) δ: 7.64-7.72 (3H, m), 8.08-8.18 (3H, m), 8.27 (1H, d), 8.56 (1H, d), 8.66 (1H, s), 9.03 (1H, d), 10.85 (1H, s). |
| 2-6 | $^1$H-NMR (CDCl$_3$) δ: 7.67 (2H, d), 7.80-7.87 (3H, m), 8.09 (1H, s), 8.25-8.34 (2H, m), 8.45-8.49 (2H, m). |
| 2-7 | $^1$H-NMR (CDCl$_3$) δ: 2.47 (3H, s), 7.50-7.55 (3H, m), 7.92 (1H, s), 8.14 (1H, dd), 8.24-8.32 (3H, m), 8.43 (1H, d), 9.04 (1H, dd). |
| 2-8 | $^1$H-NMR (CDCl$_3$) δ: 2.49 (3H, s), 7.40 (1H, dd), 7.51-7.56 (2H, m), 7.84 (1H, d), 8.10 (1H, dd), 8.20-8.25 (2H, m), 8.42 (1H, s), 8.57 (1H, d), 8.77 (1H, d). |
| 2-9 | $^1$H-NMR (CDCl$_3$) δ: 2.47 (3H, s), 7.51-7.57 (2H, m), 7.82 (1H, d), 7.88 (1H, s), 8.23-8.35 (3H, m), 8.46-8.50 (2H, m). |
| 2-10 | $^1$H-NMR (CDCl$_3$) δ: 2.39 (6H, s), 7.39 (2H, s), 7.53 (1H, dd), 7.59 (1H, s), 8.17-8.31 (3H, m), 8.47 (1H, s), 9.04 (1H, dd). |
| 2-11 | $^1$H-NMR (CDCl$_3$) δ: 2.39 (6H, s), 7.33-7.38 (3H, m), 7.80 (1H, d), 8.17 (1H, d), 8.32 (1H, s), 8.46 (1H, s), 8.50 (1H, d), 8.69 (1H, d). |
| 2-12 | $^1$H-NMR (CDCl$_3$) δ: 2.38 (6H, s), 7.39 (2H, s), 7.59 (1H, d), 7.79 (1H, s), 8.22-8.28 (2H, m), 8.81 (1H, s), 8.89 (1H, d). |
| 2-13 | $^1$H-NMR (CDCl$_3$) δ: 2.37 (6H, s), 7.39 (2H, s), 7.65 (1H, s), 8.16-8.25 (2H, m), 8.37-8.42 (2H, m), 9.02 (1H, d). |
| 2-14 | $^1$H-NMR (DMSO-d6) δ: 2.34 (6H, s), 7.47 (2H, s), 8.25 (1H, d), 8.33 (1H, d), 8.46 (1H, dd), 8.76 (1H, d), 9.22 (1H, d), 10.48 (1H, s). |
| 2-15 | $^1$H-NMR (CDCl$_3$) δ: 2.39 (6H, s), 3.35 (1H, s), 7.39 (2H, s), 7.57 (1H, br s), 7.65 (1H, d), 8.17-8.30 (3H, m), 8.45 (1H, s). |
| 2-16 | $^1$H-NMR (CDCl$_3$) δ: 2.39 (6H, s), 7.39 (2H, s), 7.55 (1H, s), 7.65 (1H, d), 8.18-8.29 (3H, m), 8.45 (1H, s). |
| 2-17 | $^1$H-NMR (CDCl$_3$) δ: 2.35 (6H, s), 7.38 (2H, s), 7.49 (1H, d), 7.70 (1H, s), 8.10-8.24 (3H, m), 8.44 (1H, s). |
| 2-18 | $^1$H-NMR (CDCl$_3$) δ: 2.36 (6H, s), 7.38 (2H, s), 7.49 (1H, d), 7.69 (1H, s), 8.11-8.22 (3H, m), 8.45 (1H, s). |
| 2-19 | $^1$H-NMR (CDCl$_3$) δ: 2.37 (6H, s), 7.40 (2H, s), 7.54 (1H, s), 7.86 (1H, d), 8.29 (1H, d), 8.39 (1H, d), 8.51-8.55 (2H, m). |
| 2-20 | $^1$H-NMR (CDCl$_3$) δ: 2.40 (6H, s), 7.40 (2H, s), 7.56 (1H, s), 7.82 (1H, d), 8.28-8.36 (2H, m), 8.47 (1H, d), 8.54 (1H, s). |

TABLE 7-continued

| Exa | NMR |
|---|---|
| 2-21 | $^1$H-NMR (CDCl$_3$) δ: 2.39 (6H, s), 7.40 (2H, s), 7.54 (1H, br s), 7.85 (1H, d), 7.98 (1H, d), 8.26 (1H, d), 8.53 (1H, s), 8.84 (1H, d). |
| 2-23 | $^1$H-NMR (DMSO-d6) δ: 2.31 (6H, s), 2.66 (3H, s), 7.44 (2H, s), 7.48 (1H, d), 7.98 (1H, d), 8.22-8.30 (2H, m), 8.57 (1H, d), 10.16 (1H, s). |
| 2-24 | $^1$H-NMR (DMSO-d6) δ: 2.18 (3H, s), 2.33 (6H, s), 7.46 (2H, s), 7.91 (1H, d), 8.24 (1H, dd), 8.39 (1H, d), 8.51 (1H, d), 8.60 (1H, d), 10.14 (1H, s), 10.96 (1H, s). |
| 2-25 | $^1$H-NMR (CDCl$_3$) δ: 2.40 (6H, s), 7.39 (2H, s), 7.49-7.66 (4H, m), 7.96-8.02 (3H, m), 8.18 (1H, d), 8.35 (1H, d), 8.43 (1H, s), 8.71 (1H, d), 8.85 (1H, s). |
| 2-26 | $^1$H-NMR (CDCl$_3$) δ: 1.25 (3H, t), 2.39 (3H, s), 2.74 (2H, q), 7.40 (2H, s), 7.52-7.53 (1H, m), 7.63 (1H, s), 8.22-8.29 (3H, m), 8.47 (1H, s), 9.04 (1H, dd). |
| 2-27 | $^1$H-NMR (CDCl$_3$) δ: 1.25 (3H, t), 2.39 (3H, s), 2.75 (3H, q), 7.36-7.39 (3H, m), 7.83 (1H, d), 8.16-8.19 (2H, m), 8.48 (1H, d), 8.52 (1H, d), 8.74 (1H, d). |
| 2-28 | $^1$H-NMR (CDCl$_3$) δ: 1.23 (3H, t), 2.35 (3H, s), 2.69-2.80 (5H, m), 7.38-7.39 (3H, m), 7.65 (1H, s), 8.13-8.16 (3H, m), 8.41 (1H, s). |
| 2-29 | $^1$H-NMR (CDCl$_3$) δ: 1.25 (3H, t), 2.39 (3H, s), 2.73 (2H, q), 7.40 (2H, q), 7.51-7.53 (2H, m), 8.18-8.26 (3H, m), 8.47 (1H, s). |
| 2-30 | $^1$H-NMR (CDCl$_3$) δ: 1.20 (3H, t), 2.35 (3H, s), 2.71 (2H, q), 3.74 (3H, s), 6.75 (1H, d), 7.38 (2H, s), 7.45 (1H, d), 7.71-7.74 (2H, m), 8.12-8.15 (2H, m). |
| 2-31 | $^1$H-NMR (CDCl$_3$) δ: 1.26 (3H, t), 2.39 (3H, s), 2.74 (2H, q), 7.41 (2H, s), 7.57 (1H, s), 7.82 (1H, d), 8.31-8.33 (2H, m), 8.47 (1H, d), 8.53 (1H, s). |
| 2-33 | $^1$H-NMR (CDCl$_3$) δ: 1.24 (3H, t), 2.16 (3H, s), 2.38 (3H, s), 2.73 (2H, q), 4.77 (2H, d), 7.38-7.44 (3H, m), 7.70 (1H, s), 8.15-8.25 (3H, m), 8.44 (1H, s). |
| 2-34 | $^1$H-NMR (CDCl$_3$) δ: 1.26 (3H, t), 2.41 (3H, s), 2.75 (2H, q), 7.41 (2H, s), 7.57 (1H, s), 8.18-8.27 (4H, m), 8.48-50 (2H, m), 9.43 (1H, s). |
| 2-35 | $^1$H-NMR (CDCl$_3$) δ: 1.26 (6H, d), 2.39 (3H, s), 3.18-3.27 (1H, m), 7.39 (1H, s), 7.45 (1H, s), 7.53 (1H, dd), 7.61 (1H, s), 8.17-8.32 (3H, m), 8.48 (1H, d), 9.04 (1H, dd). |
| 2-36 | $^1$H-NMR (CDCl$_3$) δ: 1.26 (6H, d), 2.38 (3H, s), 3.23 (1H, t), 7.35-7.45 (3H, m), 7.85 (1H, d), 8.08 (1H, s), 8.20 (1H, d), 8.50-8.55 (2H, m), 8.78 (1H, d). |
| 2-37 | $^1$H-NMR (CDCl$_3$) δ: 1.27 (6H, d), 2.39 (3H, s), 3.19-3.22 (1H, m), 7.40 (1H, s), 7.46 (1H, s), 7.54 (1H, s), 7.82 (1H, d), 8.28-8.36 (2H, m), 8.48 (1H, d), 8.54 (1H, d). |
| 2-38 | $^1$H-NMR (CDCl$_3$) δ: 2.46 (3H, s), 7.49-7.53 (2H, m), 7.75 (1H, s), 8.03 (1H, s), 8.23-8.30 (3H, m), 8.50 (1H, s), 9.03 (1H, dd). |
| 2-39 | $^1$H-NMR (CDCl$_3$) δ: 2.48 (3H, s), 7.41 (1H, dd), 7.52 (1H, s), 7.76 (1H, s), 7.86 (1H, d), 8.11 (1H, s), 8.22 (1H, d), 8.52 (1H, s), 8.60 (1H, d), 8.83 (1H, d). |
| 2-40 | $^1$H-NMR (CDCl$_3$) δ: 2.48 (3H, s), 7.53 (1H, s), 7.77 (1H, s), 7.81-7.84 (2H, m), 8.34-8.36 (2H, m), 8.49 (1H, d), 8.56 (1H, s). |
| 2-44 | $^1$H-NMR (DMSO-d6) δ: 1.15 (6H, t), 2.70 (4H, q), 7.45 (2H, s), 7.59 (1H, dd), 8.12 (1H, d), 8.31 (1H, dd), 8.66-8.73 (3H, m), 10.31 (1H, s). |
| 2-46 | $^1$H-NMR (CDCl$_3$) δ: 1.26 (6H, t), 2.74 (4H, q), 7.43 (2H, s), 7.53 (1H, s), 7.82 (1H, d), 8.29 (1H, dd), 8.34 (1H, d), 8.48 (1H, d), 8.53 (1H, d). |
| 2-47 | $^1$H-NMR (CDCl$_3$) δ: 1.28 (3H, t), 2.83 (2H, q), 7.51-7.55 (2H, m), 7.77-7.80 (2H, m), 8.20-8.33 (3H, m), 8.50 (1H, s), 9.05 (1H, dd). |
| 2-48 | $^1$H-NMR (CDCl$_3$) δ: 1.28 (3H, t), 2.82 (2H, q), 7.43 (1H, dd), 7.55 (2H, s), 7.77 (1H, s), 7.90 (1H, d), 8.13 (1H, s), 8.23 (1H, d), 8.52 (1H, s), 8.67 (1H, d), 8.82 (1H, d). |
| 2-49 | $^1$H-NMR (CDCl$_3$) δ: 1.29 (3H, t), 2.82 (2H, q), 7.56 (1H, s), 7.73 (1H, s), 7.78 (1H, s), 7.82 (1H, d), 8.33-8.35 (2H, m), 8.48 (1H, d), 8.56 (1H, s). |
| 2-56 | $^1$H-NMR (CDCl$_3$) δ: 1.26 (12H, d), 3.17-3.26 (2H, m), 7.46 (2H, s), 7.49 (1H, s), 7.54 (1H, dd), 8.17-8.34 (3H, m), 8.49 (1H, d), 9.05 (1H, dd). |
| 2-57 | $^1$H-NMR (CDCl$_3$) δ: 1.26 (12H, d), 3.16-3.25 (2H, m), 7.38-7.46 (3H, m), 7.85-7.91 (2H, m), 8.21 (1H, dd), 8.52 (1H, d), 8.61 (1H, d), 8.84 (1H, d). |
| 2-58 | $^1$H-NMR (CDCl$_3$) δ: 1.27 (12H, d), 3.15-3.22 (2H, m), 7.46-7.48 (2H, m), 7.83 (1H, d), 8.33 (1H, dd), 8.49 (1H, d), 8.54 (1H, s). |
| 2-59 | $^1$H-NMR (CDCl$_3$) δ: 7.52 (1H, dd), 7.69 (2H, s), 8.09 (1H, br s), 8.17-8.30 (3H, m), 8.50 (1H, s), 9.02 (1H, dd). |
| 2-60 | $^1$H-NMR (CDCl$_3$) δ: 7.41 (1H, dd), 7.70 (2H, s), 7.85 (1H, d), 8.15-8.22 (2H, m), 8.49 (1H, s), 8.60 (1H, d), 8.81 (1H, d). |
| 2-61 | $^1$H-NMR (CDCl$_3$) δ: 7.71 (2H, s), 7.81-7.84 (2H, m), 8.30-8.36 (2H, m), 8.48 (1H, d), 8.56 (1H, s). |
| 2-62 | $^1$H-NMR (CDCl$_3$) δ: 7.54 (1H, dd), 7.82 (1H, s), 7.90 (2H, s), 8.21-8.34 (3H, m), 8.52 (1H, d), 9.06 (1H, dd). |
| 2-63 | $^1$H-NMR (CDCl$_3$) δ: 7.39 (1H, ddz), 7.85-7.91 (3H, m), 8.19 (1H, d), 8.48 (1H, s), 8.63-8.65 (2H, m), 8.73 (1H, d). |
| 2-64 | $^1$H-NMR (CDCl$_3$) δ: 7.81-7.84 (2H, m), 7.91 (2H, s), 8.34-8.35 (2H, m), 8.49 (1H, d), 8.57 (1H, s). |
| 2-65 | $^1$H-NMR (CDCl$_3$) δ: 7.55 (1H, dd), 8.04-8.05 (2H, m), 8.20-8.36 (4H, m), 8.53 (1H, d), 9.07 (1H, d). |
| 2-66 | $^1$H-NMR (CDCl$_3$) δ: 7.84 (1H, d), 8.06 (2H, s), 8.25-8.38 (3H, m), 8.51 (1H, d), 8.58 (1H, s). |
| 2-67 | $^1$H-NMR (CDCl$_3$) δ: 7.54 (1H, dd), 7.86 (1H, s), 8.13 (2H, s), 8.24-8.36 (3H, m), 8.54 (1H, s), 9.06 (1H, dd). |
| 2-68 | $^1$H-NMR (CDCl$_3$) δ: 7.34-7.42 (1H, m), 7.84 (1H, d), 8.04-8.12 (3H, m), 8.26 (1H, d), 8.52-8.66 (2H, m), 9.23 (1H, s). |
| 2-69 | $^1$H-NMR (CDCl$_3$) δ: 7.83 (1H, d), 7.87 (1H, br s), 8.14 (2H, s), 8.36-8.37 (2H, m), 8.50 (1H, d), 8.59 (1H, s). |

TABLE 7-continued

| Exa | NMR |
|---|---|
| 2-70 | ¹H-NMR (acetone-d6) δ: 1.20 (3H, t), 2.37 (3H, s), 2.77 (2H, q), 7.58-7.62 (3H, m), 8.16 (1H, d), 8.35 (1H, dd), 8.47 (1H, d), 8.68 (1H, d), 9.01 (1H, dd), 9.38 (1H, s). |
| 2-71 | ¹H-NMR (CDCl₃) δ: 1.24 (3H, t), 2.38 (3H, s), 2.73 (2H, q), 3.28 (3H, s), 7.47-7.55 (3H, m), 7.72 (1H, s), 8.18 (2H, s), 8.30 (1H, d), 8.46 (1H, s), 9.02 (1H, dd). |
| 2-72 | ¹H-NMR (CDCl₃) δ: 1.26 (3H, t,), 1.35 (3H, t), 2.39 (3H, s), 2.74 (2H, q), 3.68 (2H, q), 7.36-7.41 (2H, m), 7.51-7.55 (2H, m), 8.17-8.33 (3H, m), 8.47 (1H, s), 9.05 (1H, dd). |
| 2-73 | ¹H-NMR (CDCl₃) δ: 1.26 (3H, t), 1.41 (3H, t), 2.38 (3H, s), 2.73 (2H, q), 3.68 (2H, q), 7.36-7.42 (3H, m), 7.84-7.86 (2H, m), 8.18 (1H, dd), 8.49 (1H, d), 8.57 (1H, d), 8.82 (1H, d). |
| 2-74 | ¹H-NMR (CDCl₃) δ: 1.26 (3H, t), 1.35 (3H, t), 2.39 (3H, s), 2.73 (2H, q), 3.68 (2H, q), 7.37-7.41 (2H, m), 7.53 (1H, s), 7.82 (1H, d), 8.27-8.36 (2H, m), 8.48 (1H, d), 8.53 (1H, s). |
| 2-75 | ¹H-NMR (CDCl₃) δ: 1.22 (3H, t), 2.37 (3H, s), 2.72 (2H, q), 4.01 (2H, q), 7.39 (1H, s), 7.41 (1H, s), 7.51 (1H, dd), 7.91 (1H, s), 8.13-8.28 (3H, m), 8.47 (1H, s), 9.01 (1H, dd). |
| 2-78 | ¹H-NMR (CDCl₃) δ: 1.17 (3H, t), 2.38 (3H, s), 2.70 (2H, q), 6.83 (2H, d), 7.16 (2H, d), 7.42-7.43 (2H, m), 7.53 (1H, dd), 7.60 (1H, br s), 8.17-8.32 (3H, m), 8.47 (1H, s), 9.04 (1H, dd). |
| 2-79 | ¹H-NMR (CDCl₃) δ 1.17 (3H, t), 2.37 (3H, s), 2.70 (2H, q), 6.82 (2H, d), 7.16 (2H, d), 7.38-7.44 (3H, m), 7.76 (1H, s), 7.86 (1H, d), 8.19 (1H, d), 8.50 (1H, s), 8.59 (1H, d), 8.84 (1H, d). |
| 2-80 | ¹H-NMR (CDCl₃) δ 1.17 (3H, t), 2.38 (3H, s), 2.70 (2H, q), 6.82 (2H, d), 7.16 (2H, d), 7.43-7.44 (2H, m), 7.54 (1H, s), 7.82 (1H, d), 8.28-8.37 (2H, m), 8.48 (1H, d), 8.53 (1H, s). |
| 2-81 | ¹H-NMR (CDCl₃) δ 1.11-1.22 (3H, m), 2.36 (3H, s), 2.68-2.75 (2H, m), 7.18-7.19 (2H, m), 7.49-7.56 (3H, m), 7.68 (1H, br s), 8.18-8.21 (2H, m), 8.31 (1H, d), 8.48 (1H, s), 9.02-9.04 (1H, m). |
| 2-82 | ¹H-NMR (CDCl₃) δ 1.21 (3H, t), 2.36 (3H, s), 2.71 (2H, q), 7.19 (2H, s), 7.44 (1H, dd), 7.56 (2H, s), 7.84 (1H, s), 7.93 (1H, d), 8.21 (1H, d), 8.52 (1H, s), 8.69 (1H, d), 8.84 (1H, d). |
| 2-83 | ¹H-NMR (CDCl₃) δ 1.21 (3H, t), 2.36 (3H, s), 2.71 (2H, q), 7.18-7.20 (2H, m), 7.54-7.56 (2H, m), 7.68 (1H, s), 7.82 (1H, d), 8.27-8.36 (2H, m), 8.48 (1H, d), 8.53 (1H, s). |
| 2-84 | ¹H-NMR (CDCl₃) δ 1.21 (3H, dd), 2.37 (3H, s), 2.72 (2H, q), 7.14 (2H, s), 7.54 (1H, s), 8.16-8.25 (5H, m), 8.33 (1H, s), 8.49-8.52 (2H, m), 9.43 (1H, s). |
| 2-85 | ¹H-NMR (CDCl₃) δ 2.26 (6H, s), 7.33 (2H, s), 7.41 (1H, dd), 8.04-8.17 (3H, m), 8.42 (1H, d), 8.92-8.93 (2H, m). |
| 2-86 | ¹H-NMR (CDCl₃) δ 2.39 (6H, s), 7.37-7.42 (3H, m), 7.84-7.90 (2H, m), 8.19 (1H, d), 8.50 (1H, s), 8.58 (1H, d), 8.80 (1H, d). |
| 2-87 | ¹H-NMR (CDCl₃) δ 2.39 (6H, s), 7.39 (2H, s), 7.56 (1H, s), 7.82 (1H, d), 8.28-8.36 (2H, m), 8.47 (1H, d), 8.53 (1H, s). |
| 2-88 | ¹H-NMR (CDCl₃) δ 1.23 (3H, t), 2.38 (3H, s), 2.73 (2H, q), 7.39 (2H, s), 7.52 (1H, q), 7.68 (1H, s), 8.16-8.30 (3H, m), 8.46 (1H, s), 9.03 (1H, dd). |
| 2-89 | ¹H-NMR (CDCl₃) δ 1.23 (3H, t), 2.38 (3H, s), 2.74 (2H, q), 7.33-7.41 (3H, m), 7.89 (1H, d), 8.19-8.24 (2H, m), 8.50 (1H, s), 8.61 (1H, d), 8.76 (1H, d). |
| 2-90 | ¹H-NMR (CDCl₃) δ 1.25 (3H, t), 2.39 (3H, s), 2.73 (2H, q), 7.40 (2H, s), 7.58 (1H, s), 7.82 (1H, d), 8.28-8.36 (2H, m), 8.47 (1H, d), 8.53 (1H, s). |
| 2-102 | ¹H-NMR (CDCl₃) δ 0.93 (3H, t), 1.61-1.73 (2H, m), 2.76 (2H, t), 7.51-7.56 (2H, m), 7.69 (1H, s), 7.97 (1H, s), 8.22-8.34 (3H, m), 8.52 (1H, s), 9.05 (1H, dd,). |
| 2-103 | ¹H-NMR (CDCl₃) δ 0.93 (3H, t), 1.56-1.74 (3H, m), 2.76 (2H, t), 7.39 (1H, dd), 7.53 (1H, s), 7.87 (1H, d), 7.97 (1H, s), 8.14 (1H, br s), 8.23 (1H, d), 8.53 (1H, s), 8.59 (1H, d), 8.80 (1H, d). |
| 2-104 | ¹H-NMR (CDCl₃) δ 0.93 (3H, t), 1.61-1.74 (2H, m), 2.75 (2H, t), 7.54 (1H, s), 7.73 (1H, s), 7.82 (1H, d), 7.98 (1H, s), 8.31-8.38 (2H, m), 8.49 (1H, d), 8.58 (1H, s). |
| 2-108 | ¹H-NMR (CDCl₃) δ 7.53 (1H, dd), 7.88-7.90 (3H, m), 8.21-8.33 (3H, m), 8.51 (1H, d), 9.05 (1H, dd). |
| 2-109 | ¹H-NMR (DMSO-d6) δ 7.59 (1H, dd), 8.05 (2H, s), 8.12 (1H, d), 8.33 (1H, d), 8.67-8.71 (2H, m), 8.75 (1H, s). |
| 2-110 | ¹H-NMR (CDCl₃) δ: 7.81-7.85 (2H, m), 7.90 (2H, s), 8.33-8.34 (2H, m), 8.48 (1H, d), 8.57 (1H, s). |
| 2-111 | ¹H-NMR (CDCl₃) δ: 7.54 (1H, dd), 7.91 (1H, s), 8.12 (2H, s), 8.23-8.34 (3H, m), 8.54 (1H, s), 9.05 (1H, dd). |
| 2-112 | ¹H-NMR (DMSO-d6) δ: 7.60 (1H, dd), 8.12-8.17 (3H, m), 8.35 (1H, dd), 8.69-8.72 (2H, m), 8.77 (1H, d), 10.96 (1H, s). |
| 2-113 | ¹H-NMR (CDCl₃) δ: 7.81-7.87 (2H, m), 8.13 (2H, s), 8.33-8.39 (2H, m), 8.49 (1H, d), 8.59 (1H, s). |
| 2-128 | ¹H-NMR (CDCl₃) δ: 1.26 (3H, t), 2.41 (3H, s), 2.75 (2H, q), 7.47-7.58 (4H, m), 8.17-8.33 (3H, m), 8.48 (1H, s), 9.05 (1H, dd). |
| 2-129 | ¹H-NMR (CDCl₃) δ: 1.22-1.29 (3H, m), 2.40 (3H, s), 2.76 (2H, q), 7.39 (1H, dd), 7.47 (2H, s), 7.84 (1H, d), 7.98 (1H, s), 8.18 (1H, d), 8.49 (1H, s), 8.56 (1H, d), 8.79 (1H, d). |
| 2-130 | ¹H-NMR (CDCl₃) δ: 1.24 (3H, t), 2.37 (3H, s), 2.73 (2H, q), 7.47 (2H, s), 7.78 (1H, d), 7.94 (1H, s), 8.26-8.32 (2H, m), 8.45 (1H, d), 8.54 (1H, s). |

TABLE 7-continued

| Exa | NMR |
|---|---|
| 2-131 | $^1$H-NMR (CDCl$_3$) δ: 7.54 (1H, dd,), 7.85 (1H, s), 7.97 (2H, s), 8.22-8.35 (3H, m), 8.52 (1H, d), 9.06 (1H, dd). |
| 2-132 | $^1$H-NMR (CDCl$_3$) δ: 7.43 (1H, dd), 7.90-7.97 (3H, m), 8.23 (1H, d), 8.33 (1H, s), 8.53 (1H, s), 8.70 (1H, d), 8.81 (1H, d). |
| 2-133 | $^1$H-NMR (CDCl$_3$) δ: 7.83 (1H, d), 7.88 (1H, s), 7.97 (2H, s), 8.34-8.36 (2H, m), 8.49 (1H, d), 8.58 (1H, s). |
| 2-137 | $^1$H-NMR (CDCl$_3$) δ: 7.52 (1H, dd), 7.57 (2H, d), 7.81 (1H, s), 8.20-8.32 (3H, m), 8.51 (1H, s), 9.04 (1H, dd). |
| 2-138 | $^1$H-NMR (DMSO-d6) δ: 7.58 (1H, dd), 7.95 (2H, s), 8.12 (1H, d), 8.33 (1H, d), 8.65-8.70 (2H, m), 8.74 (1H, s). |
| 2-139 | $^1$H-NMR (CDCl$_3$) δ: 7.58 (2H, s), 7.73 (1H, s), 7.82 (1H, d), 8.33-8.34 (2H, m), 8.48 (1H, d), 8.56 (1H, s). |
| 2-140 | $^1$H-NMR (CDCl$_3$) δ: 7.78 (1H, s), 7.82 (1H, d), 7.97 (2H, s), 8.32-8.35 (2H, m), 8.48 (1H, d), 8.56 (1H, s). |
| 2-145 | $^1$H-NMR (CDCl$_3$) δ: 7.55 (1H, dd), 8.05 (1H, br s), 8.22-8.35 (5H, m), 8.54 (1H, d), 9.07 (1H, dd). |
| 2-148 | $^1$H-NMR (CDCl$_3$) δ: 7.53 (1H, dd), 7.94-7.96 (3H, m), 8.24-8.25 (2H, m), 8.31 (1H, d), 8.52 (1H, s), 9.05 (1H, dd). |
| 2-149 | $^1$H-NMR (CDCl$_3$) δ: 7.38 (1H, dd), 7.82 (1H, d), 7.95 (2H, s), 8.16 (1H, d), 8.46 (1H, s), 8.57 (1H, d), 8.67-8.74 (1H, m). |
| 2-152 | $^1$H-NMR (CDCl$_3$) δ: 6.63 (1H, t), 7.50-7.54 (2H, m), 7.82 (1H, s), 7.91 (1H, s), 8.17-8.30 (3H, m), 8.48 (1H, d), 9.04 (1H, dd). |
| 2-153 | $^1$H-NMR (CDCl$_3$) δ: 6.65 (1H, t), 7.37 (1H, dd), 7.54 (1H, s), 7.77-7.84 (2H, m), 8.03 (1H, d), 8.32 (1H, s), 8.55-8.58 (2H, m), 9.02 (1H, s). |
| 2-154 | $^1$H-NMR (CDCl$_3$) δ: 6.62 (1H, t), 7.54 (1H, s), 7.74 (1H, s), 7.81-7.84 (2H, m), 8.28-8.36 (2H, m), 8.48 (1H, d), 8.54 (1H, s). |
| 2-158 | $^1$H-NMR (CDCl$_3$) δ: 7.40 (1H, dd), 7.85 (1H, d), 8.03-8.07 (2H, m), 8.16 (1H, d), 8.48 (1H, s), 8.58 (1H, d), 8.76-8.81 (2H, m). |
| 2-159 | $^1$H-NMR (CDCl$_3$) δ: 7.55 (1H, dd), 8.08 (1H, s), 8.17 (1H, s), 8.23-8.37 (4H, m), 8.54 (1H, d), 9.07 (1H, dd). |
| 2-160 | $^1$H-NMR (CDCl$_3$) δ: 7.43 (1H, dd), 7.88 (1H, d), 8.08 (1H, s), 8.21-8.28 (2H, m), 8.41 (1H, s), 8.54 (1H, d), 8.61 (1H, d), 8.86 (1H, d). |
| 2-161 | $^1$H-NMR (CDCl$_3$) δ: 7.84 (1H, d), 8.09 (1H, s), 8.16 (1H, s), 8.25 (1H, d), 8.33-8.39 (2H, m), 8.51 (1H, d), 8.60 (1H, s). |
| 2-162 | $^1$H-NMR (CDCl$_3$) δ: 0.93 (3H, t), 1.63-1.75 (2H, m), 2.77 (2H, t), 7.51-7.56 (2H, m), 7.73-7.76 (2H, m), 8.21-8.34 (3H, m), 8.50 (1H, s), 9.05 (1H, dd). |
| 2-163 | $^1$H-NMR (CDCl$_3$) δ: 0.94 (3H, t), 1.63-1.75 (2H, m), 2.76 (2H, t), 7.41 (1H, dd), 7.52 (1H, s), 7.77 (1H, s), 7.86 (1H, d), 7.96 (1H, br s), 8.21 (1H, d), 8.51 (1H, s), 8.60 (1H, d), 8.85 (1H, d). |
| 2-164 | $^1$H-NMR (CDCl$_3$) δ: 0.94 (3H, t), 1.62-1.75 (2H, m), 2.76 (2H, t), 7.52 (1H, s), 7.73 (1H, s), 7.77 (1H, s), 7.82 (1H, d), 8.30-8.37 (2H, m), 8.48 (1H, d), 8.55 (1H, s). |
| 2-165 | $^1$H-NMR (CDCl$_3$) δ: 1.23 (6H, d), 3.25-3.34 (1H, m), 7.48 (1H, dd), 7.59 (1H, s), 7.97 (1H, s), 8.17-8.29 (3H, m), 8.38 (1H, s), 8.55 (1H, d), 9.00 (1H, dd). |
| 2-167 | $^1$H-NMR (CDCl$_3$) δ: 1.27 (6H, d), 3.21-3.30 (1H, m), 7.61 (1H, s), 7.65 (1H, s), 7.83 (1H, d), 7.98 (1H, s), 8.34-8.38 (2H, m), 8.49 (1H, dz), 8.59 (1H, s). |
| 2-168 | $^1$H-NMR (CDCl$_3$) δ: 7.35 (1H, s), 7.44 (1H, s), 7.57 (1H, dd), 8.21-8.36 (3H, m), 8.58 (1H, d), 8.70 (1H, d), 9.09 (1H, dd), 9.96 (1H, s). |
| 2-169 | $^1$H-NMR (CDCl$_3$) δ: 7.54 (1H, dd), 7.60 (1H, s), 7.82 (1H, s), 7.96 (1H, s), 8.18-8.35 (3H, m), 8.48 (1H, s), 9.06 (1H, d). |
| 2-170 | $^1$H-NMR (CDCl$_3$) δ: 3.88 (3H, s), 7.11 (1H, s), 7.46-7.52 (2H, m), 7.99 (1H, s), 8.16-8.30 (3H, m), 8.47 (1H, s), 9.00 (1H, d). |
| 2-171 | $^1$H-NMR (CDCl$_3$) δ: 6.62 (1H, t), 7.51-7.55 (2H, m), 7.79-7.81 (2H, m), 8.19-8.32 (3H, m), 8.48 (1H, s), 9.05 (1H, d). |
| 2-172 | $^1$H-NMR (CDCl$_3$) δ: 6.63 (1H, t), 7.39 (1H, dd), 7.53 (1H, s), 7.82-7.84 (2H, m), 8.08 (1H, d), 8.37 (1H, d), 8.60-8.65 (2H, m), 8.81 (1H, s). |
| 2-173 | $^1$H-NMR (CDCl$_3$) δ: 6.61 (1H, t), 7.49 (1H, d), 7.62-7.84 (3H, m), 8.26-8.36 (2H, m), 8.44-8.53 (2H, m). |
| 2-174 | $^1$H-NMR (CDCl$_3$) δ: 6.60 (1H, t), 7.51-7.55 (2H, m), 7.78 (1H, s), 8.01 (1H, s), 8.19-8.33 (3H, m), 8.49 (1H, d), 9.05 (1H, dd). |
| 2-175 | $^1$H-NMR (CDCl$_3$) δ: 6.61 (1H, t), 7.39 (1H, dd), 7.52-7.55 (2H, m), 7.84 (1H, d), 8.03 (1H, s), 8.12 (1H, d), 8.40 (1H, s), 8.59 (1H, d), 8.70 (1H, d). |
| 2-176 | $^1$H-NMR (CDCl$_3$) δ: 6.59 (1H, t), 7.55 (1H, s), 7.74 (1H, s), 7.83 (1H, d), 8.02 (1H, s), 8.29-8.37 (2H, m), 8.49 (1H, d), 8.55 (1H, s). |
| 2-183 | $^1$H-NMR (CDCl$_3$) δ: 7.55 (1H, dd), 7.95-8.07 (3H, m), 8.21-8.34 (3H, m), 8.52 (1H, d), 9.06 (1H, d). |
| 2-184 | $^1$H-NMR (CDCl$_3$) δ: 7.39 (1H, dd), 7.82-8.18 (4H, m), 8.46 (1H, d), 8.56 (1H, d), 8.74 (1H, s), 8.90 (1H, d). |
| 2-185 | $^1$H-NMR (CDCl$_3$) δ: 7.84 (1H, d), 8.04 (1H, s), 8.06 (1H, s), 8.23 (1H, s), 8.31-8.39 (2H, m), 8.50 (1H, d), 8.57 (1H, d). |
| 2-186 | $^1$H-NMR (CDCl$_3$) δ: 7.55 (1H, dd), 8.07-8.36 (6H, m), 8.54 (1H, d), 9.07 (1H, d). |
| 2-187 | $^1$H-NMR (DMSO-d6) δ: 7.59 (1H, dd), 8.04 (1H, s), 8.12 (1H, d), 8.32-8.39 (2H, m), 8.68-8.78 (3H, m), 11.16 (1H, s). |
| 2-188 | $^1$H-NMR (CDCl$_3$) δ: 7.84 (1H, d), 8.08 (1H, s), 8.15 (1H, s), 8.23 (1H, s), 8.32-8.40 (2H, m), 8.51 (1H, d), 8.59 (1H, s). |
| 2-189 | $^1$H-NMR (CDCl$_3$) δ: 2.40 (6H, s), 7.40 (2H, s), 7.51-7.56 (2H, m), 8.18-8.32 (3H, m), 8.48 (1H, s), 9.05 (1H, dd). |

TABLE 7-continued

| Exa | NMR |
|---|---|
| 2-190 | $^1$H-NMR (CDCl$_3$) δ: 2.38 (6H, s), 7.31-7.38 (3H, m), 7.80 (1H, d), 8.18 (1H, d), 8.46-8.56 (3H, m), 8.65 (1H, d). |
| 2-191 | $^1$H-NMR (CDCl$_3$) δ: 2.40 (6H, s), 7.41 (2H, s), 7.55 (1H, s), 7.82 (1H, d), 8.28-8.36 (2H, m), 8.47 (1H, d), 8.53 (1H, s). |
| 2-192 | $^1$H-NMR (CDCl$_3$) δ: 1.26 (3H, t), 2.40 (3H, s), 2.75 (2H, q), 7.41 (2H, s), 7.51-7.56 (2H, m), 8.18-8.32 (3H, m), 8.47 (1H, s), 9.04 (1H, d). |
| 2-193 | $^1$H-NMR (CDCl$_3$) δ: 1.25 (3H, t), 2.39 (3H, s), 2.75 (2H, q), 7.34 (1H, dd), 7.41 (2H, s), 7.81 (1H, d), 8.19 (1H, d), 8.37-8.50 (3H, m), 8.70 (1H, dd). |
| 2-194 | $^1$H-NMR (CDCl$_3$) δ: 1.25 (3H, t), 2.39 (3H, s), 2.74 (2H, q), 7.42 (2H, s), 7.71 (1H, s), 7.81 (1H, d), 8.28-8.34 (2H, m), 8.46 (1H, d), 8.53 (1H, s). |
| 2-195 | $^1$H-NMR (CDCl$_3$) δ: 7.45 (1H, dd), 7.87 (2H, s), 8.11-8.23 (3H, m), 8.50 (1H, d), 9.01-8.93 (2H, m). |
| 2-196 | $^1$H-NMR (CDCl$_3$) δ: 7.36 (1H, dd), 7.82 (1H, d), 7.89 (2H, s), 8.16 (1H, d), 8.45 (1H, s), 8.57-8.66 (2H, m), 8.93 (1H, s). |
| 2-197 | $^1$H-NMR (CDCl$_3$) δ: 7.81-7.84 (2H, m), 7.91 (2H, s), 8.33-8.36 (2H, m), 8.49 (1H, d), 8.57 (1H, s). |
| 2-198 | $^1$H-NMR (CDCl$_3$) δ: 7.51 (1H, dd), 8.13 (2H, s), 8.21-8.34 (4H, m), 8.54 (1H, s), 9.02 (1H, dd). |
| 2-199 | $^1$H-NMR (CDCl$_3$) δ: 7.41 (1H, dd), 7.86 (1H, d), 8.14 (2H, s), 8.23 (1H, dd), 8.31 (1H, br s), 8.53 (1H, s), 8.60 (1H, dd), 8.82 (1H, d). |
| 2-200 | $^1$H-NMR (CDCl$_3$) δ: 7.81-7.89 (2H, m), 8.14 (2H, s), 8.32-8.36 (2H, m), 8.49 (1H, d), 8.59 (1H, s). |
| 2-201 | $^1$H-NMR (CDCl$_3$) δ: 6.63 (1H, t), 7.51-7.55 (2H, m), 7.82-7.84 (2H, m), 8.18-8.32 (3H, m), 8.48 (1H, d), 9.05 (1H, dd). |
| 2-202 | $^1$H-NMR (CDCl$_3$) δ: 6.64 (1H, t), 7.35-7.43 (1H, m), 7.54 (1H, s), 7.80-8.10 (3H, m), 8.37 (1H, s), 8.60 (1H, d), 8.67 (1H, d), 8.94 (1H, s). |
| 2-203 | $^1$H-NMR (CDCl$_3$) δ: 6.62 (1H, t), 7.55 (1H, s), 7.79-7.84 (3H, m), 8.29-8.36 (2H, m), 8.49 (1H, d), 8.54 (1H, s). |
| 2-213 | $^1$H-NMR (CDCl$_3$) δ: 2.39 (6H, s), 7.39 (2H, s), 7.55 (1H, s), 8.17-8.28 (3H, m), 8.40 (1H, s), 8.94 (1H, d). |
| 2-214 | $^1$H-NMR (CDCl$_3$) δ: 2.38 (6H, s), 6.24 (1H, s), 7.39 (2H, s), 7.59 (1H, s), 8.26-8.40 (2H, m), 9.04 (1H, d). |
| 2-215 | $^1$H-NMR (CDCl$_3$) δ: 2.38 (6H, s), 7.39 (2H, s), 7.61 (1H, s), 8.17-8.24 (2H, m), 8.38 (1H, s), 8.44 (1H, d), 9.02 (1H, d). |
| 2-216 | $^1$H-NMR (CDCl$_3$) δ: 2.38 (6H, s), 7.39 (2H, s), 7.56 (1H, s), 8.32 (1H, s), 8.45 (1H, s), 8.52 (1H, s), 9.11 (1H, s). |
| 2-217 | $^1$H-NMR (CDCl$_3$) δ: 1.24 (3H, t), 2.38 (3H, s), 2.73 (2H, q), 7.39 (2H, s), 7.55-7.65 (2H, m), 8.30-8.44 (3H, m), 9.16 (1H, d). |
| 2-218 | $^1$H-NMR (CDCl$_3$) δ: 1.25 (3H, t), 2.37 (3H, s), 2.73 (2H, q), 7.39 (2H, s), 7.56-7.63 (2H, m), 8.32 (1H, d), 8.43 (1H, s), 8.55 (1H, s), 9.17 (1H, d). |
| 2-229 | $^1$H-NMR (CDCl$_3$) δ: 6.63 (1H, t), 7.49-7.55 (2H, m), 7.66 (1H, s), 7.88 (1H, s), 8.17-8.31 (3H, m), 8.48 (1H, d), 9.04 (1H, dd). |
| 2-230 | $^1$H-NMR (CDCl$_3$) δ: 6.65 (1H, t), 7.36 (1H, dd), 7.50 (1H, s), 7.69 (1H, s), 7.78 (1H, d), 8.01 (1H, d), 8.30 (1H, s), 8.52-8.56 (2H, m), 9.10 (1H, s). |
| 2-231 | $^1$H-NMR (CDCl$_3$) δ: 6.63 (1H, t), 7.50 (1H, s), 7.67 (1H, s), 7.80-7.84 (2H, m), 8.27-8.35 (2H, m), 8.48 (1H, d), 8.53 (1H, s). |
| 2-268 | $^1$H-NMR (CDCl$_3$) δ: 1.25 (3H, t), 2.39 (3H, s), 2.72 (2H, q), 7.40 (2H, s), 7.54 (1H, s), 7.63 (1H, d), 7.85 (1H, d), 8.25 (1H, d), 8.53 (1H, d), 8.83 (1H, d). |
| 2-269 | $^1$H-NMR (CDCl$_3$) δ: 1.22-1.27 (3H, m), 2.38 (3H, s), 2.73 (2H, q), 7.40 (2H, s), 7.58 (1H, s), 8.28-8.44 (3H, m), 8.65 (1H, s). |
| a-1 | $^1$H-NMR (CDCl$_3$) δ: 3.95 (2H, s), 6.74 (2H, d), 7.42 (2H, d). |
| a-4 | $^1$H-NMR (CDCl$_3$) δ: 1.27 (3H, t), 2.22 (3H, s), 2.55 (2H, q), 3.89 (2H, s), 7.21 (2H, s). |
| a-6 | $^1$H-NMR (CDCl$_3$) δ: 4.92 (2H, s), 7.65 (2H, s). |
| b-1 | $^1$H-NMR (CDCl$_3$) δ: 2.21 (6H, s), 3.80 (2H, s), 7.14 (2H, s). |
| b-2 | $^1$H-NMR (CDCl$_3$) δ: 1.27 (3H, t), 2.22 (3H, s), 2.55 (2H, q), 3.84 (2H, s), 7.15 (2H, s). |
| b-4 | $^1$H-NMR (CDCl$_3$) δ: 4.94 (2H, s), 7.80 (2H, s). |
| b-5 | $^1$H-NMR (CDCl$_3$) δ: 4.88 (2H, s), 7.59 (2H, s). |
| b-6 | $^1$H-NMR (CDCl$_3$) δ: 4.16 (2H, s), 6.49 (1H, t), 6.83 (1H, d), 7.23-7.27 (2H, m). |
| b-8 | $^1$H-NMR (CDCl$_3$) δ: 4.62 (2H, s), 6.51 (1H, t), 7.23 (1H, s), 7.53 (1H, s). |
| c-1 | $^1$H-NMR (CDCl$_3$) δ: 4.16 (2H, s), 6.49 (1H, t), 6.84 (1H, d), 7.23-7.26 (2H, m). |
| c-2 | $^1$H-NMR (CDCl$_3$) δ: 4.57 (2H, s), 6.51 (1H, t), 7.19 (1H, s), 7.39 (1H, s). |
| c-3 | $^1$H-NMR (CDCl$_3$) δ: 4.62 (2H, s), 6.50 (1H, t), 7.22 (1H, s), 7.52 (1H, s). |
| c-5 | $^1$H-NMR (CDCl$_3$) δ: 4.17 (2H, s), 6.47 (1H, t), 6.83 (1H, d), 7.22-7.25 (2H, m). |
| c-7 | $^1$H-NMR (CDCl$_3$) δ: 4.62 (2H, s), 6.50 (1H, t), 7.23 (1H, s), 7.53 (1H, s). |
| c-8 | $^1$H-NMR (CDCl$_3$) δ: 4.65 (2H, s), 6.48 (1H, t), 7.22 (1H, s), 7.68 (1H, s). |
| 2-249 | $^1$H-NMR (CDCl$_3$) δ: 7.80-7.85 (2H, m), 7.96 (1H, s), 8.18 (1H, s), 8.28-8.37 (2H, m), 8.49 (1H, d), 8.53 (1H, s). |
| 2-259 | $^1$H-NMR (CDCl$_3$) δ: 2.45 (3H, s), 6.55 (1H, t), 7.34 (1H, s), 7.45 (1H, s), 7.53 (1H, dd), 7.84 (1H, s), 8.16-8.32 (3H, m), 8.46 (1H, d), 9.05 (1H, dd). |
| 2-260 | $^1$H-NMR (CDCl$_3$) δ: 2.48 (3H, s), 6.58 (1H, t), 7.35-7.41 (2H, m), 7.46 (1H, s), 7.81 (1H, d), 8.09 (1H, d), 8.37 (1H, s), 8.54-8.58 (2H, m), 8.67 (1H, d). |
| 2-261 | $^1$H-NMR (CDCl$_3$) δ: 2.45 (3H, s), 6.56 (1H, t), 7.35 (1H, s), 7.47 (1H, s), 7.79-7.83 (2H, m), 8.27-8.35 (2H, m), 8.46-8.52 (2H, m). |
| 2-177 | $^1$H-NMR (CDCl$_3$) δ: 7.52-7.59 (2H, m), 7.77 (1H, s), 7.88 (1H, s), 8.15-8.33 (3H, m), 8.48 (1H, d), 9.06 (1H, dd). |

TABLE 7-continued

| Exa | NMR |
|---|---|
| 2-178 | $^1$H-NMR (CDCl$_3$) δ: 7.41 (1H, dd), 7.52-7.60 (2H, m), 7.83-8.17 (4H, m), 8.42 (1H, s), 8.63 (1H, d). |
| 2-219 | $^1$H-NMR (CDCl$_3$) δ: 6.63 (1H, t), 7.49-7.54 (2H, m), 7.81 (1H, s), 7.92 (1H, s), 8.18-8.31 (3H, m), 8.48 (1H, d), 9.04 (1H, d). |
| 2-221 | $^1$H-NMR (CDCl$_3$) δ: 6.57 (1H, t), 7.46-7.57 (2H, m), 7.73-7.84 (2H, m), 8.28-8.35 (2H, m), 8.45-8.54 (2H, m). |
| 2-270 | $^1$H-NMR (CDCl$_3$) δ: 7.65 (1H, d), 7.80 (1H, s), 7.85-7.90 (3H, m), 8.29 (1H, dd), 8.56 (1H, d), 8.84 (1H, d). |
| 2-271 | $^1$H-NMR (CDCl$_3$) δ: 1.22 (3H, t), 8.14 (3H, s), 2.71 (2H, q), 7.38 (2H, s), 7.75 (1H, s), 8.14-8.22 (3H, m), 8.37 (1H, s), 8.92 (1H, d). |
| 2-272 | $^1$H-NMR (CDCl$_3$) δ: 6.62 (1H, t), 7.48-7.56 (2H, m), 7.65 (1H, s), 7.83 (1H, s), 8.17-8.32 (3H, m), 8.47 (1H, s), 9.05 (1H, d). |
| 2-273 | $^1$H-NMR (CDCl$_3$) δ: 6.63 (1H, t), 7.40 (1H, dd), 7.49 (1H, s), 7.67 (1H, s), 7.83 (1H, d), 8.10 (1H, d), 8.40 (1H, s), 8.47 (1H, s), 8.59 (1H, d), 8.70 (1H, d). |
| 2-274 | $^1$H-NMR (CDCl$_3$) δ: 6.62 (1H, t), 7.49 (1H, s), 7.66 (1H, s), 7.79-7.85 (2H, m), 8.27-8.34 (2H, m), 8.47 (1H, d), 8.53 (1H, s). |
| 2-275 | $^1$H-NMR (CDCl$_3$) δ: 6.63 (1H, t), 7.51-7.56 (2H, m), 7.67 (1H, s), 7.77 (1H, s), 8.18-8.33 (3H, m), 8.48 (1H, s), 9.05 (1H, dd). |
| 2-276 | $^1$H-NMR (CDCl$_3$) δ: 6.65 (1H, t), 7.40 (1H, dd), 7.51 (1H, s), 7.69 (1H, s), 7.83 (1H, d), 8.09 (1H, d), 8.38 (1H, s), 8.56-8.62 (2H, m), 8.68 (1H, d). |
| 2-277 | $^1$H-NMR (CDCl$_3$) δ: 6.63 (1H, t), 7.51 (1H, s), 7.68 (1H, s), 7.75 (1H, s), 7.83 (1H, d), 8.28-8.36 (2H, m), 8.48 (1H, d), 8.53 (1H, d). |
| 2-287 | $^1$H-NMR (CDCl$_3$) δ: 1.25 (3H, t), 2.39 (3H, s), 2.73 (2H, q), 7.40 (2H, s), 7.64-7.71 (2H, m), 8.40 (1H, d), 8.65 (1H, s), 8.70 (1H, s), 9.21 (1H, d). |
| 2-288 | $^1$H-NMR (CDCl$_3$) δ: 7.39 (1H, dd), 7.59 (1H, s), 7.82 (1H, d), 7.98 (1H, s), 8.11 (1H, d), 8.41 (1H, s), 8.58-8.65 (2H, m), 8.71 (1H, d). |
| 2-289 | $^1$H-NMR (CDCl$_3$) δ: 7.81-7.84 (2H, m), 7.89 (1H, s), 8.35 (1H, d), 8.49 (1H, d), 8.72 (1H, dd), 8.92 (1H, d). |
| c-9 | $^1$H-NMR (CDCl$_3$) δ: 2.23 (3H, s), 4.10 (2H, br s), 6.48 (1H, t), 7.14 (2H, s). |
| 4-1 | $^1$H-NMR (CDCl$_3$) δ: 2.38 (6H, s), 7.38 (2H, s), 7.50 (1H, s), 8.03 (1H, d), 8.19-8.28 (1H, m), 8.63 (1H, s), 9.18 (1H, s). |
| 4-33 | $^1$H-NMR (CDCl$_3$) δ: 1.23 (3H, t), 2.37 (3H, s), 2.72 (2H, q), 7.38 (2H, s), 7.53 (1H, s), 8.03 (1H, d), 8.26 (1H, d), 8.63 (1H, s), 9.17 (1H, s). |
| 4-34 | $^1$H-NMR (CDCl$_3$) δ: 1.23 (3H, t), 2.36 (3H, s), 2.71 (2H, q), 7.39 (2H, s), 7.58 (1H, s), 8.13 (1H, d), 8.35 (1H, d), 8.64 (1H, s). |
| 4-37 | $^1$H-NMR (CDCl3) δ: 7.80 (1H, s), 7.88 (2H, s), 8.09 (1H, dd), 8.28 (1H, d), 8.66 (1H, d), 9.19 (1H, s). |
| 4-38 | $^1$H-NMR (CDCl3) δ: 7.75 (1H, s), 7.89 (2H, s), 8.18 (1H, d), 8.38 (1H, d), 8.67 (1H, s). |
| 5-4 | $^1$H-NMR (CDCl3) δ: 1.24 (3H, t), 2.36 (3H, s), 2.71 (2H, q), 7.24 (2H, d), 7.37 (3H, s), 7.94 (1H, d), 8.25 (1H, s). |
| 5-5 | $^1$H-NMR (CDCl3) δ: 7.23-7.26 (1H, m), 7.63 (1H, s), 7.87 (2H, s), 7.99 (1H, dd), 8.29 (1H, d). |
| 6-4 | $^1$H-NMR (CDCl3) δ: 1.23-1.29 (3H, m), 2.42 (3H, s), 2.74 (2H, q), 7.42 (2H, s), 7.51 (1H, dd), 8.17-8.30 (3H, m), 8.42 (1H, d), 8.78 (1H, s), 9.01 (1H, dd). |

Unless not mentioned otherwise, the test solutions were prepared as follows:

Containing as solvent: Dimethylformamide, 3 parts by weight; and as emulsifier: Polyoxyethylene alkyl phenyl ether, 1 part by weight To prepare the test solution, 1 part by weight of an active compound is mixed with the above-mentioned amount of solvent containing the above-mentioned amount of emulsifier, and the mixture is diluted with water to the desired concentration.

Biological Test Example 1

Test Against Tobacco Cutworm (*Spodoptera litura*) Larvae

Leaves of sweet potato were immersed in the test solution at the appropriate concentration, and the leaves were dried in air. The leaves were then placed in a petri dish having a diameter of 9 cm, and ten *Spodoptera litura* at third instar larvae were released therein. The petri dishes were placed in a temperature-controlled chamber at 25° C. After 2 days and 4 days more sweet potato leaves were added. After 7 days, the number of dead larvae was counted to calculate the insecticidal activity. An insecticidal activity of 100% means that all larvae were killed, whereas an insecticidal activity of 0% means that no larva was killed. In the current test, the results of two petri dishes for each treatment were averaged.

In the biological test example 1, the compounds Nos. 1-4, 2-13, 2-17, 2-20, 2-21, 2-29, 2-31, 2-37, 2-40, 2-46, 2-49, 2-61, 2-64, 2-66, 2-68, 2-69, 2-74, 2-78, 2-83, 2-87, 2-88, 2-90, 2-102, 2-103, 2-104, 2-108, 2-110, 2-111, 2-113, 2-128, 2-129, 2-130, 2-133, 2-140, 2-152, 2-154, 2-161, 2-162, 2-164, 2-167, 2-173, 2-174, 2-175, 2-176, 2-185, 2-186, 2-188, 2-191, 2-194, 2-195, 2-197, 2-198, 2-200, 2-201, 2-203, 2-213, 2-214, 2-215, 2-217, 2-221, 2-231, 2-249, 2-261, 2-269, 2-270, 2-274, 4-33, 4-34 and 5-4 showed an insecticidal activity of 100% at an active compound concentration of 100 ppm.

Biological Test Example 2

Test Against Two-Spotted Spider Mite (*Tetranychus urticae*)

50 to 100 adult mites of *Tetranychus urticae* were inoculated to leaves of kidney bean at two-leaf stage planted in a pot of 6 cm in diameter. After one day, test solution at the appropriate concentration was sprayed thereon in a sufficient amount using a spray gun. After the spraying, the plant pot was placed inside a greenhouse, and after 7 days, the acaricidal activity was calculated. An acaricidal activity of 100% means that all mites were killed, whereas an acaricidal activity of 0% means that no mite was killed.

Jr. the biological test example 2, the compound Nos. 1-3, 2-29, 2-31, 2-40, 2-46, 2-49, 2-64, 2-66, 2-69, 2-72, 2-83, 2-85, 2-87, 2-90, 2-110, 2-130, 2-133, 2-154, 2-173, 2-174, 2-176, 2-184, 2-187, 2-189, 2-191, 2-192, 2-194, 2-197, 2-199, 2-201, 2-202, 2-203, 2-221, 2-231, 2-249, 2-261, 2-269, 2-274, 4-33 and 4-34 showed an acaricidal activity of 100% at an active compound concentration of 500 ppm.

Biological Test Example 3

Test Against Cucurbit Leaf Beetle (*Aulasophora femoralis*)

Leaves of cucumber were immersed in the test solution at the appropriate concentration, and the leaves were dried in air. The leaves were then put in a plastic cup containing sterilized black soil and five *Aulacophora femoralis* at second instar larvae were released in the cup. The cups were placed in a temperature-controlled chamber at 25° C. After 7 days, the number of dead larvae was counted, and thus the insecticidal activity was calculated. An insecticidal activity of 100% means that all larvae were killed, whereas an insecticidal activity of 0% means that no larva was killed.

In the biological test example 3, the compounds Nos. 2-3, 2-9, 2-13, 2-17, 2-18, 2-20, 2-21, 2-29, 2-31, 2-36, 2-37, 2-40, 2-46, 2-49, 2-57, 2-59, 2-61, 2-64, 2-66, 2-68, 2-69, 2-74, 2-78, 2-83, 2-87, 2-88, 2-89, 2-90, 2-104, 2-108, 2-110, 2-112, 2-113, 2-130, 2-133, 2-139, 2-140, 2-152, 2-154, 2-162, 2-164, 2-167, 2-173, 2-174, 2-175, 2-176, 2-185, 2-188, 2-191, 2-192, 2-193, 2-194, 2-195, 2-197, 2-199, 2-200, 2-201, 2-202, 2-203, 2-213, 2-214, 2-215, 2-217, 2-221, 2-229, 2-231, 2-249, 2-261, 2-269, 2-274 and 4-33 showed an insecticidal activity of 100% at an active compound concentration of 500 ppm.

Biological Test Example 4

*Lucilla cuprina* (48 h)

Species: *Lucilia cuprina* 1$^{st}$ instar larvae (age 24 hrs)
Solvent: dimethyl sulfoxide 10 mg active compound are dissolve in 0.5 ml dimethyl sulfoxide. Serial dilutions are made to obtain the desired rates. Approximately 20 *Lucilia* cuprina 1$^{st}$ instar larvae are transferred into a test tube containing 1 cm$^3$ of minced horse meat and 0.5 ml aqueous dilution of test compound. After 48 hrs percentage of larval mortality are recorded. 100% efficacy all larvae are killed, % efficacy normally developed larvae after 48 hrs.

In this test for example, the following compounds from the preparation examples showed good activity of 80% at application rate of 100 ppm: 2-3

In this test for example, the following compounds from the preparation examples showed good activity of 90% at application rate of 100 ppm: 2-214

In this test for example, the following compounds from the preparation examples showed good activity of 100% at application rate of 100 ppm: 2-20, 2-29, 2-31, 2-40, 2-46, 2-49, 2-61, 2-64, 2-66, 2-69, 2-74, 2-75, 2-87, 2-88, 2-90, 2-108, 2-110, 2-130, 2-133, 2-104, 2-113, 2-162, 2-164, 2-167, 2-174, 2-176, 2-185, 2-191, 2-192, 2-194, 2-197, 2-200, 2-201, 2-202, 2-203, 2-213

Biological Test Example 5

*Ctenocephalides felis*-Test (CTECFE)

Solvent: dimethyl sulfoxide

To produce a suitable preparation of active compound, 10 mg of active compound are dissolved in 0.5 ml solvent, and the concentrate is diluted with cattle blood to the desired concentration. Approximately 20 adult unfed (*Ctenocepahlides felis*) are placed in flea chambers. The blood chamber, sealed with parafilm on the bottom, are filled with cattle blood supplied with compound solution and placed on top of the flea chamber, so that the fleas are able to suck the blood. The blood chamber is heated to 37° C. whereas the flea chamber is kept at room temperature. After 2 days mortality in % is determined. 100% means that all the fleas have been killed; 0% means that none of the fleas have been killed.

In this test for example, the following compounds from the preparation examples showed good activity of 80% at application rate of 100 ppm: 2-108

In this test for example, the following compounds from the preparation examples showed good activity of 90% at application rate of 100 ppm: 2-3, 2-133, 2-176

In this test for example, the following compounds from the preparation examples showed good activity of 95% at application rate of 100 ppm: 2-40, 2-49, 2-88, 2-108, 2-202

In this test for example, the following compounds from the preparation examples showed good activity of 100% at application rate of 100 ppm: 2-20, 2-31, 2-46, 2-61, 2-64, 2-66, 2-69, 2-74, 2-87, 2-90, 2-104, 2-110, 2-113, 2-130, 2-162, 2-164, 2-167, 2-174, 2-176, 2-185, 2-191, 2-192, 2-194, 2-197, 2-200, 2-201, 2-203

Biological Test Example 6

*Boophilus microplus*-Test (Injection)

Solvent: dimethyl sulfoxide

To produce a suitable preparation of active compound, 10 mg of active compound are dissolved in 0.5 ml solvent, and the concentrate is diluted with solvent to the desired concentration. Five adult engorged female ticks (*Boophilus microplus*) are injected with 1 µl compound solution into the abdomen. Ticks are transferred into replica plates and incubated in a climate chamber for a period of time. Egg deposition of fertile eggs is monitored.

After 7 days mortality in % is determined. 100% means that all eggs are infertile; 0% means that all eggs are fertile.

In this test for example, the following compounds from the preparation examples showed good activity of 80% at application rate of 20 µg/animal: 2-9

In this test for example, the following compounds from the preparation examples showed good activity of 100% at application rate of 20 µg/animal: 2-3, 2-20, 2-31, 2-37, 2-40, 2-46, 2-49, 2-61, 2-64, 2-66, 2-69, 2-74, 2-87, 2-88, 2-90, 2-104, 2-108, 2-110, 2-113, 2-130, 2-133, 2-162, 2-164, 2-167, 2-174, 2-176, 2-185, 2-191, 2-192, 2-193, 2-194, 2-197, 2-200, 2-201, 2-202, 2-203, 2-213, 2-214

Biological Test Example 7

*Boophilus microplus* (Dip)

Solvent: Dimethylsulfoxid

To produce a suitable preparation of active compound, 10 mg of active compound are dissolved in 0.5 ml solvent, and the concentrate is diluted with water to the desired concentration. Eight to ten adult engorged female *Boophilus microplus* ticks are placed in perforated plastic beakers and immersed in aqueous compound solution for one minute. Ticks are transferred to a filter paper in a plastic tray. Egg deposition of fertile eggs is monitored after. After 7 days mortality in % is determined. 100% means that all the ticks have been killed; 0% means that none of the ticks have been killed. In this test for example, the following compounds from the preparation examples showed good activity of 90% at application rate of 100 ppm: 2-154

In this test for example, the following compounds from the preparation examples showed good activity of 100% at application rate of 100 ppm: 2-69, 2-173, 2-176, 2-203

Biological Test Example 8

*Musca domestica*-Test

Solvent: dimethyl sulfoxide

To produce a suitable preparation of active compound, 10 mg of active compound are dissolved in 0.5 ml solvent, and the concentrate is diluted with water to the desired concentration. Prior to the assay, a piece of kitchen sponge is soaked with a mixture of sugar and compound solution and placed into a container. 10 adults (*Musca domestica*) are placed into the container and closed with a perforated lid. After 2 days mortality in % is determined. 100% means that all the flies have been killed; 0% means that none of the flies have been killed.

In this test for example, the following compounds from the preparation examples showed good activity of 80% at application rate of 100 ppm: 2-90, 2-108, 2-213

In this test for example, the following compounds from the preparation examples showed good activity of 95% at application rate of 100 ppm: 2-20

In this test for example, the following compounds from the preparation examples showed good activity of 100% at application rate of 100 ppm: 2-29, 2-31, 2-40, 2-49, 2-61, 2-64, 2-66, 2-69, 2-87, 2-104, 2-110, 2-133, 2-133, 2-162, 2-164, 2-174, 2-176, 2-185, 2-191, 2-194, 2-197, 2-200, 2-201, 2-202, 2-203

Preparation Example 1

Granule Formulations

To a mixture including the compound of the present invention (10 parts by weight) (No, 2-17), bentonite (montmorillonite; 30 parts by weight), talc (58 parts by weight) and lignin sulfonate (2 parts by weight), water (25 parts by weight) is added and the resulting mixture is kneaded well, B using an extrusive granulator, granules of 10 to 40 mesh are formed and granule formulations are obtained after drying at 40 to 50° C.

Preparation Example 2

Granule Formulations

Clay Mineral having a size distribution in the range of 0.2 to 2 ram (95 parts by weight) is added to a rotary mixer. By spraying the compound of the present invention (5 parts by weight) (No. 2-17) together with a liquid diluent under rotation, the clay is moistened followed by drying at 40 to 50° C. to obtain granule formulations.

Preparation Example 3

Emulsions

By mixing the compound of the present invention (30 parts by weight) (No. 2-17), xylene (55 parts by weight), polyoxyethylenealkylphenyl ether (8 parts by weight) and calcium alkylbenzene sulfonate (7 parts by weight) with stirring, emulsion are obtained.

Preparation Example 4

Wettable Agents

By mixing and pulverization of the compound of the present invention (15 parts by weight) (No. 2-17), a mixture including white carbon (fine powders of hydrous non-crystalline silicon oxide) and powder clay (1:5 mixture; 80 parts by weight), and a condensate of sodium alkylnaphthalene sulfonate formalin (3 parts by weight) and sodium alkylbenzene sulfonate (2 parts by weight), wettable agents are obtained.

Preparation Example 5

Wettable Granules

The compound of the present invention (20 parts by weight) (No, 2-17), lignin sodium sulfonate (30 parts by weight), bentonite (15 parts by weight) and calcined diatomite powder (35 parts by weight) are thoroughly mixed, After adding water thereto, the mixture is extruded through 0.3 mm screen followed by drying to obtain wettable granules.

Industrial Applicability

The novel pesticidal carboxamides of the present invention have an excellent pesticidal activity as pesticides as shown in the above examples.

The invention claimed is:

1. A carboxamide compound of Formula (I-III), or an optical isomer thereof:

(I-III)

wherein, $R^1$ and $R^5$ each independently represent $C_{1-4}$ alkyl, $C_{1-4}$ haloalkyl, haloalkoxy, $C_{1-4}$ haloalkylthio, $C_{1-4}$ haloalkylsulfinyl, $C_{1-4}$ haloalkylsulfonyl, or halogen;

$R^2$ and $R^4$ each independently represent hydrogen;

J represents $C_{1-4}$ perfluoroalkyl-O—, $C_{1-4}$ monobromoperfluoroalkyl-O—, $C_{1-4}$ perfluoroalkyl-S—, $C_{1-4}$ monobromoperfluoroalkyl-S—, $C_{1-4}$ perfluoroalkyl-S(O)—, $C_{1-4}$ monobromoperfluoroalkyl-S(O)—, $C_{1-4}$ perfluoroalkyl-S(O)$_2$—, $C_{1-4}$ monobromoperfluoroalkyl-S(O)$_2$—, $C_{1-4}$ perfluoroalkyl, $C_{1-4}$ monobromoperfluoroalkyl, $C_{3-6}$ perfluorocycloalkyl, $C_{3-6}$ monobromoperfluorocycloalkyl, —C($J^1$)($J^2$)($J^3$), or —C($J^1$)($J^2$)($OJ^4$);

$J^1$ and $J^2$ each independently represent $C_{1-4}$ perfluoroalkyl;

$J^3$ represents any one of the following G-1 to G-9:

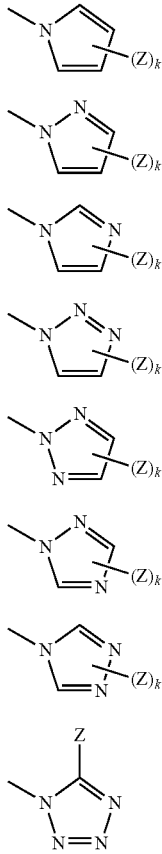

$C_{1-4}$ alkylthio, $C_{1-4}$ alkylsulfinyl, $C_{1-4}$ alkylsulfonyl, $C_{1-4}$ haloalkylthio, $C_{1-4}$ haloalkylsulfinyl, or $C_{1-4}$ haloalkylsulfonyl;

k represents 1, 2, 3 or 4;

$J^4$ represents hydrogen, $C_{1-4}$ alkyl, $C_{1-4}$ haloalkyl, $C_{1-4}$ alkylsulfonyl, $C_{1-4}$ haloalkylsulfonyl, or a phenyl group;

$R^6$ represents $C_{1-4}$ alkyl or hydrogen;

$R^7$ represents halogen or hydrogen;

$R^8$ represents halogen or hydrogen;

$R^9$ represents hydrogen, cyano, $C_{1-4}$ alkyl, $C_{1-4}$ haloalkyl, $C_{1-4}$ alkoxy, $C_{1-4}$ haloalkoxy, $C_{1-4}$ alkyl-S—, $C_{1-4}$ haloalkyl-S—, $C_{1-4}$ alkyl-S(O)—, $C_{1-4}$ haloalkyl-S(O)—, $C_{1-4}$ alkyl-S(O)$_2$—, $C_{1-4}$ haloalkyl-S(O)$_2$—, halogen, $C_{1-4}$ alkylcarbonylamino, phenylcarbonylamino, $C_{1-4}$ alkylcarbonylamino-$C_{1-4}$ alkyl, 1H-1,2,4-triazol-1-yl, or tri($C_{1-4}$ alkyl)silyl $C_{2-4}$ alkynyl;

$R^{11}$ represents hydrogen, halogen or cyano; and n''' represents 0 or 1.

2. The carboxamide compound of Formula (I-III), or an optical isomer thereof,

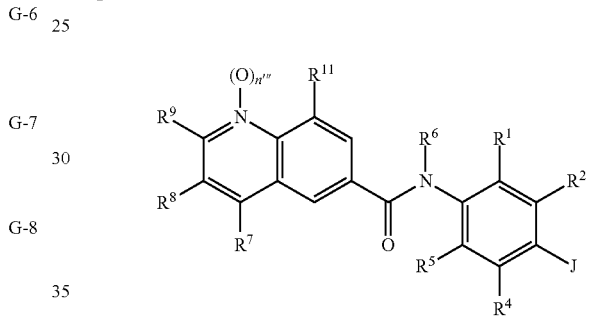

wherein:

| Compound No. | n''' | $R^1$ | $R^2$ | J | $R^4$ | $R^5$ | $R^6$ | $R^7$ | $R^8$ | $R^9$ | $R^{11}$ |
|---|---|---|---|---|---|---|---|---|---|---|---|
| 2-20 | 0 | CH$_3$ | H | 1,1,1,2,3,3,3-heptafluoropropan-2-yl | H | CH$_3$ | H | H | H | cyano | H |
| 2-29 | 0 | CH$_3$ | H | 1,1,1,2,3,3,3-heptafluoropropan-2-yl | H | ethyl | H | H | H | chloro | H |
| 2-31 | 0 | CH$_3$ | H | 1,1,1,2,3,3,3-heptafluoropropan-2-yl | H | ethyl | H | H | H | cyano | H |
| 2-37 | 0 | CH$_3$ | H | 1,1,1,2,3,3,3-heptafluoropropan-2-yl | H | propan-2-yl | H | H | H | cyano | H |
| 2-40 | 0 | CH$_3$ | H | 1,1,1,2,3,3,3-heptafluoropropan-2-yl | H | bromo | H | H | H | cyano | H |
| 2-46 | 0 | ethyl | H | 1,1,1,2,3,3,3-heptafluoropropan-2-yl | H | ethyl | H | H | H | cyano | H |
| 2-61 | 0 | chloro | H | 1,1,1,2,3,3,3-heptafluoropropan-2-yl | H | chloro | H | H | H | cyano | H |
| 2-64 | 0 | bromo | H | 1,1,1,2,3,3,3-heptafluoropropan-2-yl | H | bromo | H | H | H | cyano | H |
| 2-74 | 0 | CH$_3$ | H | 2-ethoxy-1,1,1,3,3,3-hexafluoropropan-2-yl | H | ethyl | H | H | H | cyano | H |
| 2-87 | 0 | CH$_3$ | H | 1,1,1,2,3,3,4,4,4-nonafluorobutan-2-yl | H | CH$_3$ | H | H | H | cyano | H |
| 2-130 | 0 | CH$_3$ | H | undecafluorocyclohexyl | H | ethyl | H | H | H | cyano | H |
| 2-164 | 0 | propyl | H | 1,1,1,2,3,3,4,4,4-nonafluorobutan-2-yl | H | bromo | H | H | H | cyano | H |
| 2-174 | 0 | iodo | H | 1,1,1,2,3,3,4,4,4-nonafluorobutan-2-yl | H | difluoromethoxy | H | H | H | H | H |
| 2-261 | 0 | CH$_3$ | H | 1,1,1,2,3,3,3-heptafluoropropan-2-yl | H | difluoromethoxy | H | H | H | cyano | H |
| 2-277 | 0 | chloro | H | 1-bromo-1,1,2,3,3,3-hexafluoropropan-2-yl | H | difluoromethoxy | H | H | H | cyano | H |

-continued

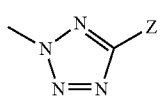

Z each independently represents hydrogen, halogen, nitro, cyano, hydroxy, thio, $C_{1-4}$ haloalkyl, $C_{1-4}$ haloalkoxy, 3. A pesticide comprising at least one compound according to claim 1.

4. A composition for controlling animal pests comprising at least one compound according to claim 1, and an extender and/or a surfactant.

5. A method for controlling parasites on animals, comprising administering to an animal an effective amount of at least one compound according to claim 1.

6. A method for controlling animal pests, comprising applying at least one compound according to claim 1 to the animal pests and/or their habitat.

7. A method for treating seed of conventional or transgenic plants, comprising applying to the seed an effective amount of at least one compound according to claim 1.

* * * * *